(12) United States Patent
Armani et al.

(10) Patent No.: US 9,090,606 B2
(45) Date of Patent: Jul. 28, 2015

(54) COMPOUNDS

(71) Applicant: CHIESI FARMACEUTICI S.p.A., Parma (IT)

(72) Inventors: Elisabetta Armani, Parma (IT); Gabriele Amari, Parma (IT); Mauro Riccaboni, Parma (IT); Charles Baker-Glenn, Essex (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 14/097,693

(22) Filed: Dec. 5, 2013

(65) Prior Publication Data

US 2014/0155428 A1    Jun. 5, 2014

(30) Foreign Application Priority Data

Dec. 5, 2012   (EP) .................................. 12195728

(51) Int. Cl.
| | |
|---|---|
| *A61K 31/44* | (2006.01) |
| *C07D 453/02* | (2006.01) |
| *C07D 401/12* | (2006.01) |
| *C07D 453/00* | (2006.01) |
| *A61K 45/06* | (2006.01) |

(52) U.S. Cl.
CPC .............. *C07D 453/02* (2013.01); *A61K 45/06* (2013.01); *C07D 401/12* (2013.01); *C07D 453/00* (2013.01)

(58) Field of Classification Search
USPC .......................................... 514/305; 546/137
See application file for complete search history.

(56) References Cited

U.S. PATENT DOCUMENTS

| | | | |
|---|---|---|---|
| 7,799,782 B2 * | 9/2010 | Munson et al. ............. | 514/234.5 |
| 7,820,698 B2 | 10/2010 | Rizzi et al. | |
| 7,923,565 B2 | 4/2011 | Delcanale et al. | |
| 7,968,724 B2 | 6/2011 | Armani et al. | |
| 8,203,000 B2 | 6/2012 | Delcanale et al. | |
| 8,383,826 B2 | 2/2013 | Delcanale et al. | |
| 8,440,834 B2 | 5/2013 | Amari et al. | |
| 8,648,204 B2 | 2/2014 | Amari et al. | |
| 8,772,314 B2 * | 7/2014 | Amari et al. .................. | 514/305 |
| 2011/0144075 A1 | 6/2011 | Delcanale et al. | |
| 2013/0005716 A1 | 1/2013 | Armani et al. | |
| 2013/0012487 A1 | 1/2013 | Amari et al. | |
| 2013/0079313 A1 | 3/2013 | Armani et al. | |
| 2013/0137648 A1 | 5/2013 | Delcanale et al. | |
| 2013/0324501 A1 | 12/2013 | Armani et al. | |

OTHER PUBLICATIONS

U.S. Appl. No. 14/097,397, filed Dec. 5, 2013, Armani, et al.
U.S. Appl. No. 14/097,586, filed Dec. 5, 2013, Armani, et al.
U.S. Appl. No. 14/097,445, filed Dec. 5, 2013, Armani, et al.
U.S. Appl. No. 14/048,651, filed Oct. 8, 2013, Armani, et al.
U.S. Appl. No. 14/164,527, filed Jan. 27, 2014, Armani, et al.
U.S. Appl. No. 14/560,140, filed Dec. 4, 2014, Amari, et al.
U.S. Appl. No. 14/560,009, filed Dec. 4, 2014, Amari, et al.

* cited by examiner

*Primary Examiner* — Rei-Tsang Shiao

(74) *Attorney, Agent, or Firm* — Oblon, McClelland, Maier & Neustadt, L.L.P.

(57) ABSTRACT

Compounds of formula (I) defined herein are both inhibitors of the phosphodiesterase 4 (PDE4) enzyme and muscarinic M3 receptor antagonists and are useful for the prevention and/or treatment of a disease of the respiratory tract characterized by airway obstruction.

14 Claims, No Drawings

COMPOUNDS

CROSS REFERENCES TO RELATED APPLICATIONS

This application claims priority to European Patent Application No. 12195728.6 filed on Dec. 5, 2012, which is incorporated herein by reference in its entirety.

BACKGROUND OF THE INVENTION

1. Field of the Invention

The present invention relates to novel compounds which are both inhibitors of the phosphodiesterase 4 (PDE4) enzyme and muscarinic M3 receptor antagonists. The present invention also relates to methods of preparing such a compound, compositions which contain such a compound, and therapeutic uses of such a compound.

2. Discussion of the Background

Chronic obstructive pulmonary disease (COPD) is a respiratory disorder characterized by progressive, not fully reversible, airflow limitation associated with an abnormal pulmonary inflammatory response to noxious particles or gases. For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into two general classes: bronchodilators, (β2-adrenoceptor agonists, antimuscarinic agents and methylxanthines) and antiinflammatory agents (glucocorticosteroids and selective phosphodiesterase-4 (PDE4) inhibitors). Bronchodilator drugs are the current mainstay of treatment for symptoms' relief.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients.

Muscarinic antagonists block the effects of ACh at muscarinic receptors. Currently, there are five known muscarinic receptor subtypes (M1-M5); human airway smooth muscle contains M1, M2, and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells. These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention and constipation. Whereas dry mouth is the most common systemic anticholinergic side effect associated with the use of antimuscarinic antagonists as a result of the systemic blockade of M1 and M3 receptors the most potentially serious systemic effect is tachycardia, which results from the blockade of cardiac M2 receptors.

Inhaled anticholinergic antimuscarinic drugs approved for the treatment of COPD include ipratropium bromide (Atrovent®), oxitropium bromide (Oxivent®) and tiotropium bromide (Spiriva®). Both ipratropium and oxitropium are short-acting agents. In contrast, tiotropium bromide is the only long-acting antimuscarinic agent (LAMA) currently marketed for COPD, proved to be suitable for once-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure. Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over 4 weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 mL) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

SUMMARY OF THE INVENTION

Accordingly, it is one object of the present invention to provide novel compounds which act both as inhibitors of the phosphodiesterase 4 (PDE4) enzyme and as muscarinic M3 receptor antagonists.

It is another object of the present invention to provide novel methods of preparing such a compound.

It is another object of the present invention to provide novel compositions which contain such a compound.

It is another object of the present invention to provide novel methods of preventing and/or treating certain diseases or conditions by administering such a compound.

These and other objects, which will become apparent during the following detailed description, have been achieved by the inventors' discovery of compounds of formula (I):

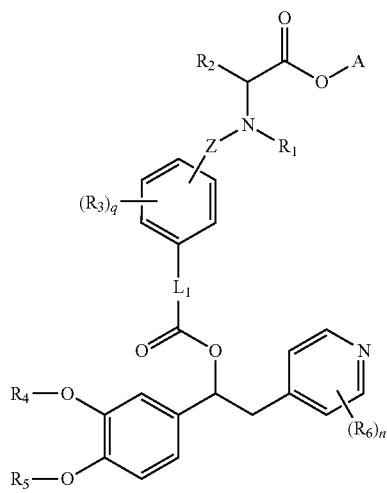

(I)

wherein $R_1$ is selected from hydrogen, ($C_1$-$C_4$) alkyl, and —$SO_2$($C_1$-$C_4$)alkyl;

$R_2$ is selected from an aryl and a 5 to 11 membered heteroaryl, wherein such aryl or heteroaryl is optionally substituted by 1 to 3 groups at each occurrence independently selected from the group consisting of: halogen, ($C_1$-$C_4$)haloalkyl, hydroxy, —$SO_2NR_8R_9$, —CN, —$NR_{10}SO_2R_{11}$, ($C_1$-$C_4$) alkyl and ($C_1$-$C_4$) alkoxy, wherein groups ($C_1$-$C_4$) alkyl or ($C_1$-$C_4$) alkoxy are optionally substituted by one group ($C_3$-$C_7$) cycloalkyl, and wherein $R_8$ is hydrogen or ($C_1$-$C_6$) alkyl;

$R_9$ is hydrogen or ($C_1$-$C_6$) alkyl;

$R_{10}$ is hydrogen or ($C_1$-$C_6$) alkyl;

$R_{11}$ is hydrogen or ($C_1$-$C_6$) alkyl;

Z is a diradical selected from the group consisting of: a bond, —($CH_2$)$_m$—, —S—, —S(O)—, —S($O_2$)—, a group —C(O)—, and a group [1]—($CH_2$)$_m$—OC(O)-[2] wherein [1] and [2] represent, respectively the point of attachment of group Z to phenyl ring and to the nitrogen atom and m is an integer ranging from 1 to 4;

$L_1$ is a divalent radical selected from the group consisting of:
a bond,
—($CH_2$)$_p$—,
[3]—($CH_2$)$_p$—O-[4]
[3]—($CH_2$)$_p$—$NR_{10}$—($CH_2$)$_t$-[4]
[3]—($CH_2$)$_p$—OC(O)-[4]
[3]—($CH_2$)$_p$—$NR_{10}$C(O)-[4]
[3]—($CH_2$)$_p$—$NR_{10}$S($O_2$)—[4]
[3]—($CH_2$)$_p$—S($O_2$)—N($R_{10}$)—[4]
wherein [3] and [4] represent, respectively the point of attachment of group $L_1$ to the carbonyl group and to the phenyl ring, and wherein $R_{10}$ is as described above, p is an integer ranging from 1 to 4 and t is an integer ranging from 1 to 4 each $R_3$ is independently hydrogen or is selected from the group consisting of: halogen, ($C_1$-$C_4$) haloalkyl, hydroxy, aminocarbonyl, di-($C_1$-$C_4$) alkylaminocarbonyl, —$SO_2NR_{12}R_{13}$, —CN, —$NR_{14}SO_2R_{15}$, —($CH_2$)$_m$—$NR_{14}SO_2R_{15}$—, ($C_1$-$C_4$) alkyl and ($C_1$-$C_4$) alkoxy, wherein groups ($C_1$-$C_4$) alkyl or ($C_1$-$C_4$) alkoxy are optionally substituted by one group ($C_3$-$C_7$) cycloalkyl, m is as described above and $R_{12}$ is hydrogen or ($C_1$-$C_6$) alkyl;

$R_{13}$ is hydrogen or ($C_1$-$C_6$) alkyl;

$R_{14}$ is hydrogen or ($C_1$-$C_6$) alkyl;

$R_{15}$ is hydrogen or ($C_1$-$C_6$) alkyl;

q is an integer ranging from 1 to 3;

$R_4$ and $R_5$ are the same or different and are independently selected from the group consisting of:

H;

($C_3$-$C_7$) cycloalkylcarbonyl;

($C_1$-$C_6$) alkyl, optionally substituted by one or more substituents selected from ($C_3$-$C_7$) cycloalkyl and ($C_5$-$C_7$) cycloalkenyl;

($C_1$-$C_6$) haloalkyl;

($C_3$-$C_7$) cycloalkyl;

($C_5$-$C_7$) cycloalkenyl;

($C_2$-$C_6$) alkenyl; and ($C_2$-$C_6$) alkynyl;

or $R_4$ and $R_5$, together with the interconnecting atoms, form a 2,2-difluoro-1,3-dioxolane ring of formula (r) fused to the phenyl moiety which bears groups —$OR_4$ and —$OR_5$, wherein asterisks indicate carbon atoms shared with the phenyl ring:

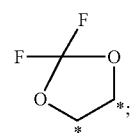

(r)

each $R_6$ is independently selected from the group consisting of: CN, $NO_2$, $CF_3$ and halogen atoms;

n is 0 or an integer ranging from 1 to 3;

A is a nitrogen containing group which may be selected from:

a group (a) which is —($CH_2$)$_s$—$NR_{16}R_{17}$ wherein s is an integer ranging from 1 to 4 and $R_{16}$ and $R_{17}$ are independently hydrogen or ($C_1$-$C_4$) alkyl; and a group (b) which is a saturated monocyclic, bicyclic or tricyclic heterocyclic ring system optionally substituted by one or two groups $R_{18}$ which are at each occurrence independently selected from ($C_1$-$C_4$) alkyl and benzyl, and N-oxides on the pyridine ring, deuterated derivativse, and pharmaceutically acceptable salts, and solvates thereof.

The present invention further provides the corresponding N-oxides on the pyridine ring of compounds of formula (I) which are represented by formula (IA)

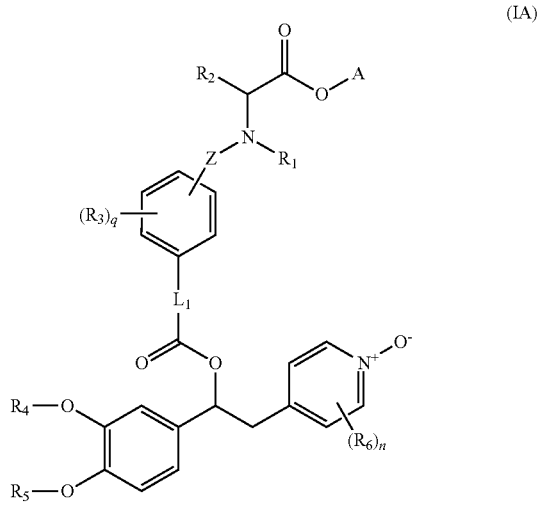

(IA)

wherein $R_1$, $R_2$, $R_3$, $R_4$, $R_5$, $R_6$, A, Z, $L_1$, n, and q are as described above.

The present invention further involves the corresponding deuterated derivatives of compounds of formula (I) wherein at least one hydrogen atom is substituted by corresponding atoms of deuterium.

The present invention also encompasses the pharmaceutically acceptable salts and/or solvates thereof.

The term "pharmaceutically acceptable salts", as used herein, refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable. Suitable examples of said salts may thus include mineral or organic acid addition salts of basic residues such as amino groups, as well as mineral or organic acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

Those skilled in the art of organic chemistry will appreciate that many organic compounds can form complexes with solvents in which they are reacted or from which they are precipitated or crystallized. These complexes are known as "solvates". Pharmaceutically acceptable solvates of compound of the invention are within the scope of the present invention.

Included within the scope of the present invention are also polymorphs and crystalline forms of compounds of formula (I), of their N-oxides on the pyridine ring, or of pharmaceutically acceptable salts, or solvates thereof.

Hereinafter, compounds of formula (I), (IA), (IB), (IC), (ID), (Ia), (Ib), (Ic), (Id), and (I)', corresponding N-oxides on the pyridine ring, enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the invention".

The present invention further provides a process for the preparation of compounds of the invention.

The present invention also provides pharmaceutical compositions of compounds of the invention either alone or in combination, in admixture with one or more pharmaceutically acceptable carriers.

In a further aspect, the present invention provides the use of the compounds of the invention as a medicament.

In one aspect, the present invention provides the use of the compounds of the invention for the manufacture of a medicament.

In particular, the present invention provides the use of the compounds of the invention for the prevention and/or treatment of any disease wherein an inhibition of PDE4 activity along with muscarinic M3 receptor antagonism is desirable.

In particular the compounds of the invention alone or combined with other active ingredients may be administered for the prevention and/or treatment of a disease the respiratory tract characterized by airway obstruction such as asthma and COPD. In one embodiment, the compounds of the invention may be administered for the prevention and/or treatment of COPD.

In a further aspect, the present invention provides the use of compounds of the invention for the preparation of a medicament for the prevention and/or treatment of any disease wherein an inhibition of PDE4 activity along with muscarinic M3 receptor antagonism is desirable.

Moreover, the present invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the invention.

A further aspect of the present invention provides a suitable inhalation device, comprising a pharmaceutical composition of a compound of the invention, which may be respectively selected from a single- or multi-dose dry powder inhaler, a pressurized metered dosed inhaler or a nebulizer and in particular a soft mist nebulizer.

A further aspect of the present invention provides a kit comprising the pharmaceutical compositions of a compound of the invention either alone or in combination with one or more active ingredient and a device which may be a single- or multi-dose dry powder inhaler, a metered dose inhaler or a nebulizer.

DETAILED DESCRIPTION OF THE PREFERRED EMBODIMENTS

The term "halogen atoms" as used herein includes fluorine, chlorine, bromine, and iodine, preferably chlorine.

As used herein, the term "$(C_1-C_x)$ alkyl" where x is an integer greater than 1 refers to straight-chained and branched alkyl groups wherein the number of constituent carbon atoms is in the range 1 to x. Particular alkyl groups are methyl, ethyl, n-propyl, i-propyl, n-butyl, sec-butyl, i-butyl, and t-butyl.

By analogy, the term "($C_1$-$C_x$)alkylene", refers to a divalent ($C_1$-$C_x$)alkyl radical, wherein ($C_1$-$C_x$)alkyl is as above defined.

The term "($C_1$-$C_X$) alkoxy" where x is an integer greater than 1 refers to straight-chained and branched alkoxy groups wherein the number of constituent carbon atoms is in the range 1 to x. Particular alkoxy groups are methoxy, ethoxy, n-propoxy, i-propoxy, n-butoxy, sec-butoxy, i-butoxy, and t-butoxy.

The expressions "($C_1$-$C_x$)haloalkyl" refer to the above defined "($C_1$-$C_x$)alkyl" groups wherein one or more hydrogen atoms are replaced by one or more halogen atoms, which can be the same or different from each other. Non-limiting examples of said ($C_1$-$C_6$)haloalkyl groups may thus include halogenated, poly-halogenated and fully halogenated alkyl groups wherein all of the hydrogen atoms are replaced by halogen atoms, e.g. trifluoromethyl or difluoro methyl groups.

The term "($C_3$-$C_y$)cycloalkyl" where y is an integer greater than or equal to 3 refers to saturated cyclic hydrocarbon groups containing from 3 to y ring carbon atoms. Non-limiting examples include cyclopropyl, cyclobutyl, cyclopentyl, cyclohexyl, and cycloheptyl.

The expression "($C_3$-$C_y$)heterocycloalkyl" refers to monocyclic ($C_3$-$C_y$)cycloalkyl groups, in which at least one ring carbon atom is replaced by a heteroatom (e.g. N, NH, S or O). Non-limiting examples of ($C_3$-$C_y$)heterocycloalkyl are represented by: pyrrolidinyl, thiazolidinyl, piperazinyl, piperidinyl, morpholinyl, thiomorpholinyl, azetidinyl.

The expression "($C_3$-$C_y$)cycloalkylcarbonyl" refers to ($C_3$-$C_y$)cycloalkylCO-groups wherein the group "($C_3$-$C_y$)cycloalkyl" has the meaning above defined.

The term "($C_2$-$C_6$)alkenyl" refers to straight or branched, conjugated or non-conjugated, carbon chains with one or more double bonds, in cis or trans configuration, wherein the number of atoms is in the range 2 to 6.

The term "($C_5$-$C_z$) cycloalkenyl" where z is an integer greater than or equal to 5 refers to cyclic hydrocarbon groups containing from 5 to z ring carbon atoms and one or more double bonds.

The term "($C_2$-$C_6$)alkynyl" refers to straight or branched carbon chains with one or more triple bonds wherein the number of atoms is in the range 2 to 6.

The expression "aryl" refers to mono or bi-cyclic ring systems which have 6 to 10 ring atoms, wherein at least one ring is aromatic.

The expression "heteroaryl" refers to mono or bi-cyclic ring systems with 5 to 11 ring atoms, in which at least one ring is aromatic and in which at least one ring atom is a heteroatom (e.g. N, NH, S or O).

Non-limiting examples of suitable aryl or 5 and 6-membered heteroaryl monocyclic systems include, for instance, benzene (phenyl), thiophene (thiophenyl), pyrrole (pyrrolyl), pyrazole (pyrazolyl), imidazole (imidazolyl), triazole (triazolyl), tetrazole (tetrazolyl), isoxazole (isoxazolyl), oxazole (oxazolyl), isothiazole (isothiazolyl), thiazole (thiazolyl), pyridine (pyridinyl), furan (furanyl) derived radicals and the like.

Non-limiting examples of suitable aryl or heteroaryl bicyclic systems include naphthalene (naphthyl), biphenylene (biphenylenyl), purine (purinyl), pteridine (pteridinyl), benzimidazole (benzimidazolyl), benzotriazole (benzotriazolyl), quinoline (quinolinyl), isoquinoline (isoquinolinyl), indole (indolyl), isoindole (isoindolyl), indazole (indazolyl), benzothiophene (benzothiophenyl), dihydrobenzo dioxin, dihydrobenzo dioxepin, benzo oxazin radicals and the like.

As used herein, the expression "heterocyclic ring system" refers to optionally substituted mono-, bi- or tri-cyclic ring systems which may be saturated, partially unsaturated or unsaturated, such as ($C_3$-$C_7$) heterocycloalkyl or heteroaryl having 5 to 11 ring atoms in which at least one ring atom is a heteroatom (e.g. N, S or O). Non-limiting examples of "heterocyclic ring system" are represented by: pyrrolidinyl, imidazolidinyl, piperazinyl, piperidinyl, quinuclidinyl, 8-azabicyclo[3.2.1]octanyl or dehydroxy scopine radical all optionally substituted by ($C_1$-$C_x$) alkyl or benzyl on a nitrogen atom.

Thus, the present invention is directed to a class of compounds acting both as inhibitors of the phosphodiesterase 4 (PDE4) enzyme and as muscarinic M3 receptor antagonists.

The present invention relates to derivatives of general formula (I), N-oxides on the pyridine ring, deuterated derivatives and pharmaceutically acceptable salts or solvates thereof,

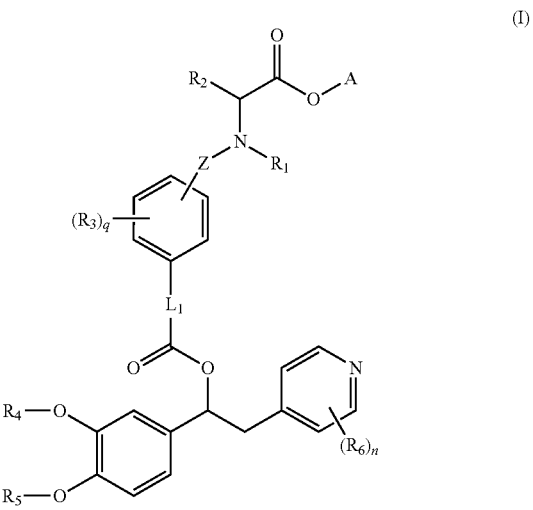

(I)

wherein $R_1$, $R_2$, $R_3$, $R_4$, $R_5$, $R_6$, A, $L_1$, n, q and Z are as above defined.

It will be apparent to those skilled in the art that compounds of general formula (I) at least contain one stereogenic center, namely represented by the carbon atom (1), and therefore exist as optical stereoisomers.

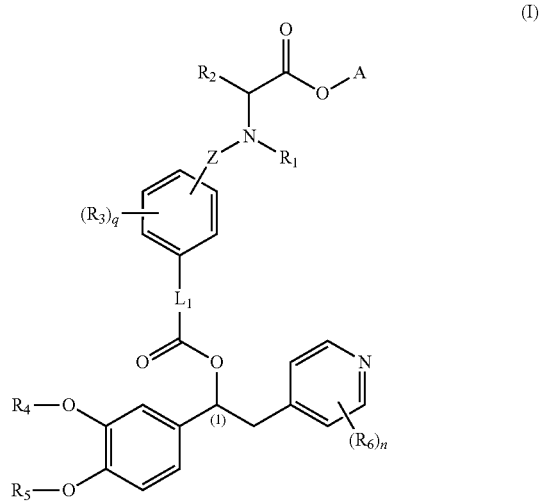

(I)

It will be apparent to the skilled person that compounds according to the invention may have at least two stereogenic centers, thus they may accordingly exist at least as four diastereoisomers. When the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon (1) is that shown below:

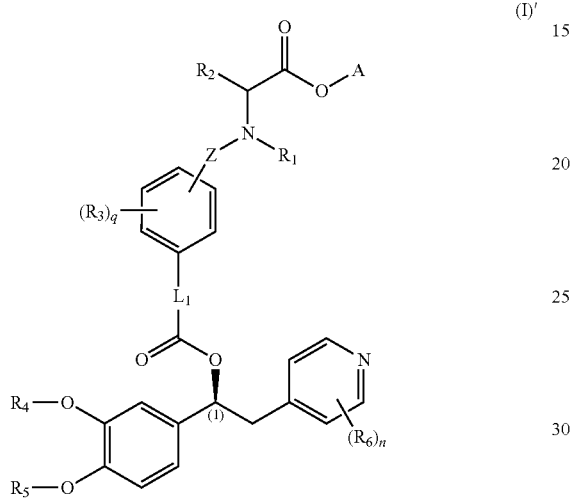

(I)'

The absolute configuration for carbon (1) is assigned on the basis of Cahn-Ingold-Prelog nomenclature based on groups' priorities.

In one preferred embodiment, for compounds of formula (I), absolute configuration at carbon (1) is (S).

In one embodiment, when A is a group of formula (I) as below defined, compounds of formula (I) may exist as at least four diastereoisomers couples (Ia), (Ib), (Ic) and (Id) herebelow reported, which are comprised within the scope of the present invention; each couple of diastereoisomers (Ia), (Ib), (Ic), and (Id) is constituted by a mixture of corresponding epimers at stereogenic center identified as (2).

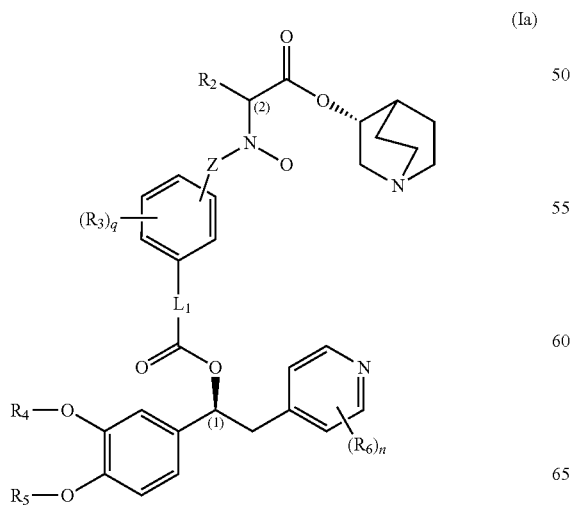

(Ia)

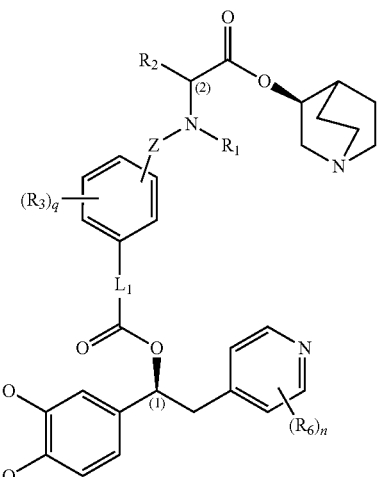

(Ib)

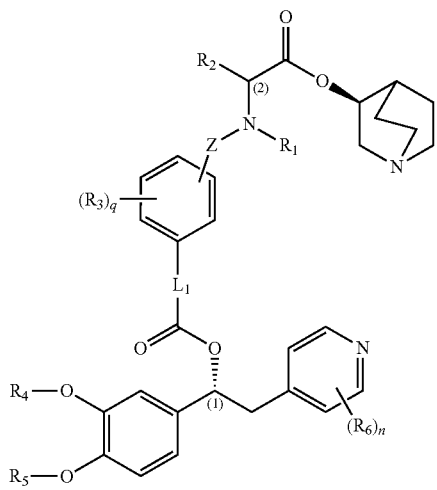

(Ic)

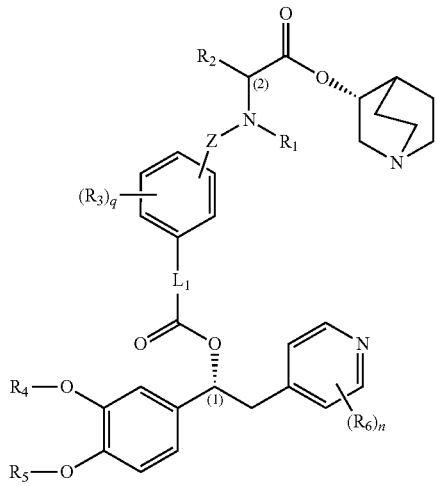

(Id)

It will be apparent to the skilled person that compounds of formula (Ia), (Ib), (Ic), and (Id) may be also obtained as single diastereoisomers wherein stereogenic center at carbon atom identified as (2) is defined as R or S.

In one embodiment, compounds of formula (Ia) are provided as above reported, or single diastereoisomers thereof.

It is to be understood that all preferred groups or embodiments described herebelow and hereabove for compounds of formula (I) may be combined among each other and apply to compounds of formula (IA), (IB), (IC), (ID), (Ia), (Ib), (Ic), (Id), and (I)' as well mutatis mutandis.

In a preferred embodiment, the invention provides compounds of formula (IA), which are N-oxides on the pyridine ring of compounds of formula (I), deuterated derivatives and pharmaceutically acceptable salts and solvates thereof:

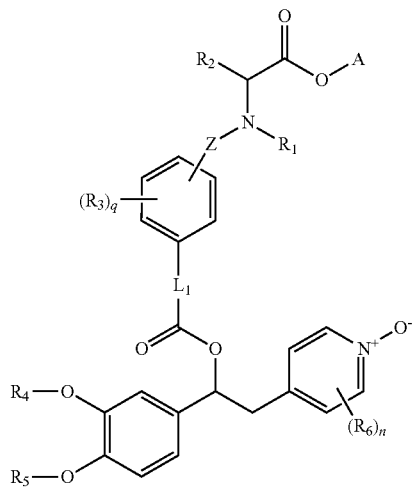

(IA)

wherein $R_1$, $R_2$, $R_3$, $R_4$, $R_5$, $R_6$, A, $L_1$, n, q and Z are as above defined.

In a preferred embodiment, n is 2 and $R_6$ are halogen atoms. In a further preferred embodiment, $R_6$ are two chlorine atoms at positions 3 and 5 of the pyridine ring.

In one preferred embodiment, $R_5$ is selected from ($C_1$-$C_6$) haloalkyl and ($C_1$-$C_6$) alkyl and $R_4$ is selected from ($C_3$-$C_7$) cycloalkyl or ($C_1$-$C_6$) alkyl which is optionally substituted by ($C_3$-$C_7$) cycloalkyl.

In another preferred embodiment, $R_4$ and $R_5$, together with the interconnecting atoms, form a 2,2-difluoro-1,3-dioxolane ring of formula (r) fused to the phenyl moiety which bears groups —$OR_4$ and —$OR_5$, wherein asterisks indicate carbon atoms shared with the phenyl ring:

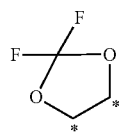

(r)

In a further preferred embodiment, $R_5$ is ($C_1$-$C_6$) haloalkyl and $R_4$ is ($C_1$-$C_6$) alkyl which is substituted by ($C_3$-$C_7$) cycloalkyl.

In another preferred embodiment, $R_4$ is ($C_1$-$C_6$) alkyl and $R_5$ is ($C_1$-$C_6$) alkyl.

A preferred group of compounds is that wherein the 4-pyridinyl ring is substituted at positions 3 and 5 with two atoms of chlorine, according to the general formula (IB)

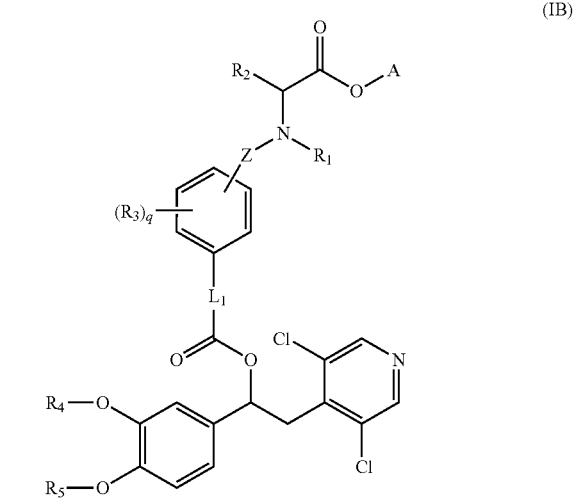

(IB)

wherein $R_1$, $R_2$, $R_3$, $R_4$, $R_5$, Z, $L_1$, A and q are as defined above for compounds of formula (I); and the corresponding N-oxide on the pyridine ring, deuterated derivatives and pharmaceutically acceptable salts and solvates thereof.

Another preferred group of compounds is that shown below according to general formula (IC):

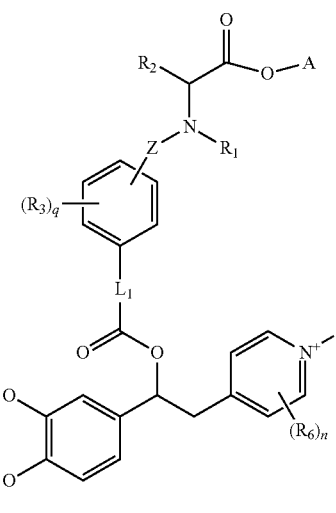

(IC)

wherein $R_1$, $R_2$, $R_3$, $R_6$, A, $L_1$, q and n are as defined above for compounds of formula (I); and the corresponding N-oxide on the pyridine ring, or pharmaceutically acceptable salts thereof.

A more preferred group of compounds is that shown below according to general formula (ID):

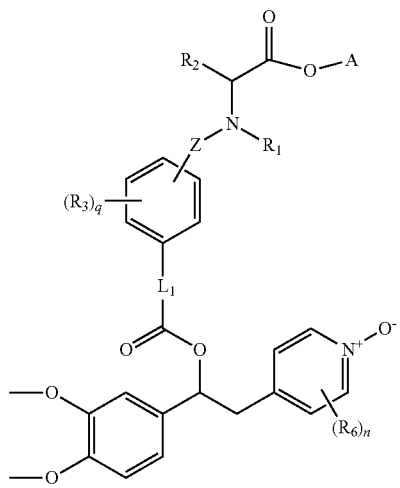

(ID)

wherein $R_1$, $R_2$, $R_3$, $R_6$, A, $L_1$, q and n are as defined above for compounds of formula (I), the corresponding N-oxide on the pyridine ring, and pharmaceutically acceptable salts and solvates thereof.

Another more preferred group of compounds is that shown below according to general formula (IE)

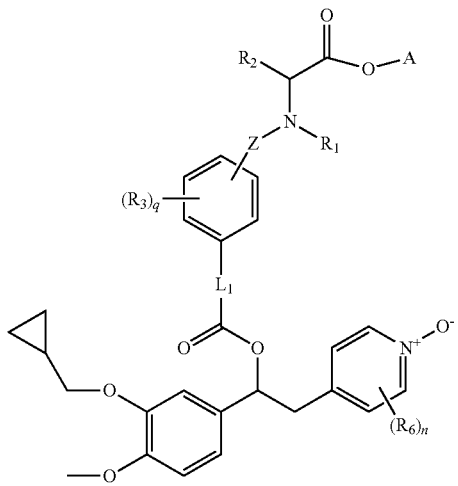

(IE)

wherein $R_1$, $R_2$, $R_3$, $R_6$, A, $L_1$, q and n are as defined above for compounds of formula (I), the corresponding N-oxide on the pyridine ring, and pharmaceutically acceptable salts and solvates thereof.

In one embodiment, A is a group (b) represented by a group of formula (I), (ii), (iii) or (iv):

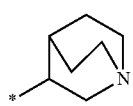

(i)

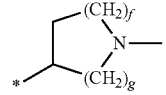

(ii)

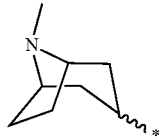

(iii)

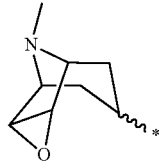

(iv)

wherein
f=1, 2 or 3;
g=1, 2 or 3.

In another embodiment, A is a group (b) represented by a group of formula (i):

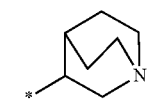

(i)

According to a preferred embodiment, the present invention provides the compounds reported below:

[(1S)-2-(3,5-dichloro-1-oxido-pyridin-1-ium-4-yl)-1-(3,4-dimethoxyphenyl)ethyl] 3-[[[2-oxo-1-phenyl-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 3-fluoro-4-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl]-4-[[1-(3-fluorophenyl)-2-oxo-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl]-4-[[1-(2-fluorophenyl)-2-oxo-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl]-4-[[1-(3-fluorophenyl)-2-oxo-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl]-4-[[2-oxo-1-phenyl-2-[(3R)-quinuclidin-3-yl]oxy-ethyl]amino]benzoate single diastereoisomer;

[(1S)-2-(3,5-dichloro-1-oxido-pyridin-1-ium-4-yl)-1-(3,4-dimethoxyphenyl)ethyl]-4-[[2-oxo-1-phenyl-2-[(3R)-quinuclidin-3-yl]oxy-ethyl]amino]benzoate; single diastereoisomer

[(1S)-2-(3,5-dichloro-1-oxido-pyridin-1-ium-4-yl)-1-(3,4-dimethoxyphenyl)ethyl]-4-[[1-(2-fluorophenyl)-2-oxo-2-[(3R)-quinuclidin-3-yl]oxy-ethyl]amino]benzoate single diastereoisomer;

[(1S)-2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]amino]benzoate single diastereoisomer;

[(1S)-2-(3,5-dichloro-1-oxido-pyridin-1-ium-4-yl)-1-(3,4-dimethoxyphenyl)ethyl] 2-fluoro-4-[[2-oxo-1-phenyl-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]sulfamoyl]benzoate single diastereoisomer;

[(1S)-2-(3,5-dichloro-1-oxido-pyridin-1-ium-4-yl)-1-(3,4-dimethoxyphenyl)ethyl] 3-[[[1-(2-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl]-4-[[[2-oxo-1-phenyl-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 4-[[[1-(2-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 3-[[[2-oxo-1-phenyl-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[2-oxo-1-phenyl-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl]-4-[[[2-oxo-1-phenyl-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl]-4-[[[1-(4-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl]-4-[[[1-(4-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl]-4-[[[1-(3-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl]-4-[[[1-(3-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl]-4-[2-[[1-(2-fluorophenyl)-2-oxo-2-[(3R)-quinuclidin-3-yl]oxy-ethyl]amino]ethyl]benzoate;

[(1S)-2-(3,5-dichloro-1-oxido-pyridin-1-ium-4-yl)-1-[4-(difluoromethoxy)-3-methoxy-phenyl]ethyl] 3-[[[1-(2-fluorophenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(4-fluorophenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(3-methoxyphenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(2-methoxyphenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(2-fluorophenyl)-2-oxo-2-[(3R)-quinuclidin-3-yl]oxy-ethyl]amino]methyl]benzoate;

[2-(3,5-dichloro-1-oxido-pyridin-1-ium-4-yl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl]-4-[[[2-oxo-1-(3-pyridyl)-2-[(3R)-quinuclidin-3-yl]oxy-ethyl]amino]methyl]benzoate;

[(3R)-quinuclidin-3-yl] 2-[[4-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-(2-fluorophenyl)acetate;

[(3R)-quinuclidin-3-yl] 2-[[3-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-(2-fluorophenyl)acetate;

[(3R)-quinuclidin-3-yl] 2-[[3-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-phenyl-acetate;

[(3R)-quinuclidin-3-yl] 2-[[3-[2-[(1S)-2-(3,5-dichloro-1-oxido-pyridin-1-ium-4-yl)-1-(3,4-dimethoxyphenyl)ethoxy]-2-oxo-ethyl]phenyl]methylamino]-2-(2-fluorophenyl)acetate;

[(1S)-2-(3,5-dichloro-1-oxido-pyridin-1-ium-4-yl)-1-[4-(difluoromethoxy)-3-isopropoxy-phenyl]ethyl] 3-[[[1-(2-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-[4-(difluoromethoxy)-3-isopropoxy-phenyl]ethyl]-4-[[[1-(2-fluorophenyl)-2-oxo-2-[(3R)-quinuclidin-3-yl]oxy-ethyl]amino]methyl]benzoate;

[(1R)-2-(3,5-dichloro-4-pyridyl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate;

[(1S)-2-(3,5-dichloro-4-pyridyl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate;

[(1R)-2-(3,5-dichloro-4-pyridyl)-1-(3,4-dimethoxyphenyl)ethyl]-4-[[[1-(2-methoxyphenyl)-2-oxo-2-[(3R)-quinuclidin-3-yl]oxy-ethyl]amino]methyl]benzoate;

[(1S)-2-(3,5-dichloro-4-pyridyl)-1-(3,4-dimethoxyphenyl)ethyl]-4-[[[1-(2-methoxyphenyl)-2-oxo-2-[(3R)-quinuclidin-3-yl]oxy-ethyl]amino]methyl]benzoate;

[(1R)-2-(3,5-dichloro-4-pyridyl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate;

[(1S)-2-(3,5-dichloro-4-pyridyl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate;

[(1S)-2-(3,5-dichloro-4-pyridyl)-1-(3,4-dimethoxyphenyl)ethyl]-4-[[[1-(3-fluorophenyl)-2-oxo-2-[(3R)-quinuclidin-3-yl]oxy-ethyl]amino]methyl]benzoate;

[(1R)-2-(3,5-dichloro-4-pyridyl)-1-(3,4-dimethoxyphenyl)ethyl]-4-[[[1-(3-fluorophenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl]-4-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl]-4-[[1-(4-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 4-[[1-(2-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 4-[[1-(3-methoxyphenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl]-4-[[1-(4-methoxyphenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl]-4-[[1-(2-methoxyphenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(benzofuran-5-yl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-furyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl]-4-[[1-(2-fluorophenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl]-4-[[1-(4-fluorophenyl)-2-oxo-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 3-[[1-(3-fluorophenyl)-2-oxo-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl]-4-[[2-oxo-1-phenyl-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 3-[[1-(4-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-(p-tolyl)-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-fluorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-methoxyphenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-methoxyphenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-methoxyphenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3,4-difluorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]-4-[[2-oxo-1-phenyl-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3S)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-fluorophenyl)-2-oxo-2-[(3R)-quinuclidin-3-yl]oxy-ethyl]sulfamoyl]benzoate;

[(1S)-2-(3,5-dichloro-1-oxido-pyridin-1-ium-4-yl)-1-[4-(difluoromethoxy)-3-methoxy-phenyl]ethyl] 3-[[[1-(2-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-[4-(difluoromethoxy)-3-methoxy-phenyl]ethyl] 3-[[[1-(2-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl]-4-[[[2-oxo-1-(3-pyridyl)-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-[4-(difluoromethoxy)-3-isopropoxy-phenyl]ethyl] 3-[[[1-(2-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-[4-(difluoromethoxy)-3-isopropoxy-phenyl]ethyl]-4-[[[1-(2-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-[4-(difluoromethoxy)-3-isopropoxy-phenyl]ethyl] 4-[[[1-(2-fluorophenyl)-2-oxo-2-[(3R)-quinuclidin-3-yl]oxy-ethyl]amino]methyl]benzoate single diastereoisomer;

[(3R)-quinuclidin-3-yl] 2-[[4-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-phenyl-acetate single diastereoisomer;

[(3R)-quinuclidin-3-yl] 2-[[4-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-phenyl-acetate single diastereoisomer;

[(1S)-1-[3-(cyclopropylmethoxy)-4-(difluoromethoxy)phenyl]-2-(3,5-dichloro-1-oxido-pyridin-1-ium-4-yl)ethyl] 2-hydroxy-3-[[[2-oxo-1-phenyl-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl]-4-[2-[[2-oxo-1-phenyl-2-[(3R)-quinuclidin-3-yl]oxy-ethyl]amino]ethyl]benzoate;

[(1S)-2-(3,5-dichloro-1-oxido-pyridin-1-ium-4-yl)-1-(3,4-dimethoxyphenyl)ethyl]-4-[2-[[1-(2-fluorophenyl)-2-oxo-2-[(3R)-quinuclidin-3-yl]oxy-ethyl]amino]ethyl]benzoate single diastereoisomer;

[(1S)-2-(3,5-dichloro-4-pyridyl)-1-(3,4-dimethoxyphenyl)ethyl] 3-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-4-pyridyl)ethyl] 3-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-methoxy-4-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[[2-oxo-1-phenyl-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-(2-dimethylaminoethyloxy)-2-oxo-1-phenyl-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]-4-methoxy-3-[[2-oxo-1-phenyl-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-methoxyphenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-(1-methylpyrrolidin-3-yl)oxy-2-oxo-1-phenyl-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-chlorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-(8-methyl-8-azabicyclo[3.2.1]octan-3-yl)oxy]-2-oxo-1-phenyl-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-fluorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]sulfamoyl]benzoate single diastereoisomer;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]sulfamoyl]benzoate single diastereoisomer;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-methoxy-5-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(benzothiophen-3-yl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[methylsulfonyl-[2-oxo-1-phenyl-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-(methanesulfonamido)-5-[[2-oxo-1-phenyl-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]carbamoyl]benzoate;

[(1S)-2-(3,5-dichloro-1-oxido-pyridin-1-ium-4-yl)-1-[4-(difluoromethoxy)-3-methoxy-phenyl]ethyl] 3-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[(1S)-2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[(1R)-2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(3-fluorophenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-(2-dimethylaminoethyloxy)-2-oxo-1-phenyl-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]carbamoyloxy methyl]benzoate;

[(1S)-2-(3,5-dichloro-1-oxido-pyridin-1-ium-4-yl)-1-(3,4-dimethoxyphenyl)ethyl] 3-[[(1R)-2-oxo-1-phenyl-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 3-[[(1S)-2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[methyl-[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-carbamoyl-5-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-(dimethylcarbamoyl)-5-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-[(8-methyl-8-azabicyclo[3.2.1]octan-3-yl)oxy]-2-oxo-1-phenyl-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(4-methoxyphenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]-4-[[1-(3-fluorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-fluorophenyl)-2-oxo-2-[(3R)-quinuclidin-3-yl]oxy-ethyl]carbamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-fluorophenyl)-2-oxo-2-[(3R)-quinuclidin-3-yl]oxy-ethyl]carbamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-2-[(3R)-quinuclidin-3-yl]oxy-1-(3-thienyl)ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 2-fluoro-4-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]oxido-pyridin-1-ium-4-yl)ethyl] 3-[[1-(6-methoxy-3-pyridyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 2-methoxy-5-[[2-oxo-1-phenyl-2-[(3R)-quinuclidin-3-yl]oxy-ethyl]sulfamoyl]benzoate;

[(1S)-2-(3,5-dichloro-1-oxido-pyridin-1-ium-4-yl)-1-(3,4-dimethoxyphenyl)ethyl] 3-[[1-(2-fluorophenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 3-[methyl-[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-methoxyphenyl)-2-oxo-2-[(3R)-quinuclidin-3-yl]oxy-ethyl]carbamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-methoxyphenyl)-2-oxo-2-[(3R)-quinuclidin-3-yl]oxy-ethyl]carbamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-methoxyphenyl)-2-oxo-2-[(3R)-quinuclidin-3-yl]oxy-ethyl]carbamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-fluorophenyl)-2-oxo-2-quinuclidin-3-yloxy-ethyl]carbamoyl]benzoate;

[2-(3,5-dichloro-1-oxido-pyridin-1-ium-4-yl)-1-(3,4-dimethoxyphenyl)ethyl]-4-[[1-(2-methoxyphenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl]-4-[[1-(3-methoxyphenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl]-4-[[1-(4-methoxyphenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl]-4-[[1-(3-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-fluoro-4-[[2-oxo-1-phenyl-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]carbamoyloxymethyl]benzoate;

[2-(3,5-dichloro-1-oxido-pyridin-1-ium-4-yl)-1-(3,4-dimethoxyphenyl)ethyl] 3-[[[1-(2-fluorophenyl)-2-oxo-2-[(3R)-quinuclidin-3-yl]oxy-ethyl]amino]methyl]benzoate;

[2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-hydroxyphenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl]-4-[[1-(3-fluorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-2-[(3R)-quinuclidin-3-yl]oxy-1-(2-thienyl)ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-(methanesulfonamidomethyl)-5-[[2-oxo-1-phenyl-2-[(3R)-quinuclidin-3-yl]oxy-ethyl]amino]benzoate;

[(3R)-quinuclidin-3-yl] 2-[3-[2-[2-(3,5-dichloro-1-oxido-pyridin-1-ium-4-yl)-1-(3,4-dimethoxyphenyl)ethoxy]-2-oxo-ethyl]anilino]-2-phenyl-acetate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[2-oxo-1-phenyl-2-[(3R)-quinuclidin-3-yl]oxy-ethyl]amino]benzoate;

[(3R)-quinuclidin-3-yl] 2-[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]carbamoyl]anilino]-2-phenyl-acetate;

[(3R)-quinuclidin-3-yl] 2-[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]sulfamoyl]anilino]-2-phenyl-acetate;

[(3R)-quinuclidin-3-yl] 2-[[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]carbamoyl]phenyl]sulfonylamino]-2-phenyl-acetate;

[(1S)-1-[3-(cyclopropylmethoxy)-4-(difluoromethoxy)phenyl]-2-(3,5-dichloro-1-oxido-pyridin-1-ium-4-yl)ethyl] 3-[[3-[[2-oxo-1-phenyl-2-[(3R)-quinuclidin-3-yl]oxy-ethyl]sulfamoyl]benzoyl]amino]propanoate;

[(3R)-quinuclidin-3-yl] 2-[3-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethoxy]anilino]-2-phenyl-acetate;

[(3R)-quinuclidin-3-yl] 2-[3-[[2-[(1S)-2-(3,5-dichloro-1-oxido-pyridin-1-ium-4-yl)-1-(3,4-dimethoxyphenyl)ethoxy]-2-oxo-ethyl]carbamoyl]anilino]-2-phenyl-acetate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(4-methoxyphenyl)-2-oxo-2-[(3R)-quinuclidin-3-yl]oxy-ethyl]amino]benzoate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(2-methoxyphenyl)-2-oxo-2-[(3R)-quinuclidin-3-yl]oxy-ethyl]amino]benzoate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(4-fluorophenyl)-2-oxo-2-[(3R)-quinuclidin-3-yl]oxy-ethyl]amino]benzoate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(3-fluorophenyl)-2-oxo-2-[(3R)-quinuclidin-3-yl]oxy-ethyl]amino]benzoate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(2-fluorophenyl)-2-oxo-2-[(3R)-quinuclidin-3-yl]oxy-ethyl]amino]benzoate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(3-methoxyphenyl)-2-oxo-2-[(3R)-quinuclidin-3-yl]oxy-ethyl]amino]benzoate;

[(3R)-quinuclidin-3-yl] 2-[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]carbamoyl]anilino]-2-(3-fluorophenyl)acetate;

[(3R)-quinuclidin-3-yl] 2-[3-[[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]-methyl-amino]methyl]anilino]-2-phenyl-acetate;

[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]sulfamoyl]anilino]-2-phenyl-acetate;

[2-(3,5-dichloro-1-oxido-pyridin-1-ium-4-yl)-1-(3,4-dimethoxyphenyl)ethyl] 3-[3-[[2-oxo-1-phenyl-2-[(3R)-quinuclidin-3-yl]oxy-ethyl]amino]propyl]benzoate;

[2-[2-(3,5-dichloro-1-oxido-pyridin-1-ium-4-yl)-1-(3,4-dimethoxyphenyl)ethoxy]-2-oxo-ethyl] 3-[[[2-oxo-1-phenyl-2-[(3R)-quinuclidin-3-yl]oxy-ethyl]amino]methyl]benzoate;

[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]carbamoyl]anilino]-2-(2-fluorophenyl)acetate;

[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]carbamoyl]anilino]-2-(3-fluorophenyl)acetate;

[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]carbamoyl]anilino]-2-(4-fluorophenyl)acetate;

[2-[2-(3,5-dichloro-1-oxido-pyridin-1-ium-4-yl)-1-(3,4-dimethoxyphenyl)ethoxy]-2-oxo-ethyl] 3-[[2-oxo-1-phenyl-2-[(3R)-quinuclidin-3-yl]oxy-ethyl]amino]benzoate;

and pharmaceutically acceptable salts and solvates thereof.

The sentence "single stereoisomer" was reported near the chemical name of each compound isolated as single diastereoisomer whose absolute configuration at stereogenic center (2) (see general formula (I) below) was not determined.

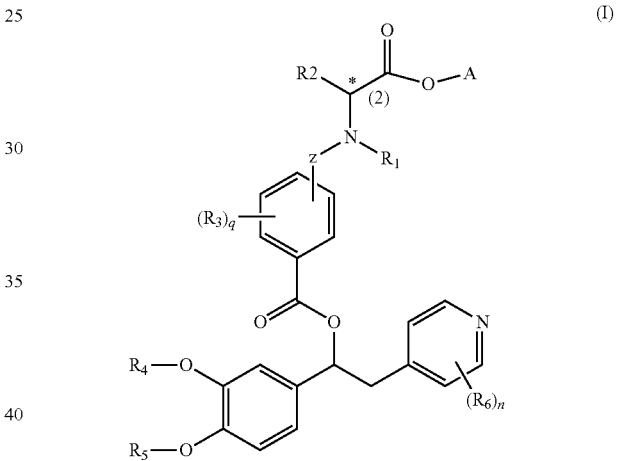

(I)

In one aspect of the present invention, a process for the preparation of compounds of the invention is provided. Processes of preparation described below and reported in the following Schemes, should not be viewed as limiting the scope of the synthetic methods available for the preparation of the compounds of the invention.

In the following Schemes, for compounds of formula (II) to (XXVIII), unless otherwise indicated, the groups $R_1$, $R_2$, $R_3$, $R_4$, $R_5$, $R_6$, A, n, q and Z have the same meanings as described for compounds of formula (I) above and $L_1$ has the meaning specified case by case.

Compounds of formula (I) can be obtained according to general synthetic routes reported in Scheme A, B, and C or by following the procedures of Scheme A, B, and C starting from slightly modified reagents, easily identifiable by the skilled person and/or following slightly modified procedures that the skilled person can easily apply. In Schemes A, B, and C below reference is made to specific synthetic schemes which are better detailed in the subsequent paragraphs.

Compounds of formula (Ie), i.e. compounds of formula (I) which are N-oxide on the pyridine ring and wherein Z is a bond, $L_1$ is a bond and $R_1$ is hydrogen, may be prepared according to the synthetic approach described in Scheme A below.

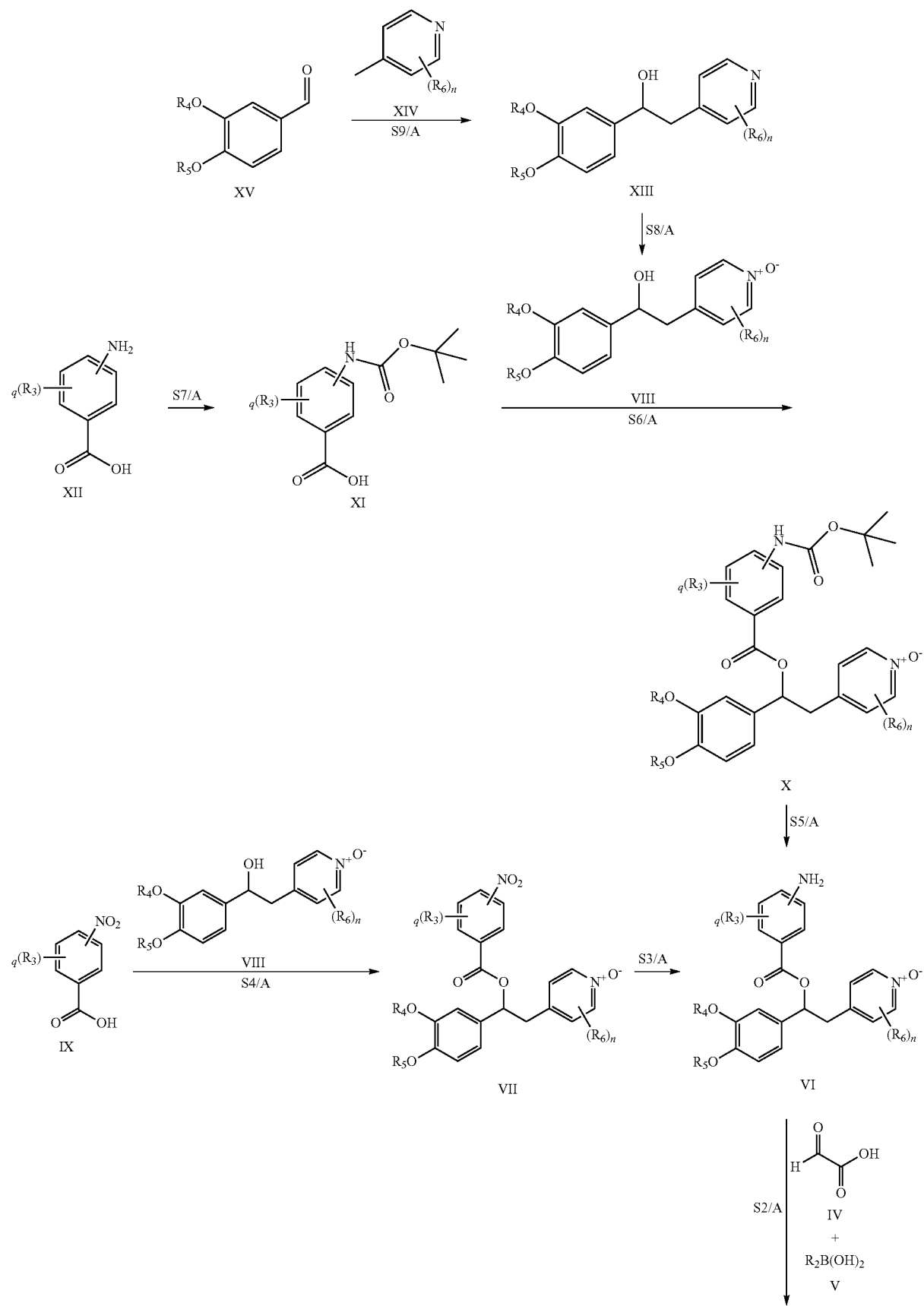
Scheme A

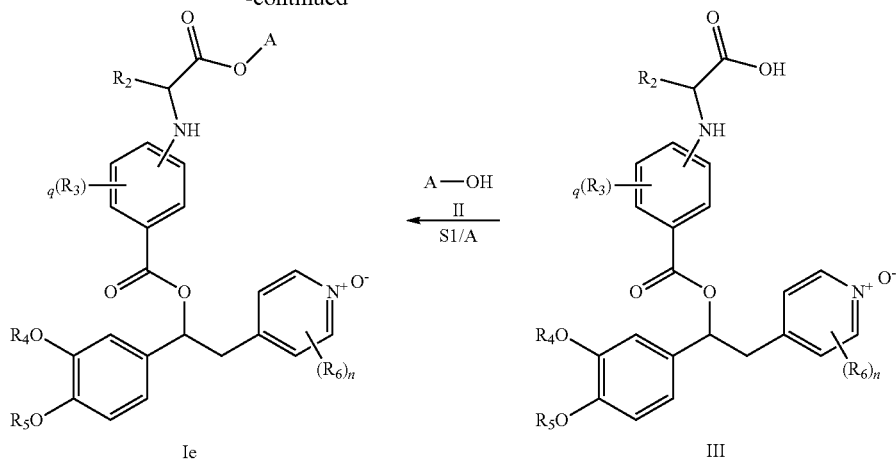
Compounds of formula (If), i.e. compounds of formula (I) which are N-oxide on the pyridine ring and wherein Z is a methylene (CH$_2$) group, L$_1$ is a bond and R$_1$ is hydrogen, may be prepared according to the synthetic approach described in Scheme B below.
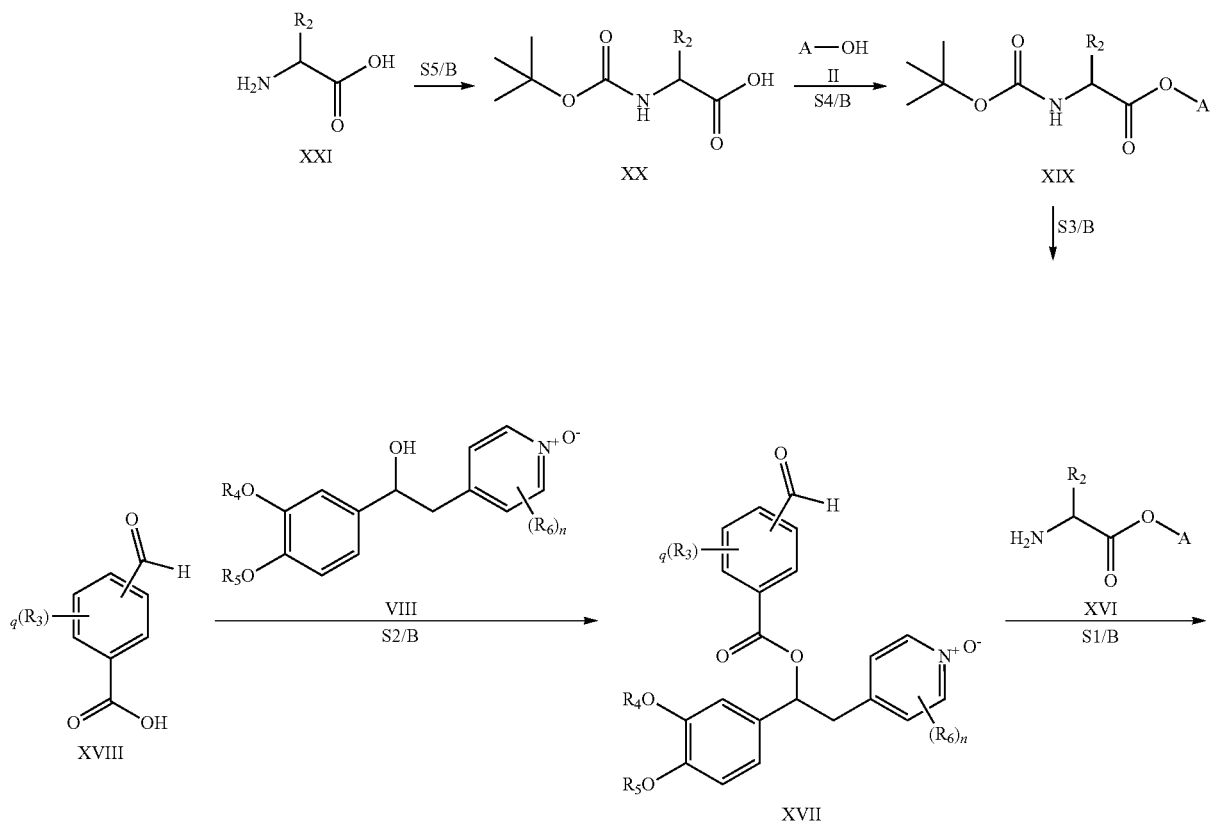

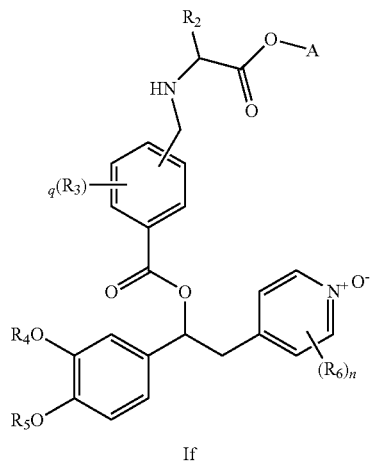
If
Compounds of formula (Ig), i.e. compounds of formula (I) which are N-oxide on the pyridine ring and wherein Z is a group —S(O₂)— and R₁ is hydrogen, may be prepared according to the synthetic approach described in Scheme C below.
Scheme C
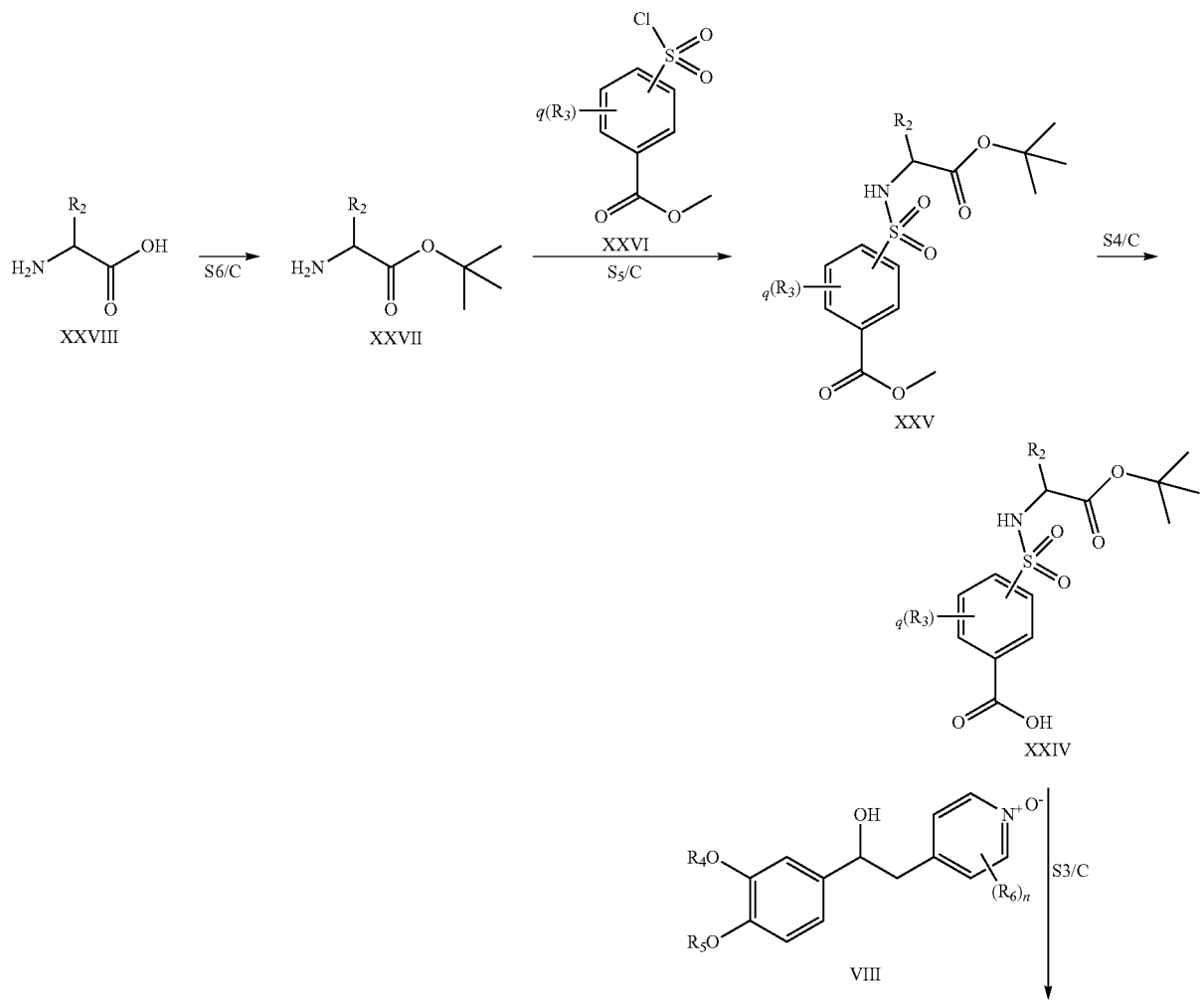

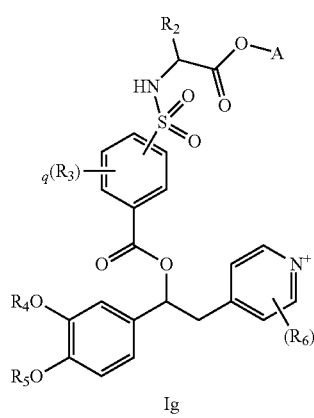

Ig

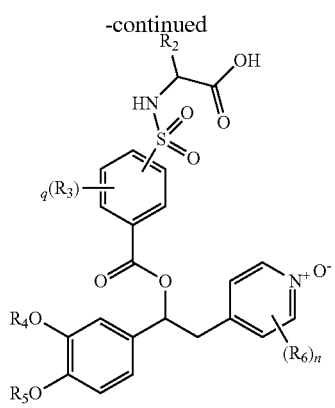

XXII

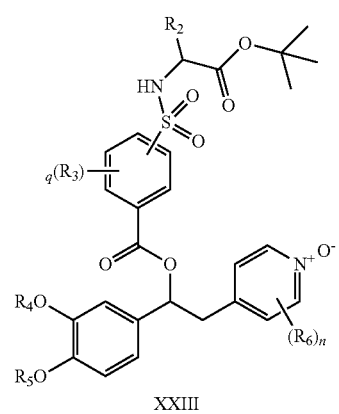

XXIII

Compounds of formula (Ie), i.e. compounds of formula (I) which are in the form of N-oxide on the pyridine ring and wherein Z is a bond, $L_1$ is a bond and $R_1$ is hydrogen, may be prepared according to Scheme 1/A (S1/A) below reported by reaction of a compound of formula (III) as below reported, with an appropriate compound of formula (II) as below reported.

solvent, such as THF in the presence of a suitable coupling agent, such as DCC/HOBt or EDC/DMAP or HATU, at an appropriate temperature, such as room (or ambient) temperature or 40° C.

Compounds of formula (III) may be prepared according to Scheme 2/A (S2/A) below reported by reaction of a compound of formula (VI) as below reported, with glyoxylic acid (IV) and an appropriate compound of formula (V) as below reported.

Scheme 1/A (S1/A)

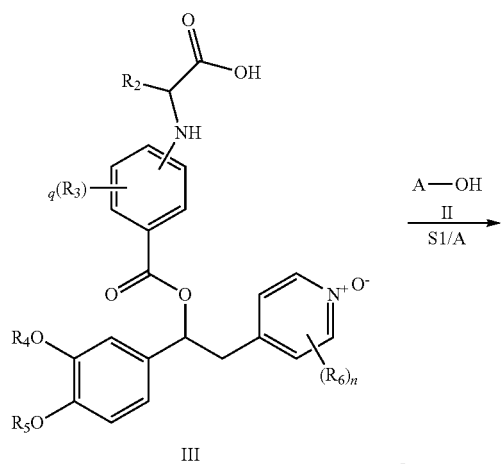

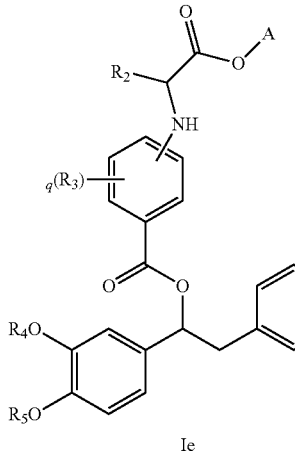

Ie

Typical reaction conditions comprise reacting a compound of formula (III) with a compound of formula (II) in a suitable Scheme 2/A (S2/A)

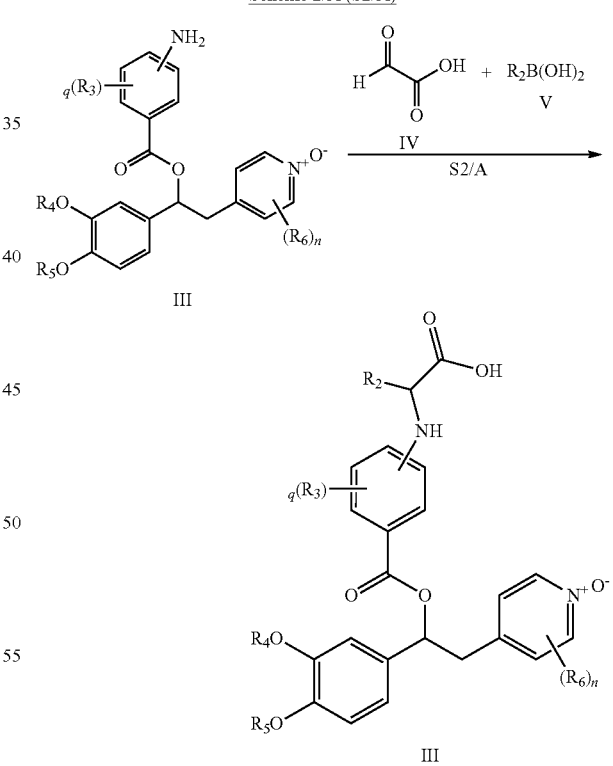

III

Typical reaction conditions comprise reacting a compound of formula (VI) with a compound of formula (V) and glyoxylic acid (IV) in a suitable solvent, such as DCM, at an appropriate temperature, such as room (or ambient) temperature.

Compounds of formula (VI) may be prepared according to Scheme 3/A (S3/A) below reported by reaction of a compound of formula (VII) as below reported.

Scheme 3/A (S3/A)

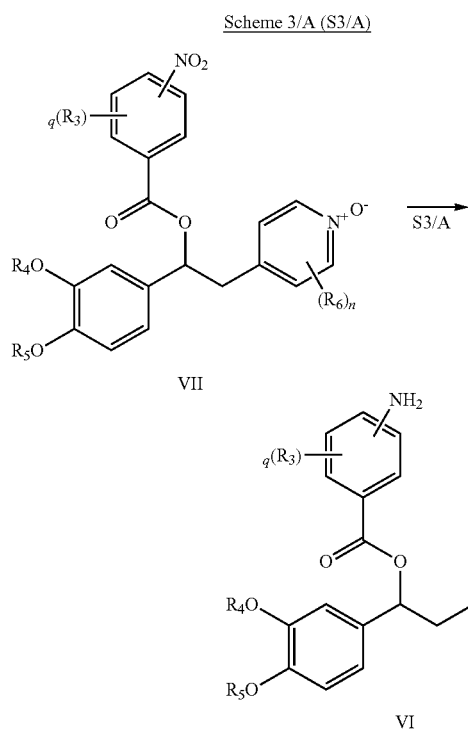

Typical reaction conditions comprise reacting a compound of formula (VII) with a suitable reducing agent, such as tin chloride dihydrate, in a suitable solvent, such as THF, at an appropriate temperature, such as room temperature to 75° C.

Compounds of formula (VII) may be prepared according to Scheme 4/A (S4/A) below reported by reaction of a compound of formula (IX) as below reported, with an appropriate compound of formula (VIII).

Scheme 4/A (S4/A)

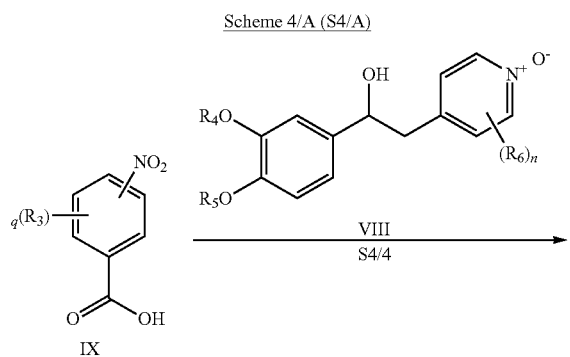

Typical reaction conditions comprise reacting a compound of formula (IX) with a compound of formula (VIII) in a suitable solvent, such as DCM, in the presence of a suitable coupling agent, such as EDC/DMAP or HATU, at an appropriate temperature, such as room (or ambient) temperature.

Compounds of formula (VI) may be also prepared according to Scheme 5/A (S5/A) below reported by reaction of a compound of formula (X) as below reported.

Scheme 5/A (S5/A)

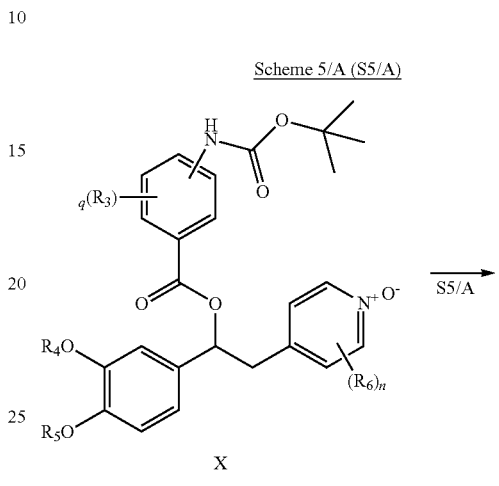

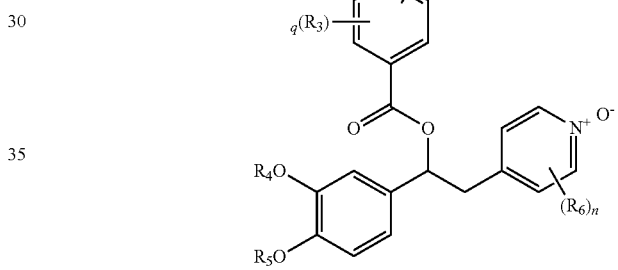

Typical reaction conditions comprise reacting a compound of formula (X) in a suitable solvent, such as 1,4-dioxane, in the presence of a suitable acid, such as hydrochloric acid, at an appropriate temperature, such as room (or ambient) temperature.

Compounds of formula (X) may be prepared according to Scheme 6/A (S6/A) below reported by reaction of a compound of formula (XI) as below reported, with an appropriate compound of formula (VIII).

Scheme 6/A (S6/A)

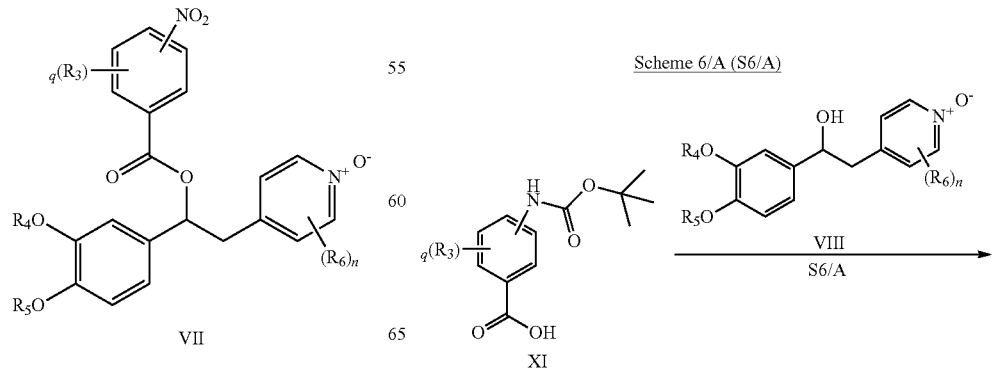

-continued

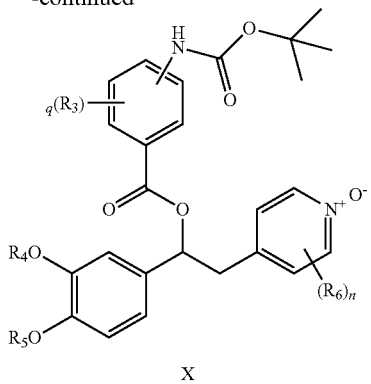

X

Typical reaction conditions comprise reacting a compound of formula (XI) with a compound of formula (VIII) in a suitable solvent, such as DCM, in the presence of a suitable coupling agent, such as EDC/DMAP or HATU, at an appropriate temperature, such as room (or ambient) temperature.

Compounds of formula (XI) may be prepared according to Scheme 7/A (S7/A) below reported by reaction of a compound of formula (XII) as below reported.

Scheme 7/A (S7/A)

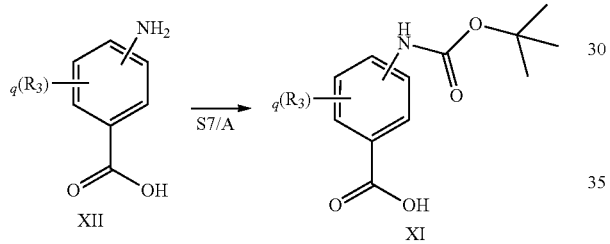

Typical reaction conditions comprise reacting a compound of formula (XII) with di-tert-butyl dicarbonate in a suitable solvent, such as 1,4-dioxane/water, in the presence of a suitable base, such as sodium hydroxide, at an appropriate temperature, such as room (or ambient) temperature.

Compounds of formula (VIII) may be prepared according to Scheme 8/A (S/A) below by reaction of a compound of formula (XIII) as below reported.

Scheme 8/A (S8/A)

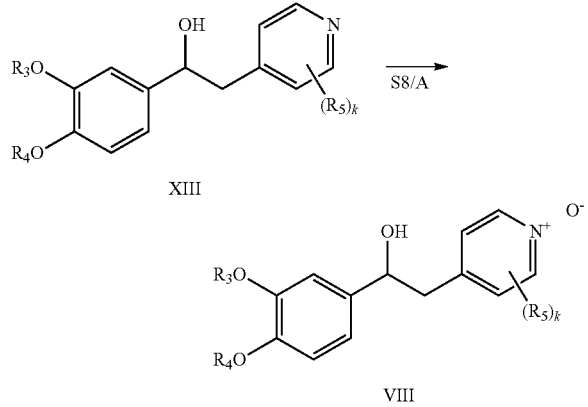

Typical reaction conditions comprise reacting a compound of formula (XIII) with a suitable oxidizing agent, such as m-CPBA or hydrogen peroxide or perbenzoic acid or peracetic acid, in a suitable solvent, such as DCM or chloroform, at an appropriate temperature, such as room (or ambient) temperature.

Compounds of formula (XIII) may be prepared according to Scheme 9/A (S9/A) below by reaction of a compound of formula (XV) as below reported, with an appropriate compound of formula (XIV) as below reported.

Scheme 9/A (S9/A)

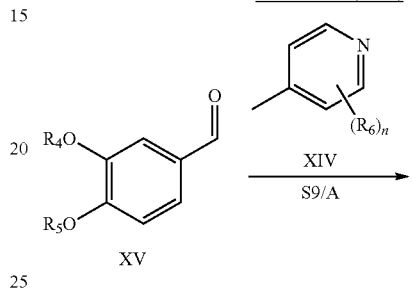

XIII

Typical reaction conditions comprise reacting a compound of formula (XV) with a compound of formula (XIV) in a suitable solvent, such as THF or other aprotic solvents, in the presence of a base, such as LHMDS or a similar strong base, at an appropriate temperature, such as −78° C.

Compounds of formula (If), i.e. compounds of formula (I) which are in the form of N-oxide on the pyridine ring and wherein Z is a methylene group (—CH2-) and $R_1$ is hydrogen, may be prepared according to Scheme 1/B (S1/B) below by reaction of a compound of formula (XVII) as below reported, with an appropriate compound of formula (XVI) as below reported.

Scheme 1/B (S1/B)

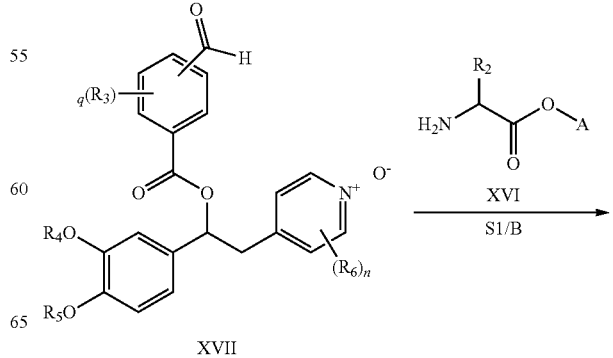

-continued

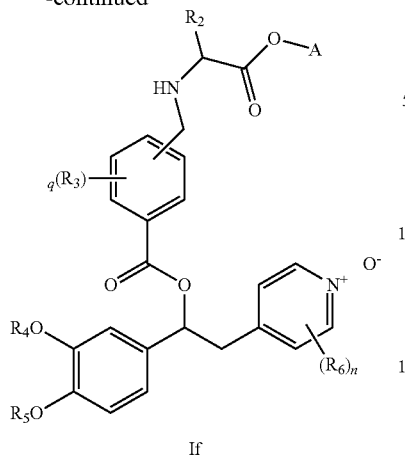

If

Typical reaction conditions comprise reacting a compound of formula (XVII) with a compound of formula (XVI) in a suitable solvent, such as acetonitrile in the presence of an acid, such as acetic acid, and a reducing agent, such as NaB(OAc)$_3$H, at an appropriate temperature, such as room (or ambient) temperature or 0° C. or 40° C.

Compounds of formula (XVII) may be prepared according to Scheme 2/B (S2/B) below by reaction of a compound of formula (XVIII) as below reported, with an appropriate compound of formula (VIII) as below reported.

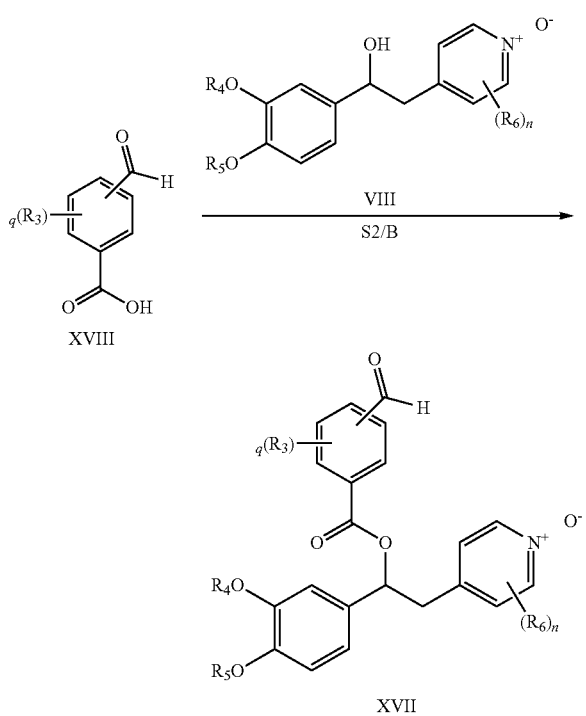

Typical reaction conditions comprise reacting a compound of formula (XVIII) with a compound of formula (VIII) in a suitable solvent, such as DCM or DMF in the presence of a coupling agent, such as EDC/DMAP or HATU, at an appropriate temperature, such as room (or ambient) temperature.

Compounds of formula (XVI) may be prepared according to Scheme 3/B (S3/B) below by reaction of a compound of formula (XIX) as below reported.

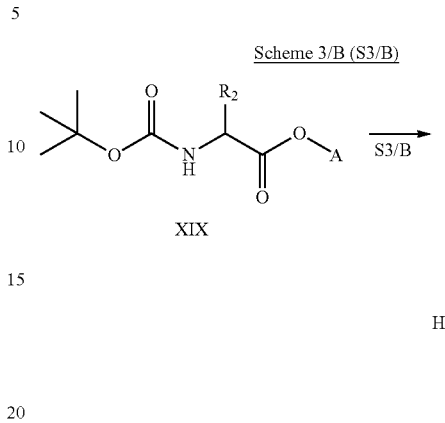

Typical reaction conditions comprise reacting a compound of formula (XIX) with an acid such as HCl or TFA in a suitable solvent, such as dioxane or DCM at an appropriate temperature, such as room (or ambient) temperature or 0° C.

Compounds of formula (XIX) may be prepared according to Scheme S4/B (S4/B) below by reaction of a compound of formula (XX) as below reported, with an appropriate compound of formula (II).

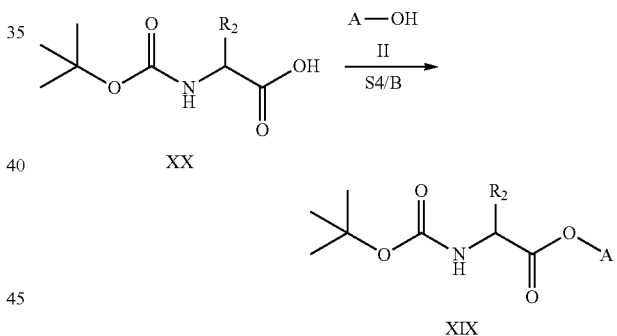

Typical reaction conditions comprise reacting a compound of formula (XX) with a compound of formula (II) in a suitable solvent, such as THF or DMF in the presence of a coupling agent, such as DCC/HOBt or HATU, at an appropriate temperature, such as room (or ambient) temperature.

Compounds of formula (XX) may be prepared according to Scheme 5/B (S5/B) below by reaction of a compound of formula (XXI) as below reported.

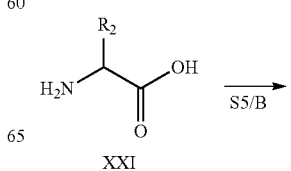

-continued

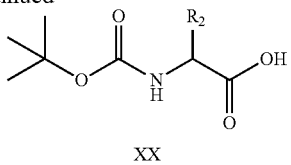

XX

Typical reaction conditions comprise reacting a compound of formula (XXI) with di-tert butyl dicarbonate in a suitable solvent, such as dioxane and water in the presence of sodium hydroxide at an appropriate temperature, such as room (or ambient) temperature or 0° C.

Compounds of formula (Ig), i.e. compounds of formula (I) which are in the form of N-oxide on the pyridine ring and wherein Z is a group —S(O$_2$)— and R$_1$ is hydrogen, may be prepared according to Scheme 1/C(S1/C) below by reaction of a compound of formula (XXII) as below reported, with a compound of formula (II).

Scheme 2/C (S2/C)

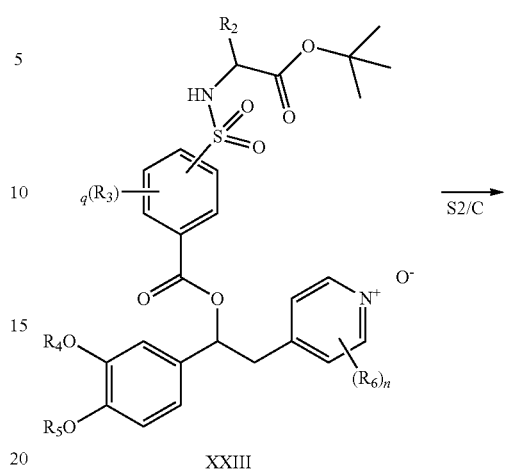

XXIII

Typical reaction conditions comprise reacting a compound of formula (XXIII) with an acid such as HCl or TFA in a suitable solvent, such as dioxane or DCM at an appropriate temperature, such as room (or ambient) temperature or 0° C.

Compounds of formula (XXIII) may be prepared according to Scheme 3/C(S3/C) below by reaction of a compound of formula (XXIV) as below reported, with an appropriate compound of formula (VIII) as below reported.

Scheme 1/C (S1/C)

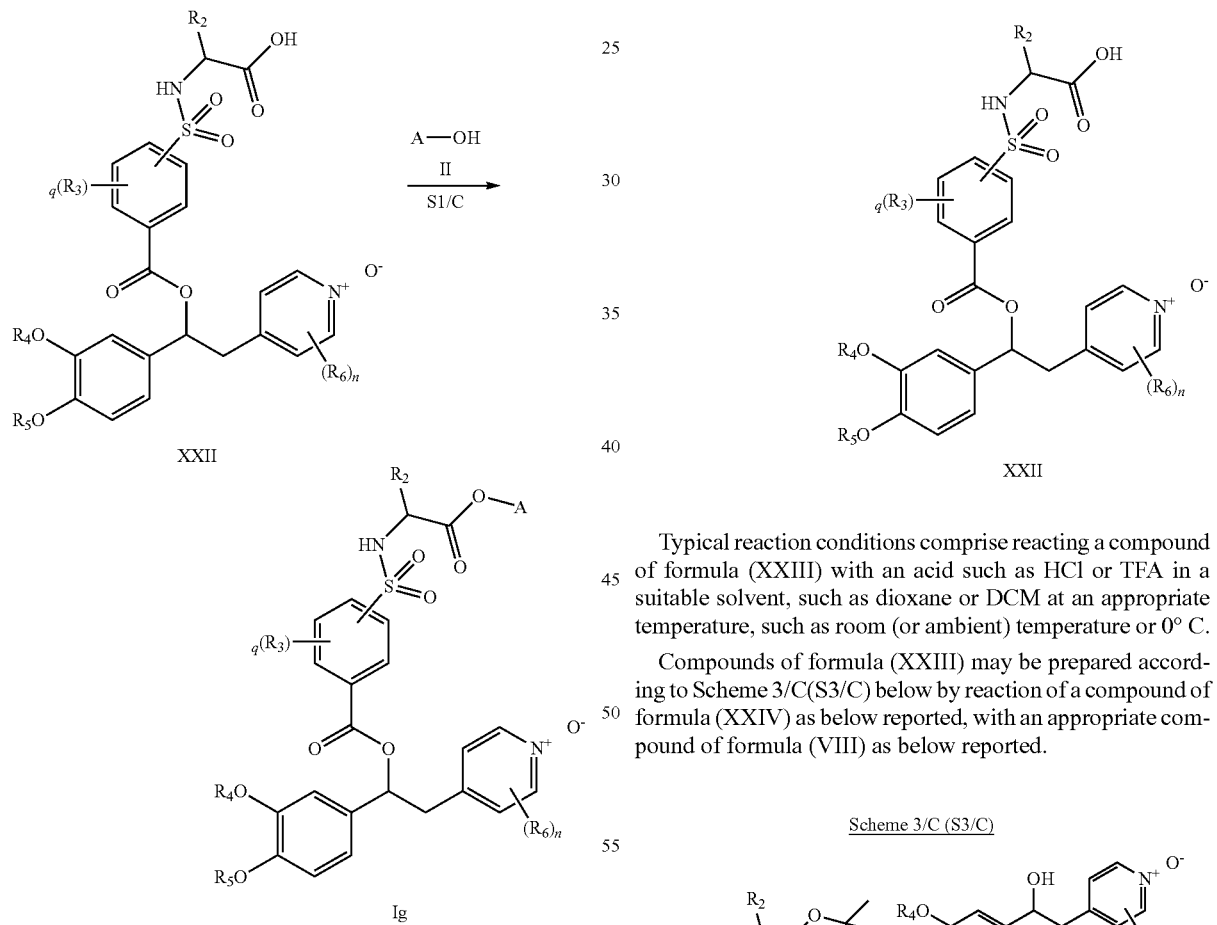

Typical reaction conditions comprise reacting a compound of formula (XXII) with a compound of formula (II) in a suitable solvent, such as THF or DMF in the presence of a coupling agent, such as DCC/HOBt or HATU, at an appropriate temperature, such as room (or ambient) temperature.

Compounds of formula (XXII) may be prepared according to Scheme 2/C(S2/C) below by reaction of a compound of formula (XXIII) as below reported.

Scheme 3/C (S3/C)

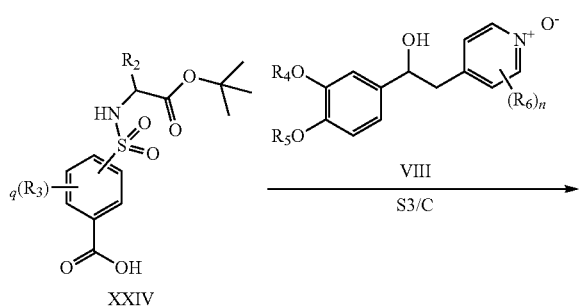

XXIV

-continued

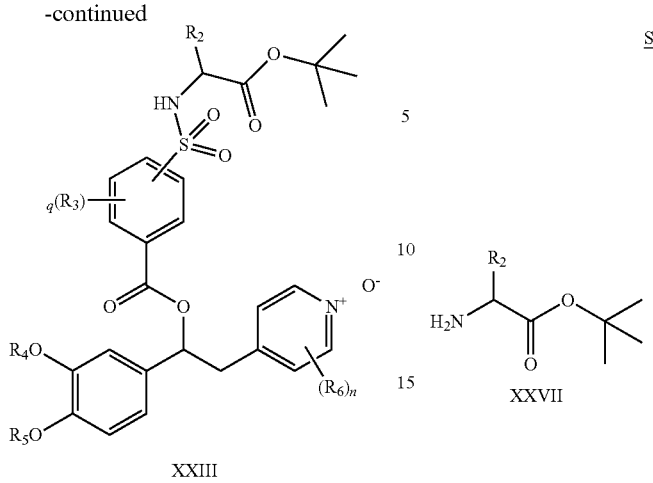

Typical reaction conditions comprise reacting a compound of formula (XXIV) with a compound of formula (VIII) in a suitable solvent, such as DCM or DMF in the presence of a coupling agent, such as EDC/DMAP or HATU, at an appropriate temperature, such as room (or ambient) temperature.

Compounds of formula (XXIV) may be prepared according to Scheme 4/C(S4/C) below by reaction of a compound of formula (XXV) as below reported.

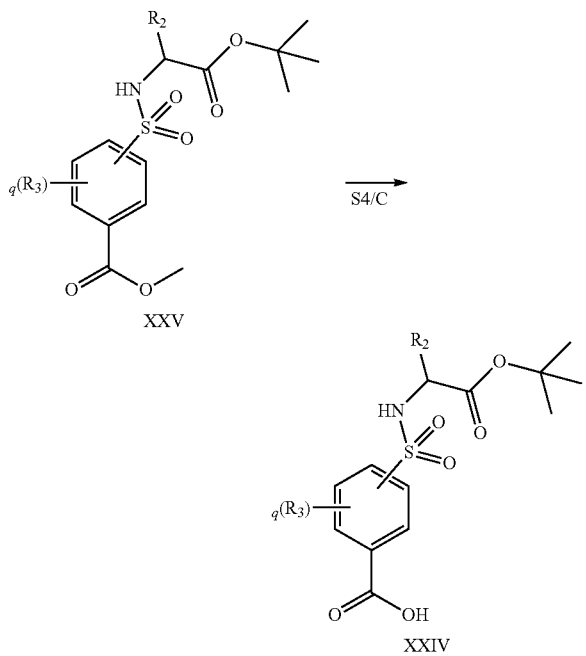

Typical reaction conditions comprise reacting a compound of formula (XXV) with a base, such as LiOH, in a suitable solvent, such as THF/methanol, at an appropriate temperature, such as room (or ambient) temperature.

Compounds of formula (XXV) may be prepared according to Scheme 5/C(S5/C) below by reaction of a compound of formula (XXVII) as below reported, with an appropriate compound of formula (XXVI) as below reported.

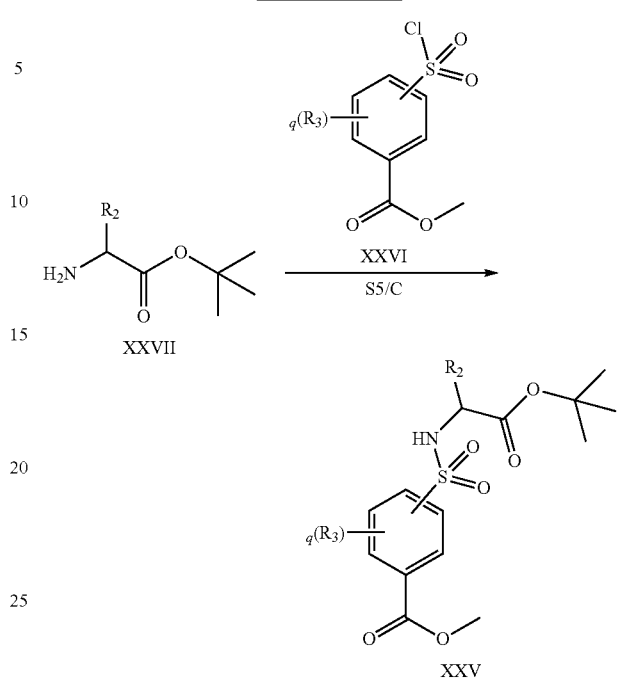

Typical reaction conditions comprise reacting a compound of formula (XXVII) with a compound of formula (XXVI), in a suitable solvent, such as THF, in the presence of triethylamine at an appropriate temperature, such as room (or ambient) temperature or 0° C.

Compounds of formula (XXVII) may be prepared according to Scheme 6/C (S6/C) below by reaction of a compound of formula (XXVIII) as below reported.

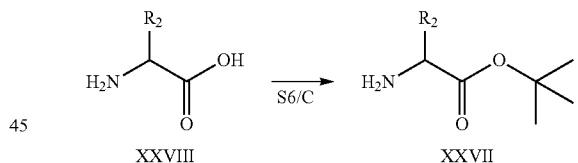

Typical reaction conditions comprise reacting a compound of formula (XXVIII) with iso-butylene in the presence of sulfuric acid in a suitable solvent, such as dioxane, at an appropriate temperature, such as room (or ambient) temperature or −78° C.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form. In particular, functional groups present in the compounds of formula (II), to (XXVIII) and which could generate unwanted side reaction and by-products, need to be properly protected before the alkylation, acylation, coupling, oxidation or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxy, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1999), which is incorporated herein by reference in its entirety).

Likewise, selective protection and deprotection of any of the said groups, for instance including carbonyl, hydroxy or amino groups, may be accomplished according to very well-known methods commonly employed in organic synthetic chemistry.

The N-oxides on the 4-pyridinyl ring of the compounds of general formula (I) and embodiments thereof may be prepared according to methods available in the literature and well known to the skilled person. For instance they may be prepared by dissolving the compound of general formula (I) or embodiments thereof in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid and peracetic acid.

Alternatively, in particular for those compounds comprising functional groups sensitive to oxidation, the corresponding N-oxides are prepared by carrying out the oxidation step before further functional groups are introduced, for example on compounds of formula (XIII) as above reported.

In a preferred embodiment, the process for preparation of compounds of formula (I) or embodiments thereof is performed starting from N-oxide on the pyridine ring of compound of formula (VIII), thus allowing the preparation of compound of formula (I) or embodiments thereof in the form of N-oxides on the pyridine ring.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The present invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y. U.S.A., which is incorporated herein by reference in its entirety.

Administration of the compounds of the present invention or may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the present invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation. Inhalable preparations include inhalable powders, propellant-containing metered aerosols or propellant-free inhalable formulations and may be administered through a suitable inhalation device which may be respectively selected from dry powder inhaler, pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (FINE) inhibitors, phosphodiesterase 4 (PDE4) inhibitors, leukotriene modulators, non-steroidal anti-inflammatory agents (NSAIDs), and mucus regulators.

The present invention also provides combinations of a compound of the invention, with a β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol, and ASF-1020 and salts thereof.

The present invention also provides combinations of a compound of the invention, with a corticosteroid selected from the group consisting of fluticasone propionate, fluticasone furoate, mometasone furoate, beclometasone dipropionate, ciclesonide, budesonide, GSK 685698, and GSK 870086.

The present invention also provides combinations of a compound of the invention, with an antimuscarinic agent selected from the group consisting of aclidinium, tiotropium, ipratropium, trospium, glycopyrronium and oxitropium salts.

The present invention also provides combinations of a compound of the invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the invention, with a P38 MAP kinase inhibitor selected from the group consisting of semapimod, talmapimod, pirfenidone, PH-797804, GSK-725, minokine, and losmapimod and salts thereof.

In a preferred embodiment, the present invention provides combinations of a compound of the invention with an IKK2 inhibitor.

The invention also provides combinations of a compound of the invention with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The invention also provides combinations of a compound of the invention with a leukotriene modulator selected from the group consisting of montelukast, zafirlukast, and pranlukast.

The invention also provides combinations of a compound of the invention with a NSAID selected from the group consisting of ibuprofen and ketoprofen.

The invention also provides combinations of a compound of the invention with a mucus regulator selected from the group consisting of INS-37217, diquafosol, sibenadet, CS-003, talnetant, DNK-333, MSI-1956, and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage comprised between 0.001 and 1000 mg/day, preferably between 0.1 and 500 mg/day.

When they are administered by inhalation route, the dosage of the compounds of the invention is advantageously comprised between 0.01 and 20 mg/day, preferably between 0.1 and 10 mg/day.

Preferably, the compounds of the invention alone or combined with other active ingredients may be administered for the prevention and/or treatment of any obstructive respiratory disease such as asthma, chronic bronchitis and chronic obstructive pulmonary disease (COPD).

However the compounds of the invention may be administered for the prevention and/or treatment of any disease wherein PDE4 inhibition or M3 antagonism is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia greata, hypertrophic scars, discoid lupus erythematosus, systemic lupus erythematosus, follicular and wide-area pyodermias, endogenous and exogenous acne, acne rosacea, Behçet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Abbreviations

DCC=N,N'-dicyclohexylcarbodiimide;
HOBt=hydroxybenzotriazole;
HATU=(dimethylamino)-N,N-dimethyl(3H-[1,2,3]triazolo[4,5-b]pyridin-3-yloxy) methaniminium hexafluorophosphate;
EDC=1-ethyl-3-(3-dimethylaminopropyl) carbodiimide hydrochloride;
DMAP=4-dimethylaminopyridine;
DMF=dimethylformamide;
EtOAc=ethyl acetate;
RT=room temperature;
THF=tetrahydrofuran;
DCM=dichloromethane;
MeOH=methyl alcohol;
EtOH=ethylic alcohol;
LHMDS=lithium bis(trimethylsilyl)amide;
m-CPBA=meta-chloroperoxybenzoic acid;
TFA=trifluoroacetic acid;
LC-MS=liquid chromatography/mass spectrometry;
HPLC=high pressure liquid chromatography;
MPLC=medium pressure liquid chromatography;
SFC=supercritical fluid chromatography
General Experimental Details
Analytical Methods
Liquid Chromatography-Mass Spectrometry
Method 1

LC-MS was performed on a Waters 2795 Alliance HT HPLC with Waters 2996 Diode Array Detector coupled to a Micromass ZQ, single quadrupole mass spectrometer using a Phenomenex Luna C18 (2) column (5 µm, 100×4.6 mm plus guard cartridge) with a linear gradient of 5-95% acetonitrile/water (with 0.1% formic acid in each mobile phase) within 3.5 minutes and held at 95% for 2.0 minutes.
Method 2

LC-MS was performed on a Waters 2795 Alliance HT HPLC with Waters 2996 Diode Array Detector coupled to a Micromass ZQ, single quadrapole mass spectrometer using a Waters Xterra MS C18 column (5 μm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.
NMR $^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.
Preparative Reverse-Phase HPLC Conditions Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector.

The columns used for the preparative purification of the compounds were a Waters Sunfire OBD Phenomenex Luna Phenyl Hexyl or Waters Xbridge Phenyl at 10 μM 19×150 mm or Waters CSH Phenyl Hexyl, 19×150, 5 μm column.

Appropriate focused gradients were selected based on acetonitrile and methanol solvent systems under either acidic or basic conditions. The modifiers used under acidic/basic conditions were formic acid or trifluoroacetic acid (0.1% V/V) and ammonium bicarbonate (10 mM) respectively. The purification was controlled by Waters Fractionlynx software through monitoring at 210-400 nm, and triggered a threshold collection value at 260 nm and, when using the Fractionlynx, the presence of target molecular ion as observed under APi conditions. Collected fractions were analysed by LCMS (Waters Acquity systems with Waters SQD).
Compound Preparation Where the preparation of starting materials is not described, these are commercially available, known in the literature, or readily obtainable by those skilled in the art using standard procedures. Where it is stated that compounds were prepared "analogously" or "similarly" to earlier examples or intermediates, it will be appreciated by the skilled person that the reaction time, number of equivalents of reagents and temperature can be modified for each specific reaction and that it may be necessary or desirable to employ different work-up or purification techniques.

Flash chromatography refers to silica gel chromatography and is carried out using an Isolera MPLC system (manufactured by Biotage); pre-packed silica gel cartridges (supplied by Biotage); or using conventional glass column chromatography.

In the procedures that follow, after each starting material, reference to a compound number may be provided. This is provided merely for assistance to the skilled chemist. The starting material may not necessarily have been prepared from the batch referred to.

Many of the Compounds described in the following Examples have been prepared from stereochemically pure starting materials, for example 95% enantiomeric excess (ee). The stereochemistry of the compounds in the Examples, where indicated, has been assigned on the assumption that absolute configuration at resolved stereogenic centers of staring materials is maintained throughout any subsequent reaction conditions.

Compounds isolated as single diastereoisomers whose absolute configuration at stereogenic center (2) was not determined, are herebelow referred to as Single Diastereoisomers without mention in their chemical name of absolute configuration for the unknown stereogenic center.

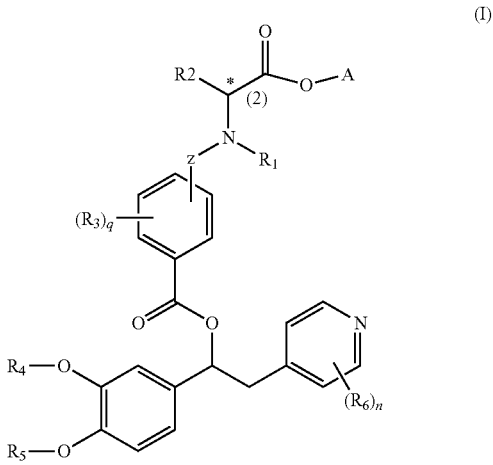

(I)

Intermediate 1/A (I-1/A). (S)-3,5-Dichloro-4-(2-(3,4-dimethoxyphenyl)-2-hydroxyethyl)pyridine 1-oxide

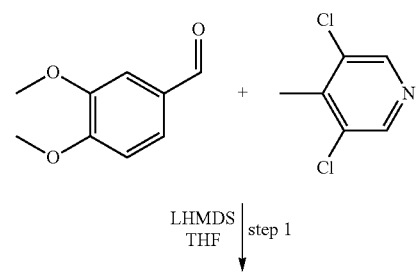

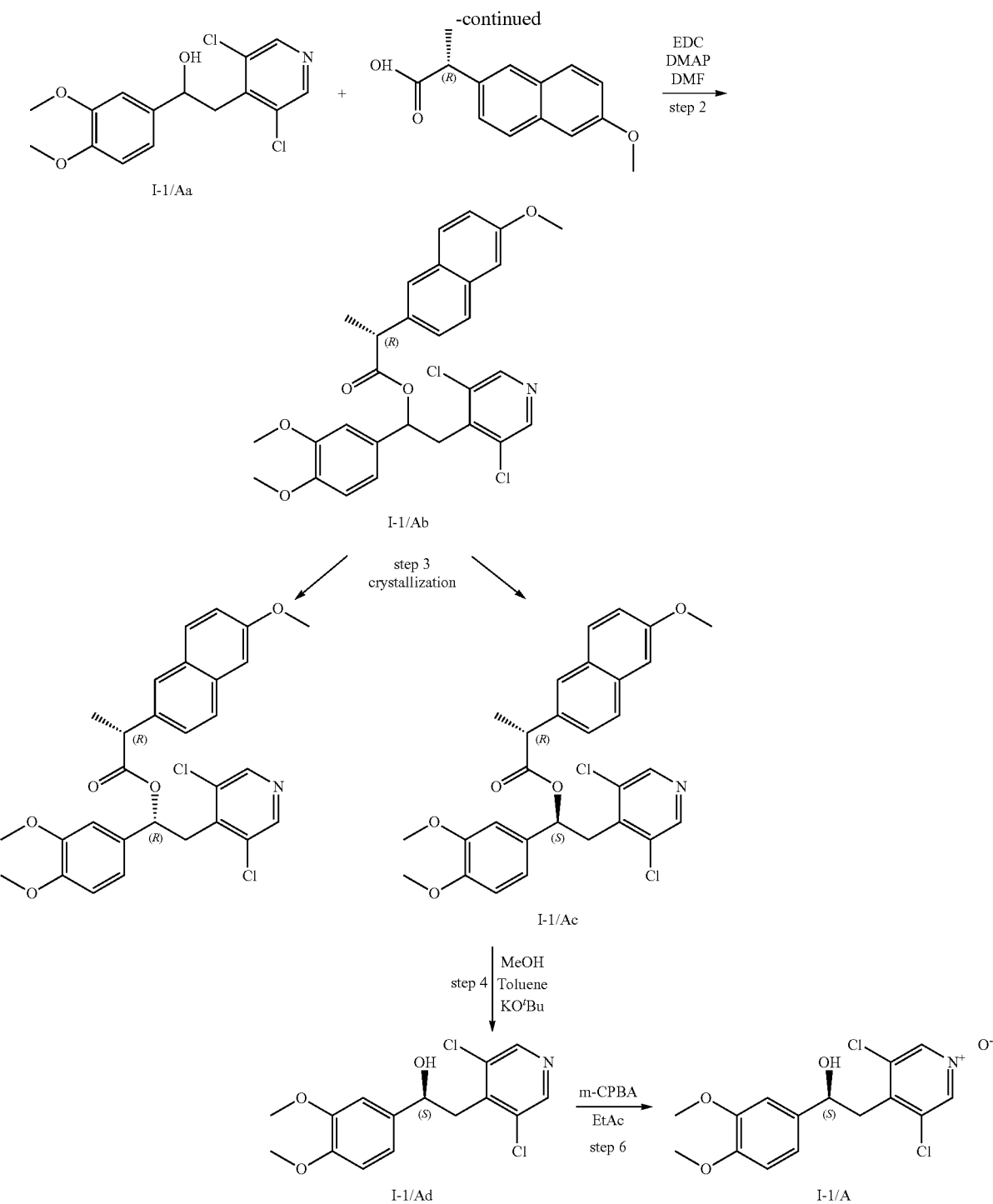

Step 1: Preparation of (R,S)-2-(3,5-dichloropyridin-4-yl)-1-(3,4-dimethoxyphenyl)ethanol (I-1/Aa)

3,5-dichloro-4-methylpyridine (54 g, 331 mmol) was dissolved in dry THF (480 mL) under argon atmosphere and cooled at −78° C. in dry-ice/acetone bath. LHMDS IN THF solution (331 mL, 331 mmol) was added drop-wise keeping the temperature at −78°. The mixture was stirred at −78° for 1 hour. Thereafter, a solution of 3,4-dimethoxybenzaldehyde (50 g, 301 mmol) in dry THF (120 mL) was added drop-wise keeping the temperature at −78° C. When the addition was completed, the mixture was allowed to warm at RT. The reaction was poured into ice and water (1 L), and the mixture was stirred until a copious precipitate formed. The solid was filtered, and dissolved in ethyl acetate (500 mL), dried over $Na_2SO_4$ and the solvent evaporated under vacuum. The crude was crystallized in $CHCl_3$/hexane. The precipitate was filtered, washed with hexane and dried under vacuum at 40° C. for 8 hours to give 55 g of the title compound (45% yield). The mother liquor solution was evaporated under vacuum at 40°

C., dissolved in ethyl acetate (200 mL) and extracted with 200 mL of water. The organic solution was dried over Na₂SO₄ and the solvent evaporated under vacuum at 40° C. The crude was crystallized in CHCl₃/hexane, and additional 15 g of the title product were obtained (70% overall yield).

Step 2: Preparation of (R,S)-2-(3,5-dichloropyridin-4-yl)-1-(3,4-dimethoxyphenyl)ethyl) (R)-2-(6-methoxynaphthalen-2-yl)propanoate (I-1/Ab)

(R,S)-2-(3,5-dichloropyridin-4-yl)-1-(3,4-dimethoxyphenyl)ethanol (50 g, 152 mmol), (R)-2-(6-methoxynaphthalen-2-yl)propanoic acid (38.6 g, 168 mmol), DMAP (20.5 g, 168 mmol), and EDC (43.8 g, 229 mmol) were dissolved in DMF (300 mL), and the reaction mixture was stirred at RT for 2 hours Thereafter, water (500 mL) was added, and the solution stirred till complete precipitation occurs. The solid was filtered and dissolved in DCM (500 mL). The organic solution was washed with aqueous HCl 1N (2×500 mL), saturated aqueous NaHCO₃ solution (500 mL) and dried over Na₂SO₄. The solvent was evaporated under vacuum and the solid residue sonicated in EtOH (300 mL) and triturated for 1 hour. The resulting precipitate was collected by filtration and dried under vacuum at 40° C. for 4 h to give 79 g (99% yield) of the title compound, as diastereoisomeric mixture.

Step 3: Preparation of (S)-2-(3,5-dichloropyridin-4-yl)-1-(3,4-dimethoxyphenyl)ethyl) (R)-(2-(6-methoxynaphthalen-2-yl)propanoate (I-1/Ac)

(R,S)-2-(3,5-dichloropyridin-4-yl)-1-(3,4-dimethoxyphenyl)ethyl) (R)-(6-methoxy naphthalen-2-yl)propanoate (diastereoisomeric mixture, 79 g, 146 mmol) was dissolved in CHCl₃ (100 mL), and MeOH (30 mL) was slowly added up to persistent opalescence and the mixture left at RT for 2 hours. The solid formed was collected by filtration and re-crystallized by CHCl₃/MeOH (70 mL/20 mL) solvent system to obtain 35 g of the desired compound (yield 88%, ee 98%). Chiral HPLC analysis: Chiralcel OD column, 10 μm, 250×4.6 mm; Flow=0.8 ml/min; eluent=hexane:isopropanol 97/3; $R_t$=42.33 min; ¹H NMR (600 MHz, CHLOROFORM-d) δ ppm 8.04 (s, 2H), 7.67 (d, J=8.79 Hz, 1H), 7.58 (d, J=8.52 Hz, 1H), 7.53 (m, 1H), 7.12-7.20 (m, 3H), 6.95 (dd, J=8.24, 1.92 Hz, 1H), 6.78-6.88 (m, 2H), 6.14 (dd, J=10.44, 4.12 Hz, 1H), 3.95 (s, 3H), 3.88 (s, 3H), 3.78-3.81 (m, 4H), 3.55 (dd, J=13.73, 10.44 Hz, 1H), 3.14 (dd, J=13.60, 4.26 Hz, 1H), 1.44 (d, J=7.14 Hz, 3H).

Step 4: Preparation of (S)-2-(3,5-dichloropyridin-4-yl)-1-(3,4-dimethoxyphenyl)ethanol, (I-1/Ad)

(S)-2-(3,5-dichloropyridin-4-yl)-1-(3,4-dimethoxyphenyl)ethyl) (R)-2-(6-methoxynaphthalen-2-yl)propanoate (30 g, 56 mmol) was dissolved in MeOH, and toluene was slowly added. Potassium tert-butoxide was slowly added to the suspension. The mixture was stirred for 24 hours at RT. The reaction was diluted with water (500 mL), and the aqueous mixture was extracted with CHCl₃ (500 mL). The organic layer was dried over Na₂SO₄ and the solvent was evaporated under vacuum. The residue was crystallized from CHCl₃ (100 mL) and hexane (20 mL). The mother liquor was concentrated and recrystallized with an analogous procedure giving a second crop of desired compound. In total, 16 g of the title compound (87% yield) were obtained. Chiral HPLC analysis: Chiralcel OD column, 10 μm, 250×4.6 mm; flow=0.8 ml/min; eluent=hexane:isopropanol 95/5; $R_t$=58.03 min; $[\alpha]_D^{20}$=+10.21 (c=0.506, Methanol); ¹H NMR (400 MHz, acetone) δ ppm 8.47 (s, 2H), 6.96-7.15 (m, 1H), 6.87 (m, 2H), 4.93-5.21 (m, 1H), 4.50 (d, J=3.97 Hz, 1H), 3.78 (s, 6H), 3.44 (dd, J=12.79, 8.38 Hz, 1H), 3.22 (dd, J=13.01, 5.51 Hz, 1H). MS/ESI⁺ [MH]⁺: 328.19

Step 5: Preparation of (S)-3,5-dichloro-4-(2-(3,4-dimethoxyphenyl)-2-hydroxyethyl)pyridine 1-oxide (I-1/A)

(S)-2-(3,5-dichloropyridin-4-yl)-1-(3,4-dimethoxyphenyl)ethanol (4 g, 12 mmol) was dissolved in ethyl acetate, and m-CPBA was added to the solution. The mixture was stirred at RT for 5 hours. The formed solid was collected by filtration, washed with ethyl acetate and dried under vacuum to give 1.72 g of (S)-2-(3,5-dichloropyridin-4-yl)-1-(3,4-dimethoxyphenyl)ethanol (41% yield). Chiral HPLC analysis: Chiralcel OD column, 10 μm, 250×4.6 mm; Flow=0.8 ml/min; eluent=hexane:isopropanol 60/40; $R_t$ 22.16 min; $[\alpha]_D^{20}$=+68.91 (c=0.253, Methanol/CHCl₃ 1:1); ¹H NMR (400 MHz, CHLOROFORM-d) δ ppm 8.15 (s, 2H), 6.99 (m, 1H), 6.79-6.88 (m, 2H), 5.03 (dd, J=8.50, 5.32 Hz, 1H), 3.75-3.98 (m, 6H), 3.42 (dd, J=13.57, 8.56 Hz, 1H), 3.19 (dd, J=13.51, 5.32 Hz, 1H), 2.06-2.15 (m, 1H); MS/ESI⁺ [MH]⁺: 344

Intermediates I-1/B, I-1/C, I-1/D, I-1/E, I-1/F

The racemic alcohol intermediates reported in table below are described in patent application WO2009/018909, which is incorporated herein by reference in its entirety, and may be obtained following the above procedure (only step 1 followed by step 5) substituting 3,4-dimethoxybenzaldehyde with the suitable 3,4-dialkoxybenzaldehyde.

Table of racemic alcohol intermediates

| Structure | Name | Intermediate | Analytical data |
|---|---|---|---|
| (structure shown) | (R,S)-3,5-dichloro-4-(2-(3,4-dimethoxyphenyl)-2-hydroxyethyl)pyridine 1-oxide | I-1/B | ¹H NMR (400 MHz, (CDCl₃) δ ppm 8.15 (s, 2 H), 6.99 (m, 1 H), 6.79-6.88 (m, 2 H), 5.03 (dd, J = 8.50, 5.32 Hz, 1 H), 3.75-3.98 (m, 6 H), 3.42 (dd, J = 13.57, 8.56 Hz, 1 H), 3.19 (dd, J = 13.51, 5.32 Hz, 1 H), 2.06-2.15 (m, 1 H); MS/ESI⁺ [MH]⁺: 344 |

Table of racemic alcohol intermediates

| Structure | Name | Intermediate | Analytical data |
|---|---|---|---|
| 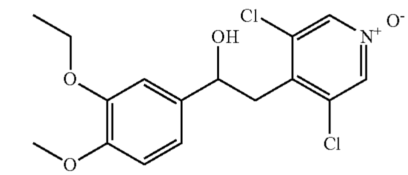 | (R,S)-3,5-dichloro-4-(2-(3-ethoxy-4-methoxyphenyl)-2-hydroxyethyl)pyridine 1-oxide | I-1/C | MS/ESI⁺ [MH]⁺: 358 |
| 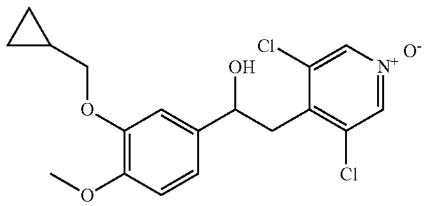 | (R,S)-3,5-dichloro-4-(2-(3-cyclopropylmethoxy-4-methoxyphenyl)-2-hydroxyethyl)pyridine 1-oxide | I-1/D | $^1$H NMR (400 MHz, CDCl$_3$): δ 8.13 (s, 2 H), 6.97 (s, 1 H), 6.83-6.81 (m, 2 H), 5.00-4.97 (m, 1 H), 3.87-3.84 (m, 5 H), 3.41-3.13 (m, 1 H), 3.18-3.13 (m, 1 H), 2.13-2.11 (br s, 1 H), 1.35-1.31 (m, 1 H), 0.68-0.63 (m, 2 H), 0.37-0.35 (m, 2H).<br>LCMS (Method 1): [MH+] = 384 at 3.21 min. |
| 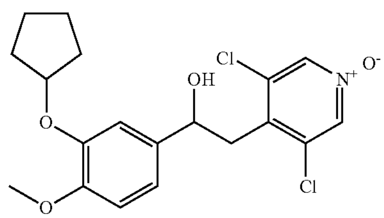 | (R,S)-3,5-dichloro-4-(2-(3-(cyclopentyloxy)-4-methoxyphenyl)-2-hydroxyethyl)pyridine 1-oxide | I-1/E | $^1$H NMR (400 MHz, CDCl$_3$): δ 8.13 (s, 2 H), 6.94 (s, 1 H), 6.82-6.81 (m , 2 H), 5.01-4.80 (m, 1 H), 4.79-4.76 (m, 1 H), 3.42 (s, 3 H), 3.41-3.36 (m, 1 H), 3.19-3.14 (m, 1 H), 1.95-1.79 (m, 6 H), 1.65-1.57 (m, 3 H).<br>LCMS (Method 2): [MH+] = 398 at 3.13 min. |
| 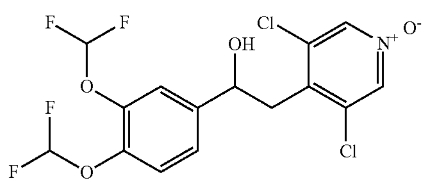 | (R,S)-4-(2-(3,4-bis(difluoromethoxy)phenyl)-2-hydroxyethyl)-3,5-dichloropyridine 1-oxide | I-1/F | $^1$H NMR (400 MHz, CDCl$_3$): δ 8.15 (s, 2 H), 7.33 (s, 1 H), 7.28-7.19 (m, 2 H), 6.55 (t, J = 73.4 Hz, 1 H), 6.53 (t, J = 73.4 Hz, 1 H), 5.08 (app t, J = 6.4 Hz, 1 H), 3.38 (dd, J = 13.6, 8.7 Hz, 1 H), 3.17 (dd, J = 13.6, 5.2 Hz, 1 H), 2.29 (s, 1 H).<br>LCMS (Method 1): [MH+] = 416 at 3.54 min. |

Intermediate 1/G (I-1/G). (S)-3,5-dichloro-4-(2-(3-(cyclopropylmethoxy)-4-(difluoromethoxy)phenyl)-2-hydroxyethyl)pyridine 1-oxide The intermediate I-1/G may be obtained following the procedure described in patent application WO2010/089107, which is incorporated herein by reference in its entirety.

Intermediate 1/H (I-1/H). (S)-3,5-dichloro-4-(2-(4-(difluoromethoxy)-3-methoxyphenyl)-2-hydroxyethyl)pyridine 1-oxide

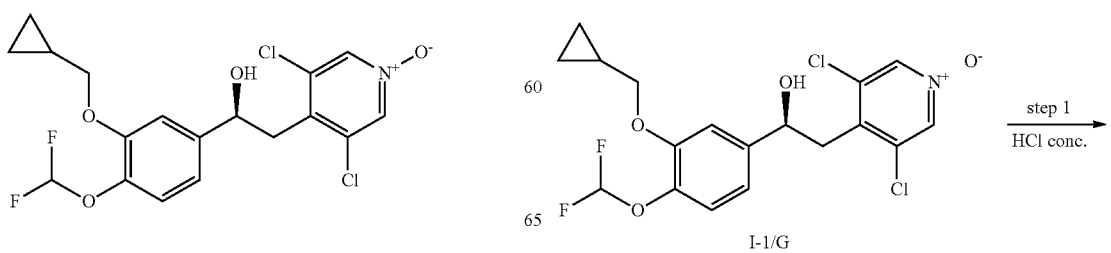

I-1/G

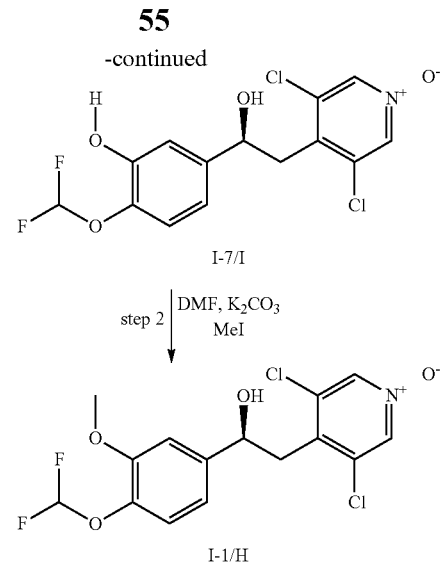

Step 1: (S)-3,5-dichloro-4-(2-(4-(difluoromethoxy)-3-hydroxyphenyl)-2-hydroxyethyl)pyridine 1-oxide (I-1/I)

(S)-3,5-dichloro-4-(2-(3-(cyclopropylmethoxy)-4-(difluoromethoxy)phenyl)-2-hydroxyethyl)pyridine 1-oxide (5 g, 11.90 mmol) was added to 100 mL of 37% HCl and stirred at room temperature for about 3 minutes, obtaining a yellow solution. After stirring for further 3 minutes the solution was poured into a solution of NaOH (48 g) in water (500 mL). The red solution was added with 1 M HCl to pH 1. The brown solid was filtered, washed with water and triturated with hot EtOH (50 mL). After stirring at r.t. for 1 hour, the solid was filtered, washed with EtOH and dried under vacuum at 40 C yielding 2.4 of the title compound. MS/ESI$^+$ [MH]$^+$:366

Step 2: S)-3,5-dichloro-4-(2-(4-(difluoromethoxy)-3-methoxyphenyl)-2-hydroxyethyl)pyridine 1-oxide (I-1/H)

(S)-3,5-dichloro-4-(2-(4-(difluoromethoxy)-3-hydroxyphenyl)-2-hydroxyethyl)-pyridine 1-oxide (2 g, 5.46 mmol) was dissolved in DMF (16 mL) then K$_2$CO$_3$ (2 g, 14.47 mmol) and iodomethane (1.72 g, 12.12 mmol) were added and the mixture was stirred at r.t. for 4 hours. The mixture was poured into 200 mL of water, filtered, washed with water and dried under vacuum at 40° C. 1.98 g of whitish solid was obtained.

$^1$H NMR (400 MHz, DMSO-d6): δ ppm 8.53 (s, 2H), 7.08-7.13 (m, 2H), 7.01 (t, J=75.00 Hz, 1H), 6.88 (dd, J=7.94, 1.76 Hz, 1H), 5.64 (d, J=4.41 Hz, 1H), 4.77-4.94 (m, 1H), 3.81 (s, 3H), 3.17 (d, J=8.38 Hz, 1H), 3.05 (d, J=5.73 Hz, 1H) MS/ESI$^+$ [MH]$^+$:380

Intermediates I-1/J, I-1/K, I-1/L, I-1/M, I-1/N

The intermediates reported in table below, I-1/J, I-1/K, I-1/L, I-1/M, I-1/N, may be obtained following the procedure described above for intermediate 1/H, by reacting intermediate 1/I with a suitable alkylating agent.

| Structure | Name | Intermediate | Analytical data |
|---|---|---|---|
| 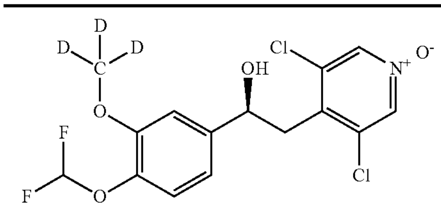 | (S)-3,5-dichloro-4-(2-(4-(difluoromethoxy)-3-trideuteromethoxyphenyl)-2-hydroxyethyl)pyridine 1-oxide | I-1/J | $^1$H NMR (400 MHz, DMSO-d6): δ ppm 8.53 (s, 2 H), 7.06-7.13 (m, 2 H), 7.01 (t, J = 75.00 Hz, 1 H), 6.88 (dd, J = 8.38, 1.76 Hz, 1 H), 5.63 (d, J = 4.41 Hz, 1 H), 4.64-4.91 (m, 1 H), 3.19 (dd, J = 13.23, 8.38 Hz, 1 H), 3.05 (d, J = 5.73 Hz, 1 H) MS/ESI+ [MH]$^+$: 383 |
| 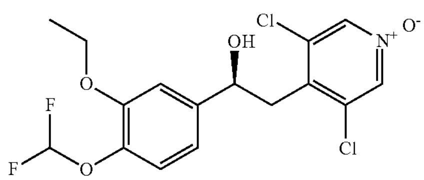 | (S)-3,5-dichloro-4-(2-(4-(difluoromethoxy)-3-ethoxyphenyl)-2-hydroxyethyl)pyridine 1-oxide | I-1/K | $^1$H NMR (400 MHz, DMSO-d6): δ ppm 8.53 (s, 2 H), 7.06-7.13 (m, 2 H), 7.01 (t, J = 75.00 Hz, 1 H), 6.86 (dd, J = 8.16, 1.54 Hz, 1 H), 5.62 (d, J = 3.97 Hz, 1 H), 4.72-4.97 (m, 1 H), 3.91-4.19 (m, 2 H), 3.18 (dd, J = 13.23, 8.38 Hz, 1 H), 3.02 (dd, J = 13.23, 5.29 Hz, 1 H), 1.33 (t, J = 7.06 Hz, 3 H) MS/ESI+ [MH]$^+$: 394 |
| 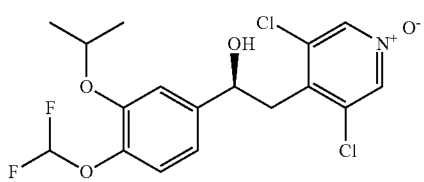 | (S)-3,5-dichloro-4-(2-(4-(difluoromethoxy)-3-isopropoxyphenyl)-2-hydroxyethyl)pyridine 1-oxide | I-1/L | $^1$H NMR (400 MHz, DMSO-d6): δ ppm 8.52 (s, 2 H), 7.04-7.13 (m, 2 H), 6.97 (t, J = 75.00 Hz, 1 H), 6.86 (dd, J = 7.94, 1.76 Hz, 1 H), 5.63 (d, J = 3.53 Hz, 1 H), 4.81-4.90 (m, 1 H), 4.46-4.65 (m, 1 H), 3.16 (d, J = 7.94 Hz, 1 H), 3.04 (d, J = 6.17 Hz, 1 H), 1.26 (dd, J = 13.67, 6.17 Hz, 6 H) MS/ESI+ [MH]$^+$: 408 |
| 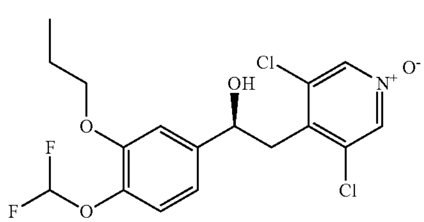 | (S)-3,5-dichloro-4-(2-(4-(difluoromethoxy)-3-propoxyphenyl)-2-hydroxyethyl)pyridine 1-oxide | I-1/M | MS/ESI+ [MH]$^+$: 408 |

| Structure | Name | Intermediate | Analytical data |
|---|---|---|---|
| 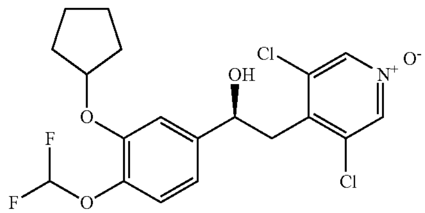 | (S)-3,5-dichloro-4-(2-(3-(cyclopentyloxy)-4-(difluoromethoxy)phenyl)-2-hydroxyethyl)pyridine 1-oxide | I-1/N | MS/ESI+ [MH]+: 434 |

Alcohol intermediates from I-1/B to I-1/N are used as below or may be coupled with any suitable acidic portion to obtain the compound of the invention or intermediates thereof.

Intermediate 2. (S)-3,5-dichloro-4-(2-(3,4-dimethoxyphenyl)-2-((3-formylbenzoyl)oxy)ethyl)pyridine 1-oxide (I-2)

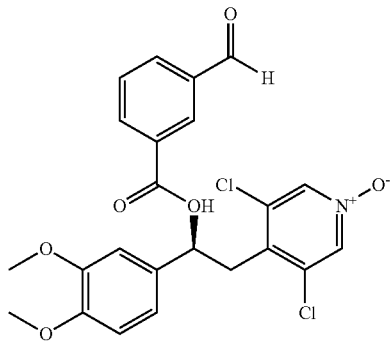 [SMILES: COc1ccc([C@H](Cc2c(Cl)c[n+]([O-])cc2Cl)OC(=O)c2cccc(C=O)c2)cc1OC]

A solution of (S)-3,5-dichloro-4-(2-(3,4-dimethoxyphenyl)-2-hydroxyethyl)-pyridine 1-oxide (0.688 g, 2 mmol), 3-formylbenzoic acid (0.300 g, 2 mmol), N-(3-dimethylaminopropyl)-N'-ethylcarbodiimide hydrochloride (0.767 g, 4 mmol) and 4-(dimethylamino)pyridine (0.122 g, 1 mmol) in anhydrous DCM (30 mL) was stirred at RT for 21 hours. The reaction mixture was partitioned between saturated NaHCO$_3$ (20 mL) and DCM (10 mL) and filtered through a phase separator cartridge. The cartridge was washed thoroughly with DCM and the solvent was removed in vacuo. The crude material was purified by silica gel column chromatography eluting with 1:1 DCM:EtOAc to afford the title compound as an off-white solid (0.863 g, 91%).

$^1$H NMR (400 MHz, CDCl$_3$): δ 10.08 (s, 1H), 8.54 (t, J=1.7 Hz, 1H), 8.27 (dt, J=7.8, 1.5 Hz, 1H), 8.14 (s, 2H), 8.09 (dt, J=7.7, 1.5 Hz, 1H), 7.63 (t, J=7.7 Hz, 1H), 7.05 (dd, J=8.2, 2.1 Hz, 1H), 7.00 (d, J=2.1 Hz, 1H), 6.87 (d, J=8.3 Hz, 1H), 6.33 (dd, J=9.7, 4.6 Hz, 1H), 3.92 (s, 3H), 3.88 (s, 3H), 3.76 (dd, J=14.0, 9.8 Hz, 1H), 3.39 (dd, J=14.0, 4.6 Hz, 1H). LCMS (Method 1): [MH+]=476 at 3.55 min.

The following intermediates were synthesized following the same procedure as that described for intermediate 2 using the appropriate alcoholic intermediate.

| Structure | Intermediate number | Analytical Data |
|---|---|---|
| 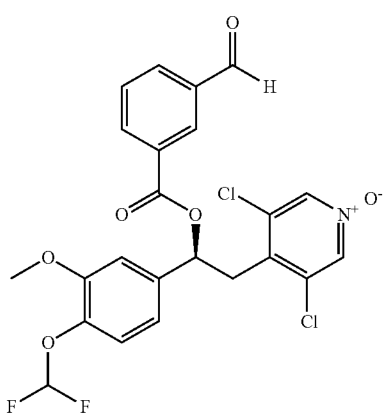 | Intermediate 34 | $^1$H NMR (400 MHz, CDCl$_3$): δ 10.08 (s, 1 H), 8.54 (t, J = 1.7 Hz, 1 H), 8.27 (dt, J = 7.8, 1.5 Hz, 1 H), 8.15 (s, 2 H), 8.10 (dt, J = 7.7, 1.4 Hz, 1 H), 7.65 (t, J = 7.7 Hz, 1 H), 7.20 (d, J = 8.0 Hz, 1 H), 7.10-7.06 (m, 2 H), 6.55 (t, J = 74.9 Hz, 1 H), 6.32 (dd, J = 10.0, 4.3 Hz, 1 H), 3.92 (s, 3 H), 3.75 (dd, J = 14.1, 10.0 Hz, 1 H), 3.37 (dd, J = 14.1, 4.3 Hz, 1 H). |

-continued

| Structure | Intermediate number | Analytical Data |
|---|---|---|
| 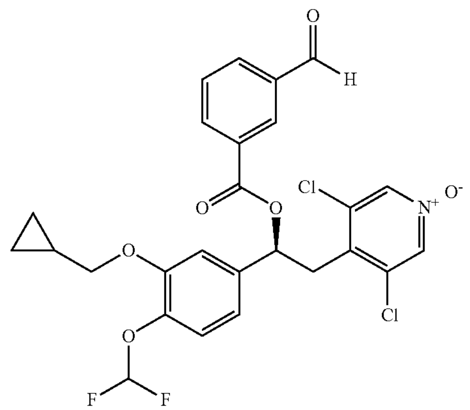 | Intermediate 35 | ¹H NMR (400 MHz, CDCl₃): δ 10.08 (s, 1 H), 8.53 (t, J = 1.7 Hz, 1 H), 8.26 (dt, J = 7.8, 1.5 Hz, 1 H), 8.15 (s, 2 H), 8.10 (dt, J = 7.7, 1.5 Hz, 1 H), 7.64 (t, J = 7.7 Hz, 1 H), 7.19 (d, J = 8.1 Hz, 1 H), 7.10-7.03 (m, 2 H), 6.62 (t, J = 75.3 Hz, 1 H), 6.30 (dd, J = 10.0, 4.3 Hz, 1 H), 3.91 (d, J = 6.9 Hz, 2 H), 3.73 (dd, J = 14.1, 10.0 Hz, 1 H), 3.35 (dd, J = 14.1, 4.3 Hz, 1 H), 1.32-1.23 (m, 1 H), 0.69-0.63 (m, 2 H), 0.40-0.35 (m, 2 H). LCMS (Method 2): [MH+] = 552 at 4.00 min. |
| 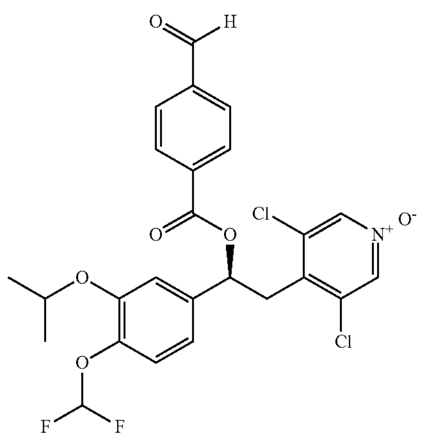 | Intermediate 36 | ¹H NMR (400 MHz, CDCl₃): δ 10.10 (s, 1 H), 8.18-8.14 (m, 2 H), 8.12 (s, 2 H), 7.97-7.95 (m, 2 H), 7.19-7.17 (m, 1 H), 7.07-7.04 (m, 2 H), 6.55 (t, J = 75.2 Hz, 1 H), 6.29 (dd, J = 4.4, 9.6 Hz, 1 H), 4.60-4.54 (m, 1 H), 3.70 (dd, J = 9.6, 14.0 Hz, 1 H), 3.34 (dd, J = 4.4, 14.0 Hz, 1 H), 1.38-1.27 (m, 6 H). LCMS (Method 2): [MH+] = 540 at 4.02 min. |
| 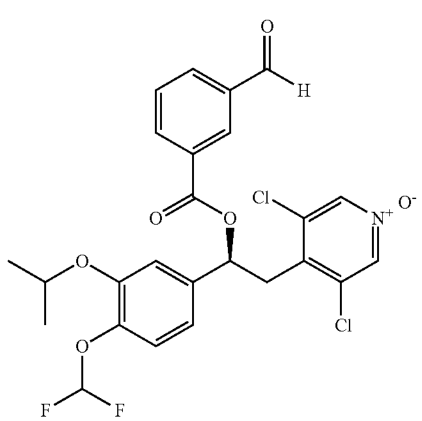 | Intermediate 37 | ¹H NMR (400 MHz, CDCl₃): δ 10.08 (s, 1 H), 8.54 (t, J = 1.7 Hz, 1 H), 8.26 (dt, J = 7.8, 1.5 Hz, 1 H), 8.15 (s, 2 H), 8.10 (dt, J = 7.7, 1.5 Hz, 1 H), 7.65 (t, J = 7.7 Hz, 1 H), 7.19 (d, J = 8.0 Hz, 1 H), 7.09-7.04 (m, 2 H), 6.56 (t, J = 75.2 Hz, 1 H), 6.30 (dd, J = 9.8, 4.4 Hz, 1 H), 4.62-4.54 (m, 1 H), 3.73 (dd, J = 14.1, 9.8 Hz, 1 H), 3.37 (dd, J = 14.1, 4.4 Hz, 1 H), 1.38 (d, J = 6.1 Hz, 3 H), 1.35 (d, J = 6.0 Hz, 3 H). LCMS (Method 1): [MH+] = 540 at 4.18 min. |

The following intermediates were synthesized following the same procedure as that described for intermediate 2, starting from (R,S)-2-(3,5-dichloropyridin-4-yl)-1-(3,4-dimethoxyphenyl)ethanol (Intermediate 1/Aa). Single diastereoisomers were obtained by SFC purification.

| Structure | Intermediate number | Analytical Data |
|---|---|---|
| 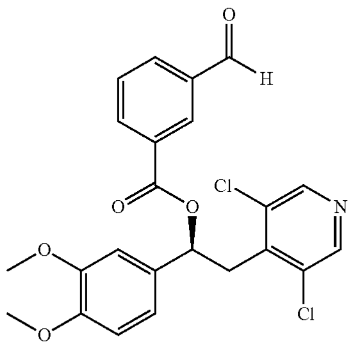 [SMILES: COc1ccc([C@H](Cc2c(Cl)cncc2Cl)OC(=O)c2cccc(C=O)c2)cc1OC] | Intermediate 38 | ¹H NMR (400 MHz, CDCl₃): δ 10.07 (s, 1 H), 8.54 (t, J = 1.7 Hz, 1 H), 8.45 (s, 2 H), 8.27 (dt, J = 7.8, 1.5 Hz, 1 H), 8.08 (dt, J = 7.7, 1.5 Hz, 1 H), 7.62 (t, J = 7.7 Hz, 1 H), 7.09 (dd, J = 8.3, 2.0 Hz, 1 H), 7.00 (d, J = 2.0 Hz, 1 H), 6.87 (d, J = 8.3 Hz, 1 H), 6.36 (dd, J = 10.0, 4.3 Hz, 1 H), 3.91 (s, 3 H), 3.88 (s, 3 H), 3.85 (dd, J = 13.9, 10.2 Hz, 1 H), 3.44 (dd, J = 13.7, 4.4 Hz, 1 H). LCMS (Method 1): [MH+] = 460 at 4.41 min. |
| 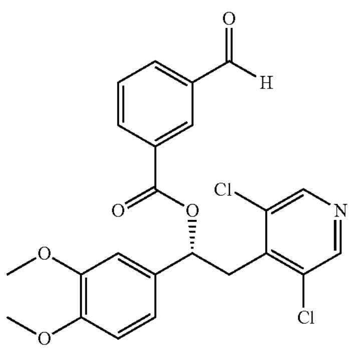 [SMILES: COc1ccc([C@@H](Cc2c(Cl)cncc2Cl)OC(=O)c2cccc(C=O)c2)cc1OC] | Intermediate 39 | ¹H NMR (400 MHz, CDCl₃): δ 10.07 (s, 1 H), 8.54 (t, J = 1.7 Hz, 1 H), 8.45 (s, 2 H), 8.27 (dt, J = 7.8, 1.5 Hz, 1 H), 8.08 (dt, J = 7.7, 1.5 Hz, 1 H), 7.62 (t, J = 7.7 Hz, 1 H), 7.09 (dd, J = 8.3, 2.0 Hz, 1 H), 7.00 (d, J = 2.0 Hz, 1 H), 6.87 (d, J = 8.3 Hz, 1 H), 6.36 (dd, J = 10.0, 4.3 Hz, 1 H), 3.91 (s, 3 H), 3.88 (s, 3 H), 3.85 (dd, J = 13.9, 10.2 Hz, 1 H), 3.44 (dd, J = 13.7, 4.4 Hz, 1 H). LCMS (Method 1): [MH+] = 460 at 4.41 min. |
| 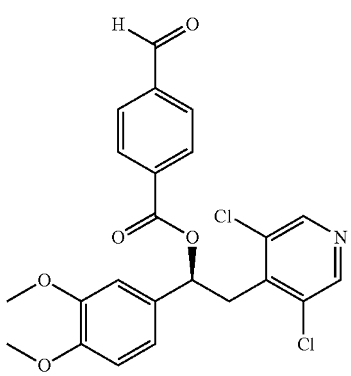 [SMILES: COc1ccc([C@H](Cc2c(Cl)cncc2Cl)OC(=O)c2ccc(C=O)cc2)cc1OC] | Intermediate 40 | ¹H NMR (400 MHz, CDCl₃): δ 10.09 (s, 1 H), 8.45 (s, 2 H), 8.19 (d, J = 8.1 Hz, 2 H), 7.94 (d, J = 8.1 Hz, 2 H), 7.08 (dd, J = 8.2, 2.1 Hz, 1 H), 6.99 (d, J = 2.0 Hz, 1 H), 6.87 (d, J = 8.3 Hz, 1 H), 6.36 (dd, J = 10.0, 4.3 Hz, 1 H), 3.90 (s, 3 H), 3.88 (s, 3 H), 3.83 (dd, J = 13.7, 10.0 Hz, 1 H), 3.43 (dd, J = 13.7, 4.4 Hz, 1 H). LCMS (Method 1): [MH+] = 460 at 4.45 min. |
| 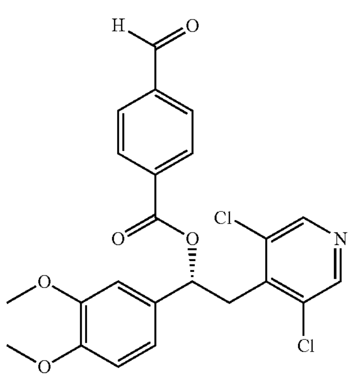 [SMILES: COc1ccc([C@@H](Cc2c(Cl)cncc2Cl)OC(=O)c2ccc(C=O)cc2)cc1OC] | Intermediate 41 | ¹H NMR (400 MHz, CDCl₃): δ 10.09 (s, 1 H), 8.45 (s, 2 H), 8.19 (d, J = 8.1 Hz, 2 H), 7.94 (d, J = 8.1 Hz, 2 H), 7.08 (dd, J = 8.2, 2.1 Hz, 1 H), 6.99 (d, J = 2.0 Hz, 1 H), 6.87 (d, J = 8.3 Hz, 1 H), 6.36 (dd, J = 10.0, 4.3 Hz, 1 H), 3.90 (s, 3 H), 3.88 (s, 3 H), 3.83 (dd, J = 13.7, 10.0 Hz, 1 H), 3.43 (dd, J = 13.7, 4.4 Hz, 1 H). LCMS (Method 1): [MH+] = 460 at 4.45 min. |

Intermediate 3. (S)-3,5-dichloro-4-(2-(3,4-dimethoxyphenyl)-2-((4-formylbenzoyl)oxy)ethyl)pyridine 1-oxide (I-3)

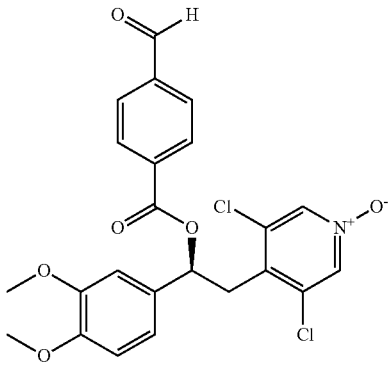 [SMILES: COc1ccc([C@H](Cc2c(Cl)c[n+]([O-])cc2Cl)OC(=O)c2ccc(C=O)cc2)cc1OC]

A solution of (S)-3,5-dichloro-4-(2-(3,4-dimethoxyphenyl)-2-hydroxyethyl)-pyridine 1-oxide (0.688 g, 2 mmol), 4-carboxybenzaldehyde (0.300 g, 2 mmol), N-(3-dimethylaminopropyl)-N'-ethylcarbodiimide hydrochloride (0.767 g, 4 mmol) and 4-(dimethylamino)pyridine (0.122 g, 1 mmol) in anhydrous DCM (30 mL) was stirred at RT for 17 hours. The reaction mixture was partitioned between saturated NaHCO₃ (20 mL) and DCM (10 mL) and filtered through a phase separator cartridge. The cartridge was washed thoroughly with DCM and the solvent was removed in vacuo. The crude material was purified by silica gel column chromatography eluting with 2:3 DCM:EtOAc to afford the title compound as a white solid (0.724 g, 76%).

$^{1}$H NMR (400 MHz, CDCl₃): δ 10.10 (s, 1H), 8.18 (d, J=8.1 Hz, 2H), 8.13 (s, 2H), 7.98-7.93 (m, 2H), 7.04 (dd, J=8.2, 2.1 Hz, 1H), 6.99 (d, J=2.1 Hz, 1H), 6.87 (d, J=8.3 Hz, 1H), 6.33 (dd, J=9.7, 4.6 Hz, 1H), 3.91 (s, 3H), 3.88 (s, 3H), 3.78-3.70 (m, 1H), 3.38 (dd, J=14.0, 4.6 Hz, 1H). LCMS (Method 1): [MH+]=476/478 at 3.65 min.

Intermediate 4. (R)-2-((tert-butoxycarbonyl)amino)-2-phenylacetic acid (I4)

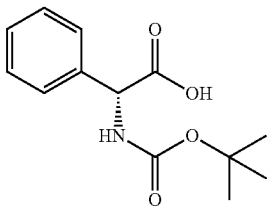 [SMILES: CC(C)(C)OC(=O)N[C@@H](C(=O)O)c1ccccc1]

Phenylglycine (1.51 g, 10 mmol) was dissolved in a mixture of dioxane and water (2:1, 30 mL) and 1.0 N aqueous sodium hydroxide, and the resulting mixture was cooled to 0° C. Di-tert-butyl dicarbonate (3.27 g, 15 mmol) and sodium hydrogen carbonate (0.84 g, 10 mmol) were added in one portion and the mixture was stirred at 0° C. for 10 minutes. The ice bath was removed and the reaction mixture was stirred at ambient temperature for 24 hours. After this time, the reaction mixture was concentrated under reduced pressure and partitioned between ethyl acetate and water. The aqueous layer was acidified with 1.0 N aqueous potassium hydrogen sulphate solution (pH 2.5) and subsequently washed with ethyl acetate (2×40 mL). The combined organic fractions were dried over magnesium sulfate and the solvent was removed in vacuo to yield the title compound (1.8 g, 72%) as a clear oil, which solidified on standing.

$^{1}$H NMR (400 MHz, CDCl₃): δ 8.08 (s, 1H), 7.47-7.27 (m, 5H), 5.48*$^{or\,†}$ (dd, J=72.0 Hz, 6.5 Hz, 1H), 5.13*$^{or\,†}$ (d, J=5.6 Hz, 1H), 3.71 (s, 1H), 1.43 (s, 3H), 1.21 (s, 6H). * and † refer to different isomers.

The following intermediates were synthesized via a similar method.

| Structure | Intermediate number | Analytical Data |
|---|---|---|
| (4-fluorophenyl Boc-phenylglycine structure) | Intermediate 5 | $^{1}$H NMR (400 MHz, CDCl₃): δ 7.79-7.69* $^{or\,†}$ (m, 1 H), 7.43-7.35 (m, 2 H), 7.09-6.99 (m, 2 H), 5.55-5.46* $^{or\,†}$ (m, 1 H), 5.36-5.28* $^{or\,†}$ (m, 1 H), 5.15-5.06* $^{or\,†}$ (m, 1 H), 1.43 (s, 3H), 1.23 (s, 6 H). |
| (3-fluorophenyl Boc-phenylglycine structure) | Intermediate 25 | $^{1}$H NMR (400 MHz, CDCl₃): δ 7.37-7.30 (m, 1 H), 7.17 (d, J = 7.8 Hz, 1 H), 7.12-7.07 (m, 1 H), 7.05-6.99 (m, 1 H), 5.63 (br s, 1 H), 5.32 (d, J = 7.0 Hz, 1 H), 4.84-4.79 (m, 1 H), 3.10 (ddd, J = 14.9, 8.2, 2.3 Hz, 1 H), 2.79-2.62 (m, 3 H), 2.61-2.51 (m, 1 H), 2.32 (d, J = 14.9 Hz, 1 H), 2.05-1.99 (m, 1 H), 1.78-1.62 (m, 2 H), 1.56-1.47 (m, 1 H), 1.44 (s, 9 H), 1.41-1.31 (m, 1 H). LCMS (Method 1): [MH+] = 379 at 2.62 min. |

-continued

| Structure | Intermediate number | Analytical Data |
|---|---|---|
| (2-fluorophenyl, Boc-amino acetic acid structure) | Intermediate 26 | $^1$H NMR (400 MHz, CDCl$_3$): δ 7.38-7.27 (m, 2 H), 7.17-7.05 (m, 2 H), 5.67-5.60 (m, 1 H), 5.57 (d, J = 8.0 Hz, 1 H), 4.84-4.79 (m, 1 H), 3.10 (dd, J = 14.9, 8.1 Hz, 1 H), 2.77-2.61 (m, 3 H), 2.52-2.42 (m, 1 H), 2.36 (d, J = 15.1 Hz, 1 H), 2.01-1.96 (m, 1 H), 1.73-1.61 (m, 2 H), 1.54-1.46 (m, 1 H), 1.44 (s, 9 H), 1.39-1.25 (m, 1 H). LCMS (Method 2): [MH+] = 379 at 3.65 min. |
| (2-methoxyphenyl, Boc-amino acetic acid structure) | Intermediate 27 | $^1$H NMR (400 MHz, CDCl$_3$): δ 7.34-7.27 (m, 2 H), 6.95 (t, J = 7.5 Hz, 1 H), 6.87 (d, J = 8.1 Hz, 1 H), 5.69 (d, J = 9.0 Hz, 1 H), 5.46 (d, J = 9.1 Hz, 1 H), 4.79-4.74 (m, 1 H), 3.83 (s, 3 H), 3.13 (ddd, J = 14.8, 8.0, 2.3 Hz, 1 H), 2.76-2.62 (m, 3 H), 2.40 (d, J = 14.7 Hz, 2 H), 1.97-1.89 (m, 1 H), 1.73-1.63 (m, 1 H), 1.54-1.46 (m, 1 H), 1.44 (s, 9 H), 1.30-1.17 (m, 2 H). LCMS (Method 1): [MH+] = 391 at 2.57 min. |

Intermediate 6. (R)—(R)-quinuclidin-3-yl 2-((tert-butoxycarbonyl)amino)-2-phenylacetate (I-6)

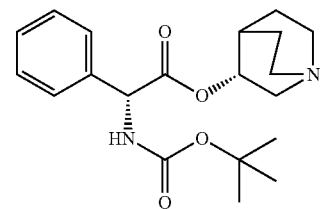 [SMILES: CC(C)(C)OC(=O)N[C@@H](C(=O)O[C@H]1CN2CCC1CC2)c1ccccc1]

(R)-2-((tert-Butoxycarbonyl)amino)-2-phenylacetic acid (5.0 g, 19.9 mmol), (R)-quinuclidin-3-ol (3.8 g, 29.8 mmol), N,N'-Dicyclohexylcarbodiimide (4.72 g, 22.9 mmol) and 1-hydroxybenzotriazole hydrate (3.09 g, 22.9 mmol) where mixed together in tetrahydrofuran (175 mL) and stirred at ambient temperature for 18 hours. After this time the reaction mixture was filtered through a pad of Celite® and concentrated in vacuo. The resulting crude was partitioned between ethyl acetate (100 mL) and 10% aqueous sodium carbonate solution (50 mL), the resulting organic fractions were dried over magnesium sulfate, filtered and the solvent was removed in vacuo. Trituration with cold methanol gave the title compound as a white solid (898 mg, 17%) as a single diastereoisomer.

$^1$H NMR (400 MHz, CDCl3): δ 7.84 (d, J=7.8 Hz, 1H), 7.49-7.31 (m, 5H), 5.22 (d, J=8.2 Hz, 1H), 4.73-4.66 (m, 1H), 3.02 (ddd, J=14.5 Hz, 7.8 Hz, 1.5 Hz, 1H), 2.69-2.51 (m, 3H), 2.46-2.33 (m, 1H), 2.19 (d, J=14.5, 1H), 1.98-1.87 (m, 1H), 1.70-1.53 (m, 2H), 1.53-1.30 (m, 1H), 1.43 (s, 9H), 1.34-1.23 (m, 1H).

The following intermediates were synthesized via a similar method.

| Structure | Intermediate number | Analytical Data |
|---|---|---|
| (4-fluorophenyl quinuclidinyl ester, Boc-amino structure) | Intermediate 7 | $^1$H NMR (400 MHz, CDCl$_3$): δ 7.38-7.32 (m, 2 H), 7.09-7.02 (m, 2 H), 5.59 (br s, 1 H), 5.29 (d, J = 7.0 Hz, 1 H), 4.83-4.78 (m, 1 H), 3.14-3.06 (m, 1 H), 2.80-2.62 (m, 3 H), 2.59-2.50 (m, 1 H), 2.35-2.28 (m, 1 H), 2.04-1.98 (m, 1 H), 1.76-1.28 (m, 13 H). LCMS (Method 2): [MH+] = 379 at 3.65 min. |
| (3-fluorophenyl quinuclidinyl ester, Boc-amino structure) | Intermediate 28 | $^1$H NMR (400 MHz, DMSO): δ 10.50 (br s, 1 H), 9.30 (br s, 3 H), 7.62-7.52 (m, 2 H), 7.48 (d, J = 7.7 Hz, 1 H), 7.40-7.32 (m, 1 H), 5.41 (s, 1 H), 5.17 (brs, 1 H). 3.69-3.59 (m, 1 H), 3.30-3.11 (m, 5 H), 2.38-2.31 (m, 1 H), 2.15-2.05 (m, 1 H), 1.99-1.89 (m, 1 H), 1.88-1.80 (m, 1 H), 1.80-1.70 (m, 1 H). LCMS (Method 2): [MH+] = 279 at 2.57 min. |

-continued

| Structure | Intermediate number | Analytical Data |
|---|---|---|
| 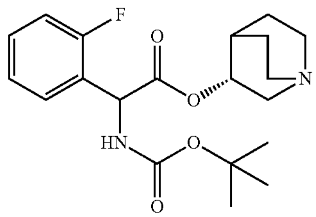 [SMILES: CC(C)(C)OC(=O)NC(C(=O)O[C@H]1CN2CCC1CC2)c1ccccc1F] | Intermediate 29 | ¹H NMR (400 MHz, DMSO): δ 10.81 (br s, 1 H), 9.32 (br s, 3 H), 7.78-7.72 (m, 1 H), 7.62-7.55 (m, 1 H), 7.44-7.34 (m, 2 H), 5.52 (s, 1 H), 5.23-5.17 (m, 1 H), 3.66 (dd, J = 14.0, 8.5 Hz, 1 H), 3.32-3.10 (m, 5 H), 2.36-2.29 (m, 1 H), 2.12-2.00 (m, 1 H), 1.99-1.90 (m, 1 H), 1.90-1 79 (m, 1 H), 1.79-1.71 (m, 1 H). LCMS (Method 2): [MH+] = 279 at 2.59 min. |
| 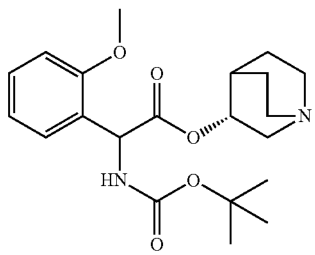 [SMILES: COc1ccccc1C(NC(=O)OC(C)(C)C)C(=O)O[C@H]1CN2CCC1CC2] | Intermediate 30 | ¹H NMR (400 MHz, DMSO): δ 10.82 (s, 1 H), 8.91 (s, 3 H), 7.54-7.47 (m, 2 H), 7.17 (d, J = 8.2 Hz, 1 H), 7.08 (t, J = 7.5 Hz, 1 H), 5.42-5.35 (m, 1 H), 5.21-5.15 (m, 1 H), 3.86 (s, 3 H), 3.72-3.63 (m, 1 H), 3.30-3.07 (m, 4 H), 3.03-2.92 (m, 1 H), 2.32-2.26 (m, 1 H), 1.98-1.79 (m, 3 H), 1.79-1.65 (m, 1 H). LCMS (Method 2): [MH+] = 291 at 2.49 min. |
| 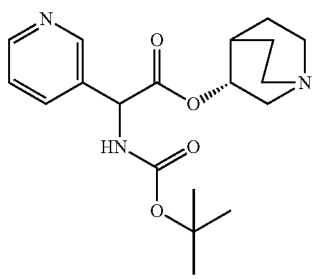 [SMILES: CC(C)(C)OC(=O)NC(C(=O)O[C@H]1CN2CCC1CC2)c1cccnc1] | Intermediate 47 | ¹H NMR (400 MHz, DMSO): δ 8.63 (t, J = 2.50 Hz, 1 H), 8.52 (td, J = 4.55, 1.60 Hz, 1 H), 7.95 (d, J = 8.08 Hz, 1 H), 7.86-7.81 (m, 1 H), 7.43-7.36 (m, 1 H), 5.31 (dd, J = 8.04, 3.97 Hz, 1 H), 4.72 (t, J = 9.02 Hz, 1 H), 3.11-2.96 (m, 1 H), 2.65-2.53 (m, 4 H), 2.47-2.10 (m, 1 H), 1.89-1.65 (m, 1 H), 1.63-1.47 (m, 2 H), 1.41 (s, 9 H), 1.36-1.22 (m, 2 H), |

Intermediate 8, (R)—(R)-quinuclidin-3-yl 2-amino-2-phenylacetate bis hydrochloride salt

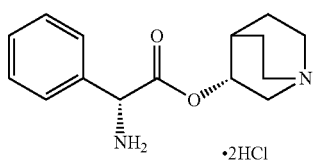 [SMILES: N[C@@H](C(=O)O[C@H]1CN2CCC1CC2)c1ccccc1]

To a solution of (R)—(R)-quinuclidin-3-yl 2-((tert-butoxycarbonyl)amino)-2-phenylacetate (0.608 g, 1.687 mmol) in anhydrous dioxane (6 mL) was added 2M HCl in diethyl ether (5.2 mL, 10.4 mmol). The reaction mixture was stirred at room temperature for 20 hours. The solvent was removed in vacuo to afford the title compound as a white solid (0.564 g, quantitative yield).

¹H NMR (400 MHz, DMSO): δ 10.56 (br s, 1H), 9.24 (br s, 3H), 7.65-7.59 (m, 2H), 7.56-7.49 (m, 3H), 5.34 (s, 1H), 5.20-5.15 (m, 1H), 3.69-3.60 (m, 1H), 3.32-3.10 (m, 5H), 2.37-2.30 (m, 1H), 2.15-2.04 (m, 1H), 1.99-1.89 (m, 1H), 1.89-1.80 (m, 1H), 1.79-1.70 (m, 1H). LCMS (Method 12): [MH+]=261 at 2.11 min.

The following intermediates were synthesized via a similar method.

| Structure | Intermediate number | Analytical Data |
|---|---|---|
| 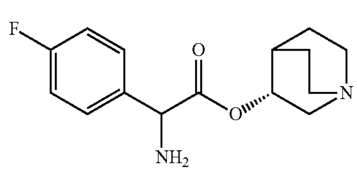 | Intermediate 9 | ¹H NMR (400 MHz, DMSO): δ 10.74 (br s, 1 H), 9.33 (br s, 3 H), 7.73-7.67 (m, 2 H), 7.41-7.34 (m, 2 H), 5.37 (s, 1 H), 5.19-5.13 (m, 1 H), 3.68-3.60 (m, 1 H), 3.30-3.10 (m, 5 H), 2.35-2.30 (m, 1 H), 2.19-2.08 (m, 1 H), 1.99-1.60 (m, 3 H). LCMS (Method 2): [MH+] = 279 at 2.62 min. |

| Structure | Intermediate number | Analytical Data |
|---|---|---|
| (3-fluorophenyl)glycine quinuclidinyl ester · 2HCl | Intermediate 31 | $^1$H NMR (400 MHz, DMSO): δ 10.50 (br s , 1 H), 9.30 (br s, 3 H), 7.62-7.52 (m, 2 H), 7.48 (d, J = 7.7 Hz, 1 H), 7.40-7.32 (m, 1 H), 5.41 (s, 1 H), 5.17 (br s, 1 H), 3.69-3.59 (m, 1 H), 3.30-3.11 (m, 5 H), 2.38-2.31 (m, 1 H), 2.15-2.05 (m, 1 H), 1.99-1.89 (m, 1 H), 1.88-1.80 (m, 1 H), 1.80-1.70 (m, 1 H). LCMS (Method 2): [MH+] = 279 at 2.57 min. |
| (2-fluorophenyl)glycine quinuclidinyl ester · 2HCl | Intermediate 32 | $^1$H NMR (400 MHz, DMSO): 10.81 (br s, 1 H), 9.32 (br s, 3 H), 7.78-7.72 (m, 1 H), 7.62-7.55 (m, 1 H), 7.44-7.34 (m, 2 H), 5.52 (s, 1 H), 5.23-5.17 (m, 1 H), 3.66 (dd, J = 14.0, 8.5 Hz, 1 H), 3.32-3.10 (m, 5 H), 2.36-2.29 (m, 1 H), 2.12-2.00 (m, 1 H), 1.99-1.90 (m, 1 H), 1.90-1 79 (m, 1 H), 1.79-1.71 (m, 1 H). LCMS (Method 2): [MH+] = 279 at 2.59 min. |
| (2-methoxyphenyl)glycine quinuclidinyl ester · 2HCl | Intermediate 33 | $^1$H NMR (400 MHz, DMSO): δ 10.82 (s, 1 H), 8.91 (s, 3 H), 7.54-7.47 (m, 2 H), 7.17 (d, J = 8.2 Hz, 1 H), 7.08 (t, J = 7.5 Hz, 1 H), 5.42-5.35 (m, 1 H), 5.21-5.15 (m, 1 H), 3.86 (s, 3 H), 3.72-3.63 (m, 1 H), 3.30-3.07 (m, 4 H), 3.03-2.92 (m, 1 H), 2.32-2.26 (m, 1 H), 1.98-1.79 (m, 3 H), 1.79-1.65 (m, 1 H). LCMS (Method 2): [MH+] = 291 at 2.49 min. |
| (pyridin-3-yl)glycine quinuclidinyl ester · 2HCl | Intermediate 48 | LCMS (Method 2): [MH+] = 262 at 2.13 min. |

Intermediate 10. [(1S)-2-(3,5-dichloro-1-oxidopyridin-1-ium-4-yl)-1-(3,4-dimethoxyphenyl)ethyl]-3-nitrobenzoate (I-10)

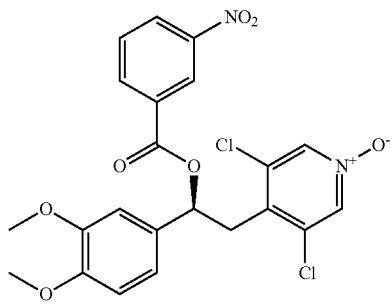 [SMILES: COc1ccc([C@H](Cc2c(Cl)c[n+]([O-])cc2Cl)OC(=O)c2cccc([N+](=O)[O-])c2)cc1OC]

To a stirred solution of (1S)-2-(3,5-dichloro-1-oxidopyridin-1-ium-4-yl)-1-(3,4-dimethoxyphenyl)ethanol (0.500 g, 1.45 mmol) and 3-nitrobenzoic acid (0.242 g, 1.45 mmol) in dichloromethane (15.0 mL) was added 1-ethyl-3-(3-dimethylaminopropyl) carbodiimide (0.560 g, 2.91 mmol) and N,N-dimethylpyridin-4-amine (0.089 g, 0.73 mmol). The reaction was stirred at room temperature for 16 hours. The reaction was quenched by addition of saturated aqueous sodium bicarbonate solution (25.0 mL) and extracted with dichloromethane (×2). The combined organic extracts were dried on magnesium sulphate, filtered and the solvent removed in vacuo to afford a yellow oil. The crude material was purified by silica gel chromatography eluting sequentially with isohexane, ethyl acetate and 10% methanol in ethyl acetate to afford the title compound as a yellow solid (0.642 g, 90% yield).

1H NMR (400 MHz, CDCl3): δ 8.89 (d, J=2.0 Hz, 1H), 8.44-8.41 (m, 1H), 8.33-8.30 (m, 1H), 8.14 (s, 2H), 7.63 (t, J=8.0 Hz, 1H), 7.06-7.03 (m, 2H), 6.88 (d, J=8.4 Hz, 1H), 6.30 (dd, J=9.6, 4.4 Hz, 1H), 3.92 (s, 3H), 3.90 (s, 3H), 3.78 (dd, J=9.6, 14.0 Hz, 1H), 3.38 (dd, J=14.0, 4.4 Hz, 1H).

LCMS (Method 1): [MH+]=493 at 3.77 min.

The following compounds were synthesized via a similar method.

| Structure | Intermediate | Analytical data |
|---|---|---|
| 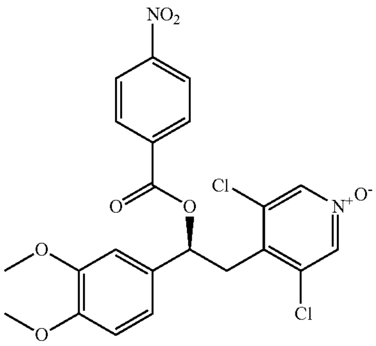 | Intermediate 11 | 1H NMR (400 MHz, CDCl3): δ 8.30 (d, J = 9.0 Hz, 2 H), 8.18 (d, J = 9.0 Hz, 2 H), 8.14 (s, 2 H), 7.03 (dd, J = 8.4, 2.0 Hz, 1 H), 6.98 (d, J = 2.0 Hz, 1 H), 6.32 (d, J = 8.4 Hz, 1 H), 6.31 (dd, J = 9.6, 4.4 Hz, 1 H), 3.91 (s, 3 H), 3.88 (s, 3 H), 3.75 (dd, J = 9.6, 14.0 Hz, 1 H), 3.38 (dd, J = 14.0, 4.4 Hz, 1 H). LCMS (Method 1): [MH+] = 493 at 3.78 min. |
| 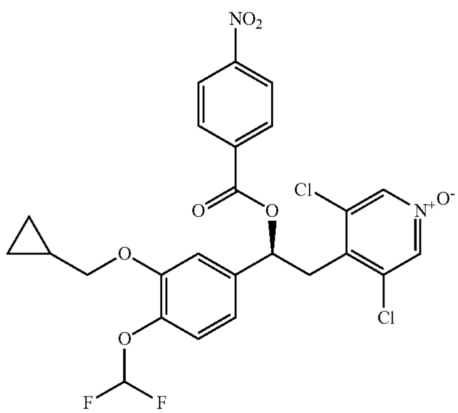 | Intermediate 12 | 1H NMR (400 MHz, CDCl3): δ 8.30 (m, 2 H), 8.19 (m, 2 H), 8.15 (s, 2 H), 7.20 (d, J = 8.4 Hz, 1 H), 7.06 (dd, J = 8.4, 2.0 Hz, 1 H), 7.03 (d, J = 2.0 Hz, 1 H), 6.63 (t, J = 75.0 Hz, 1 H), 6.30 (dd, J = 10.0, 4.4 Hz, 1 H), 3.89 (d, J = 7.2 Hz, 2 H), 3.72 (dd, J = 10.0, 14.4 Hz, 1 H), 3.35 (dd, J = 4.4, 14.4 Hz, 1 H), 1.29-1.24 (m, 1 H), 0.68-0.64 (m, 2 H), 0.39-0.35 (m, 2 H). LCMS (Method 1): [MH+] = 569 at 4.35 min. |
| 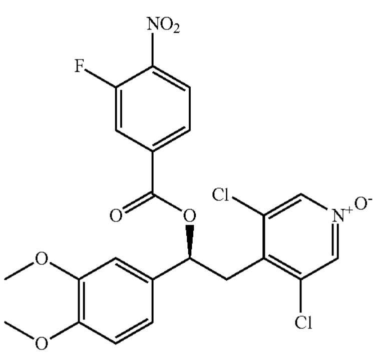 | Intermediate 13 | $^1$HNMR (400 MHz, DMSO): δ 8.58 (s, 2 H); 8.35-8.29 (m, 1 H); 8.11 (dd, J = 11.5, 1.8 Hz, 1 H); 8.03 (dd, J = 8.6, 1.1 Hz, 1 H); 7.13 (d, J = 2.0 Hz, 1 H); 7.08 (dd, J = 8.2, 1.8 Hz, 1 H); 7.00 (d, J = 8.3 Hz, 1 H); 6.24 (dd, J = 9.4, 4.5 Hz, 1 H); 3.80 (d, J = 14.1 Hz, 6 H); 3.76 (dd, J = 14.1, 9.4 Hz, 1 H); 3.45-3.42 (m, 1 H). LCMS (Method 1): [MH+] = 511 at 3.83 min. |

Intermediate 14. [(1S)-2-(3,5-dichloro-1-oxidopyridin-1-ium-4-yl)-1-(3,4-dimethoxyphenyl)ethyl] 3-aminobenzoate (I-14)

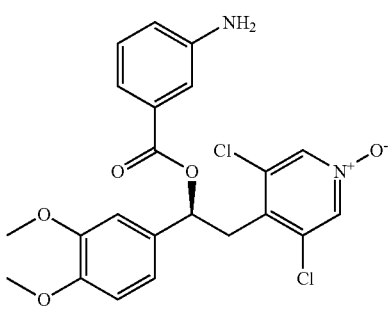 [SMILES: COc1ccc([C@H](Cc2c(Cl)c[n+]([O-])cc2Cl)OC(=O)c2cccc(N)c2)cc1OC]

To a stirred solution of [(1S)-2-(3,5-dichloro-1-oxidopyridin-1-ium-4-yl)-1-(3,4-dimethoxyphenyl)ethyl]-3-nitrobenzoate (0.640 g, 1.30 mmol) in anhydrous tetrahydrofuran (30.0 mL) was added tin chloride dihydrate (1.18 g, 5.2 mmol). After heating at 75° C. for 16 hours, the reaction was allowed to cool to room temperature. The reaction was partitioned between ethyl acetate and sodium bicarbonate and extracted with ethyl acetate (×2). The combined organic extracts were dried on magnesium sulphate, filtered and the solvent was removed in vacuo to afford the title compound as a brown solid (0.520 g, 87% yield).

$^1$H NMR (400 MHz, DMSO): δ 8.58 (s, 2H), 7.20-7.15 (m, 3H), 7.04-6.98 (m, 3H), 6.83-6.81 (m, 1H), 6.22-6.19 (dd, J=4.4, 9.6 Hz, 1H), 5.39 (s, 2H), 3.82 (s, 3H), 3.78 (s, 3H), 3.63-3.59 (dd, J=9.6, 14.0 Hz, 1H), 3.33-3.29 (m, 1H). LCMS (Method 1): [MH+]=463 at 3.28 min.

The following compounds were synthesized via a similar method.

| Structure | Intermediate | Analytical data |
|---|---|---|
| (structure with NH₂-phenyl benzoate, 3,4-dimethoxyphenyl, 3,5-dichloropyridine N-oxide) | Intermediate 15 | ¹H NMR (400 MHz, DMSO): δ 8.59 (s, 2 H), 7.71 (d, J = 8.4 Hz, 2 H), 7.05-7.01 (m, 3 H), 6.59 (d, J = 8.4 Hz, 2 H), 6.21-6.19 (dd, J = 4.4, 9.6 Hz, 1 H), 6.06 (s, 2 H), 3.82 (s, 3 H), 3.79 (s, 3 H), 3.64-3.58 (dd, J = 9.6, 14.0 Hz, 1 H), 3.34-3.30 (m, 1 H). LCMS (Method 1): [MH+] = 463 at 3.38 min. |
| (structure with NH₂-phenyl benzoate, cyclopropylmethoxy/difluoromethoxy-phenyl, 3,5-dichloropyridine N-oxide) | Intermediate 16 | 1H NMR (400 MHz, CDCl3): δ 8.13 (s, 2H), 8.12-7.80 (m, 2 H), 7.16-7.14 (m, 1 H), 7.04-7.01 (m, 2 H), 6.79-6.41 (m, 3 H), 6.23 (dd, J = 10.0, 4.4 Hz, 1 H), 4.13 (brs, 2 H), 3.88-3.86 (m, 2 H), 3.64 (dd, J = 10.0, 14.0 Hz, 1 H), 3.28 (dd, J = 14.0, 4.4 Hz, 1 H), 1.29-1.22 (m, 1 H), 0.66-0.61 (m, 2 H), 0.37-0.34 (m, 2 H). LCMS (Method 1): [MH+] = 539 at 3.97 min. |
| (structure with F, NH₂-phenyl benzoate, 3,4-dimethoxyphenyl, 3,5-dichloropyridine N-oxide) | Intermediate 17 | ¹H NMR (400 MHz, DMSO): δ 8.58 (s, 2 H); 7.62-7.51 (m, 2 H); 7.08-6.95 (m, 3 H); 6.79 (t, J = 9.1 Hz, 1 H); 6.23-6.13 (m, 2 H); 4.06 (dd, J = 14.2, 7.1 Hz, 1 H); 3.79 (t, J = 10.9 Hz, 6 H); 3.65-3.58 (m, 1 H); 3.35-3.29 (m, 1 H). LCMS (Method 2): [MH+] = 481 at 3.30 min. |

Intermediate 18.
4-(tert-butoxycarbonylamino)-2-fluoro-benzoic acid
(I-18)

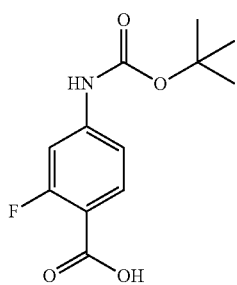 [SMILES: CC(C)(C)OC(=O)Nc1ccc(C(=O)O)c(F)c1]

To a stirred solution of 4-amino-2-fluorobenzoic acid (2.00 g, 12.89 mmol) in water (20.0 mL) was added a solution of sodium hydroxide (1.58 g, 39.51 mmol) in water (3.4 mL) followed by a solution of di-tert-butyl dicarbonate (6.99 g, 32.03 mmol) in 1,4-dioxane (20.0 mL). The reaction was stirred at room temperature for 48 hours. The reaction was washed with diethyl ether. The mixture was acidified to pH=5.8 by addition of citric acid. The mixture was cooled to 0° C. using an ice bath and stirred at 0° C. for 1 hour. The solid was filtered off and washed with water (10 mL×3) to afford the title compound as a white solid (0.447 g, 13%). ¹H NMR (400 MHz, DMSO): δ 7.94 (t, J=8.4 Hz, 1H), 7.48 (dd, J=13.4, 1.9 Hz, 1H), 7.03 (dd, J=8.4, 1.9 Hz, 1H), 6.74 (s, 1H), 0.00 (s, 9H). LCMS (Method 1): [MH-]=254 at 3.55 min.

Intermediate 19. [(1S)-2-(3,5-dichloro-1-oxido-pyridin-1-ium-4-yl)-1-(3,4-dimethoxyphenyl)ethyl]-4-(tert-butoxycarbonylamino)-2-fluoro-benzoate (I-19)

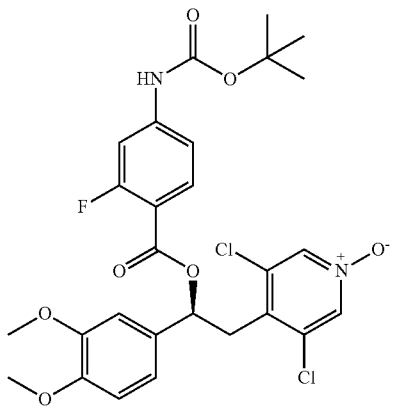

To a stirred solution of 4-(tert-butoxycarbonylamino)-2-fluorobenzoic acid (0.200 g, 0.78 mmol) and (1S)-2-(3,5-dichloro-1-oxidopyridin-1-ium-4-yl)-1-(3,4-dimethoxyphenyl)ethanol (0.270 g, 0.78 mmol) in dichloromethane (10.0 mL) was added 1-ethyl-3-(3-dimethylaminopropyl) carbodiimide (0.300 g, 1.57 mmol) and N,N-dimethylpyridin-4-amine (0.048 g, 0.39 mmol). The reaction was stirred at room temperature for 16 hours. The reaction was quenched by addition of saturated aqueous sodium bicarbonate solution (25.0 mL) and extracted with dichloromethane (×2). The combined organic extracts were dried on magnesium sulphate, filtered, and the solvent removed in vacuo to afford a yellow oil. The crude material was purified by silica gel chromatography eluting sequentially with iso-hexane and 10% methanol in ethyl acetate to afford the title compound as a yellow solid (0.351 g, 77%).

$^1$H NMR (400 MHz, DMSO): δ 10.04 (s, 1H), 8.58 (s, 2H), 7.87 (t, J=8.7 Hz, 1H), 7.48 (dd, J=14.1, 1.9 Hz, 1H), 7.35 (dd, J=8.8, 2.1 Hz, 1H), 7.09-6.96 (m, 3H), 6.24 (dd, J=4.6, 4.4 Hz, 1H), 3.80 (s, 3H), 3.78 (s, 3H), 3.60 (dd, 9.3, 4.7 Hz, 1H), 3.35 (m, 1H), 1.52 (s, 9H). LCMS (Method 1): [MH+]=581 at 4.12 min.

Intermediate 20. [(1S)-2-(3,5-dichloro-1-oxido-pyridin-1-ium-4-yl)-1-(3,4-dimethoxyphenyl)ethyl]-4-amino-2-fluoro-benzoate (I-20)

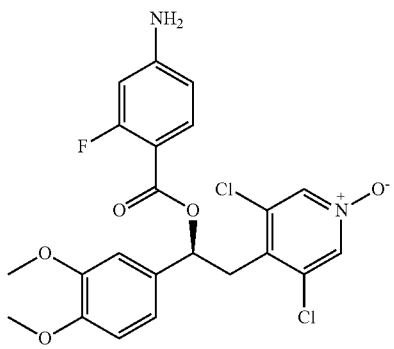

[(1S)-2-(3,5-dichloro-1-oxidopyridin-1-ium-4-yl)-1-(3,4-dimethoxyphenyl)ethyl]-4-(tert-butoxycarbonylamino)-2-fluorobenzoate (0.690 g, 1.19 mmol) was stirred in a 4N HCl in 1,4-dioxane solution (14.8 mL, 5.94 mmol). The reaction was stirred at room temperature for 3 hours. The solvent was removed in vacuo. The residue was purified by silica gel chromatography eluting sequentially with iso-hexane and 10% methanol in ethyl acetate to afford the title compound as a beige solid (0.451 g, 79%).

$^1$H NMR (400 MHz, DMSO): δ 8.57 (s, 2H), 7.64 (t, J=8.7 Hz, 1H), 7.03 (s, 1H), 6.99 (s, 1H), 6.42 (dd, J=8.6, 2.2 Hz, 1H), 6.36 (s, 1H), 6.31 (dd, J=14.2, 2.0 Hz, 1H), 6.20 (dd, J=8.7, 4.9 Hz, 1H), 3.79 (s, 3H), 3.78 (s, 3H), 3.55 (dd, J=13.9, 9.1 Hz, 1H), 3.36-3.30 (m, 1H).
LCMS (Method 1): [MH+]=481 at 3.43 min.

Intermediate 21. tert-Butyl 2-amino-2-phenylacetate (I-21)

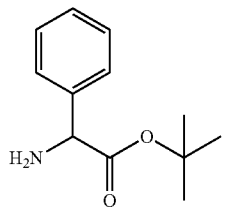

A stirring suspension of phenylglycine (2.0 g, 13.2 mmol) and concentrated sulfuric acid (2.0 mL) in dioxane (15 mL) was cooled to −78° C. iso-Butylene was gently bubbled through the suspension, until the volume of solution was doubled, after which the reaction vessel was sealed and allowed to warm to ambient temperature. The reaction was allowed to stir for 48 hours and subsequently concentrated under reduced pressure; the resulting crude was partitioned between diethyl ether (2×30 mL) and 2 N aqueous solution of sodium hydroxide (60 mL). The resulting organic phases were combined, dried over magnesium sulfate and concentrated under reduced pressure to yield the title compound as a clear oil which crystallised on standing (2.63 g, 96%).

$^1$H NMR (400 MHz, CDCl$_3$): δ 7.39-7.24 (m, 5H), 4.48 (s, 1H), 1.39 (s, 9H).

Intermediate 22. Methyl 3-[(2-tert-butoxy-2-oxo-1-phenylethyl)sulfamoyl]benzoate (I-22)

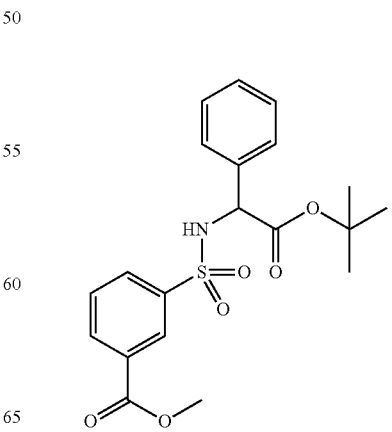

To a stirred solution of tert-butyl-2-amino-2-phenylacetate (1.34 g, 6.45 mmol) and methyl 3-(chlorosulfonyl)benzoate (1.53 g, 6.51 mmol) in tetrahydrofuran (15 mL) was added triethylamine (0.90 mL, 6.45 mmol) in one portion at ambient temperature. The reaction mixture was stirred for 30 minutes, after which time, the reaction mixture was concentrated under reduced pressure and partitioned between ethyl acetate (30 mL) and 10% citric acid solution (10 mL). The resulting organic phases were dried over magnesium sulfate and concentrated under reduced pressure to yield a crude solid. The solid was triturated in diethyl ether (5 mL) and cold methanol (5 mL) to yield the title compound as a white solid (1.13 g, 43%).

$^1$H NMR (400 MHz, CDCl$_3$): δ 8.32 (t, J=1.9 Hz, 1H), 8.12 (dt, J=7.9, 1.5 Hz, 1H), 7.86 (ddd, J=7.9, 1.9, 1.2 Hz, 1H), 7.44 (t, J=7.9 Hz, 1H), 7.22-7.13 (m, 5H), 5.79 (d, J=7.6 Hz, 1H), 5.00 (d, J=7.7 Hz, 1H), 3.94 (s, 3H), 1.26 (s, 9H). LCMS (Method 2): [M−H]=404 at 4.12 min.

Intermediate 23. 3-[(2-tert-Butoxy-2-oxo-1-phenyl-ethyl)sulfamoyl]benzoic acid (I-23)

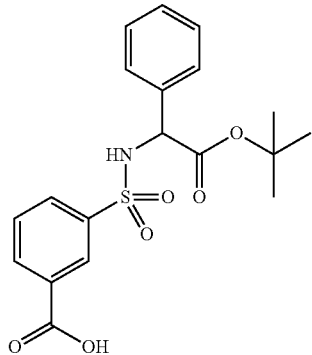 [SMILES: CC(C)(C)OC(=O)C(NS(=O)(=O)c1cccc(C(=O)O)c1)c1ccccc1]

To a stirring solution of methyl 3-[(2-tert-butoxy-2-oxo-1-phenylethyl)-sulfamoyl]benzoate (2.2 g, 5.4 mmol) in tetrahydrofuran (33.7 mL) and methanol (33.7 mL) was added 1.0 N aqueous lithium hydroxide (13.5 mL, 13.5 mmol) in one portion. The reaction mixture was stirred for 18 hours at ambient temperature, after which time the mixture was concentrated under reduced pressure. The resulting crude was partitioned between ethyl acetate (20 mL) and water (40 mL); the resulting aqueous was acidified with concentrated sulphuric acid (c. 1.0 mL) and washed with ethyl acetate (2×20 mL). The organic phases were combined, dried over magnesium sulfate and concentrated under reduced pressure to yield the title compound as a white solid (1.21 g, 57%).

$^1$H NMR (400 MHz, MeOD-d$_4$): δ 8.40 (t, J=1.7 Hz, 1H), 8.17 (dt, J=7.9, 1.3 Hz, 1H), 8.03 (ddd, J=7.9, 2.1, 1.3 Hz, 1H), 7.59 (t, J=7.9 Hz, 1H), 7.29-7.20 (m, 5H), 4.97 (s, 1H), 1.25 (s, 9H). LCMS (Method 1): [M−H]=390 at 3.83 min.

Intermediate 42. 2-(4-Formylphenyl)acetic acid

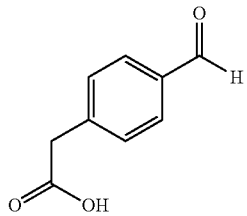 [SMILES: O=Cc1ccc(CC(=O)O)cc1]

To a solution of 2-[4-(bromomethyl)phenyl]acetic acid (770 mg, 3.36 mmol) in ethanol (6 mL) and water (6 mL) was added hexamethylenetetramine (1.26 g, 9.0 mmol) and the mixture was heated to reflux for 4 hours. Concentrated HCl (1.5 mL) was added cautiously to the mixture at reflux. The mixture was heated to reflux for 30 minutes and then allowed to cool. Water (20 mL) and DCM (20 mL) were added and the organic phase was passed through a hydrophobic fit and the solvent was removed in vacuo to afford the title compound as an off-white solid (479 mg, 87%). $^1$H NMR (400 MHz, CDCl$_3$): δ 10.01 (s, 1H), 7.86 (d, J=7.9 Hz, 2H), 7.47 (d, J=7.9 Hz, 2H), 3.75 (s, 2H).

Note: OH not visible. LCMS (Method 1): [MH+]=165 at 2.80 min.

Intermediate 43. 2-(3-Formylphenyl)acetic acid

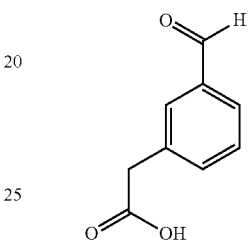

To a solution of 2-(m-tolyl)acetic acid in chloroform (30 mL) was added N-bromosuccinimide (2.37 g, 13.32 mmol). The mixture was heated to reflux for 8 hours and the solvent was removed in vacuo. The residue was dissolved in ethanol (30 mL) and water (30 mL) and hexamethylenetetramine (5 g, 35.7 mmol) was added. The mixture was heated to reflux for 4 hours. Concentrated HCl (5.9 mL) was added cautiously to the mixture at reflux. The mixture was heated to reflux for 30 minutes and then allowed to cool. Water (30 mL) and DCM (30 mL) were added and the organic phase was passed through a hydrophobic frit and the solvent was removed in vacuo. The residue was taken up into saturated aqueous sodium bicarbonate solution, and washed with DCM (2×15 mL). The aqueous phase was acidified with 2M aqueous HCl. The mixture was extracted with DCM (2×15 mL) and the combined organic fractions were passed through a hydrophobic frit. The solvent was removed in vacuo to afford a mixture of the title compound as an off-white solid (1.35 g, 62%). $^1$H NMR (400 MHz, CDCl$_3$): δ 10.01 (s, 1H), 7.84-7.79 (m, 2H), 7.60-7.48 (m, 2H), 3.75 (s, 2H). LCMS (Method 1): [MH+]=165 at 2.77 min.

Intermediate 44. 2-(4-formylphenyl)acetic acid

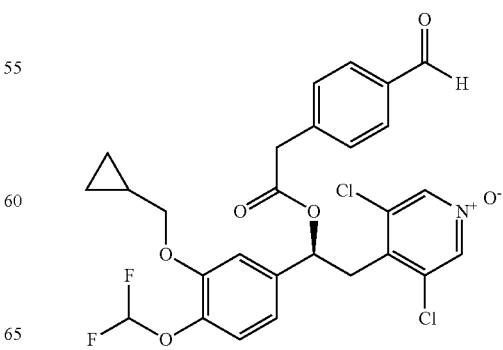

To a solution of 2-(4-formylphenyl)acetic acid (394 mg, 2.4 mmol) in DMF (5 mL) was added (1S)-1-[3-(cyclopropylmethoxy)-4-(difluoromethoxy)phenyl]-2-(3,5-dichloro-1-oxido-pyridin-1-ium-4-yl)ethanol (1.0 g, 2.4 mmol) followed by DMAP (147 mg, 1.2 mmol) and EDC.HCl (930 mg, 4.8 mmol). The mixture was allowed to stir a room temperature for 18 hours and then saturated sodium bicarbonate solution (10 mL) was added. The organic phase was passed through a hydrophobic fit and the solvent was removed in vacuo. The crude material was purified by silica gel column chromatography, eluting with 0-100% EtOAc in DCM, to afford the title compound as an off-white solid (312 mg, 23%). $^1$H NMR (400 MHz, CDCl3): δ 10.00 (s, 1H), 8.04 (s, 2H), 7.81 (d, J=7.5 Hz, 1H), 7.72 (s, 1H), 7.52-7.42 (m, 2H), 7.13 (d, J=8.1 Hz, 1H), 6.91-6.85 (m, 2H), 6.62 (t, J=75.3 Hz, 1H), 6.05 (dd, J=9.9, 4.4 Hz, 1H), 3.85-3.76 (m, 2H), 3.72-3.59 (m, 2H), 3.49 (dd, J=14.0, 9.9 Hz, 1H), 3.18 (dd, J=14.0, 4.4 Hz, 1H), 1.32-1.19 (m, 1H), 0.70-0.63 (m, 2H), 0.40-0.34 (m, 2H). LCMS (Method 2): [MH+]=566 at 3.54 min.

The following intermediate was prepared via a similar method.

| Reference | Compound | Analytical data |
|---|---|---|
| Intermediate 46 | 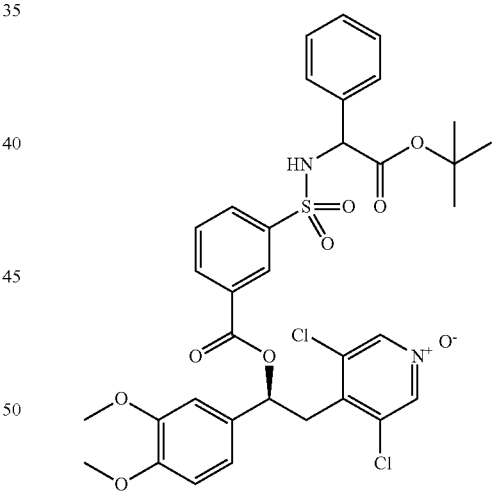 | LCMS (Method 1): [MH+] = 490 at 3.53 min. | afford the title compound as an off-white solid (317 mg, 23%). $^1$H NMR (400 MHz, CDCl$_3$): δ 10.02 (s, 1H), 8.05 (s, 2H), 7.83 (d, J=8.0 Hz, 2H), 7.34 (d, J=8.0 Hz, 2H), 7.13 (d, J=8.2 Hz, 1H), 6.90-6.82 (m, 2H), 6.61 (t, J=75.3 Hz, 1H), 6.04 (dd, J=9.9, 4.5 Hz, 1H), 3.79 (dd, J=7.0, 3.7 Hz, 2H), 3.66 (d, J=3.5 Hz, 2H), 3.48 (dd, J=14.1, 9.9 Hz, 1H), 3.17 (dd, J=14.1, 4.5 Hz, 1H), 1.32-1.19 (m, 1H), 0.70-0.63 (m, 2H), 0.40-0.32 (m, 2H). LCMS (Method 2): [MH+]=566 at 3.73 min.

Intermediate 45. 2-(4-Formylphenyl)acetic acid

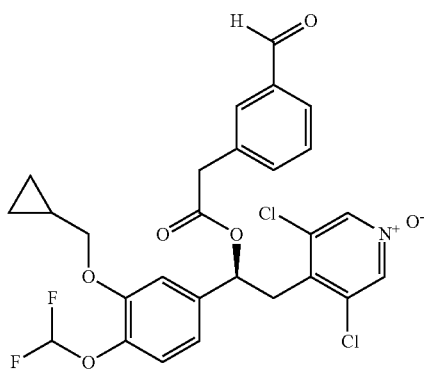

To a solution of 2-(3-formylphenyl)acetic acid (394 mg, 2.4 mmol) in DMF (5 mL) was added (1S)-1-[3-(cyclopropylmethoxy)-4-(difluoromethoxy)phenyl]-2-(3,5-dichloro-1-oxido-pyridin-1-ium-4-yl)ethanol (1.0 g, 2.4 mmol) followed by DMAP (147 mg, 1.2 mmol) and EDC.HCl (930 mg, 4.8 mmol). The mixture was allowed to stir a room temperature for 18 hours. The solvent was removed in vacuo and the residue was partitioned between DCM (10 mL) and waturated sodium bicarbonate solution (10 mL). The organic phase was passed through a hydrophobic fit and the solvent was removed in vacuo. The crude material was purified by silica gel column chromatography, eluting with 0-100% EtOAc in DCM, to afford the title compound as an off-white solid (312 mg, 23%).

Intermediate 49. [(1S)-2-(3,5-Dichloro-1-oxido-pyridin-1-ium-4-yl)-1-(3,4-dimethoxyphenyl)ethyl] 3-[(2-tert-butoxy-2-oxo-1-phenyl-ethyl)sulfamoyl]benzoate (I-49)

3-[(2-tert-Butoxy-2-oxo-1-phenyl-ethyl)sulfamoyl]benzoic acid (1.216 g, 3.11 mmol) was added to a stirred suspension of (S)-3,5-dichloro-4-(2-(3,4-dimethoxyphenyl)-2-hydroxyethyl)pyridine 1-oxide (1.07 g, 3.11 mmol) in N,N-dimethylformamide (12 mL). To the resultant solution was added N,N-4-(dimethylamino)pyridine (0.189 g, 1.55 mmol) followed by N-(3-dimethylaminopropyl)-N'-ethylcarbodiimide hydrochloride (1.192 g, 6.22 mmol) and the reaction was stirred at room temperature for 18 hours. After this time, the reaction mixture was concentrated under reduced pressure and water (30 mL) was added; the resulting off-white precipitate was filtered and dried in air. The crude material was purified over a 50 g silica cartridge on an ISOLERA system; eluting initially with iso-hexane with an increasing solvent gradient to 100% ethyl acetate over four column volumes, after which 100% ethyl acetate was maintained for six column volumes. The desired fractions were combined and concentrated under reduced pressure to yield the title product as a white solid (1.340 g, 60%).

$^1$H NMR (400 MHz, CDCl$_3$): δ 8.33 (dt, J=7.9, 1.6 Hz, 1H), 8.18 (s, 1H), 8.16 (s, 1H), 8.19-8.05 (m, 1H), 7.90-7.82 (m, 1H), 7.43 (q, J=7.6 Hz, 1H), 7.21-7.08 (m, 5H), 7.07-6.98 (m, 2H), 6.88 (d, J=8.3 Hz, 1H), 6.26 (dd, J=9.5, 4.8 Hz, 1H), 6.07 (dd, J=33.2, 7.9 Hz, 1H), 4.96 (t, J=7.8 Hz, 1H), 3.93 (s, 2H), 3.92 (s, 1H), 3.89 (s, 3H), 3.8-3.69 (m, 1H), 3.39 (dt, J=14.0, 4.2 Hz, 1H), 1.22 (s, 6H), 1.21 (s, 3H). LCMS (Method 1): [M+H]=717 at 4.03 min.

Example 1

[(1S)-2-(3,5-dichloro-1-oxido-pyridin-1-ium-4-yl)-1-(3,4-dimethoxyphenyl)-ethyl] 3-[[[2-oxo-1-phenyl-2-[(3R)-quinuclidin-3-yl]oxy-ethyl]amino]methyl] benzoate (Ex. 1)

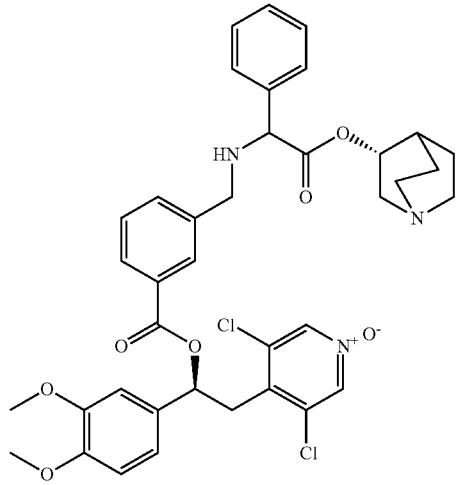

To a suspension of (R)—(R)-quinuclidin-3-yl 2-amino-2-phenylacetate bis hydrochloride salt (0.200 g, 0.600 mmol) in EtOAc (5 mL) was added Et$_3$N (0.176 mL, 1.26 mmol). The reaction mixture was stirred at room temperature for 2 hours. The precipitate obtained was filtered, washed with EtOAc (~5 mL) and the solvent was removed in vacuo. This residue was dissolved in CH$_3$CN (4 mL) and to the solution was added (S)-3,5-dichloro-4-(2-(3,4-dimethoxyphenyl)-2-(3-formyl-benzoyl)oxy)ethyl)-pyridine 1-oxide (0.286 g, 0.6 mmol) followed by acetic acid (0.034 mL, 0.6 mmol). The reaction mixture was stirred at room temperature for 20 hours. NaBH(OAc)$_3$ (0.318 g, 1.5 mmol) was added and the reaction mixture was stirred at room temperature for a further 24 hours. The excess solvent was removed in vacuo and the residue was partitioned between EtOAc (70 mL) and saturated aqueous NaHCO$_3$ solution (15 mL). The organic layer was washed with saturated brine (2×15 mL), dried (MgSO$_4$), filtered and the solvent was removed in vacuo. Purification by preparative HPLC gave a yellow gum (0.158 g). This was dissolved in EtOAc (25 mL), washed with saturated aqueous NaHCO$_3$ solution (5 mL) and saturated brine (5 mL) dried (MgSO$_4$) and filtered. The solvent was removed in vacuo and trituration with diethyl ether gave the title compound (1:1 mixture of diastereoisomers) as a yellow solid (126.9 mg, 29%).

$^1$H NMR (400 MHz, CDCl3): δ 8.12*$^{or}$ $^+$ (s, 2H), 8.11*$^{or}$ $^+$ (s, 2H), 8.00-7.97 (m, 1H), 7.92 (d, J=7.8 Hz, 1H), 7.54-7.52 (m, 1H), 7.42-7.30 (m, 6H), 7.03-6.98 (m, 2H), 6.85 (d, J=8.2 Hz, 1H), 6.30-6.28 (m, 1H), 4.88-4.78 (m, 1H), 4.40*$^{or}$ $^+$ (s, 1H), 4.38*$^{or}$ $^+$ (s, 1H), 3.89 (s, 3H), 3.88 (s, 3H), 3.78-3.71 (m, 3H), 3.38-3.34 (m, 1H), 3.25-3.10 (m, 1H), 2.81-2.65 (m, 4H), 2.60-2.35 (m, 1H), 2.00-1.88 (m, 1H), 1.75-1.45 (m, 3H), 1.40-1.10 (m, 2H). * and † refer to different isomers. LCMS (Method 1): [MH+]=720/722 at 2.41 min.

The following compounds were synthesized via a similar method as that for compound of Example 1 and obtained as mixtures of diastereoisomers.

| Ref. | Compound | Analytical Data |
|---|---|---|
| Ex. 2 | [(1S)-2-(3,5-dichloro-1-oxido-pyridin-1-ium-4-yl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate | $^1$H NMR (400 MHz, CDCl3): δ 8.12 (s, 2 H), 7.97 (d, J = 7.2 Hz, 1 H), 7.91 (d, J = 7.8 Hz, 1 H), 7.58-7.51 (m, 1 H), 7.38 (t, J = 7.7 Hz, 1 H), 7.33-7.19 (m, 2 H), 7.03-6.83 (m, 5 H), 6.31-6.25 (m, 1 H), 5.04-4.98* or $^+$ (m, 1 H), 4.94-4.88* or $^+$ (m, 1 H), 4.67* or $^+$ (s, 1 H), 4.58* or $^+$ (s, 1 H), 3.93-3.86 (m, 6 H), 3.83-3.77 (m, 5 H), 3.71 (dd, J = 14.0, 9.6 Hz, 1H), 3.39-3.25 (m, 2 H), 2.97-2.84 (m, 3H), 2.84-2.40 (m, 2 H), 2.15-2.05 (m, 1 H), 1.85-1.36 (m, 3 H), 1.30 (t, J = 7.9 Hz, 1 H). * and † refer to different isomers. LCMS (Method 1): [MH+] = 750 at 2.37 min. |

-continued

| Ref. | Compound | Analytical Data |
|---|---|---|
| Ex. 14 | [(1S)-2-(3,5-dichloro-1-oxido-pyridin-1-ium-4-yl)-1-(3,4-dimethoxyphenyl)ethyl] 3-[[[1-(2-fluorophenyl)-2-oxo-2-[(3R)-quinuclidin-3-yl]oxy-ethyl]amino]methyl]benzoate 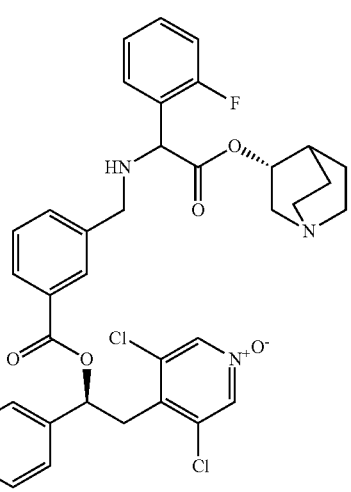 | 1H NMR (400 MHz, CDCl3): δ 8.12 (s, 2H), 7.98 (d, J = 5.1 Hz, 1 H), 7.92 (d, J = 7.8 Hz, 1 H), 7.53 (t, J = 5.9 Hz, 1 H), 7.39 (t, J = 7.6 Hz, 2 H), 7.36-7.27 (m, 1 H), 7.19-7.12 (m, 1 H), 7.12-7.05 (m, 1 H), 7.04-6.98 (m, 2 H), 6.86 (dd, J = 8.2, 2.7 Hz, 1 H), 6.32-6.25 (m, 1 H), 4.97-4.92* or † (m, 1 H), 4.91-4.85* or † (m, 1 H), 4.73* or † (s, 1 H), 4.71* or † (s, 1H), 3.90 (s, 3 H), 3.89 (s, 3 H), 3.80 (s, 2 H), 3.77-3.67 (m, 1 H), 3.39-3.31 (m, 1 H), 3.31-3.17 (m, 1 H), 2.87-2.77 (m, 4 H). 2.61-2.43 (m, 1 H), 2.10-1.94 (m, 1 H), 1.80-1.65 (m, 2 H), 1.65-1.53 (m, 1 H), 1.33-1.24 (m, 1 H). * and † refer to different isomers.<br>LCMS (Method 2): [MH+] =738 at 3.26 min. |
| Ex. 15 | [(1S)-2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate 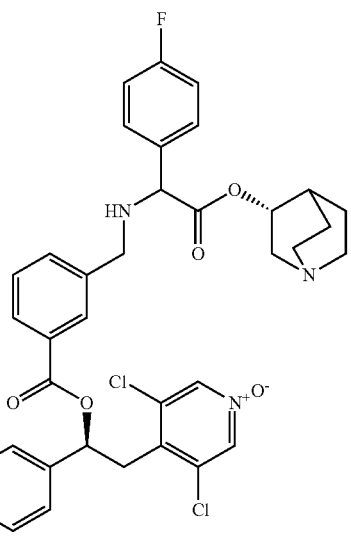 | ¹H NMR (400 MHz, CDCl3): δ 8.13 (s, 2 H), 7.98-7.90 (m, 2 H), 7.52 (d, J = 7.5 Hz, 1 H), 7.42-7.33 (m, 3 H), 7.07 (t, J = 8.5 Hz, 2 H), 7.04-6.98 (m, 2 H), 6.86 (d, J = 8.2 Hz, 1 H), 6.29 (dd, J = 9.7, 4.6 Hz, 1 H), 4.90-4.84 (m, 1 H), 4.37 (s, 1 H), 3.90 (s, 3 H), 3.88 (s, 3 H), 3.75 (s, 2 H), 3.72-3.67 (m, 1 H), 3.36 (dd, J = 14.0, 4.7 Hz, 1 H), 3.27-3.18 (m, 1 H), 2.92-2.80 (m, 3 H), 2.70-2.59 (m, 1 H), 2.55-2.45 (m, 1 H), 2.13-2.06 (m, 1H), 1.80-1.66 (m, 2 H), 1.66-1.55 (m, 1 H), 1.48-1.39 (m, 1 H).<br>LCMS (Method 1): [MH+] =738 at 2.53 min. |

-continued

| Ref. | Compound | Analytical Data |
| --- | --- | --- |
| Ex. 16 | [(1S)-2-(3,5-dichloro-1-oxido-pyridin-1-ium-4-yl)-1-(3,4-dimethoxyphenyl)ethyl] 4-[[[2-oxo-1-phenyl-2-[(3R)-quinuclidin-3-yl]oxy-ethyl]amino]methyl]benzoate | $^1$H NMR (400 MHz, CDCl3): δ 8.12 (s, 2H), 7.97 (m, 2H), 7.41-7.29 (m, 7H), 7.04-6.98 (m, 2H), 6.86-6.82 (m, 1H), 6.32-6.28 (m, 1H), 4.83-4.77 (m, 1H), 4.37 (s, 1H), 3.90 (s, 3H), 3.87 (s, 3H), 3.79 (s, 2H), 3.73-3.67 (m, 1H), 3.39-3.33 (m, 1H), 3.21-3.09 (m, 1H), 2.69-2.51 (m, 4H), 2.50-2.31 (m, 1H), 2.04-1.83 (m, 1H), 1.64-1.52 (m, 2H), 1.29-1.25 (m, 1H), 1.24-1.14 (m, 1H).<br>LCMS (Method 1): [MH+] =720 at 2.45 min |
| Ex. 17 | [(1S)-2-(3,5-dichloro-1-oxido-pyridin-1-ium-4-yl)-1-(3,4-dimethoxyphenyl)ethyl]4-[[[1-(2-fluorophenyl)-2-oxo-2-[(3R)-quinuclidin-3-yl]oxy-ethyl]amino]methyl]benzoate | $^1$H NMR (400 MHz, CDCl3): δ 8.37 (s, 1 H), 8.13 (s, 2 H), 8.00-7.95 (m, 2 H), 7.42-7.27 (m, 4 H), 7.21-6.97 (m, 4 H), 6.86 (d, J = 8.2 Hz, 1 H), 6.30 (dd, J = 9.6, 4.6 Hz, 1 H), 5.03-4.97*or† (m, 1 H), 4.97-4.91*or† (m, 1 H), 4.71*or† (s, 1 H), 4.70*or† (s, 1 H), 3.90 (s, 3 H), 3.88 (s, 3 H); 3.82-3.79 (m, 2 H), 3.71 (dd, J = 13.9, 9.7 Hz, 1 H), 3.39-3.24 (m, 2 H), 3.00-2.78 (m, 4 H), 2.66-2.52 (m, 1 H), 2.20-2.04 (m, 1 H), 1.87-1.44 (m, 3 H), 1.41-1.32 (m, 1 H). * and † refer to different isomers. LCMS (Method 1): [MH+] = 738 at 2.6 min |

-continued

| Ref. | Compound | Analytical Data |
|---|---|---|
| Ex. 18 | [(1S)-2-(3,5-dichloro-1-oxido-pyridin-1-ium-4-yl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate 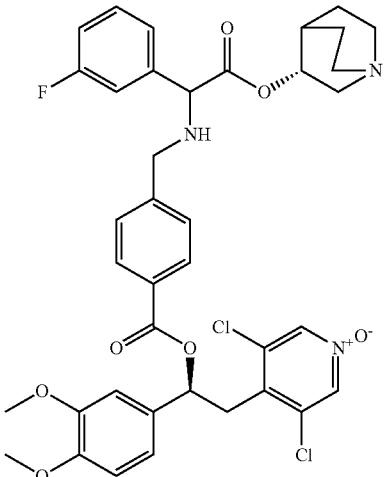 | $^1$H NMR (400 MHz, CDCl3): δ 8.13 (s, 2 H), 8.01-7.96 (m, 2 H), 7.41-7.27 (m, 3 H), 7.19-7.10 (m, 2 H), 7.06-6.97 (m, 3 H), 6.86 (d, J = 8.2 Hz, 1 H), 6.31 (dd, J = 9.7, 4.6 Hz, 1 H), 4.96-4.90*or† (m, 1 H), 4.90-4.85*or† (m, 1 H), 4.37*or† (s, 1 H), 4.37*or† (s, 1 H), 3.91 (s, 3 H), 3.88 (s, 3 H), 3.81-3.77 (m, 2 H), 3.76-3.67 (m, 1 H), 3.39-3.18 (m, 2 H), 2.92-2.75 (m, 4 H), 2.68-2.44 (m, 1 H), 2.13-1.95 (m, 1 H), 1.80-1.39 (m, 3 H), 1.37-1.27 (m, 1 H). * and † refer to different isomers. LCMS (Method 1): [MH+] = 738 at 2.55 min |

Example 3

[(1S)-2-(3,5-dichloro-1-oxidopyridin-1-ium-4-yl)-1-(3,4-dimethoxyphenyl)-ethyl]-3-[[2-oxo-1-phenyl-2-[(3R)-quinuclidin-3-yl]oxyethyl]amino]benzoate (Ex. 3)

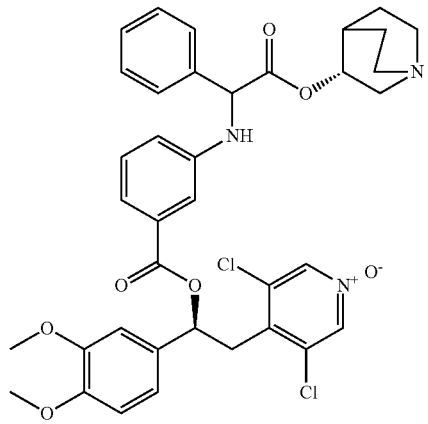

To a stirred solution of [(1S)-2-(3,5-dichloro-1-oxidopyridin-1-ium-4-yl)-1-(3,4-dimethoxyphenyl)ethyl] 3-aminobenzoate (0.850 g, 1.83 mmol) in dichloromethane (20 mL) was added phenylboronic acid (0.225 g, 1.83 mmol) and glyoxylic acid (205 μL, 1.83 mmol). The reaction was stirred at room temperature for 16 hours. The reaction was quenched by addition of water and extracted with dichloromethane (×2). The combined organic extracts were dried on magnesium sulfate, filtered and the solvent was removed in vacuo. A small sample of crude residue (90 mg) was purified by prep-HPLC to provide 2-[3-[(1S)-2-(3,5-dichloro-1-oxidopyridin-1-ium-4-yl)-1-(3,4-dimethoxyphenyl)ethoxy]-carbonylanilino]-2-phenylacetic acid as a white solid (33.6 mg).

$^1$H NMR (400 MHz, DMSO): δ 8.54*$^{or}$ † (s, 2H), 8.53*$^{or}$ † (s, 2H), 7.51-7.49 (m, 2H), 7.39-7.35 (m, 2H), 7.32-7.30 (m, 1H), 7.26-7.24 (m, 1H), 7.18-7.16 (m, 2H), 7.01-6.92 (m, 4H), 6.68-6.51 (brs, 1H), 6.18-6.14 (m, 1H), 5.08 (s, 1H), 3.59 (s, 3H), 3.58 (s, 3H), 3.56-3.51 (m, 1H), 3.32-3.27 (m, 1H). † and * refer to different isomers. LCMS (Method 2): [MH+]=597 at 2.84 min.

The remaining amount of crude residue (0.940 g) was taken on to the next step without further purification. To a stirred solution of crude 2-[3-[(1S)-2-(3,5-dichloro-1-oxidopyridin-1-ium-4-yl)-1-(3,4-dimethoxyphenyl)ethoxy]-carbonylanilino]-2-phenylacetic acid (0.940 g, 1.57 mmol) in anhydrous tetrahydrofuran (30.0 mL) was added (R)-quinuclidin-3-ol (0.300 g, 2.35 mmol), N,N'-dicyclohexylcarbodiimide (0.375 g, 1.80 mmol) and 1-hydroxybenzotriazole (0.245 g, 1.80 mmol). The reaction was stirred at room temperature under nitrogen for 16 hours. The reaction was filtered through fine sintered glass and the filtrate was removed in vacuo. The residue was partitioned between ethyl acetate and sodium bicarbonate and extracted with ethyl acetate (×2). The combined organic layers were dried on magnesium sulfate, filtered and the solvent was removed in vacuo and the residue was purified by prep HPLC to afford [(1S)-2-(3,5-dichloro-1-oxidopyridin-1-ium-4-yl)-1-(3,4-dimethoxyphenyl)ethyl]-3-[[2-oxo-1-phenyl-2-[(3R)-quinuclidin-3-yl]oxyethyl]amino]benzoate (Ex. 3) as a white solid (118 mg, 9% yield over two steps).

$^1$H NMR (400 MHz, DMSO): δ 8.61*$^{or}$ † (s, 2H), 8.57*$^{or}$ † (s, 2H), 7.57 (d, J=7.5 Hz, 2H), 7.47-7.31 (m, 4H), 7.28-7.20 (m, 2H), 7.06-6.97 (m, 4H), 6.78-6.71 (m, 1H), 6.21 (dd, J=9.4, 4.7 Hz, 1H), 5.37-5.29 (m, 1H), 4.80-4.71 (m, 1H), 3.83-3.76 (m, 6H), 3.65-3.56 (m, 1H), 3.18-3.10 (m, 1H), 3.07-2.96 (m, 1H), 2.68-2.57 (m, 3H), 2.32-2.22 (m, 1H), 2.11 (d, J=14.5 Hz, 1H), 1.93 (s, 1H), 1.68-1.60 (m, 1H), 1.60-1.54 (m, 1H), 1.53-1.43 (m, 1H), 1.34-1.17 (m, 1H). † and * refer to different isomers. LCMS (Method 1): [MH+]=706 at 2.75 min.

Compounds herebelow reported were prepared starting from the appropriate starting materials according to analogous procedures as those hereabove described to obtain the compound of Example 3.

| Ref. | Compound | Analytical Data |
|---|---|---|
| Ex. 4 | 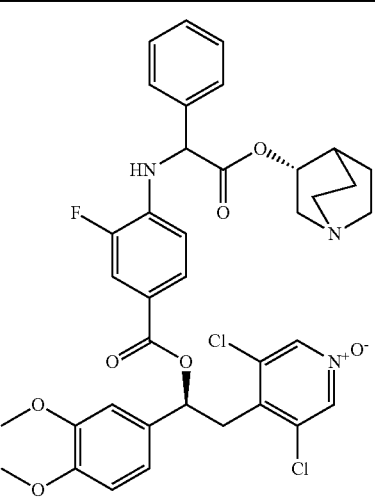<br>[(1S)-2-(3,5-dichloro-1-oxido-pyridin-1-ium-4-yl)-1-(3,4-dimethoxyphenyl)ethyl] 3-fluoro-4-[[2-oxo-1-phenyl-2-[(3R)-quinuclidin-3-yl]oxy-ethyl]amino]benzoate | 1H NMR (400 MHz, CDCl3): 8.12*or† (s, 2 H), 8.10*or† (s, 2 H), 7.64 (m, 1 H), 7.56-7.55 (m, 1 H), 7.47 (d, J = 7.3 Hz, 2 H), 7.40-7.33 (m, 3 H), 6.99-6.94 (m, 1 H), 6.93 (s, 1 H), 6.83 (d, J = 8.2 Hz, 1 H), 6.37 (t, J = 8.3 Hz, 1 H), 6.23-6.17 (m, 1 H), 5.75 (s, 1 H), 5.13 (t, J = 4.8 Hz, 1 H), 4.89-4.78 (m, 1 H), 3.88 (d, J = 2.7 Hz, 3 H), 3.86 (s, 3 H), 3.65 (ddd, J = 13.7, 9.9, 3.5 Hz, 1 H), 3.30 (dd, J = 14.0, 3.9 Hz, 1 H), 3.22-3.05 (m, 1 H), 2.81-2.68 (m, 4 H), 2.25 (d, J = 14.8 Hz, 1 H), 1.77-1.59 (m, 2 H), 1.48-1.32 (m, 2 H), 1.21-1.13 (m, 1 H). † and * refer to different isomers. LCMS (Method 2): [MH+] = 724 at 3.89 min. |
| Ex. 5 | 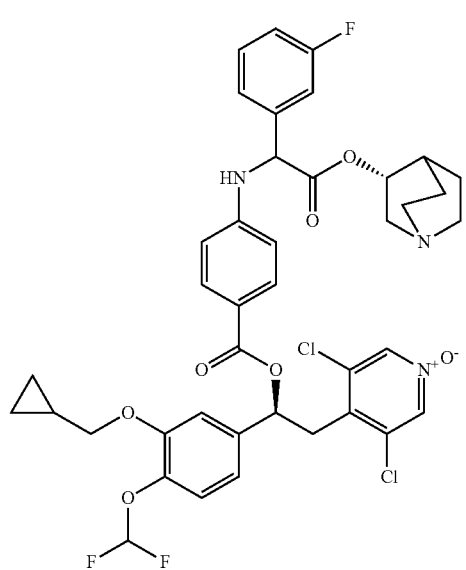<br>[(1S)-1-[3-(cyclopropylmethoxy)-4-(difluoromethoxy)phenyl]-2-(3,5-dichloro-1-oxidopyridin-1-ium-4-yl)ethyl]4-[[1-(3-fluorophenyl)-2-oxo-2-[(3R)-quinuclidin-3-yl]oxyethyl]amino]benzoate | $^1$H NMR (400 MHz, CDCl3): δ 8.29 (brs, 1 H), 8.12 (s, 2 H), 8.11* or † (s, 2 H), 7.80-7.78 (m, 2 H), 7.40-7.35 (m, 1 H), 7.34-7.29 (m, 2 H), 7.18-7.13 (m, 2 H), 7.06-6.98 (m, 2 H), 6.59 (t, J = 75.4 Hz, 1 H), 6.58* or † (t, J = 75.4 Hz, 1 H), 6.51-6.49 (m, 2 H), 6.23-6.18 (m, 1 H), 5.52-5.50 (m, 1 H), 5.13-5.12 (m, 1 H), 5.04-5.03 (m, 1 H), 5.00-4.99* or † (m, 1 H), 3.87-3.84 (m, 2 H), 3.65-3.59 (m, 1 H), 3.42-3.25 (m, 2 H), 3.09-2.92 (m, 4 H), 2.73-2.51 (m, 1 H), 2.27-2.05 (m, 1 H), 2.00-1.64 (m, 3 H), 1.43-1.23 (m, 2 H), 0.66-0.60 (m, 2 H), 0.37-0.32 (m, 2 H). * and † refer to different isomers. LCMS (Method 1): [MH+] = 800 at 3.11 min. |

-continued

| Ref. | Compound | Analytical Data |
|---|---|---|
| Ex. 6 | 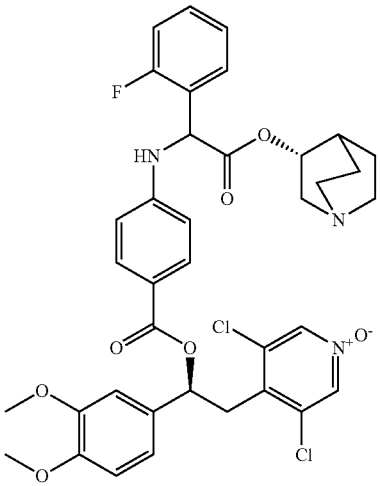<br>[(1S)-2-(3,5-dichloro-1-oxidopyridin-1-ium-4-yl)-1-(3,4-dimethoxyphenyl)ethyl] 4-[[1-(2-fluorophenyl)-2-oxo-2-[(3R)-quinuclidin-3-yl]oxy-ethyl]amino]benzoate | 1H NMR (400 MHz, CDCl3): δ 8.10*or† (s, 2 H), 8.09*or† (s, 2 H), 7.80 (d, J = 8.4 Hz, 2 H), 7.38-7.26 (m, 2 H), 7.16-7.11 (m, 2 H), 6.98-6.94 (m, 2 H), 6.83-6.81 (m, 1 H), 6.53 (d, J = 8.4 Hz, 2 H), 6.24-6.22 (m, 1 H), 5.51-5.48 (m, 2 H), 4.99-4.82 (m, 1 H), 3.88*or† (s, 3 H), 3.87*or† (s, 3 H), 3.86*or† (s, 3 H), 3.85*or† (s, 3 H), 3.64-3.60 (m, 1 H), 3.32-3.25 (m, 1 H), 3.20-3.14 (m, 1 H), 2.90-2.76 (m, 4 H), 2.49-2.44 (m, 1 H), 2.13-1.92 (m, 1 H), 1.83-1.41 (m, 3 H), 1.25-1.20 (m, 1 H). † and * refer to different isomers.<br>LCMS (Method 1): [MH+] = 724 at 2.83 min. |
| Ex. 7 | 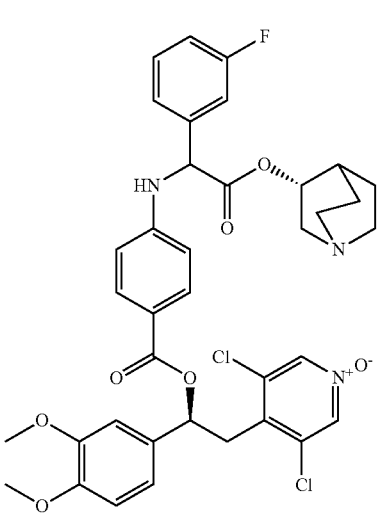<br>[(1S)-2-(3,5-dichloro-1-oxidopyridin-1-ium-4-yl)-1-(3,4-dimethoxyphenyl)ethyl] 4-[[1-(3-fluorophenyl)-2-oxo-2-[(3R)-quinuclidin-3-yl]oxy-ethyl]amino]benzoate | 1H NMR (400 MHz, CDCl3): δ 8.11*or† (s, 2 H), 8.10*or† (s, 2 H), 7.80 (d, J = 8.8 Hz, 2 H), 7.36-7.18 (m, 3 H), 7.03-6.96 (m, 3 H), 6.83-6.81 (m, 1 H), 6.49 (d, J = 8.8 Hz, 2 H), 6.25-6.22 (m, 1 H), 5.54-5.53 (m, 1 H), 5.12-5.10 (m, 1 H), 4.86-4.84 (m, 1 H), 3.88*or† (s, 3 H), 3.87*or† (s, 3 H), 3.86*or† (s, 3 H), 3.85*or† (s, 3 H), 3.67-3.61 (m, 1 H), 3.32-3.07 (m, 2 H), 2.78-2.65 (m, 4 H), 2.55-2.24 (m, 1 H), 2.07-1.84 (m, 1 H), 1.77-1.40 (m, 3 H), 1.27-1.19 (m, 1 H). † and * refer to different isomers.<br>LCMS (Method 1): [MH+] = 724 at 2.83 min. |

Compounds herebelow reported were prepared starting from the appropriate starting materials according to analogous procedures hereabove described to obtain the compound of Example 3; separation of isomers was achieved by supercritical fluid chromatography (SFC).

| Ref. | Compound | Analytical Data |
|---|---|---|
| Ex. 8 (Single Diastereoisomer 1) | 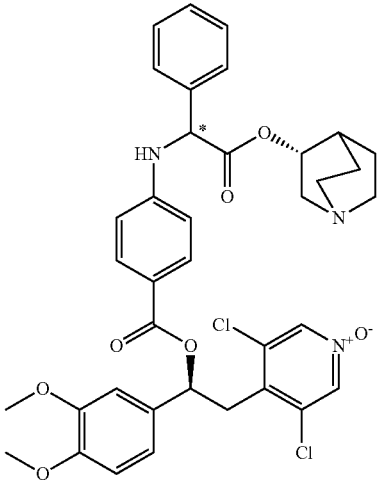 [(1S)-2-(3,5-dichloro-1-oxido-pyridin-1-ium-4-yl)-1-(3,4-dimethoxyphenyl)ethyl] 4-[[2-oxo-1-phenyl-2-[(3R)-quinuclidin-3-yl]oxy-ethyl]amino]benzoate single diastereoisomer | $^1$H NMR (400 MHz, CDCl3): δ 8.11 (s, 2 H), 7.79 (d, J = 8.8 Hz, 2 H), 7.48-7.46 (m, 2 H), 7.39-7.32 (m, 3 H), 6.98-6.93 (m, 2 H), 6.83-6.80 (m, 1 H), 6.52 (d, J = 8.8 Hz, 2 H), 6.22 (dd, J = 4.4, 9.6 Hz, 1 H), 5.52 (d, J = 5.6 Hz, 1 H), 5.12 (d, J = 5.6 Hz, 1 H), 4.84-4.82 (m, 1 H), 3.87 (s, 3 H), 3.85 (s, 3 H), 3.64 (dd, J = 9.6, 14.0 Hz, 1 H), 3.28 (dd, J = 4.4, 14.0 Hz, 1 H), 3.10-3.08 (m, 1 H), 2.76-2.68 (m, 3 H), 2.51-2.49 (m, 1 H), 2.28-2.24 (m, 1 H), 2.05-2.04 (m, 1 H), 1.75-1.67 (m, 1 H), 1.53-1.52 (m, 1 H), 1.40-1.22 (m, 2 H). LCMS (Method 2): [MH+] = 706 at 3.22 min. |
| Ex. 9 (Single Diastereoisomer 2) | 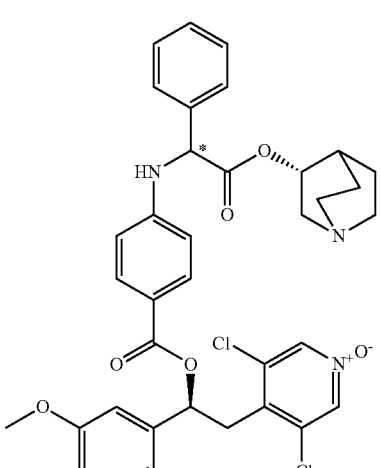 Single diastereoisomer of [(1S)-2-(3,5-dichloro-1-oxido-pyridin-1-ium-4-yl)-1-(3,4-dimethoxyphenyl)ethyl] 4-[[2-oxo-1-phenyl-2-[(3R)-quinuclidin-3-yl]oxy-ethyl]amino]benzoate single diastereoisomer | $^1$H NMR (400 MHz, CDCl3): δ 8.09 (s, 2 H), 7.79 (d, J = 8.8 Hz, 2 H), 7.48-7.46 (m, 2 H), 7.38-7.31 (m, 3 H), 6.98-6.97 (m, 2 H), 6.83-6.81 (m, 1 H), 6.501 (d, J = 8.8 Hz, 2 H), 6.24 (dd, J = 4.4, 9.6 Hz, 1 H), 5.52 (d, J = 5.6 Hz, 1 H), 5.12 (d, J = 5.6 Hz, 1 H), 4.88-4.86 (m, 1 H), 3.88 (s, 3 H), 3.86 (s, 3 H), 3.63 (dd, J = 9.6, 14.0 Hz, 1 H), 3.29 (dd, J = 4.4, 14.0 Hz, 1 H), 3.25-3.19 (m, 1 H), 2.81-2.73 (m, 4 H), 1.85-1.84 (m, 1 H), 1.62-1.58 (m, 1 H), 1.51-1.49 (m, 1 H), 1.25-1.15 (m, 3 H). LCMS (Method 2): [MH+] = 706 at 3.24 min. |

| Ref. | Compound | Analytical Data |
|---|---|---|
| Ex. 10 (Single Diastereoisomer 1) | 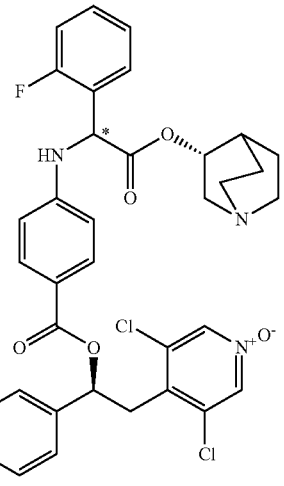<br>[(1S)-2-(3,5-dichloro-1-oxidopyridin-1-ium-4-yl)-1-(3,4-dimethoxyphenyl)ethyl] 4-[[1-(2-fluorophenyl)-2-oxo-2-[(3R)-quinuclidin-3-yl]oxyethyl]amino]benzoate single diastereoisomer | 1H NMR (400 MHz, CDCl3): δ 8.10 (s, 2 H), 7.80 (d, J = 8.8 Hz, 2 H), 7.36-7.27 (m, 2 H), 7.16-7.12 (m, 2 H), 6.98-6.93 (m, 2 H), 6.83-6.80 (m, 1 H), 6.53 (d, J = 8.8 Hz, 2 H), 6.23 (dd, J = 4.4, 9.6 Hz, 1 H), 5.51-5.50 (m, 2 H), 4.86-4.85 (m, 1 H), 3.87 (s, 3 H), 3.85 (s, 3 H), 3.67-3.61 (dd, J = 9.6, 14.0 Hz, 1 H), 3.31-3.27 (dd, J = 4.4, 14.0 Hz, 1 H), 3.12-3.06 (m, 1 H), 2.80-2.65 (m, 3 H), 2.45-2.38 (m, 1 H), 2.30-2.23 (m, 1 H), 2.10-2.03 (m, 1 H), 1.65-1.61 (m, 2 H), 1.53-1.47 (m, 1 H), 1.39-1.25 (m, 1 H).<br>LCMS (Method 2): [MH+] = 724 at 3.23 min. |
| Ex. 11 (Single Diastereoisomer 1) | 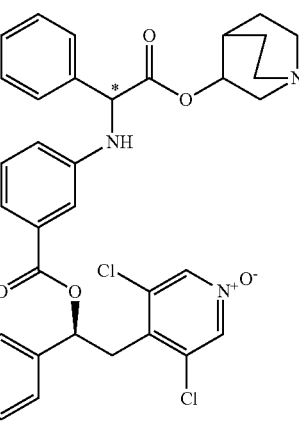<br>[(1S)-2-(3,5-dichloro-1-oxidopyridin-1-ium-4-yl)-1-(3,4-dimethoxyphenyl)ethyl]-3-[[2-oxo-1-phenyl-2-[(3R)-quinuclidin-3-yl]oxyethyl]amino]benzoate single diastereoisomer | $^1$H NMR (400 MHz, CDCl3): δ 8.11 (s, 2 H), 7.49-7.47 (m, 2 H), 7.38-7.14 (m, 6 H), 6.94-6.91 (m, 2 H), 6.82 (d, J = 8.4 Hz, 1 H), 6.75-6.73 (m, 1 H), 6.22 (dd, J = 4.7, 9.6 Hz, 1 H), 5.16 (d, J = 5.6 Hz, 1 H), 5.10 (d, J = 5.6 Hz, 1 H), 4.82-4.80 (m, 1 H), 3.87 (s, 3 H), 3.86 (s, 3 H), 3.65 (dd, J = 9.6, 14.0 Hz, 1 H), 3.30 (dd, J = 4.7, 14.0 Hz, 1 H), 3.10-3.04 (m, 1 H), 2.77-2.61 (m, 3 H), 2.50-2.43 (m, 1 H), 2.26-2.22 (m, 1 H), 2.05-2.01 (m, 1 H), 1.75-1.47 (m, 3 H), 1.39-1.34 (m, 1 H).<br>LCMS (Method 1): [MH+] = 706 at 2.81 min. |

Example 12

[(1S)-2-(3,5-dichloro-1-oxido-pyridin-1-ium-4-yl)-1-(3,4-dimethoxyphenyl)ethyl] 2-fluoro-4-[[2-oxo-1-phenyl-2-[(3R)-quinuclidin-3-yl]oxy-ethyl]amino]benzoate (Ex. 12)

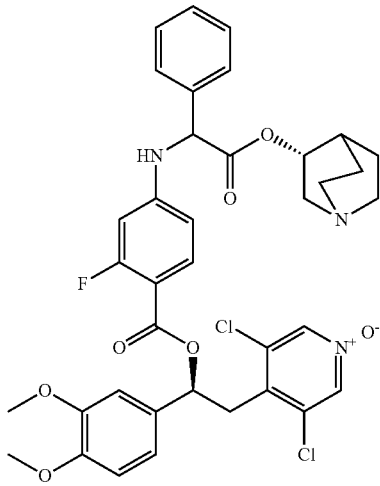

Example 12 was prepared according to an analogous synthetic procedure to that described in Example 3, starting from aniline intermediate (I-20).

NMR (400 MHz, CDCl3) δ 8.10*$^{or\,\dagger}$ (s, 2H), 8.09*$^{or\,\dagger}$ (s, 2H), 7.69 (t, J=8.5 Hz, 1H), 7.45 (d, J=7.5 Hz, 2H), 7.41-7.28 (m, 3H), 6.99 (dd, J=5.0, 2.0 Hz, 1H), 6.94-6.89 (m, 1H), 6.81 (d, J=8.3 Hz, 1H), 6.34 (dd, J=8.8, 2.3 Hz, 1H), 6.28 (dt, J=9.1, 4.5 Hz, 1H), 6.16 (dd, J=13.1, 2.2 Hz, 1H), 5.63 (d, J=5.4 Hz, 1H), 5.08 (d, J=5.4 Hz, 1H), 4.95-4.84 (m, 1H), 3.88*$^{or\,\dagger}$ (s, 3H), 3.88*$^{or\,\dagger}$ (s, 3H), 3.86*$^{or\,\dagger}$ (s, 3H), 3.86*$^{or}$ † (s, 3H), 3.61 (ddd, J=13.9, 9.1, 4.4 Hz, 1H), 3.34-3.25 (m, 1H), 3.29-3.22*$^{or\,\dagger}$ (m, 1H), 3.14*$^{or\,\dagger}$ (ddd, J=14.9, 8.2, 2.3 Hz, 1H), 2.90-2.73 (m, 4H), 2.55-2.45*$^{or\,\dagger}$ (m, 1H), 2.30*or † (d, J=15.4 Hz, 1H), 2.11*$^{or\,\dagger}$ (s, 1H), 1.91*$^{or\,\dagger}$ (s, 1H), 1.83-1.39 (m, 3H), 1.25-1.09 (m, 1H). * and † refer to different isomers.

LC MS (Method 1): [MH+]=724 at 2.77 min.

Example 13

Single diastereoisomer of [(1S)-2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]sulfamoyl]benzoate (Ex. 13, diast 1)

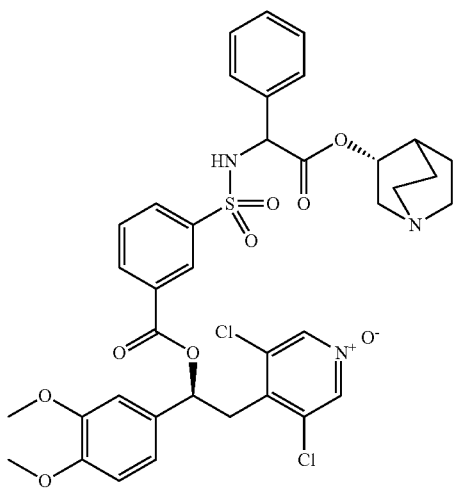

Trifluoroacetic acid (5.0 mL) was added to a stirred solution of [(1S)-2-(3,5-dichloro-1-oxido-pyridin-1-ium-4-yl)-1-(3,4-dimethoxyphenyl)ethyl] 3-[(2-tert-butoxy-2-oxo-1-phenyl-ethyl)sulfamoyl]benzoate (1.0 g, 1.39 mmol) in dichloromethane (5.0 mL) at 0° C., and stirring was maintained at 0° C. for 2.5 hours. The reaction mixture was then stirred at ambient temperature for 30 minutes, after which time toluene (50 mL) was added and the solvent removed under reduced pressure to yield a yellow solid, inferred as the intermediate 2-[[3-[(1S)-2-(3,5-dichloro-1-oxido-pyridin-1-ium-4-yl)-1-(3,4-dimethoxyphenyl)ethoxy]carbonylphenyl]sulfonylamino]-2-phenyl-acetic acid. The crude was subsequently dissolved in THF (20 mL), and N,N'-dicyclohexylcarbodiimide (431 mg, 2.09 mmol), 1-hydroxybenzotriazole hydrate (282 mg, 2.09 mmol) and (R)-quinuclidin-3-ol (355 mg, 2.79 mmol) were sequentially added. The resulting reaction mixture was stirred at ambient temperature for 18 hours, after which time the reaction mixture was filtered through a pad of Celite®, washing with tetrahydrofuran (10 mL). The filtrate was concentrated under reduced pressure and the resulting crude was partitioned between ethyl acetate (20 mL) and water (10 mL), the organic phases were dried over magnesium sulfate and concentrated under reduced pressure. The resulting crude was triturated in diethyl ether, and final purification was achieved by preparative HPLC and subsequent SFC to afford the title compound as a pale yellow solid (17.9 mg, de=100%).

$^{1}$H NMR (400 MHz, CDCl$_3$): δ 8.30 (s, 1H), 8.16 (s, 2H), 8.06 (d, J=7.4 Hz, 1H), 7.82 (d, J=8.0 Hz, 1H), 7.42 (t, J=8.0 Hz, 1H), 7.20-7.08 (m, 5H), 7.07-6.98 (m, 2H), 6.88 (d, J=8.5 Hz, 1H), 6.26 (dd, J=9.6, 4.8 Hz, 1H), 5.10 (s, 1H), 4.72-4.62 (m, 1H), 3.94 (s, 3H), 3.89 (s, 3H), 3.73 (dd, J=14.0, 9.6 Hz, 1H), 3.39 (dd, J=14.0, 4.7 Hz, 1H), 2.99 (ddd, J=13.0, 8.1, 2.0 Hz, 1H), 2.74-2.53 (m, 3H), 2.48-2.35 (m, 1H), 2.23 (d, J=14.8 Hz, 1H), 1.90-1.81 (m, 1H) 1.76-1.2 (m, 4H). LCMS (Method 1): [MH+]=770 at 2.71 min.

Example 19 and Example 20

Single diastereoisomers of [(1S)-2-(3,5-dichloro-1-oxido-pyridin-1-ium-4-yl)-1-(3,4-dimethoxyphenyl)ethyl] 3-[[[2-oxo-1-phenyl-2-[(3R)-quinuclidin-3-yl]oxy-ethyl]amino]methyl]benzoate (Ex. 19, diast 1 and Ex. 20, diast 2)

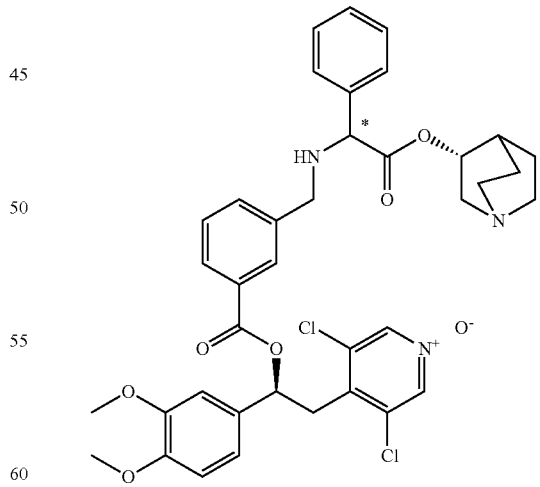

Purification of the 1:1 mixture of diastereoisomers of Example 1 by chiral preparative SFC afforded the single diastereoisomers. The absolute configurations of these were not determined.

Title compound (Example 19, Single diastereoisomer 1) was obtained as a light brown solid (43.5 mg, 10%).

¹H NMR (400 MHz, CDCl3): δ 8.12 (s, 2H), 7.99 (s, 1H), 7.92 (d, J=7.8 Hz, 1H), 7.55 (d, J=7.7 Hz, 1H), 7.42-7.29 (m, 6H), 7.03-6.97 (m, 2H), 6.85 (d, J=8.2 Hz, 1H), 6.29 (dd, J=9.6, 4.7 Hz, 1H), 4.82-4.76 (m, 1H), 4.40 (s, 1H), 3.89 (s, 3H), 3.87 (s, 3H), 3.78 (s, 2H), 3.71 (dd, J=13.9, 9.7 Hz, 1H), 3.35 (dd, J=13.9, 4.7 Hz, 1H), 3.10 (ddd, J=14.8, 8.2, 2.3 Hz, 1H), 2.78-2.61 (m, 2H), 2.56-2.47 (m, 1H), 2.34 (d, J=15.0 Hz, 1H), 2.04-1.95 (m, 2H), 1.69-1.59 (m, 2H), 1.55-1.45 (m, 1H), 1.35-1.25 (m, 2H). LCMS (Method 1): [MH+]=720/722 at 2.48 min.

Title compound (Example 20, Single diastereoisomer 2) was obtained as a light brown solid (51.5 mg, 12%).

¹H NMR (400 MHz, CDCl3): δ 8.12 (s, 2H), 8.00 (s, 1H), 7.92 (d, J=7.8 Hz, 1H), 7.53 (d, J=7.7 Hz, 1H), 7.42-7.27 (m, 6H), 7.04-6.97 (m, 2H), 6.85 (d, J=8.2 Hz, 1H), 6.28 (dd, J=9.7, 4.6 Hz, 1H), 4.87-4.82 (m, 1H), 4.38 (s, 1H), 3.89 (s, 3H), 3.88 (s, 3H), 3.78 (d, J=3.6 Hz, 2H), 3.71 (dd, J=13.8, 9.6 Hz, 1H), 3.35 (dd, J=14.0, 4.6 Hz, 1H), 3.19 (dd, J=14.7, 8.4 Hz, 1H), 2.80-2.65 (m, 4H), 2.27-2.05 (m, 2H), 1.89-1.83 (m, 1H), 1.66-1.55 (m, 1H), 1.54-1.44 (m, 1H), 1.30-1.21 (m, 1H), 1.21-1.10 (m, 1H). LCMS (Method 1): [MH+]=720/722 at 2.48 min.

Compounds reported in the table herebelow were made according to the analogous procedures as that described in Example 19 and Example 20. Chiral preparative SFC or chiral preparative HPLC afforded the single diastereoisomers.

| Reference | Compound | Analytical Data |
| --- | --- | --- |
| Ex. 21 (Single Diastereoisomer 1) | [(1S)-2-(3,5-dichloro-1-oxido-pyridin-1-ium-4-yl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate single diastereoisomer | ¹H NMR (400 MHz, CDCl3): δ 8.12 (s, 2 H), 7.98 (s, 1 H), 7.93 (d, J = 7.8 Hz, 1 H), 7.54 (d, J = 7.7 Hz, 1 H), 7.42-7.29 (m, 2 H), 7.17 (t, J = 9.6 Hz, 2 H), 7.05-6.97 (m, 3 H), 6.86 (d, J = 8.2 Hz, 1 H), 6.29 (dd, J = 9.6, 4.6 Hz, 1 H), 4.83-4.78 (m, 1 H), 4.39 (s, 1 H), 3.90 (s, 3 H), 3.88 (s, 3 H), 3.78 (s, 2 H), 3.71 (dd, J = 13.9, 9.7 Hz, 1 H), 3.35 (dd, J = 13.9, 4.6 Hz, 1 H), 3.13 (dd, J = 14.8, 8.3 Hz, 1 H), 2.81-2.65 (m, 3 H), 2.62-2.51 (m, 1 H), 2.37 (d, J = 14.9 Hz, 1 H), 2.02-1.95 (m, 1 H), 1.72-1.59 (m, 2 H), 1.57-1.46 (m, 1 H), 1.39-1.28 (m, 1 H). LCMS (Method 2): [MH+] = 738 at 3.34 min. |
| Ex. 22 (Single Diastereoisomer 2) | [(1S)-2-(3,5-dichloro-1-oxido-pyridin-1-ium-4-yl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate single diastereoisomer | ¹H NMR (400 MHz, CDCl3): δ 8.13 (s, 2 H), 7.99 (s, 1 H), 7.93 (d, J = 7.8 Hz, 1 H), 7.53 (d, J = 7.6 Hz, 1 H), 7.40 (t, J = 7.7 Hz. 1 H), 7.36-7.28 (m, 1 H), 7.20-7.12 (m, 2 H), 7.05-6.98 (m, 3 H), 6.86 (d, J = 8.2 Hz, 1 H), 6.29 (dd, J = 9.7, 4.6 Hz, 1 H), 4.87-4.82 (m, 1 H), 4.37 (s, 1 H), 3.90 (s, 3 H), 3.88 (s, 3 H), 3.82-3.67 (m, 3 H), 3.35 (dd, J = 14.0, 4.6 Hz, 1 H), 3.20 (dd, J = 14.7, 8.4 Hz, 1 H), 2.79-2.64 (m, 5H), 1.90-1.84 (m, 1 H), 1.67-1.56 (m, 1 H), 1.55-1.44 (m, 1 H), 1.34-1.14 (m, 2 H). LCMS (Method 2): [MH+] = 738 at 3.36 min. |

| Reference | Compound | Analytical Data |
|---|---|---|
| Ex. 23 (Single Diastereoisomer 1) | [(1S)-2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate single diastereoisomer 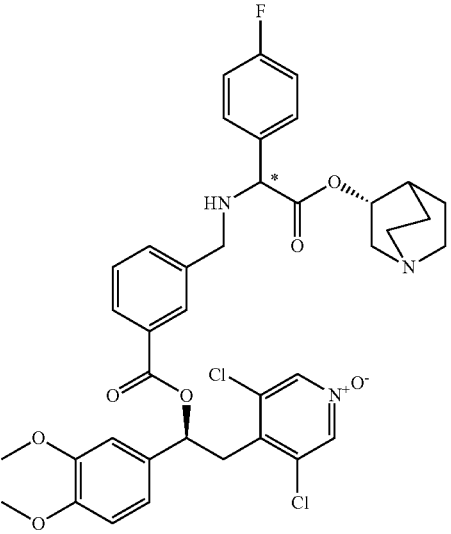 | ¹H NMR (400 MHz, CDCl3): δ 8.12 (s, 2 H), 7.98-7.90 (m, 2H), 7.53 (d, J = 7.7 Hz, 1 H), 7.42-7.34 (m, 3 H), 7.10-6.97 (m, 4 H), 6.86 (d, J = 8.2 Hz, 1 H), 6.29 (dd, J = 9.7, 4.6 Hz, 1 H), 4.83-4.78 (m, 1 H), 4.37 (s, 1 H), 3.90 (s, 3 H), 3.88 (s, 3 H), 3.76 (s, 2 H), 3.71 (dd, J = 14.0, 9.7 Hz, 1 H), 3.36 (dd, J = 14.0, 4.7 Hz, 1 H), 3.14 (ddd, J = 14.8, 8.2, 2.3 Hz, 1 H), 2.82-2.65 (m, 3 H), 2.67-2.51 (m, 1 H), 2.37 (d, J = 14.9 Hz, 1 H), 2.04-1.96 (m, 1 H), 1.72-1.59 (m, 2 H), 1.58-1.47 (m, 1 H), 1.39-1.29 (m, 1 H). LCMS (Method 1): [MH+] =738 at 2.58 min. |
| Ex. 24 (Single Diastereoisomer 2) | [(1S)-2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate single diastereoisomer 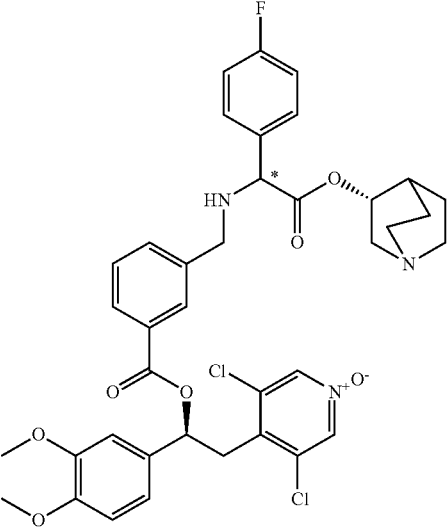 | ¹H NMR (400 MHz, CDCl3): δ 8.13 (s, 2 H), 7.97 (s, 1 H), 7.93 (d, J = 7.8 Hz, 1 H), 7.52 (d, J = 7.6 Hz, 1 H), 7.42-7.33 (m, 3 H), 7.08-6.97 (m, 4 H), 6.86 (d, J = 8.2 Hz, 1 H), 6.29 (dd, J = 9.7, 4.6 Hz, 1 H), 4.87-4.81 (m, 1 H), 4.36 (s, 1 H), 3.90 (s, 3 H), 3.88 (s, 3 H), 3.81-3.67 (m, 3 H), 3.35 (dd, J = 14.0, 4.6 Hz, 1 H), 3.20 (dd, J = 14.7, 8.4 Hz, 1 H), 2.82-2.65 (m, 5 H), 1.89-1.83 (m, 1 H), 1.66-1.57 (m, 1 H), 1.55-1.45 (m, 1 H), 1.32-1.14 (m, 2 H). LCMS (Method 1): [MH+] = 738 at 2.59 min. |

-continued

| Reference | Compound | Analytical Data |
| --- | --- | --- |
| Ex. 25 (Single Diastereoisomer 1) | [(1S)-2-(3,5-dichloro-1-oxido-pyridin-1-ium-4-yl)-1-(3,4-dimethoxyphenyl)ethyl] 3-[[[1-(2-methoxyphenyl)-2-oxo-2-[(3R)-quinuclidin-3-yl]oxy-ethyl]amino)methyl]benzoate single diastereoisomer 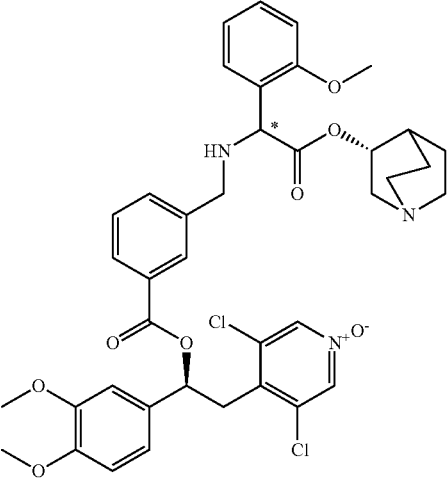 | $^1$H NMR (400 MHz, CDCl3): δ 8.11 (s, 2 H), 7.98 (s, 1 H), 7.91 (d, J = 7.8 Hz, 1 H), 7.57 (d, J = 7.7 Hz, 1 H), 7.38 (t, J = 7.7 Hz, 1 H), 7.32-7.27 (m, 1 H), 7.23 (dd, J = 7.5, 1.7 Hz, 1 H), 7.04-6.98 (m, 2 H), 6.96 (t, J = 7.5 Hz, 1 H), 6.90 (d, J = 8.2 Hz, 1 H), 6.85 (d, J = 8.1 Hz, 1 H), 6.28 (dd. J = 9.6, 4.7 Hz, 1 H), 4.84-4.78 (m, 1 H), 4.62 (s, 1 H), 3.89 (s, 3 H), 3.87 (s, 3 H), 3.81 (s, 5 H), 3.70 (dd, J = 13.9, 9.6 Hz, 1 H), 3.35 (dd, J = 13.9, 4.7 Hz, 1 H), 3.18 (ddd, J = 14.8, 8.1, 2.3 Hz, 1 H), 2.80-2.70 (m, 3 H), 2.51-2.40 (m, 2 H), 2.01-1.95 (m, 1 H), 1.73-1.63 (m, 1 H), 1.60-1.50 (m, 2 H), 1.35-1.24 (m, 1 H). LCMS (Method 2): [MH+] =750 at 3.23 min. |
| Ex. 26 (Single Diastereoisomer 2) | [(1S)-2-(3,5-dichloro-1-oxido-pyridin-1-ium-4-yl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate single diastereoisomer 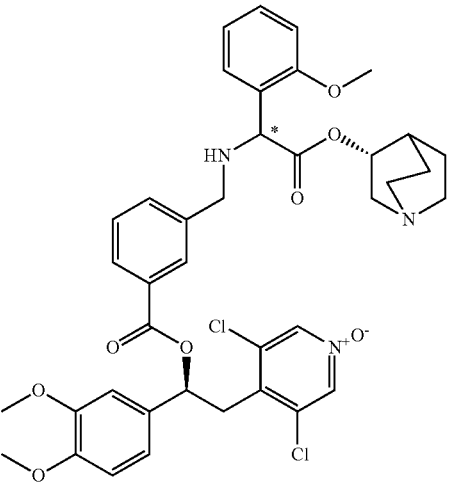 | $^1$H NMR (400 MHz, CDCl3): δ 8.12 (s, 2 H), 7.99 (s, 1 H), 7.91 (d, J = 7.8 Hz, 1 H), 7.55 (d, J = 7.5 Hz, 1 H), 7.38 (t, J = 7.7 Hz, 1 H), 7.31-7.23 (m, 2 H), 7.03-6.98 (m, 2 H), 6.94 (t, J = 7.4 Hz, 1 H), 6.86 (t, J = 8.3 Hz, 2 H), 6.28 (dd, J = 9.6, 4.6 Hz, 1 H), 4.93-4.88 (m, 1 H), 4.67 (s, 1 H), 3.89 (s, 3 H), 3.88 (s, 3 H), 3.82-3.77 (m, 5 H), 3.71 (dd, J = 13.9, 9.7 Hz, 1 H), 3.35 (dd, J = 14.0, 4.6 Hz, 1 H), 3.22 (dd, J = 14.5, 8.5 Hz, 1 H), 2.84-2.65 (m, 5 H), 1.96-1.91 (m, 1 H), 1.71-1.61 (m, 1H), 1.61-1.51 (m, 1 H), 1.31-1.14 (m, 2 H). LCMS (Method 2): [MH+] = 750 at 3.24 min. |

-continued

| Reference | Compound | Analytical Data |
|---|---|---|
| Ex. 27 (Single Diastereoisomer 1) | [(1S)-2-(3,5-dichloro-1-oxido-pyridin-1-ium-4-yl)-1-(3,4-dimethoxyphenyl)ethyl] 4-[[[2-oxo-1-phenyl-2-[(3R)-quinuclidin-3-yl]oxy-ethyl]amino]methyl]benzoate single diastereoisomer 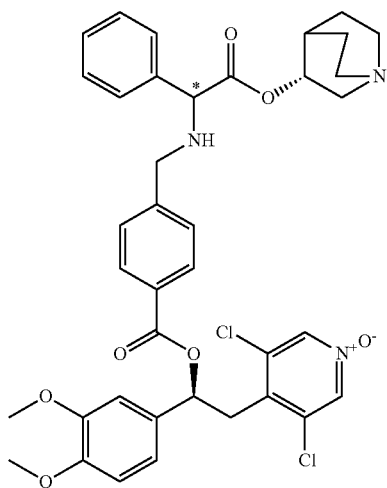 | $^1$H NMR (400 MHz, CDCl3): δ 8.12 (s, 2 H), 7.98 (d, J = 8.1 Hz, 2 H), 7.43-7.27 (m, 7 H), 7.04-6.97 (m, 2 H), 6.85 (d, J = 8.2 Hz, 1 H), 6.30 (dd, J = 9.7, 4.6 Hz, 1 H), 4.82-4.76 (m, 1 H), 4.37 (s, 1 H), 3.90 (s, 3 H), 3.88 (s, 3 H), 3.80 (s, 2 H), 3.75-3.67 (m, 1 H), 3.35 (dd, J = 14.0, 4.6 Hz, 1 H), 3.14-3.06 (m, 1 H), 2.79-2.62 (m, 3 H), 2.56-2.46 (m, 1 H), 2.37-2.30 (m, 1 H), 2.00-1.95 (m, 1 H), 1.69-1.58 (m, 2 H), 1.55-1.45 (m, 1 H), 1.36-1.22 (m, 1 H). LCMS (Method 2): [MH+] =720 at 3.27 min |
| Ex. 28 (Single Diastereoisomer 1) | [(1S)-2-(3,5-dichloro-1-oxido-pyridin-1-ium-4-yl)-1-(3,4-dimethoxyphenyl)ethyl] 4-[[[1-(4-fluorophenyl)-2-oxo-2-[(3R)-quinuclidin-3-yl)oxy-ethyl]amino]methyl]benzoate single diastereoisomer 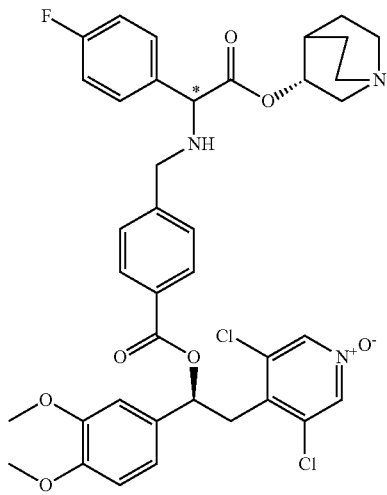 | $^1$H NMR (400 MHz, CDCl3): δ 8.12 (s, 2 H), 7.98 (d, J = 8.1 Hz, 2 H), 7.43-7.33 (m, 4 H), 7.10-6.97 (m, 4 H), 6.85 (d, J = 8.2 Hz, 1 H), 6.30 (dd, J = 9.7, 4.6 Hz, 1 H), 4.81-4.76 (m, 1 H), 4.35 (s, 1 H), 3.90 (s, 3 H), 3.88 (s, 3 H), 3.78 (s, 2 H), 3.71 (dd, J = 14.0, 9.7 Hz, 1 H), 3.35 (dd, J = 13.9, 4.6 Hz, 1 H), 3.17-3.08 (m, 1 H), 2.81-2.63 (m, 3 H), 2.60-2.49 (m, 1 H), 2.39-2.31 (m, 1 H), 2.02-1.96 (m, 1 H), 1.71-1.57 (m, 2H), 1.56-1.45 (m, 1 H), 1.39-1.27 (m, 1 H). LCMS (Method 2): [MH+] = 738 at 3.29 min |

-continued

| Reference | Compound | Analytical Data |
| --- | --- | --- |
| Ex. 29 (Single Diastereoisomer 2) | [(1S)-2-(3,5-dichloro-1-oxido-pyridin-1-ium-4-yl)-1-(3,4-dimethoxyphenyl)ethyl] 4-[[[1-(4-fluorophenyl)-2-oxo-2-[(3R)-quinuclidin-3-yl]oxy-ethyl]amino]methyl]benzoate single diastereoisomer | ¹H NMR (400 MHz, CDCl3): δ 8.12 (s, 2 H), 7.98 (d, J = 8.1 Hz, 2 H), 7.42-7.33 (m, 4 H), 7.08-6.97 (m, 4 H), 6.86 (d, J = 8.2 Hz, 1 H), 6.31 (dd, J = 9.7, 4.5 Hz, 1 H). 4.87-4.81 (m, 1 H), 4.35 (s, 1 H), 3.91 (s, 3 H), 3.88 (s, 3 H), 3.78 (s, 2 H), 3.71 (dd, J = 14.0, 9.7 Hz, 1 H), 3.35 (dd, J = 13.9, 4.6 Hz, 1 H), 3.24-3.16 (m, 1 H), 2.82-2.64 (m, 5 H), 1.88-1.82 (m, 1 H), 1.66-1.56 (m, 1 H), 1.54-1.44 (m, 1 H), 1.33-1.15 (m, 2 H). LCMS (Method 2): [MH+] =738 at 3.32 min |
| Ex. 30 (Single Diastereoisomer 1) | [(1S)-2-(3,5-dichloro-1-oxido-pyridin-1-ium-4-yl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate single diastereoisomer | ¹H NMR (400 MHz, CDCl3): δ 8.13 (s, 2 H), 7.98 (d, J = 8.1 Hz, 2 H), 7.42-7.27 (m, 3 H), 7.19-7.11 (m, 2 H), 7.05-6.98 (m, 3 H), 6.85 (d, J = 8.2 Hz, 1 H), 6.30 (dd, J = 9.7, 4.6 Hz, 1 H), 4.84-4.79 (m, 1 H), 4.36 (s, 1 H), 3.91 (s, 3 H), 3.88 (s, 3 H), 3.80 (s, 2 H), 3.71 (dd, J = 14.0, 9.7 Hz, 1 H), 3.35 (dd, J = 14.0, 4.6 Hz, 1 H), 3.18-3.10 (m, 1 H), 2.82-2.66 (m, 3 H), 2.62-2.52 (m, 1 H), 2.42-2.35 (m, 1 H), 2.02-1.97 (m, 1 H), 1.73-1.59 (m, 2 H), 1.58-1.47 (m, 1 H), 1.41-1.24 (m, 1 H). LCMS (Method 1): [MH+] = 738 at 2.64 min |

-continued

| Reference | Compound | Analytical Data |
|---|---|---|
| Ex. 31 (Single Diastereoisomer 2) | [(1S)-2-(3,5-dichloro-1-oxido-pyridin-1-ium-4-yl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate single diastereoisomer 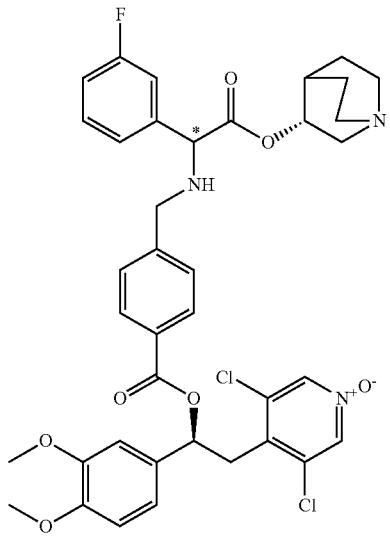 | $^1$H NMR (400 MHz, CDCl3): δ 8.13 (s, 2 H), 7.98 (d, J = 8.1 Hz, 2 H), 7.39 (d, J = 8.0 Hz, 2 H), 7.36-7.27 (m, 1 H), 7.19-7.11 (m, 2 H), 7.06-6.96 (m, 3 H), 6.86 (d, J = 8.2 Hz, 1 H), 6.30 (dd, J = 9.7, 4.6 Hz, 1 H), 4.88-4.81 (m, 1 H), 4.37 (s, 1 H), 3.91 (s, 3 H), 3.88 (s, 3 H), 3.79 (s, 2 H), 3.71 (dd, J = 14.0, 9.7 Hz, 1 H), 3.35 (dd, J = 14.0, 4.6 Hz, 1 H), 3.26-3.17 (m, 1 H), 2.83-2.65 (m, 5 H), 1.90-1.84 (m, 1 H), 1.67-1.56 (m, 1 H), 1.55-1.44 (m, 1 H), 1.36-1.15 (m, 2 H). LCMS (Method 1): [MH+] = 738 at 2.65 min |

Example 32
[(1S)-2-(3,5-dichloro-1-oxido-pyridin-1-ium-4-yl)-1-(3,4-dimethoxyphenyl)ethyl]-4-[2-[[1-(2-fluorophenyl)-2-oxo-2-[(3R)-quinuclidin-3-yl]oxy-ethyl]amino]ethyl]benzoate (Ex. 32)

Step 1: Preparation of [(1S)-2-(3,5-dichloro-1-oxido-pyridin-1-ium-4-yl)-1-(3,4-dimethoxyphenyl)ethyl] 4-(1,3-dioxolan-2-ylmethyl)benzoate

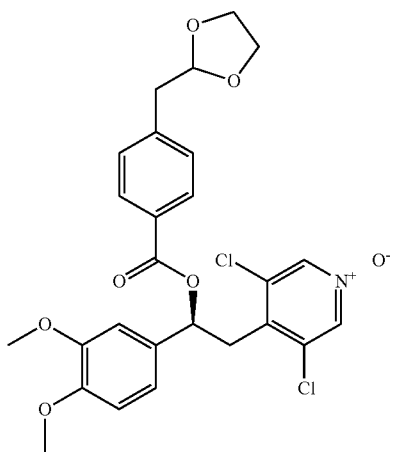

To a solution of 4-((1,3-dioxolan-2-yl)methyl)benzoic acid (362 mg, 1.05 mmol) in DCM (9 mL) was added (1S)-2-(3,5-dichloro-1-oxido-pyridin-1-ium-4-yl)-1-(3,4-dimethoxyphenyl)ethanol (200 mg, 0.96 mmol) followed by DMAP (58 mg, 0.48 mmol) and EDC.HCl (396 mg, 1.9 mmol). The mixture was allowed to stir a room temperature for 18 hours and then water (20 mL) and DCM (20 mL) were added and the organic phase was passed through a hydrophobic frit. The solvent was removed in vacuo and the crude material was purified by silica gel column chromatography, eluting with 30-100% EtOAc in DCM, to afford the title compound as an off-white solid (497 mg, 97%).

$^1$H NMR (400 MHz, CDCl$_3$): δ 8.13 (s, 2H), 7.96 (d, J=8.1 Hz, 2H), 7.34 (d, J=8.1 Hz, 2H), 7.02-6.97 (m, 2H), 6.85 (d, J=8.2 Hz, 1H), 6.29 (dd, J=9.7, 4.6 Hz, 1H), 5.08 (t, J=4.6 Hz, 1H), 3.95-3.80 (m, 10H), 3.76-3.66 (m, 1H), 3.34 (dd, J=14.0, 4.6 Hz, 1H), 3.02 (d, J=4.6 Hz, 2H).

LCMS (Method 1): [MH+]=534 at 3.70 min.

Step 2: Preparation of [(1S)-2-(3,5-dichloro-1-oxido-pyridin-1-ium-4-yl)-1-(3,4-dimethoxyphenyl)ethyl]-4-[2-[[1-(2-fluorophenyl)-2-oxo-2-[(3R)-quinuclidin-3-yl]oxy-ethyl]amino]ethyl]benzoate

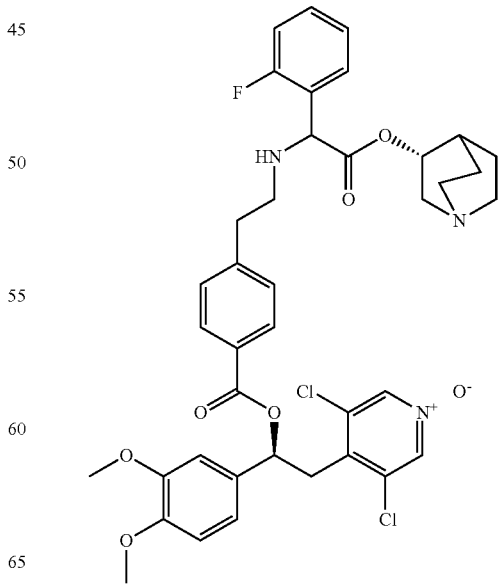

[(1S)-2-(3,5-dichloro-1-oxido-pyridin-1-ium-4-yl)-1-(3,4-dimethoxyphenyl)ethyl]-4-(1,3-dioxolan-2-ylmethyl)benzoate (500 mg, 0.93 mmol) was dissolved in THF (18.76 mL) and 2N aqueous HCl (18.76 mL). The mixture was stirred at 40° C. until the starting material had been consumed. The mixture was neutralized using saturated aqueous sodium bicarbonate solution, and washed with EtOAc (2×40 mL). The combined organic extracts were dried over MgSO₄, filtered, and the solvent was removed in vacuo to give the crude aldehyde intermediate as an off-white foam. The crude product was used directly in the next step without purification.

The title compound was synthesized from the above obtained crude aldehyde intermediate (215 mg, 0.44 mmol) and Intermediate 32 (154 mg, 0.44 mmol) via the same method described for Example 1. Purification by preparative HPLC gave the desired product as a pale yellow solid (53 mg, 16%, formate salt, 1:1 mixture of diastereoisomers).

¹H NMR (400 MHz, CDCl₃):) δ 8.37 (s, 1H), 8.13 (s, 2H), 7.94 (dd, J=8.0, 2.4 Hz, 2H), 7.36-7.17 (m, 4H), 7.17-6.96 (m, 4H), 6.85 (d, J=8.2 Hz, 1H), 6.29 (dd, J=9.6, 4.6 Hz, 1H), 4.99 (s, 1H, * or †), 4.94 (s, 1H, * or †), 4.73 (s, 1H), 3.93-3.84 (m, 6H), 3.71 (dd, J=14.0, 9.6 Hz, 1H), 3.38-3.27 (m, 2H), 3.00-2.49 (m, 9H), 2.19 (s, 1H, * or †), 2.05 (s, 1H, * or †), 1.92-1.40 (m, 5H). * and † refer to different isomers.

LCMS (Method 1): [MH+]=752 at 2.42 min.

Compounds herebelow reported were prepared as mixtures of diastereoisomers starting from the appropriate aldehyde and the appropriate amine according to the procedure described in Example 1.

| Ref. | Compound | Analytical Data |
|---|---|---|
| Ex. 33 | [(1S)-2-(3,5-dichloro-1-oxido-pyridin-1-ium-4-yl)-1-[4-(difluoromethoxy)-3-methoxy-phenyl]ethyl] 3-[[[1-(2-fluorophenyl)-2-oxo-2-[(3R)-quinuclidin-3-yl]oxy-ethyl]amino]methyl]benzoate Formate salt 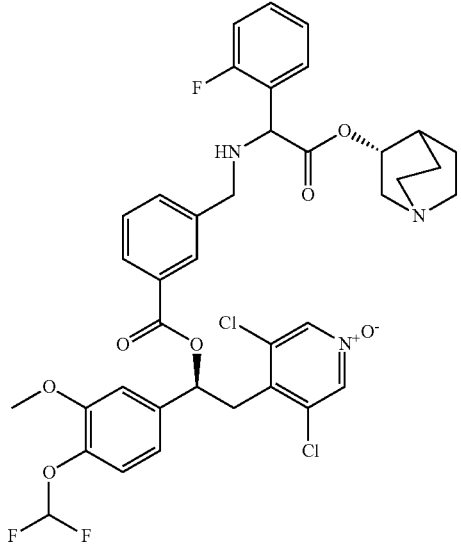 | ¹H NMR (400 MHz, CDCl₃): δ 8.39 (s, 1 H), 8.14 (s, 2 H), 8.02-7.97 (m, 1 H), 7.92 (d, J = 7.7 Hz, 1 H), 7.57-7.51 (m, 1 H), 7.44-7.28 (m, 3 H), 7.21-7.03 (m, 5 H), 6.54 (t, J = 75.0 Hz, 1 H), 6.31-6.25 (m, 1 H), 5.01-4.96*or† (m, 1 H), 4.94-4.89*or† (m, 1 H), 4.73*or† (s, 1 H), 4.70*or† (s, 1 H), 3.90*or† (s, 3 H), 3.89*or† (s, 3 H), 3.82-3.78 (m, 2 H), 3.70 (dd, J = 14.1, 9.8 Hz, 1 H), 3.37-3.21 (m, 2 H), 2.94-2.74 (m, 4 H), 2.63-2.47 (m, 1 H), 2.15-1.99 (m, 1 H), 1.83-1.40 (m, 3 H), 1.36-1.27 (m, 1 H). * and † refer to different isomers. LCMS (Method 1): [MH+] =774 at 2.75 min |

| Ref. | Compound | Analytical Data |
|---|---|---|
| Ex. 34 | 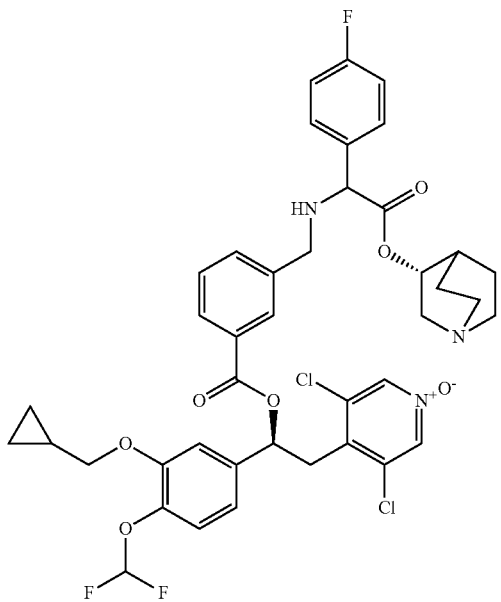<br>[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(4-fluorophenyl)-2-oxo-2-[(3R)-quinuclidin-3-yl]oxy-ethyl]amino]methyl]benzoate | $^1$H NMR (300 MHz, DMSO) δ 8.52 (d, 2 H), 7.94 (s, 1 H), 7.87 (d, 1 H), 7.59 (d, 1 H), 7.39-7.54 (m, 3 H), 7.14-7.27 (m, 4 H), 7.06-7.11 (m, 1 H), 7.06 (t, 1 H), 6.21 (dd, 1 H), 4.67 (dt, 1 H), 4.38 (t, 1 H), 3.93 (d, 2 H), 3.72 (br. s., 2 H), 3.61 (dd, 1 H), 3.35 (dd, 1 H), 2.90-3.16 (m, 1 H), 2.54-2.69 (m, 4 H), 2.33-2.47 (m, 1 H), 1.64-1.79 (m, 1 H), 1.36-1.60 (m, 3 H), 1.09-1.34 (m, 3 H), 0.45-0.62 (m, 2 H), 0.24-0.41 (m, 2 H).<br>LCMS (Method 1): [MH+] = 814 at 2.91 min. |
| Ex. 35 | 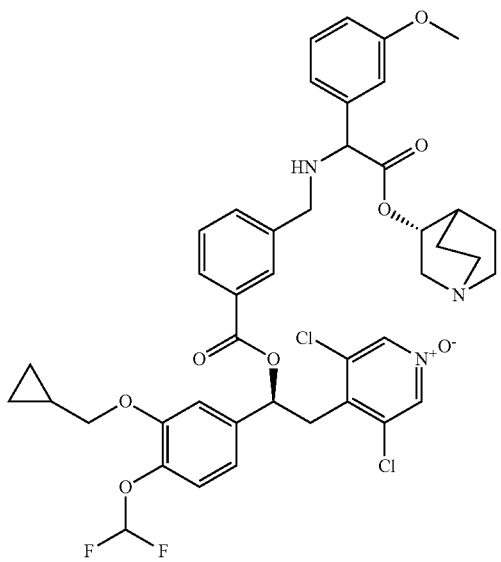<br>[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(3-methoxyphenyl)-2-oxo-2-[(3R)-quinuclidin-3-yl]oxy-ethyl]amino]methyl]benzoate trifluoroacetate salt | $^1$H NMR (300 MHz, DMSO) δ 9.72 and 9.83 (br. s., 1 H), 8.54 (s, 2 H), 7.94-8.14 (m, 2 H), 7.65-7.75 (m, 1 H), 7.59 (t, 1 H), 7.41 (t, 1 H), 7.18-7.27 (m, 2 H), 6-97-7.17 (m, 4 H), 7.07 (t, 1 H), 6.11-6.35 (m, 1 H), 5.00-5.42 (m, 2 H), 3.99-4.25 (m, 2 H), 3.94 (d, 2 H), 3.77 (s, 3 H), 3.64-3.76 (m, 1 H), 3.63 (dd, 1 H), 3.36 (dd, 1 H), 2.81-3.30 (m, 5 H), 2.02-2.13 and 2.20-2.35 (m, 1 H), 1.32-1.96 (m, 4 H), 1.05-1.30 (m, 1 H), 0.46-0.70 (m, 2 H), 0.20-0.44 (m, 2 H).<br>LCMS (Method 1): [MH+] = 826 at 2.85 min. |

| Ref. | Compound | Analytical Data |
|---|---|---|
| Ex. 36 | 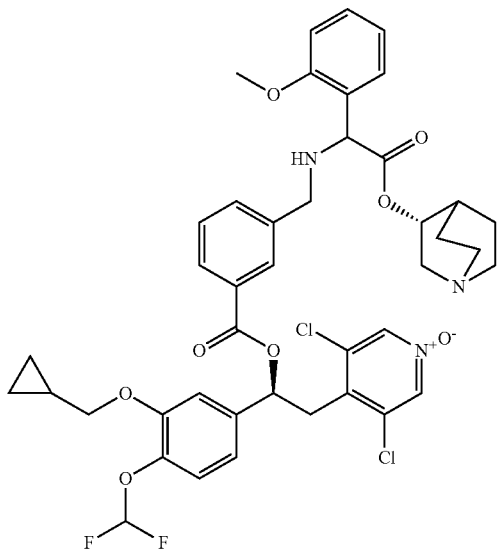<br>[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(2-methoxyphenyl)-2-oxo-2-[(3R)-quinuclidin-3-yl]oxy-ethyl]amino]methyl]benzoate trifluoroacetate salt | $^1$H NMR (300 MHz, DMSO) δ 9.82 (br. s., 1 H), 8.55 (s, 2 H), 8.05 (d, 1 H), 8.00 and 8.01 (t, 1 H), 7.66-7.77 (m, 1 H), 7.57 (t, 1 H), 7.34-7.51 (m, 2 H), 7.18-7.27 (m, 2 H), 6.77-7.33 (m, 4 H), 6.17-6.36 (m, 1 H), 5.23-5.48 (m, 1 H), 5.04-5.23 (m, 1 H), 4.05-4.29 (m, 2 H), 3.94 (d, 2 H), 3.73 and 3.77 (s, 3 H), 3.65-3.72 (m, 1 H), 3.63 (dd, 1 H), 3.37 (dd, 1 H), 2.65-3.31 (m, 5 H), 1.99-2.13 and 2.17-2.35 (m, 1 H), 1.30-1.95 (m, 4 H), 1.08-1.28 (m, 1 H), 0.46-0.69 (m, 2 H), 0.20-0.44 (m, 2 H). LCMS (Method 1): [MH+] = 826 at 2.71 min. |
| Ex. 37 | 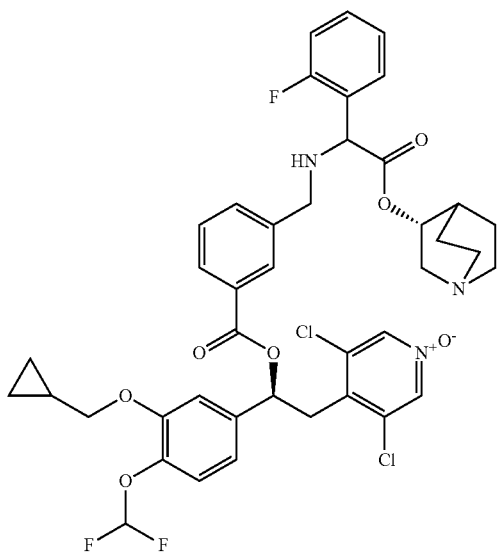<br>[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(2-fluorophenyl)-2-oxo-2-[(3R)-quinuclidin-3-yl]oxy-ethyl]amino]methyl]benzoate trifluoroacetate salt | $^1$H NMR (300 MHz, DMSO) δ 9.66 and 9.75 (br. s., 1 H), 8.54 (s, 2 H), 7.89-8.08 (m, 2 H), 7.42-7.76 (m, 4 H), 6.73-7.39 (m, 6 H), 6.10-6.32 (m, 1 H), 4.97-5.32 (m, 2 H), 4.05 (br. s., 2 H), 3.93 and 3.94 (d, 2 H), 3.65-3.75 (m, 1 H), 3.62 (dd, 1 H), 3.36 (dd, 1 H), 2.56-3.31 (m, 5 H), 1.99-2.15 and 2.18-2.32 (m, 1 H), 1.34-1.97 (m. 4 H), 1.04-1.33 (m, 1 H), 0.46-0.71 (m, 2 H), 0.18-0.43 (m, 2 H). LCMS (Method 1): [MH+] = 814 at 2.97 min. |

| Ref. | Compound | Analytical Data |
|---|---|---|
| Ex. 38 | 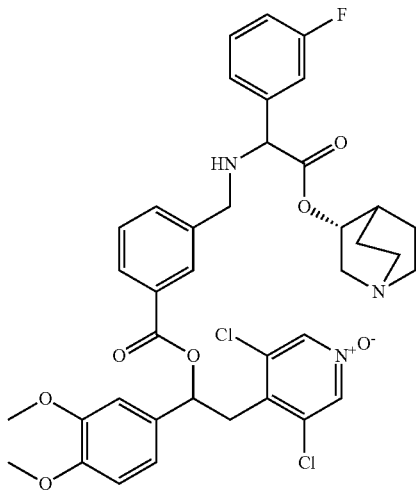<br>[2-(3,5-dichloro-1-oxido-pyridin-1-ium-4-yl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate trifluoroacetate salt | $^1$H NMR (300 MHz, DMSO) δ 9.60 and 9.73 (br. s., 1 H), 8.53 (s, 2 H), 7.93-8.11 (m, 2 H), 7.62-7.72 (m, 1 H), 7.46-7.62 (m, 2 H), 7.23-7.46 (m, 3 H), 7.07 (d, 1 H), 7.03 (dd, 1 H), 6.97 (d, 1 H), 6.11-6.37 (m, 1 H), 4.96-5.25 (m, 2 H), 3.88-4.17 (m, 3 H), 3.78 (s, 3 H), 3.76 (s, 3 H), 3.64 (dd, 2 H), 3.36 (dd, 1 H), 2.99-3.30 (m, 4 H), 2.86-2.99 (m, 1 H), 2.00-2.16 and 2.21 2.30 (m, 1 H), 1.32-1.99 (m, 4 H). LCMS (Method 1): [MH+] = 738 at 2.63 min. |
| Ex. 39 | 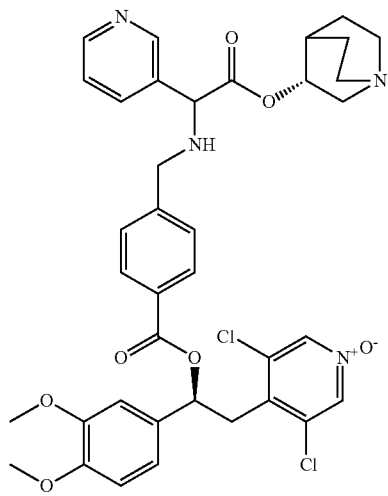<br>[(1S)-2-(3,5-dichloro-1-oxido-pyridin-1-ium-4-yl)-1-(3,4-dimethoxyphenyl)ethyl] 4-[[[2-oxo-1-(3-pyridyl)-2-[(3R)-quinuclidin-3-yl]oxy-ethyl]amino]methyl]benzoate formate salt | $^1$H NMR (400 MHz, DMSO): δ 8.55 (s, 1 H), 8.48 (s, 2 H), 8.46-8.41 (m, 1 H), 8.12 (s, 1 H), 7.86 (d, J = 7.9 Hz, 2 H), 7.79 (dq, J = 7.9, 2.0 Hz, 1 H), 7.40 (d, J = 8.0 Hz, 2 H), 7.33 (dt, J = 7.9, 4.9 Hz, 1 H), 7.00-6.86 (m, 3 H), 6.14 (dd, J = 9.6, 4.4 Hz, 1 H), 4.67-4.58 (m, 1 H), 4.39 (d, J = 2.1 Hz, 1 H), 3.71 (s, 3 H), 3.68 (s, 3 H), 3.56 (dd, J = 14.2, 9.4 Hz, 1 H), 3.28 (dd, J = 14.2, 4.5 Hz, 1 H), 3.21-2.78 (m, 3 H), 2.65-2.08 (m, 5 H), 1.82-1.61 (m, 1 H), 1.53-1.03 (m, 4 H). LCMS (Method 1): [MH+] = 721 at 2.42 min. |

-continued

| Ref. | Compound | Analytical Data |
|---|---|---|
| Ex. 40 | 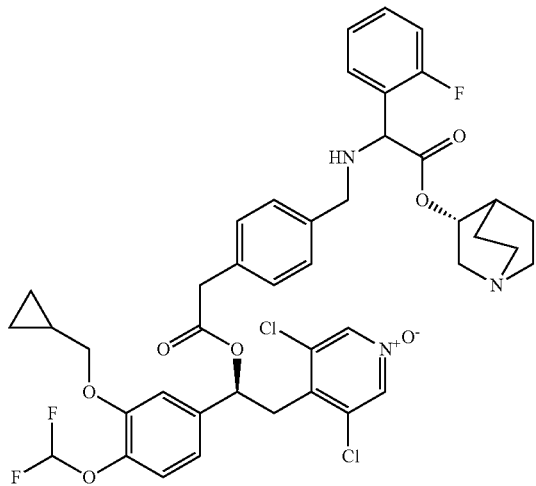<br>[(3R)-quinuclidin-3-yl] 2-[[4-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-(2-fluorophenyl)acetate formate salt | $^1$H NMR (400 MHz, CD$_3$CN): δ 8.31 (br s, 1 H), 8.10 (s, 2 H), 7.60-7.51 (m, 1 H), 7.43-7.34 (m, 1 H), 7.31-6.09 (m, 7 H), 6.98 (d, J = 28.3 Hz, 2 H), 6.78 (t, J = 74.3 Hz, 1 H), 6.01 (dd, J = 9.8, 4.7 Hz, 1 H), 4.96-4.86 (m, 1 H), 4.75 (d, J = 4.1 Hz, 1 H), 3.87 (d, J = 7.1 Hz, 2 H), 3.76 (s, 2 H), 3.65-3.55 (m, 2 H), 3.46 (dd, J = 14.1, 9.9 Hz, 1 H), 3.33-3.19 (m, 1 H), 3.21 (dd, J = 13.8, 4.8 Hz, 1 H), 2.94-2.74 (m, 5 H), 2.77-2.67 (m, 1 H), 2.10-1.17 (m, 5 H), 0.67-0.59 (m, 2 H), 0.41-0.34 (m, 2 H).<br>LCMS (Method 1): [MH+] = 828 at 2.74 min. |
| Ex. 41 | 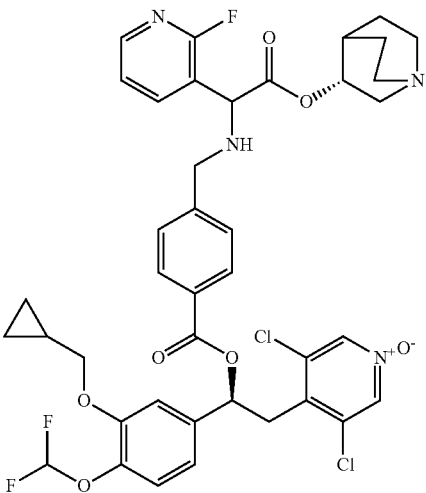<br>[(3R)-quinuclidin-3-yl] 2-[[3-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-(2-fluorophenyl)acetate formate salt | $^1$H NMR (400 MHz, DMSO): δ 8.47* (s, 2 H), 8.46† (s, 2 H), 8.20 (s, 1 H), 7.55 (t, J = 7.5 Hz, 1 H), 7.40-7.32 (m, 1 H), 7.26-6.85 (m, 10 H), 5.96 (dd, J = 9.4, 4.6 Hz, 1 H), 4.75-4.66 (m, 1 H), 4.64 (s, 1 H), 3.86-2.80 (m, 9 H), 2.79-2.09 (m, 6 H), 1.88-1.06 (m, 5 H), 0.60-0.53 (m, 2 H), 0.37-0.31 (m, 2 H). * and † refer to different isomers. LCMS (Method 1): [MH+] = 828 at 2.82 min. |

| Ref. | Compound | Analytical Data |
|---|---|---|
| Ex. 42 | 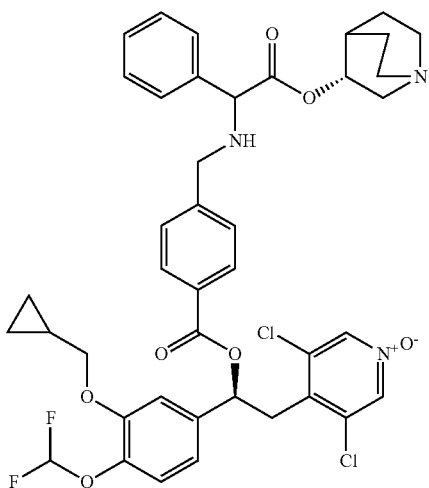<br>[(3R)-quinuclidin-3-yl] 2-[[3-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-phenyl-acetate formate salt | $^1$H NMR (400 MHz, DMSO): δ 8.47* (s, 2 H), 8.46† (s, 2 H), 8.21 (s, 1 H), 7.45-6.84 (m, 13 H), 5.96 (dd, J = 9.3, 4.6 Hz, 1 H), 4.73-4.64 (m, 1 H), 4.36 (s, 1 H), 3.89-2.72 (m, 9 H), 2.69-2.12 (m, 6 H), 1.98-1.07 (m, 5 H), 0.60-0.54 (m, 2 H), 0.37-0.31 (m, 2 H). * and † refer to different isomers. LCMS (Method 1); [MH+] = 810 at 2.71 min. |
| Ex. 43 | 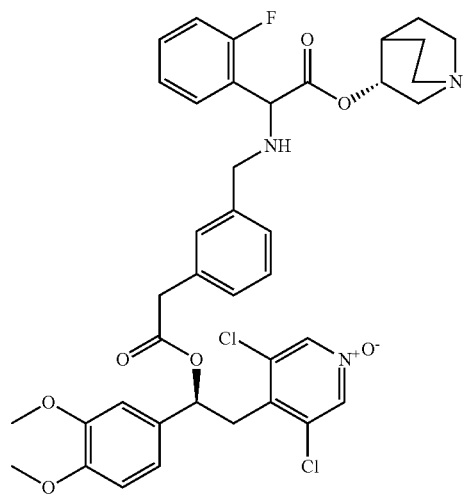<br>[(3R)-quinuclidin-3-yl] 2-[[3-[2-[(1S)-2-(3,5-dichloro-1-oxido-pyridin-1-ium-4-yl)-1-(3,4-dimethoxyphenyl)ethoxy]-2-oxo-ethyl]phenyl]methylamino]-2-(2-fluorophenyl)acetate formal salt | $^1$H NMR (400 MHz, DMSO): δ 8.47* (s, 2 H), 8.45† (s, 2 H), 8.19 (s, 1 H), 7.55 (t, J = 7.6 Hz, 1 H), 7.41-7.30 (m, 1 H), 7.27-7.10 (m, 5 H), 7.03 (d, J = 7.3 Hz, 1 H), 6.94-6.81 (m, 3 H), 5.96 (dd, J = 9.4, 4.6 Hz, 1 H), 4.76-4.66 (m, 1 H), 4.64 (s, 1 H), 3.73 (s, 3 H), 3.69 (s, 3 H), 3.67-2.91 (m, 6 H), 2.71-2.12 (m, 5 H), 1.89-1.69 (m, 1 H), 1.60-1.06 (m, 5 H). * and † refer to different isomers. LCMS (Method 1): [MH+] = 752 at 2.50 min. |

| Ref. | Compound | Analytical Data |
| --- | --- | --- |
| Ex. 44 | 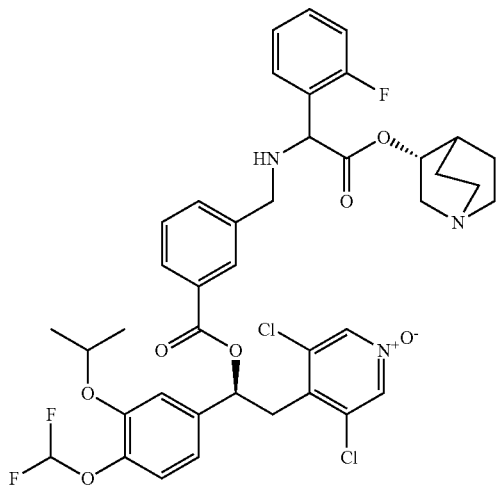<br>[(1S)-2-(3,5-dichloro-1-oxido-pyridin-1-ium-4-yl)-1-[4-(difluoromethoxy)-3-isopropoxy-phenyl]ethyl] 3-[[[1-(2-fluorophenyl)-2-oxo-2-[(3R)-quinuclidin-3-yl]oxy-ethyl)amino]methyl]benzoate formate salt | ¹H NMR (400 MHz, DMSO): δ 8.54* (s, 2 H), 8.53† (s, 2 H), 8.20 (s, 1 H), 7.96 (s, 1 H), 7.88 (d, J = 7.7 Hz, 1 H), 7.62-7.52 (m, 2 H), 7.47 (t, J = 7.7 Hz, 1 H), 7.41-7.32 (m, 1 H), 7.26-7.16 (m, 4 H), 7.07 (d, J = 8.2 Hz, 1 H), 7.03* (t, J = 74.7 Hz, 1 H), 7.03† (t, J = 74.7 Hz, 1 H), 6.22-6.16 (m, 1 H), 4.75-4.59 (m, 3 H), 3.82-3.71 (m, 2 H), 3.60 (dd, J = 15.4, 11.2 Hz, 1 H), 3.39-3.32 (m, 1 H), 3.12-2.96 (m, 1 H), 2.69-2.13 (m, 5 H), 1.87-1.70 (m, 1 H), 1.58-1.37 (m, 3 H), 1.29 (d, J = 6.0 Hz, 3 H), 1.22 (d, J = 6.1 Hz, 3 H), 1.20-1.17 (m, 1 H).<br>* and † refer to different isomers. LCMS (Method 1): [MH+] = 802 at 2.93 min. |
| Ex. 45 | 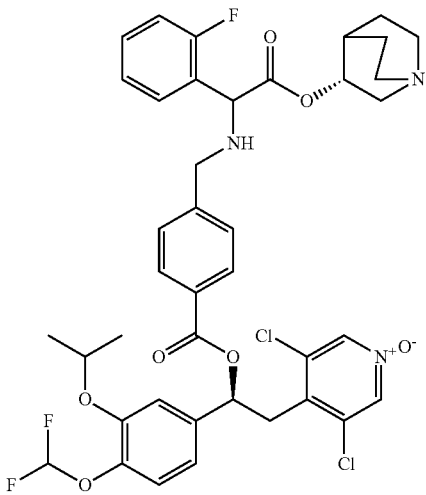<br>[(1S)-2-(3,5-dichloro-1-oxido-pyridin-1-ium-4-yl)-1-[4-(difluoromethoxy)-3-isopropoxy-phenyl]ethyl] 4-[[[1-(2-fluorophenyl)-2-oxo-2-[(3R)-quinuclidin-3-yl]oxy-ethyl]amino]methyl]benzoate formate salt | ¹H NMR (400 MHz, DMSO): δ 8.56 (s, 2 H), 8.20 (s, 1 H), 7.95 (dd, J = 8.0, 1.7 Hz, 2 H), 7.56 (t, J = 7.5 Hz, 1 H), 7.47 (d, J = 7.9 Hz, 2 H), 7.41-7.32 (m, 1 H), 7.26-7.17 (m, 4 H), 7.08 (dd, J = 8.3, 1.9 Hz, 1 H), 7.03 (t, J = 74.6 Hz, 1 H), 6.20 (dd, J = 9.2, 4.7 Hz, 1 H), 4.76-4.60 (m, 3 H), 3.83-3.72 (m, 2 H), 3.61 (dd, J = 14.9, 8.9 Hz, 1 H), 3.36 (dd, J = 14.1, 4.7 Hz, 1 H), 3.25-3.01 (m, 1 H), 2.70-2.14 (m, 5 H), 1.88-1.71 (m, 1 H), 1.60-1.38 (m, 3 H), 1.29 (d, J = 6.0 Hz, 3 H), 1.23 (d, J = 6.0 Hz, 3 H), 1.20-1.07 (m, 1 H). LCMS (Method 1): [MH+] = 802 at 2.90 min. |

| Ref. | Compound | Analytical Data |
|---|---|---|
| Ex. 46 | 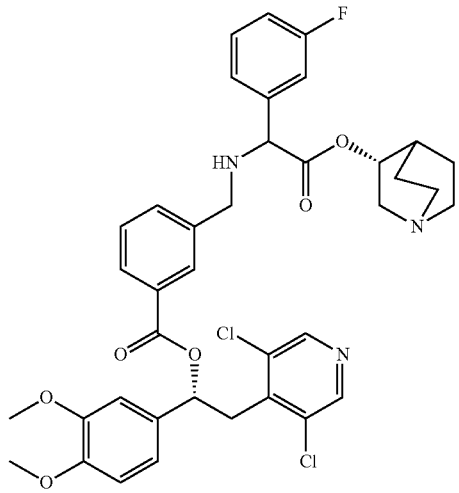 [SMILES: COc1ccc([C@@H](Cc2c(Cl)cncc2Cl)OC(=O)c2cccc(CNC(C(=O)O[C@H]3CN4CCC3CC4)c3cccc(F)c3)c2)cc1OC]<br>[(1R)-2-(3,5-dichloro-4-pyridyl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate formate salt | $^1$H NMR (400 MHz, DMSO): δ 8.57 (s, 2 H), 8.23 (s, 1 H), 7.94 (s, 1 H), 7.84 (d, J = 7.8 Hz, 1 H), 7.58 (d, J = 7.7 Hz, 1 H), 7.49-7.24 (m, 4 H), 7.18-7.11 (m, 1 H), 7.05-6.94 (m, 3 H), 6.59 (br s, 1 H), 6.28 (dt, J = 9.7, 3.4 Hz, 1 H), 4.70-4.64 (m, 1 H), 4.41 (d, J = 5.7 Hz, 1 H), 3.76 (s, 3 H), 3.75 (s, 3 H), 3.75-3.68 (m, 2 H), 3.42 (dd, J = 13.7, 4.5 Hz, 1 H), 3.08-2.93 (m, 3 H), 2.69-2.12 (m, 4 H), 1.89-1.70 (m, 1 H), 1.68-1.08 (m, 4 H). LCMS (Method 1): [MH+] = 722 at 2.86 min. |
| Ex. 47 | 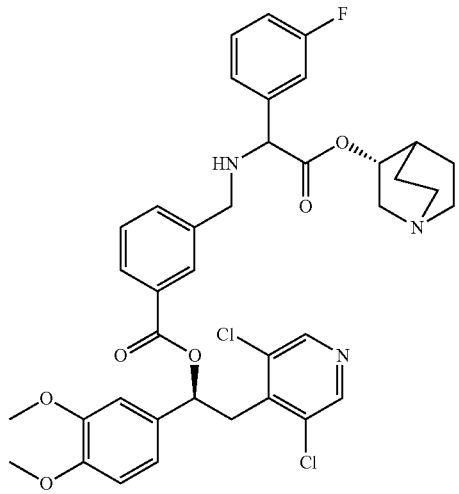 [SMILES: COc1ccc([C@H](Cc2c(Cl)cncc2Cl)OC(=O)c2cccc(CNC(C(=O)O[C@H]3CN4CCC3CC4)c3cccc(F)c3)c2)cc1OC]<br>[(1S)-2-(3,5-dichloro-4-pyridyl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate formate salt | $^1$H NMR (400 MHz, DMSO): δ 8.57 (s, 2 H), 8.24 (s, 1 H), 7.94 (s, 1 H), 7.84 (d, J = 7.8 Hz, 1 H), 7.58 (d, J = 7.5 Hz, 1 H), 7.48-7.24 (m, 4 H), 7.18-7.11 (m, 1 H), 7.06-6.95 (m, 3 H), 6.59 (br s, 1 H), 6.32-6.26 (m, 1 H), 4.72-4.63 (m, 1 H), 4.41 (d, J = 6.1 Hz, 1 H), 3.77 (s, 3 H), 3.75 (s, 3 H), 3.72 (q, J = 4.5 Hz, 2 H), 3.41 (dd, J = 13.9, 4.3 Hz, 1 H), 3.09-2.95 (m, 3 H), 2.69-2.13 (m, 4 H), 1.87-1.69 (m, 1 H), 1.67-1.07 (m, 4 H). LCMS (Method 1): [MH+] = 722 at 2.86 min. |

-continued

| Ref. | Compound | Analytical Data |
|---|---|---|
| Ex. 48 | 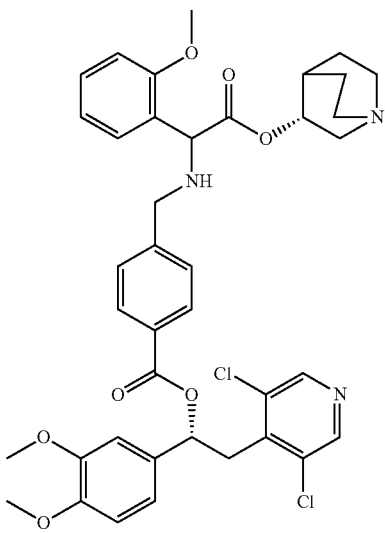 [SMILES: COc1ccc([C@@H](Cc2c(Cl)cncc2Cl)OC(=O)c2ccc(CNC(C(=O)O[C@H]3CN4CCC3CC4)c3ccccc3OC)cc2)cc1OC]<br>[(1R)-2-(3,5-dichloro-4-pyridyl)-1-(3,4-dimethoxyphenyl)ethyl] 4-[[[1-(2-methoxyphenyl)-2-oxo-2-[(3R)-quinuclidin-3-yl]oxy-ethyl]amino]methyl]benzoate formate salt | $^1$H NMR (400 MHz, DMSO): δ 8.59 (s, 2 H), 8.19 (s, 1 H), 7.90 (dd, J = 8.0, 1.7 Hz, 2 H), 7.44 (d, J = 8.0 Hz, 2 H), 7.38 (dt, J = 7.6, 1.8 Hz, 1 H), 7.32-7.24 (m, 1 H), 7.06-6.92 (m, 5 H), 6.56 (br s, 1 H), 6.29 (dd, J = 9.8, 4.2 Hz, 1 H), 4.73-4.61 (m, 1 H), 4.59 (s, 1 H), 3.79-3.70 (m, 11 H), 3.41 (dd, J = 13.5, 4.3 Hz, 1 H), 3.20-2.88 (m, 3 H), 2.70-2.16 (m, 4 H), 1.86-1.71 (m, 1 H), 1.60-1.08 (m. 4 H).<br>LCMS (Method 1): [MH+] = 734 at 2.59 min. |
| Ex. 49 | 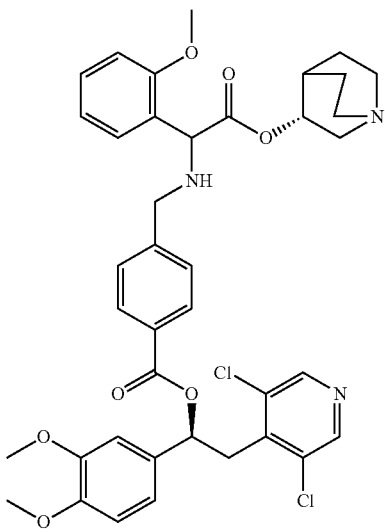 [SMILES: COc1ccc([C@H](Cc2c(Cl)cncc2Cl)OC(=O)c2ccc(CNC(C(=O)O[C@H]3CN4CCC3CC4)c3ccccc3OC)cc2)cc1OC]<br>[(1S)-2-(3,5-dichloro-4-pyridyl)-1-(3,4-dimethoxyphenyl)ethyl] 4-[[[1-(2-methoxyphenyl)-2-oxo-2-[(3R)-quinuclidin-3-yl]oxy-ethyl]amino]methyl]benzoate formate salt | $^1$H NMR (400 MHz, DMSO): δ 8.59 (s, 2 H), 8.20 (s, 1 H), 7.90 (d, J = 7.9 Hz, 2 H), 7.44 (dd, J = 7.9, 3.3 Hz, 2 H), 7.41-7.35 (m, 1 H), 7.32-7.24 (m, 1 H), 7.06-6.92 (m, 5 H), 6.54 (br s, 1 H), 6.29 (dd, J = 9.8, 4.3 Hz, 1 H), 4.73-4.62 (m, 1 H), 4.59 (d, J = 2.5 Hz, 1 H), 3.79-3.70 (m, 11 H), 3.41 (dd, J = 14.6, 4.9 Hz, 1 H), 3.19-2.88 (m, 3 H), 2.69-2.15 (m, 4 H), 1.86-1.71 (m, 1 H), 1.59-1.07 (m, 4 H). LCMS (Method 1): [MH+] = 734 at 2.59 min. |

| Ref. | Compound | Analytical Data |
|---|---|---|
| Ex. 50 | 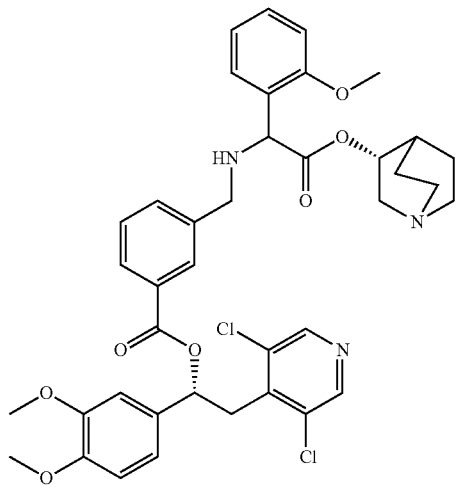 [SMILES: COc1ccc([C@@H](Cc2c(Cl)cncc2Cl)OC(=O)c2cccc(CNC(C(=O)O[C@H]3CN4CCC3CC4)c3ccccc3OC)c2)cc1OC]<br>[(1R)-2-(3,5-dichloro-4-pyridyl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate formate salt | $^1$H NMR (400 MHz, DMSO): δ 8.57 (s, 2 H), 8.18 (s, 1 H), 7.91 (s, 1 H), 7.84 (d, J = 7.7 Hz, 1 H), 7.57 (t, J = 5.8 Hz, 1 H), 7.45 (td, J = 7.7, 2.1 Hz, 1 H), 7.41-7.36 (m, 1 H), 7.31-7.25 (m, 1 H), 7.05-6.92 (m, 5 H), 6.55 (br s, 1 H), 6.28 (dd, J = 9.8, 4.3 Hz, 1 H), 4.72-4.63 (m, 1 H), 4.59 (d, J = 6.4 Hz, 1 H), 3.79-3.64 (m, 11 H), 3.41 (dd, J = 14.8, 4.9 Hz, 1 H), 3.16-2.90 (m, 3 H), 2.69-2.17 (m, 4 H), 1.86-1.71 (m, 1 H), 1.59-1.08 (m, 4 H). LCMS (Method 1): [MH+] = 734 at 2.54 min. |
| Ex. 51 | 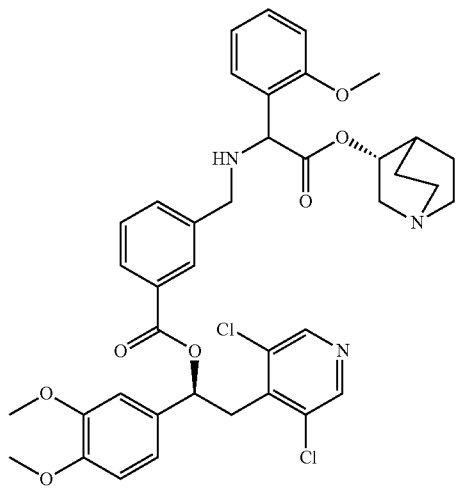 [SMILES: COc1ccc([C@H](Cc2c(Cl)cncc2Cl)OC(=O)c2cccc(CNC(C(=O)O[C@H]3CN4CCC3CC4)c3ccccc3OC)c2)cc1OC]<br>[(1S)-2-(3,5-dichloro-4-pyridyl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate format salt | $^1$H NMR (400 MHz, DMSO): δ 8.57 (s, 2 H), 8.20 (s, 1 H), 7.91 (s, 1 H), 7.83 (d, J = 7.7 Hz, 1 H), 7.57 (d, J = 7.7 Hz, 1 H), 7.45 (t, J = 7.6 Hz, 1 H), 7.41-7.35 (m, 1 H), 7.32-7.24 (m, 1 H), 7.05-6.91 (m, 5 H), 6.57 (br s, 1 H), 6.28 (dd, J = 9.6, 4.2 Hz, 1 H), 4.73-4.61 (m, 1 H), 4.58 (s, 1 H), 3.80-3.62 (m, 11 H), 3.41 (dd, J = 13.9, 4.3 Hz, 1 H), 3.19-2.85 (m, 3 H), 2.69-2.15 (m, 4 H), 1.84-1.71 (m, 1 H), 1.59-1.07 (m, 4 H). LCMS (Method 1): [MH+] = 734 at 2.58 min. |

| Ref. | Compound | Analytical Data |
|---|---|---|
| Ex. 52 | 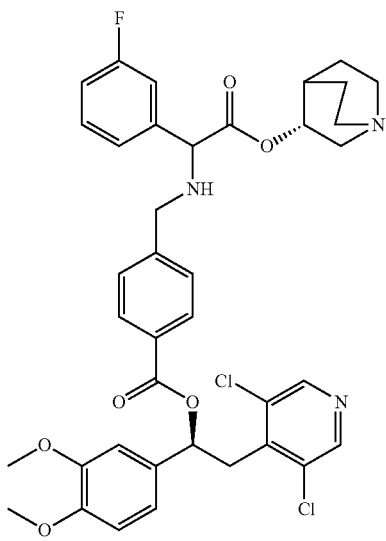 [SMILES: COc1ccc([C@H](Cc2c(Cl)cncc2Cl)OC(=O)c2ccc(CNC(C(=O)O[C@H]3CN4CCC3CC4)c3cccc(F)c3)cc2)cc1OC]<br>[(1S)-2-(3,5-dichloro-4-pyridyl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate formate salt | $^1$H NMR (400 MHz, DMSO): δ 8.59 (s, 2 H), 8.21 (s, 1 H), 7.91 (d, J = 7.9 Hz, 2 H), 7.49-7.21 (m, 5 H), 7.18-7.11 (m, 1 H), 7.03 (d, J = 9.9 Hz, 2 H), 6.97 (d, J = 8.1 Hz, 1 H), 6.59 (br s, 1 H), 6.29 (dd, J = 9.8, 4.2 Hz, 1 H), 4.72-4.63 (m, 1 H), 4.42 (d, J = 3.4 Hz, 1 H), 3.78 (s, 3 H), 3.75 (s, 3 H), 3.75-3.68 (m, 2 H), 3.42 (dd, J = 13.8, 4.5 Hz, 1 H), 3.12-2.92 (m, 3 H), 2.70- 2.12 (m, 4H), 1.89-1.69 (m, 1 H), 1.60-1.10 (m, 4 H).<br>LCMS (Method 1): [MH+] = 722 at 2.89 min. |
| Ex. 53 | 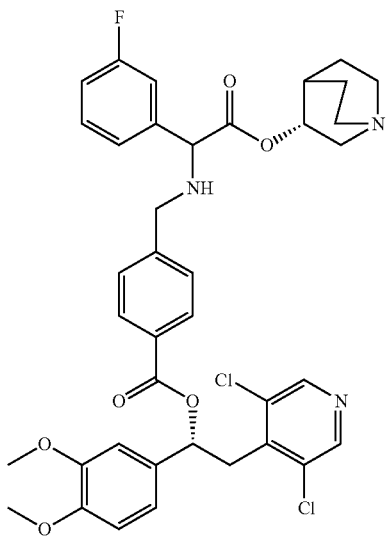 [SMILES: COc1ccc([C@@H](Cc2c(Cl)cncc2Cl)OC(=O)c2ccc(CNC(C(=O)O[C@H]3CN4CCC3CC4)c3cccc(F)c3)cc2)cc1OC]<br>[(1R)-2-(3,5-dichloro-4-pyridyl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate formate salt | $^1$H NMR (400 MHz, DMSO): δ 8.59 (s, 2 H), 8.19 (s, 1 H), 7.91 (d, J = 8.0 Hz, 2 H), 7.48-7.24 (m, 5 H), 7.18-7.11 (m, 1 H), 7.03 (d, J = 10.2 Hz, 2 H), 6.97 (d, J = 8.1 Hz, 1 H), 6.55 (br s, 1 H), 6.29 (dd, J = 9.8, 4.3 Hz, 1 H), 4.73-4.63 (m, 1 H), 4.42 (s, 1 H), 3.78 (s, 3 H), 3.75 (s, 3 H), 3.75-3.68 (m, 2 H), 3.41 (dd, J = 13.9, 4.0 Hz, 1 H), 3.11-2.95 (m, 3 H), 2.71-2.13 (m, 4 H), 1.88-1.70 (m, 1 H), 1.60-1.11 (m, 4 H). LCMS (Method 1): [MH+] = 722 at 2.88 min. |

Compounds herebelow reported were prepared as mixtures of diastereoisomers starting from the appropriate aniline and the appropriate phenylboronic acid according to the procedure described in Example 3.

| Ref. | Compound | Analytical Data |
|---|---|---|
| Ex. 54 | 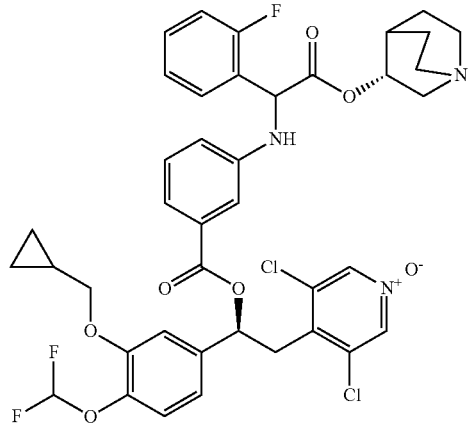<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-fluorophenyl)-2-oxo-2-[(3R)-quinuclidin-3-yl]oxy-ethyl]amino]benzoate trifluoroacetate salt | $^1$H NMR (300 MHz, DMSO) δ 9.36 and 9.50 (br. s., 1 H), 8.52 and 8.54 (s, 2 H), 7.49-7.62 (m, 1 H), 7.36-7.49 (m, 1 H), 6.94-7.12 (m, 3 H), 6.78-7.37 (m, 7 H), 6.63-6.86 (m, 1 H), 6.09-6.30 (m, 1 H), 5.62 (d, 1 H), 4.85-5.18 (m, 1 H), 3.87-3.98 (m, 2 H), 3.46-3.79 (m, 2 H), 3.06-3.40 (m, 5 H), 2.78-2.93 (m, 1 H), 1.97-2.11 and 2.20-2.30 (m, 1 H), 1.37-1.97 (m, 4 H), 1.11-1.37 (m, 1 H), 0.45-0.68 (m, 2 H), 0.18-0.45 (m, 2 H).<br>LCMS (Method 1): [MH+] = 800 at 3.11 min. |
| Ex. 55 | 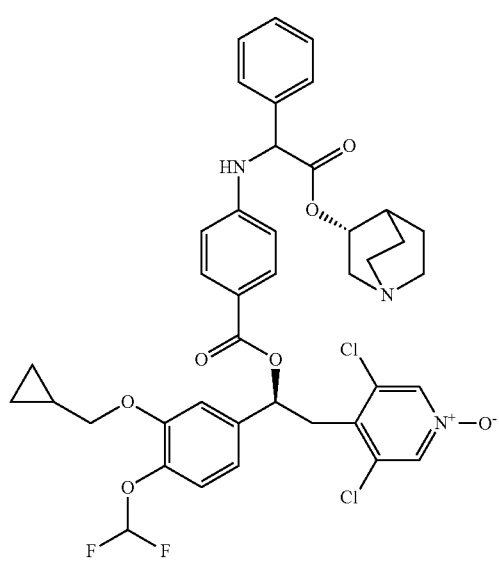 [SMILES: O=C(O[C@@H](Cc1c(Cl)c[n+]([O-])cc1Cl)c1ccc(OC(F)F)c(OCC2CC2)c1)c1ccc(NC(C(=O)O[C@H]2CN3CCC2CC3)c2ccccc2)cc1]<br>[(1S)-1-[3-(cyclopropylmethoxy)-4-(difluoromethoxy)phenyl]-2-(3,5-dichloro-1-oxido-pyridin-1-ium-4-yl)ethyl] 4-[[2-oxo-1-phenyl-2-[(3R)-quinuclidin-3-yl]oxy-ethyl]amino]benzoate | $^1$H NMR (300 MHz, DMSO) δ 8.53 (s, 2 H), 6.96-7.80 (m, 12 H), 6.72-6.85 (m, 2 H), 6.15 (dd, 1 H), 5.33-5.64 (m, 1 H), 4.61-4.86 (m, 1 H), 3.91 (d, 2 H), 3.55 (dd, 1 H), 3.33-3.40 (m, 1 H), 2.90-3.21 (m, 1 H), 2.57-2.68 (m, 4 H), 2.02-2.41 (m, 1 H), 0.90-1.97 (m, 6 H), 0.49-0.64 (m, 2 H), 0.22-0.43 (m, 2 H).<br>LCMS (Method 1): [MH+] = 782 at 3.10 min. |

| Ref. | Compound | Analytical Data |
|---|---|---|
| Ex. 56 | 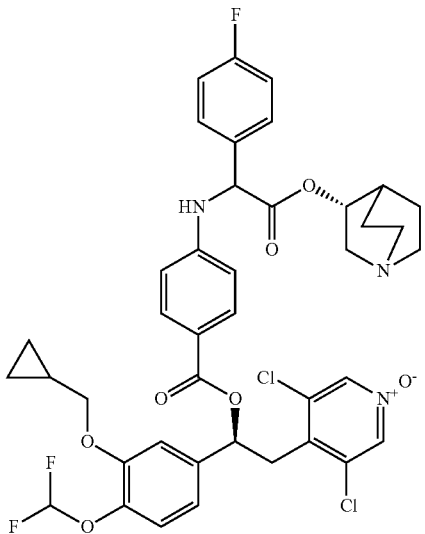<br>[(1S)-1-[3-(cyclopropylmethoxy)-4-(difluoromethoxy)phenyl]-2-(3,5-dichloro-1-oxido-pyridin-1-ium-4-yl)ethyl] 4-[[1-(4-fluorophenyl)-2-oxo-2-[(3R)-quinuclidin-3-yl]oxy-ethyl]amino]benzoate trifluoroacetate salt | $^1$H NMR (300 MHz, DMSO) δ 9.44 and 9.58 (br. s., 1 H), 8.53 (s, 2 H), 7.69-7.80 (m, 2 H), 7.51-7.64 (m, 2 H), 6.79-7.35 (m, 7 H), 6.68-6.82 (m, 2 H), 6.04-6.23 (m, 1H), 5.48 and 5.54 (d, 1 H), 4.95-5.17 (m, 1 H), 3.91 (d, 2 H), 3.60-3.77 (m, 1 H), 3.55 (dd, 1 H), 3.30 (dd, 1 H), 3.02-3.26 (m, 4 H), 2.76-2.90 (m, 1 H), 2.00-2.11 and 2.21-2.31 (m, 1 H), 1.32-1.99 (m, 4 H), 1.07-1.34 (m, 1 H), 0.47-0.69 (m, 2 H), 0.25-0.39 (m, 2 H). LCMS (Method 1): [MH+] = 800 at 3.1 min. |
| Ex. 57 | 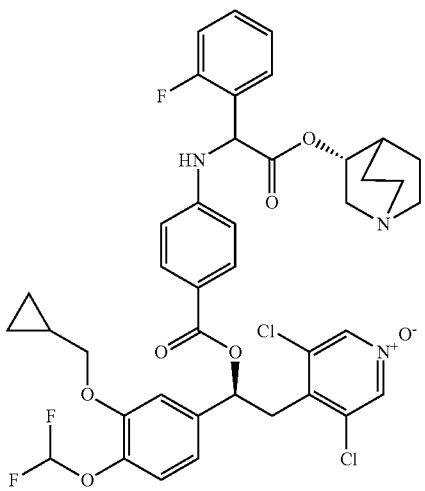<br>[(1S)-1-[3-(cyclopropylmethoxy)-4-(difluoromethoxy)phenyl]-2-(3,5-dichloro-1-oxido-pyridin-1-ium-4-yl)ethyl] 4-[[1-(2-fluorophenyl)-2-oxo-2-[(3R)-quinuclidin-3-yl]oxy-ethyl]amino]benzoate trifluoroacetate salt | $^1$H NMR (300 MHz, DMSO) δ 9.43 and 9.56 (br. s., 1 H), 8.53 and 8.54 (s, 2 H), 7.67-7.78 (m, 2 H), 7.37-7.61 (m, 2 H), 7.04 (dd, 1 H), 6.78-7.36 (m, 7 H), 6.70-6.86 (m, 2 H), 5.66 and 5.69 (d, 1 H), 5.00-5.24 (m, 1 H), 3.91 (d, 2 H), 3.62-3.77 (m, 1 H), 3.55 (dd, 1 H), 3.30 (dd, 1 H), 2.69-3.24 (m, 5 H), 1.98-2.13 and 2.22-2.32 (m, 1 H), 1.39-1.99 (m, 4 H), 1.08-1.35 (m, 1 H), 0.48-0.65 (m, 2 H), 0.26-0.44 (m, 2 H). LCMS (Method 1): [MH+] = 800 at 3.10 min. |

| Ref. | Compound | Analytical Data |
|---|---|---|
| Ex. 58 | 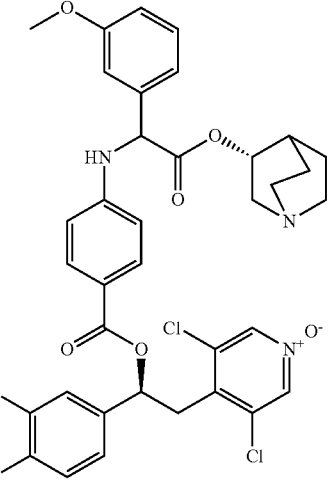<br>[(1S)-1-[3-(cyclopropylmethoxy)-4-(difluoromethoxy)phenyl]-2-(3,5-dichloro-1-oxido-pyridin-1-ium-4-yl)ethyl] 4-[[1-(3-methoxyphenyl)-2-oxo-2-[(3R)-quinuclidin-3-yl]oxy-ethyl]amino]benzoate trifluoroacetate salt | $^1$H NMR (300 MHz, DMSO) δ ppm 9.41 and 9.54 (br. s., 1 H), 8.53 and 8.54 (s, 2 H), 7.63-7.81 (m, 2 H), 7.32 and 7.34 (t, 1 H), 6.89-6.97 (m, 1 H), 6.79-7.31 (m, 7 H), 6.69-6.79 (m, 2 H), 6.07-6.23 (m, 1 H), 5.41 and 5.46 (d, 1 H), 4.93-5.20 (m, 1 H), 3.91 (d, 2 H), 3.76 and 3.77 (s, 3 H), 3.60-3.72 (m, 1 H), 3.55 (dd, 1 H), 3.30 (dd, 1 H), 3.02-3.26 (m, 4 H), 2.70-2.86 (m, 1 H), 1.98-2.09 (m, 1 H), 1.41-1.99 (m, 4 H), 1.03-1.32 (m, 1 H), 0.47-0.64 (m, 2 H), 0.14-0.43 (m, 2 H). LCMS (Method 1): [MH+] = 812 at 3.11 min. |
| Ex. 59 | 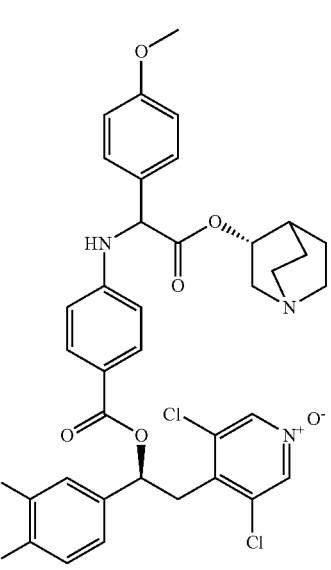<br>[(1S)-1-[3-(cyclopropylmethoxy)-4-(difluoromethoxy)phenyl]-2-(3,5-dichloro-1-oxido-pyridin-1-ium-4-yl)ethyl] 4-[[1-(4-methoxyphenyl)-2-oxo-2-[(3R)-quinuclidin-3-yl]oxy-ethyl]amino]benzoate trifluoroacetate salt | $^1$H NMR (300 MHz, DMSO) δ 9.54 and 9.67 (br. s., 1 H), 8.53 and 8.54 (s, 2 H), 7.72 (m, 2 H), 7.40-7.53 (m, 2 H), 6.79-7.39 (m, 7 H), 6.75 (m, 2 H), 6.06-6.26 (m, 1 H), 5.35 and 5.40 (d, 1 H), 4.96-5.12 (m, 1 H), 3.91 (d, 2 H), 3.75 and 3.76 (s, 3 H), 3.60-3.72 (m, 1 H), 3.55 (dd, 1 H), 3.30 (dd, 1 H), 3.00-3.25 (m, 4 H), 2.68-2.90 (m, 1 H), 1.97-2.10 and 2.21-2.31 (m, 1 H), 1.41-1.99 (m, 4 H), 1.02-1.28 (m, 1 H), 0.48-0.64 (m, 2 H), 0.12-0.43 (m, 2 H). LCMS (Method 1): [MH+] = 812 at 3.11 min. |

| Ref. | Compound | Analytical Data |
|---|---|---|
| Ex. 60 | 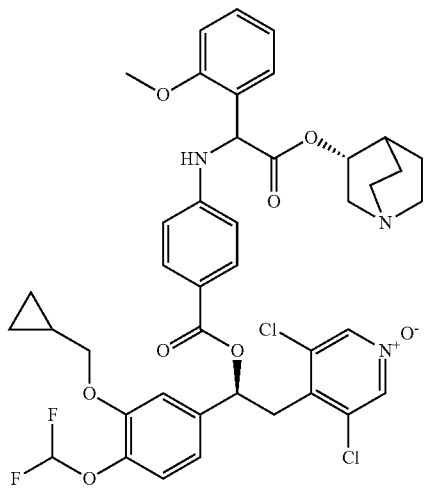<br>[(1S)-1-[3-(cyclopropylmethoxy)-4-(difluoromethoxy)phenyl]-2-(3,5-dichloro-1-oxido-pyridin-1-ium-4-yl)ethyl] 4-[[1-(2-methoxyphenyl)-2-oxo-2-[(3R)-quinuclidin-3-yl]oxy-ethyl]amino]benzoate trifluoroacetate salt | $^1$H NMR (300 MHz, DMSO) δ 9.47 and 9.55 (br. s., 1 H), 8.53 and 8.54 (s, 2 H), 7.62-7.86 (m, 2 H), 7.31-7.47 (m, 2 H), 6.78-7.31 (m, 7 H), 6.67-6.78 (m, 2 H), 6.07-6.29 (m, 1 H), 5.59 and 5.61 (br. s., 1 H), 4.95-5.17 (m, 1 H), 3.92 (d, 2 H), 3.86 (s, 3 H), 3.61-3.74 (m, 1 H), 3.55 (dd, 1 H), 3.30 (dd, 1 H), 2.94-3.25 (m, 4 H), 2.60-2.89 (m, 1 H), 1.97-2.06 and 2.19-2.31 (m, 1 H), 1.34-1.98 (m, 4 H), 1.00-1.29 (m, 1 H), 0.46-0.70 (m, 2 H), 0.12-0.43 (m, 2 H). LCMS (Method 1): [MH+] = 812 at 3.12 min. |
| Ex. 61 | 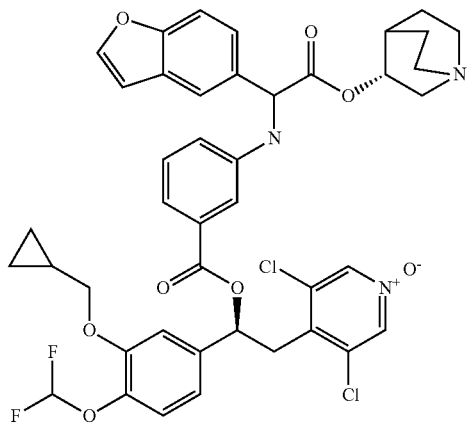<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(benzofuran-5-yl)-2-oxo-2-[(3R)-quinuclidin-3-yl]oxy-ethyl]amino]benzoate trifluoroacetate salt | $^1$H NMR (300 MHz, DMSO) δ 9.38 and 9.54 (br. s., 1 H), 8.53 and 8.55 (s, 2 H), 8.01 and 8.03 (d, 1 H), 7.83 (s, 1 H), 7.63 and 7.64 (d, 1 H), 7.47-7.56 (m, 1 H), 7.31 (d, 1 H), 7.19-7.29 (m, 2 H), 7.11-7.19 (m, 2 H), 6.79-7.11 (m, 4 H), 6.79 (br. s., 1 H), 6.18 (dd, 1 H), 5.44 and 5.48 (d, 1 H), 4.97-5.12 (m, 1 H), 3.91 and 3.93 (d, 2 H), 3.47-3.76 (m, 2 H), 3.33 (dd, 1 H), 2.96-3.25 (m, 4 H), 2.65-2.82 (m, 1 H), 1.97-2.06 and 2.20-2.30 (m, 1 H), 1.57-1.97 (m, 3 H), 1.36-1.57 (m, 1 H), 1.10-1.29 (m, 1 H), 0.50-0.64 (m, 2 H), 0.28-0.40 (m, 2 H). LCMS (Method 1): [MH+] = 822 at 3.15 min. |

-continued

| Ref. | Compound | Analytical Data |
|---|---|---|
| Ex. 62 | 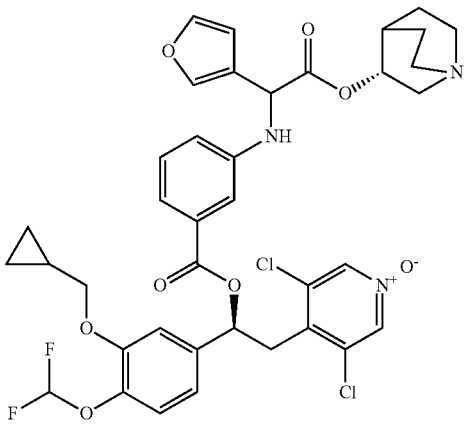<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-furyl)-2-oxo-2-[(3R)-quinuclidin-3-yl]oxy-ethyl]amino]benzoate trifluoroacetate salt | $^1$H NMR (300 MHz, DMSO) δ 9.44 and 9.52 (br. s., 1 H), 8.55 and 8.56 (s, 2 H), 7.81 (s, 1 H), 7.69 and 7.70 (dd, 1 H), 7.25-7.37 (m, 2 H), 7.22 (d, 1 H), 7.19 (d, 1 H), 7.04-7.12 (m, 2 H), 6.93-7.04 (m, 1 H), 7.07 (t, 1 H), 6.63 (dd, 1 H), 6.52-6.61 (m, 1 H), 6.13-6.25 (m, 1 H), 5.32 and 5.36 (d, 1 H), 4.90-5.16 (m, 1 H), 3.93 (d, 2 H), 3.53-3.76 (m, 2 H), 3.34 (dd, 1 H), 3.01-3.27 (m, 4 H), 2.77-2.96 (m, 1 H), 2.02-2.14 and 2.16-2.26 (m, 1 H), 1.44-1.98 (m, 4 H), 1.11-1.35 (m, 1 H), 0.47-0.67 (m, 2 H), 0.23-0.42 (m, 2 H). LCMS (Method 1): [MH+] = 772 at 3.08 min. |
| Ex. 63 | 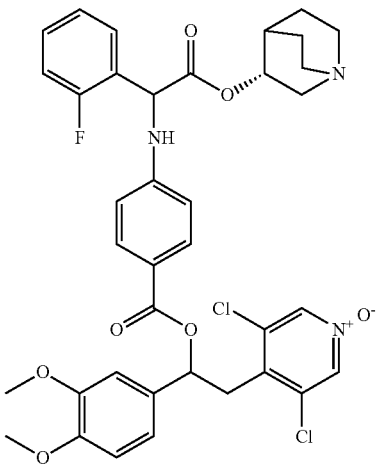<br>[2-(3,5-dichloro-1-oxido-pyridin-1-ium-4-yl)-1-(3,4-dimethoxyphenyl)ethyl] 4-[[1-(2-fluorophenyl)-2-oxo-2-[(3R)-quinuclidin-3-yl]oxy-ethyl]amino]benzoate trifluoroacetate salt | $^1$H NMR (300 MHz, DMSO) δ 9.40 and 9.52 (br. s., 1 H), 8.53 (s, 2 H), 7.65-7.82 (m, 2 H), 7.19-7.61 (m, 5 H), 6.89-7.08 (m, 3 H), 6.67-6.86 (m, 2 H), 6.06-6.27 (m, 1 H), 5.54-5.79 (m, 1 H), 4.97-5.23 (m, 1 H), 3.77 (s, 3 H), 3.75 (s, 3 H), 3.53-3.71 (m, 2 H), 3.29 (dd, 1 H), 2.71-3.23 (m, 5 H), 1.98-2.12 (m, 1 H), 1.37-1.98 (m, 4 H).<br>LCMS (Method 1): [MH+] = 724 at 2.81 min. |

| Ref. | Compound | Analytical Data |
|---|---|---|
| Ex. 64 | 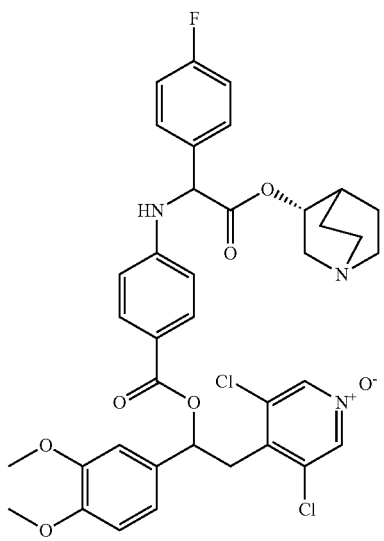<br>[2-(3,5-dichloro-1-oxido-pyridin-1-ium-4-yl)-1-(3,4-dimethoxyphenyl)ethyl] 4-[[1-(4-fluorophenyl)-2-oxo-2-[(3R)-quinuclidin-3-yl]oxy-ethyl]amino]benzoate trifluoroacetate salt | $^1$H NMR (300 MHz, DMSO) δ 9.37 and 9.51 (br. s., 1 H), 8.53 (s, 2 H), 7.66-7.80 (m, 2 H), 7.51-7.65 (m, 2 H), 7.16-7.36 (m, 3 H), 6.88-7.08 (m, 3 H), 6.66-6.82 (m, 2 H), 6.01-6.25 (m, 1 H), 5.39-5.62 (m, 1 H), 4.97-5.15 (m, 1 H), 3.77 (s, 3 H), 3.74 (s, 3 H), 3.55-3.70 (m, 2 H), 2.97-3.35 (m, 5 H), 2.22-2.33 and 2.75-2.86 (m, 1 H), 2.05 (m, 1 H), 1.36-1.98 (m, 4 H). LCMS (Method 1): [MH+] = 724 at 2.83 min. |
| Ex. 65 | 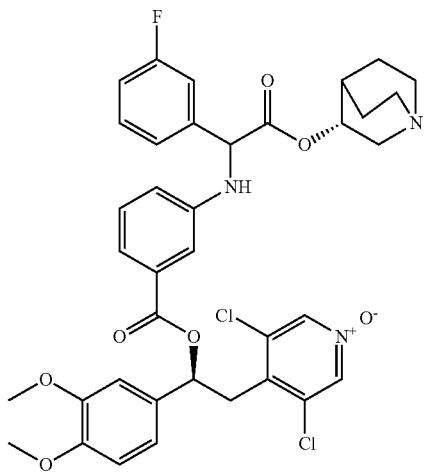<br>[(1S)-2-(3,5-dichloro-1-oxido-pyridin-1-ium-4-yl)-1-(3,4-dimethoxyphenyl)ethyl] 3-[[1-(3-fluorophenyl)-2-oxo-2-[(3R)-quinuclidin-3-yl]oxy-ethyl]amino]benzoate trifluoroacetate salt | $^1$H NMR (300 MHz, DMSO) δ 9.45 and 9.58 (br. s., 1 H), 8.53 and 8.54 (s, 2 H), 7.35-7.58 (m, 3 H), 7.12-7.35 (m, 4 H), 6.90-7.06 (m, 4 H), 6.66-6.89 (m, 1 H), 5.98-6.28 (m, 1 H), 5.45 and 5.48 (d, 1 H), 4.93-5.16 (m, 1 H), 3.79 (s, 3 H), 3.76 and 3.77 (s, 3 H), 3.49-3.71 (m, 2 H), 3.00-3.40 (m, 5 H), 2.75-2.87 (m, 1 H), 2.00-2.12 and 2.20-2.30 (m, 1 H), 1.39-1.97 (m, 4 H). LCMS (Method 1): [MH+] = 724 at 2.83 min. |

| Ref. | Compound | Analytical Data |
|---|---|---|
| Ex. 66 | 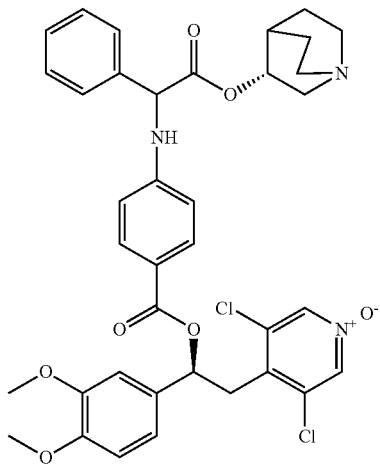<br>[(1S)-2-(3,5-dichloro-1-oxido-pyridin-1-ium-4-yl)-1-(3,4-dimethoxyphenyl)ethyl] 4-[[2-oxo-1-phenyl-2-[(3R)-quinuclidin-3-yl]oxy-ethyl]amino]benzoate trifluoroacetate salt | $^1$H NMR (300 MHz, DMSO) δ 8.52 and 8.53 (s, 2 H), 7.66-7.83 (m, 2 H), 7.48-7.60 (m, 2 H), 7.30-7.47 (m, 3 H), 7.26 (d, 1 H), 6.90-7.06 (m, 3 H), 6.67-6.84 (m, 2 H), 6.02-6.27 (m, 1 H), 5.43 and 5.49 (d, 1 H), 4.92-5.17 (m, 1 H), 3.76 (s, 3 H), 3.74 (s, 3 H), 3.48-3.67 (m, 2 H), 3.02-3.38 (m, 5 H), 2.67-2.85 (m, 1 H), 1.98-2.07 and 2.22-2.33 (m, 1 H), 1.30-1.96 (m, 4 H). LCMS (Method 1): [MH+] = 706 at 2.80 min. |
| Ex. 67 | 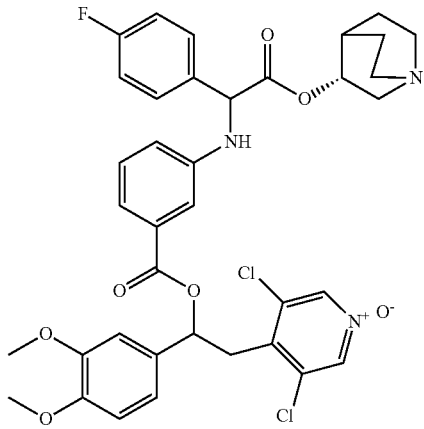<br>[2-(3,5-dichloro-1-oxido-pyridin-1-ium-4-yl)-1-(3,4-dimethoxyphenyl)ethyl] 3-[[1-(4-fluorophenyl)-2-oxo-2-[(3R)-quinuclidin-3-yl]oxy-ethyl]amino]benzoate trifluoroacetate salt | $^1$H NMR (300 MHz, DMSO) δ 9.40 and 9.55 (br. s., 1 H), 8.54 (s, 2 H), 7.47-7.68 (m, 2 H), 7.15-7.38 (m, 5 H), 6.86-7.07 (m, 4 H), 6.76 (br. s., 1 H), 6.06-6.35 (m, 1 H), 5.26-5.53 (m, 1 H), 4.90-5.18 (m, 1 H), 3.77 and 3.79 (s, 3 H), 3.76 (s, 3 H), 3.48-3.69 (m, 2 H), 2.99-3.41 (m, 5 H), 2.68-2.85 (m, 1 H), 1.99-2.06 and 2.19-2.30 (m, 1 H), 1.40-1.97 (m, 4 H). LCMS (Method 1): [MH+] = 724 at 2.84 min. |

Compounds herebelow reported were prepared as mixtures of diastereoisomers according to analogous procedures as those hereabove described in Example 13, starting from the appropriate analogs of Intermediate 22.

| Ref. | Compound | Analytical Data |
|---|---|---|
| Ex. 68 | 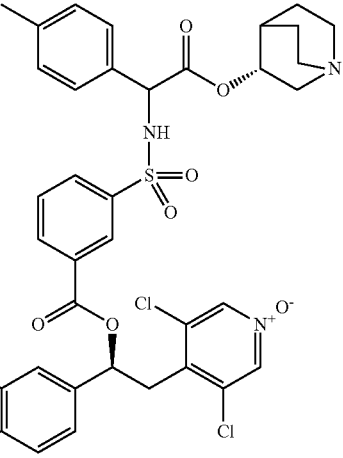<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-(p-tolyl)-2-[(3R)-quinuclidin-3-yl]oxy-ethyl]sulfamoyl]benzoate trifluoroacetate salt | $^1$H NMR (300 MHz, DMSO) δ 9.35-9.64 (m, 1 H), 9.06 (d, 1 H), 8.55 (s, 2 H), 8.05-8.23 (m, 2 H), 7.89-8.04 (m, 1 H), 7.67 (t, 1 H), 6.85-7.29 (m, 7 H), 7.08 (t, 1 H), 6.10-6.30 (m, 1 H), 5.10 (d, 1 H), 4.77-4.99 (m, 1 H), 3.86-4.03 (m, 2 H), 3.58-3.72 (m, 1 H), 3.28-3.41 (m, 1 H), 3.00-3.27 (m, 4 H), 2.86-3.00 (m, 1 H), 2.80 (m, 1 H), 2.14 (s, 3 H), 1.89-2.00 (m, 1 H), 1.68-1.88 (m, 2 H), 1.55-1.68 (m, 1 H), 1.49 (t, 1 H), 1.14-1.32 (m, 1 H), 0.49-0.67 (m, 2 H), 0.19-0.44 (m, 2 H). LCMS (Method 1): [MH+] = 860 at 3.08 min. |
| Ex. 69 | 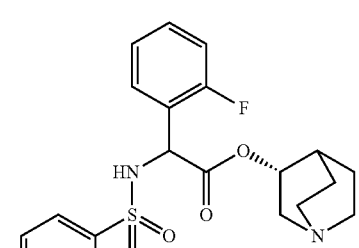<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-fluorophenyl)-2-oxo-2-[(3R)-quinuclidin-3-yl]oxy-ethyl]sulfamoyl]benzoate trifluoroacetate salt | $^1$H NMR (300 MHz, DMSO) δ 9.45 and 9.53 (br. s., 1 H), 9.18 and 9.19 (d, 1 H), 8.55 and 8.56 (s, 2 H), 8.08 and 8.22 (t, 1 H), 7.92 and 8.13 (dt, 1 H), 7.58 and 7.65 (t, I H), 7.65 (t, 1 H), 6.80-7.39 (m, 7 H), 7.09 (t, 1 H), 6.13-6.27 (m, 1 H), 5.40 and 5.46 (d, I H), 4.86-5.06 (m, I H), 3.97 (dd, 1 H), 3.93 (dd, 1 H), 3.54-3.75 (m, 2 H), 3.37 (dd, I H), 2.95-3.26 (m, 4 H), 2.78-2.93 (m, 1 H), 1.91-2.00 and 2.06-2.19 (m, I H), 1.32-1.88 (m, 4 H), 1.09-1.30 (m, 1 H), 0.46-0.70 (m, 2 H), 0.21-0.43 (m, 2 H). LCMS (Method 1): [MH+] = 864 at 3.04 min. |

| Ref. | Compound | Analytical Data |
|---|---|---|
| Ex. 70 | 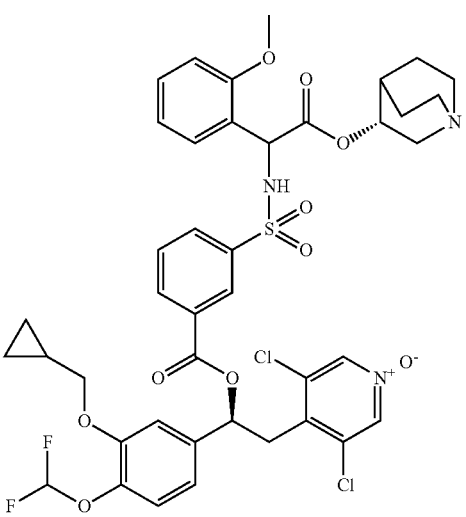<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-methoxyphenyl)-2-oxo-2-[(3R)-quinuclidin-3-yl]oxy-ethyl]sulfamoyl]benzoate trifluoroacetate salt | $^1$H NMR (300 MHz, DMSO) δ 9.49 (br. s., 1 H), 8.80 and 8.83 (d, 1 H), 8.55 and 8.56 (s, 2 H), 8.19 (t, 1 H), 8.04-8.16 (m, 1 H), 7.84-8.00 (m, 1 H), 7.59 and 7.64 (t, 1 H), 6.81-7.38 (m, 6 H), 6.59-6.81 (m, 2 H), 6.09-6.31 (m, 1 H), 5.35 and 5.39 (d, 1 H), 4.87-5.06 (m, 2 H), 3.95 (d, 2 H), 3.65 (dd, 1 H), 3.53-3.63 (m, 1 H), 3.50 and 3.55 (s, 3 H), 3.37 (dd, 1 H), 2.90-3.30 (m, 3 H), 2.68-2.90 (m, 1 H), 1.90-2.02 and 2.10-2.28 (m, 1 H), 1.38-1.91 (m, 4 H), 1.06-1.31 (m, 1 H), 0.49-0.70 (m, 2 H), 0.22-0.44 (m, 2 H). LCMS (Method 1): [MH+] = 876 at 3.05 min. |
| Ex. 71 | 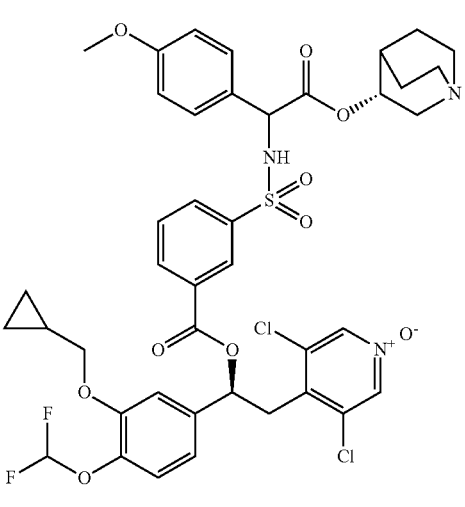<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-methoxyphenyl)-2-oxo-2-[(3R)-quinuclidin-3-yl]oxy-ethyl]sulfamoyl]benzoate trifluoroacetate salt | $^1$H NMR (300 MHz, DMSO) δ 9.42 and 9.49 (br. s., 1 H), 9.02 and 9.04 (d, 1 H), 8.54 and 8.56 (s, 2 H), 8.20 and 8.23 (t, 1 H), 8.05-8.17 (m, 1 H), 7.87-8.03 (m, 1 H), 7.60 and 7.67 (t, 1 H), 6.81-7.39 (m, 6 H), 6.53-6.68 and 6.70-6.78 (m, 2 H), 6.14-6.28 (m, 1 H), 5.07 and 5.10 (d, 1 H), 4.76-4.98 (m, 1 H), 3.95 (d, 2 H), 3.59 and 3.65 (s, 3 H), 2.75-3.58 (m, 8 H), 1.89-1.99 and 2.00-2.11 (m, 1 H), 1.42-1.89 (m, 4 H), 1.03-1.33 (m, 1 H), 0.50-0.65 (m, 2 H), 0.21-0.45 (m, 2 H). LCMS (Method 1): [MH+] = 876 at 3.03 min. |

| Ref. | Compound | Analytical Data |
|---|---|---|
| Ex. 72 | 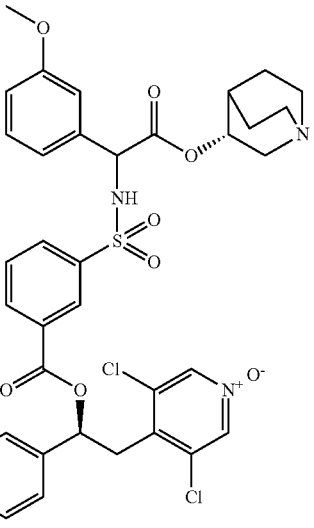 [(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-methoxyphenyl)-2-oxo-2-[(3R)-quinuclidin-3-yl]oxy-ethyl]sulfamoyl]benzoate trifluoroacetate salt | $^1$H NMR (300 MHz, DMSO) δ 9.46 and 9.54 (br. s., 1 H), 9.07 and 9.10 (d, 1 H), 8.55 and 8.57 (s, 2 H), 8.18 and 8.21 (t, 1 H), 8.05 and 8.14 (dt, 1 H), 7.89 and 7.98 (ddd, 1 H), 7.55 and 7.68 (t, 1 H), 6.79-7.39 (m, 5 H), 6.54-6.89 (m, 3 H), 6.11-6.30 (m, 1 H), 5.13 and 5.16 (d, 1 H), 4.83-5.02 (m, 1 H), 3.86-4.03 (m, 2 H), 3.64 (dd, 1 H), 3.54-3.59 (m, 1 H), 3.52 and 3.60 (s, 3 H), 3.30-3.43 (m, 1 H), 2.76-3.27 (m, 5 H), 1.89-2.02 and 2.05-2.15 (m, 1 H), 1.37-1.88 (m, 4 H), 1.06-1.32 (m, 1 H), 0.48-0.66 (m, 2 H), 0.25-0.41 (m, 2 H). LCMS (Method 1): [MH+] = 876 at 3.04 min. |
| Ex. 73 | 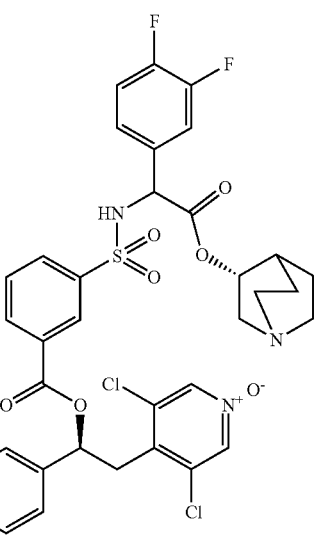 [(1S)-1-[3-(cyclopropylmethoxy)-4-(difluoromethoxy)phenyl]-2-(3,5-dichloro-1-oxido-pyridin-1-ium-4-yl)ethyl] 3-[[1-(3,4-difluorophenyl)-2-oxo-2-[(3R)-quinuclidin-3-yl]oxy-ethyl]sulfamoyl]benzoate trifluoroacetate salt | $^1$H NMR (300 MHz, DMSO) δ 9.40 and 9.51 (br. s., 1 H), 9.16 and 9.17 (d, 1 H), 8.54 and 8.56 (s, 2 H), 8.18-8.23 (m, 1 H), 8.11 and 8.16 (dt, 1 H), 7.92 and 7.98 (ddd, 1 H), 7.61 and 7.67 (t, 1 H), 6.74-7.43 (m, 7 H), 6.07-6.31 (m, 1 H), 5.29 and 5.31 (d, 1 H), 4.77-5.05 (m, 1 H), 3.88-4.06 (m, 2 H), 3.51-3.71 (m, 2 H), 3.37 (dd, 1 H), 2.78-3.29 (m, 5 H), 1.91-2.02 and 2.03-2.13 (m, 1 H), 1.38-1.88 (m, 4 H), 1.06-1.31 (m, 1 H), 0.49-0.68 (m, 2 H), 0.19-0.44 (m, 2 H). LCMS (Method 1): [MH+] = 882 at 3.09 min. |

| Ref. | Compound | Analytical Data |
|---|---|---|
| Ex. 74 | 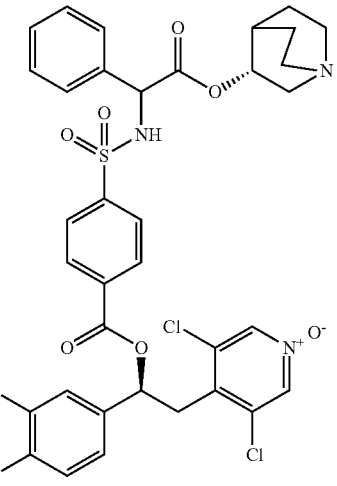<br><br>[(1S)-1-[3-(cyclopropylmethoxy)-4-(difluoromethoxy)phenyl]-2-(3,5-dichloro-1-oxido-pyridin-1-ium-4-yl)ethyl] 4-[[2-oxo-1-phenyl-2-[(3R)-quinuclidin-3-yl]oxy-ethyl]sulfamoyl]benzoate trifluoroacetate salt | $^1$H NMR (300 MHz, DMSO) δ 9.58 and 9.62 (br. s., 1 H), 9.18 and 9.19 (d, 1 H), 8.56 and 8.57 (s, 2 H), 7.95-8.14 (m, 2 H), 7.73-7.91 (m, 2 H), 7.17-7.43 (m, 7 H), 7.09-7.16 (m, 1 H), 7.07 (t, 1 H), 6.07-6.33 (m, 1 H), 5.17 and 5.23 (d, 1 H), 4.85-5.02 (m, 1 H), 3.94 (d, 2 H), 3.47-3.75 (m, 2 H), 3.37 (dd, 1 H), 2.97-3.31 (m, 4 H), 2.70-3.01 (m, 1 H), 1.87-1.98 and 2.02-2.16 (m, 1 H), 0.98-1.88 (m, 5 H), 0.47-0.72 (m, 2 H), 0.20-0.43 (m, 2 H). LCMS (Method 1): [MH+] = 846 at 3.07 min. |
| Ex. 75 | 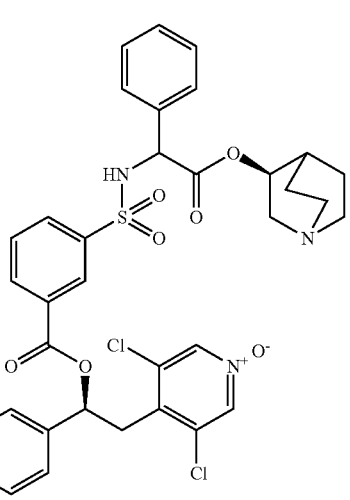<br><br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3S)-quinuclidin-3-yl]oxy-ethyl]sulfamoyl]benzoate trifluoroacetate salt | $^1$H NMR (300 MHz, DMSO) δ 9.45 (s, 1 H), 9.13 (d, I H), 8.56 (s, 2 H), 8.22 (dt, 1 H), 8.12 (m, 1 H), 7.98 (t, 1 H), 7.64 (dd, 1 H), 7.09-7.29 (m, 8 H), 7.08 (t, 1 H), 6.21 (dd, 1 H), 5.18 (d, 1 H), 4.86-4.93 (m, 1 H), 3.95 (d, 2 H), 3.64 (dd, 1 H), 3.53 (d, 1 H), 2.99-3.26 (m, 5 H), 2.80 (d, 1 H), 1.92 (br. s., 1 H), 1.67-1.87 (m, 3 H), 1.32-1.58 (m, 1 H), 1.08-1.32 (m, 1 H), 0.57 (d, 2 H), 0.23-0.43 (m, 2 H). LCMS (Method 1): [MH+] = 846 at 3.05 min. |

| Ref. | Compound | Analytical Data |
|---|---|---|
| Ex. 76 | 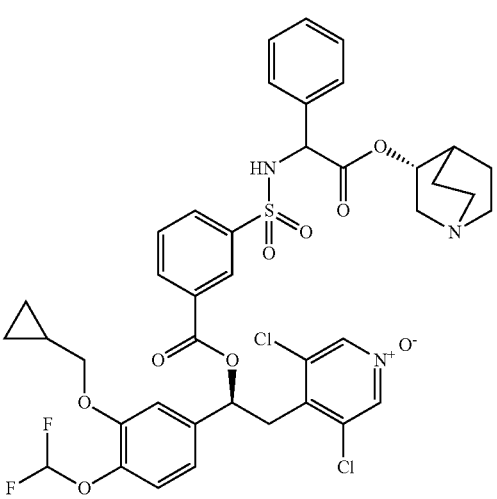<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]sulfamoyl]benzoate trifluoroacetate salt | $^1$H NMR (300 MHz, DMSO) δ 9.52 and 9.59 (br. s., 1 H), 9.14 (d, 1 H), 8.55 and 8.57 (s, 2 H), 8.23 (t, 1 H), 8.07 and 8.14 (dt, 1 H), 7.93 and 8.01 (dt, 1 H), 7.58 and 7.66 (t, 1 H), 7.09-7.32 (m, 8 H), 7.08 (t, 1 H), 6.10-6.30 (m, 1 H), 5.15 and 5.19 (d, 1 H), 4.81-4.99 (m, 1 H), 3.95 (d, 2 H), 3.46-3.75 (m, 2 H), 3.30-3.45 (m, 1 H), 2.74-3.27 (m, 5 H), 1.89-1.98 and 1.98-2.10 (m, 1 H), 0.99-1.87 (m, 5 H), 0.47-0.66 (m, 2 H), 0.30-0.42 (m, 2 H). LCMS (Method 1): [MH+] = 846 at 3.03 min. |
| Ex. 77 | 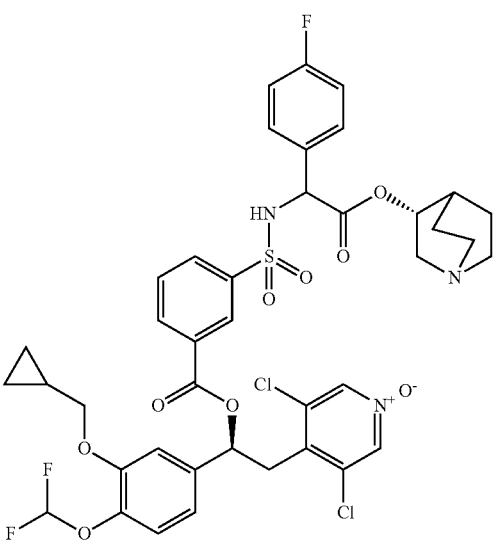<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-fluorophenyl)-2-oxo-2-[(3R)-quinuclidin-3-yl]oxy-ethyl]sulfamoyl]benzoate trifluoroacetate salt | $^1$H NMR (300 MHz, DMSO) δ 9.53 and 9.61 (br. s., 1 H), 9.15 and 9.16 (d, 1 H), 8.55 and 8.56 (s, 2 H), 8.22 (t, 1 H), 8.11 and 8.16 (dt, 1 H), 7.93 and 8.00 (ddd, 1 H), 7.60 and 7.67 (t, 1 H), 7.19-7.40 (m, 4 H), 7.07-7.14 (m, 1 H), 6.88-7.06 (m, 2 H), 7.08 (t, 1 H), 6.20 (dd, 1 H), 5.22 and 5.25 (d, 1 H), 4.77-5.00 (m, 1 H), 3.95 (d, 2 H), 3.48-3.72 (m, 2 H), 3.37 (dd, 1 H), 2.69-3.30 (m, 5 H), 1.89-2.00 and 2.00-2.13 (m, 1 H), 1.34-1.90 (m, 4 H), 1.14-1.31 (m, 1 H), 0.47-0.69 (m, 2 H), 0.15-0.44 (m, 2 H). LCMS (Method 1): [MH+] = 864 at 3.05 min. |

Compounds reported in the table herebelow were obtained as a mixture of diastereoisomers according to the procedure described in Example 1 and subsequently separated as single diastereoisomers as described in Examples 19 and 20 by chiral preparative SFC or chiral preparative HPLC.

| Ref. | Compound | Analytical Data |
| --- | --- | --- |
| Ex. 78 (Single Diastereo-isomer 1) | 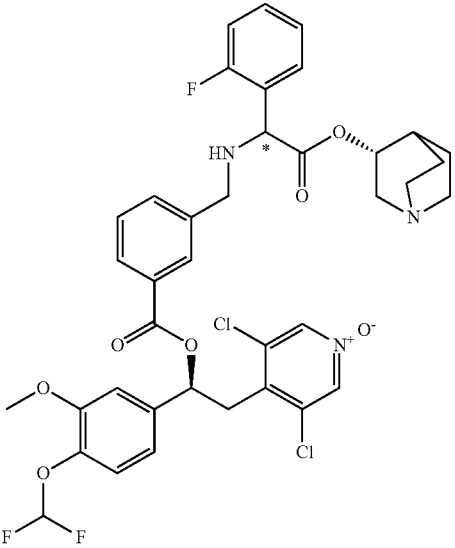<br>[(1S)-2-(3,5-dichloro-1-oxido-pyridin-1-ium-4-yl)-1-[4-(difluoromethoxy)-3-methoxy-phenyl]ethyl] 3-[[[1-(2-fluorophenyl)-2-oxo-2-[(3R)-quinuclidin-3-yl]oxy-ethyl]amino]methyl]benzoate single diastereoisomer | $^1$H NMR (400 MHz, CDCl$_3$): δ 8.13 (s, 2 H), 8.00 (s, 1 H), 7.91 (d, J = 7.8 Hz, 1 H), 7.54 (d, J = 7.7 Hz, 1 H), 7.42-7.36 (m, 2 H), 7.33-7.26 (m, 1 H), 7.20-7.02 (m, 5 H), 6.54 (t, J = 75.0 Hz, 1 H), 6.28 (dd, J = 9.9, 4.3 Hz, 1 H), 4.88-4.82 (m, 1 H), 4.71 (s, 1 H), 3.90 (s, 3 H), 3.81 (s, 2 H), 3.69 (dd, J = 14.0, 9.9 Hz, 1 H), 3.33 (dd, J = 14.0, 4.3 Hz, 1 H), 3.22-3.14 (m, 1 H), 2.78-2.63 (m, 5 H), 1.88-1.81 (m, 1 H), 1.64-1.43 (m, 2 H), 1.30-1.09 (m, 2 H).<br>LCMS (Method 2): [MH+] = 774 at 3.68 min |
| Ex. 79 (Single diastereo-isomer 2) | 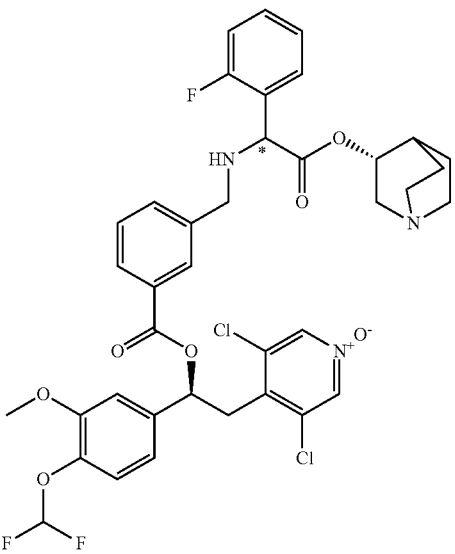<br>[(1S)-2-(3,5-dichloro-1-oxido-pyridin-1-ium-4-yl)-1-[4-(difluoromethoxy)-3-methoxy-phenyl]ethyl] 3-[[[1-(2-fluorophenyl)-2-oxo-2-[(3R)-quinuclidin-3-yl]oxy-ethyl]amino]methyl]benzoate single diastereoisomer | $^1$H NMR (400 MHz, CDCl$_3$): δ 8.14 (s, 2 H), 8.00 (s, 1 H), 7.91 (d, J = 7.8 Hz, 1 H), 7.55 (d, J = 7.7 Hz, 1 H), 7.43-7.36 (m, 2 H), 7.35-7.27 (m, 1 H), 7.20-7.03 (m, 5 H), 6.54 (t, J = 75.0 Hz, 1 H), 6.28 (dd, J = 9.8, 4.4 Hz, 1 H), 4.84-4.78 (m, 1 H), 4.73 (s, 1 H), 3.89 (s, 3 H), 3.85-3.76 (m, 2 H), 3.70 (dd, J = 14.1, 9.9 Hz, 1 H), 3.34 (dd, J = 14.0, 4.4 Hz, 1 H), 3.16-3.09 (m, 1 H), 2.79-2.63 (m, 3 H), 2.54-2.44 (m, 1 H), 2.40-2.33 (m, 1 H), 2.00-1.95 (m, 1 H), 1.70-1.56 (m, 2 H), 1.55-1.45 (m, 1 H), 1.35-1.24 (m, 1 H). LCMS (Method 1): [MH+] = 774 at 2.75 min. |

| Ref. | Compound | Analytical Data |
| --- | --- | --- |
| Ex. 80 (Single Diastereo-isomer 1) | [(1S)-2-(3,5-dichloro-1-oxido-pyridin-1-ium-4-yl)-1-(3,4-dimethoxyphenyl)ethyl] 4-[[[2-oxo-1-(3-pyridyl)-2-[(3R)-quinuclidin-3-yl]oxy-ethyl]amino]methyl]benzoate single diastereoisomer | $^1$H NMR (400 MHz, DMSO): δ 8.62 (d, J = 2.2 Hz, 1 H), 8.56 (s, 2 H), 8.52 (dd, J = 4.8, 1.6 Hz, 1 H), 7.93 (d, J = 8.0 Hz, 2 H), 7.86 (dt, J = 8.0, 1.9 Hz, 1 H), 7.47 (d, J = 8.1 Hz, 2 H), 7.41 (dd, J = 7.9, 4.8 Hz, 1 H), 7.08-6.93 (m, 3 H), 6.22 (dd, J = 9.6, 4.4 Hz, 1 H), 4.71-4.63 (m, 1 H), 4.47 (d, J = 8.5 Hz, 1 H), 3.78 (s, 3 H), 3.75 (s, 3 H), 3.63 (dd, J = 14.2, 9.7 Hz, 1 H), 3.34 (dd, J = 14.1, 4.1 Hz, 1 H), 3.25-2.78 (m, 2 H), 2.99 (dd, J = 14.9, 8.2 Hz, 2 H), 2.69-2.11 (m, 5 H), 1.88-1.81 (m, 1 H), 1.59-1.17 (m, 4 H). LCMS (Method 1): [MH+] = 721 at 2.39 min. |
| Ex. 81 (Single Diastereo-isomer 1) | [(1S)-2-(3,5-dichloro-1-oxido-pyridin-1-ium-4-yl)-1-[4-(difluoromethoxy)-3-isopropoxy-phenyl]ethyl] 3-[[[1-(2-fluorophenyl)-2-oxo-2-[(3R)-quinuclidin-3-yl]oxy-ethyl]amino]methyl]benzoate single diastereoisomer | $^1$H NMR (400 MHz, DMSO): δ 8.53 (s, 2 H), 7.96 (s, 1 H), 7.88 (d, J = 7.7 Hz, 1 H), 7.62-7.52 (m, 2 H), 7.47 (t, J = 7.7 Hz, 1 H), 7.40-7.32 (m, 1 H), 7.25-7.16 (m, 4 H), 7.09-7.05 (m, 1 H), 7.03 (t, J = 74.6 Hz, 1 H), 6.19 (dd, J = 9.2, 4.6 Hz, 1 H), 4.73-4.59 (m, 3 H), 3.82-3.70 (m, 2 H), 3.60 (dd, J = 14.3, 9.3 Hz, 1 H), 3.35 (dd, J = 15.5, 4.6 Hz, 1 H), 3.12-2.80 (m, 1 H), 2.69-2.32 (m, 5 H), 1.74-1.35 (m, 3 H), 1.29 (d, J = 6.0 Hz, 3 H), 1.22 (d, J = 6.0 Hz, 3 H), 1.26-1.05 (m, 2 H). LCMS (Method 2): [MH+] = 802 at 3.85 min. |

| Ref. | Compound | Analytical Data |
|---|---|---|
| Ex. 82 (single diastereoisomer 1) | 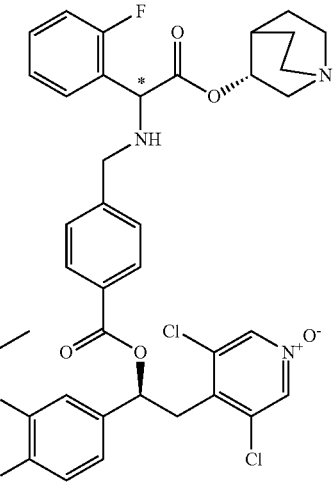<br>[(1S)-2-(3,5-dichloro-1-oxido-pyridin-1-ium-4-yl)-1-[4-(difluoromethoxy)-3-isopropoxy-phenyl]ethyl] 4-[[[1-(2-fluorophenyl)-2-oxo-2-[(3R)-quinuclidin-3-yl]oxy-ethyl]amino]methyl]benzoate single diastereoisomer | $^1$H NMR (400 MHz, DMSO): δ 8.56 (s, 2 H), 7.95 (d, J = 8.0 Hz, 2 H), 7.56 (t, J = 7.5 Hz, 1 H), 7.47 (d, J = 8.1 Hz, 2 H), 7.41-7.33 (m, 1 H), 7.25-7.17 (m, 4 H), 7.11-7.06 (m, 1 H), 7.03 (t, J = 74.6 Hz, 1 H), 6.20 (dd, J = 9.1, 4.6 Hz, 1 H), 4.74-4.59 (m, 3 H), 3.79 (d, J = 6.0 Hz, 2 H), 3.61 (dd, J = 14.2, 9.2 Hz, 1 H), 3.36 (dd, J = 14.5, 5.1 Hz, 1 H), 3.10-2.99 (m, 2 H), 2.71-2.31 (m, 4 H), 1.75-1.69 (m, 1 H), 1.56-1.36 (m, 2 H), 1.30-1.09 (m, 2 H), 1.29 (d, J = 6.0 Hz, 3 H), 1.23 (d, J = 6.0 Hz, 3 H). LCMS (Method 2): [MH+] = 802 at 3.84 min. |
| Ex. 83 (Single Diastereoisomer 2) | 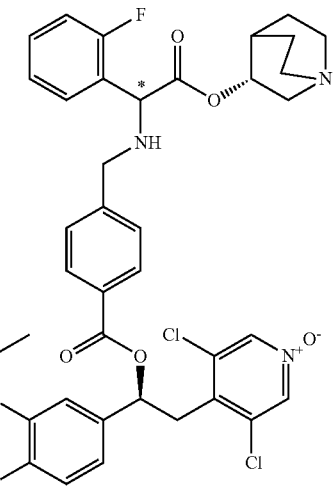<br>[(1S)-2-(3,5-dichloro-1-oxido-pyridin-1-ium-4-yl)-1-[4-(difluoromethoxy)-3-isopropoxy-phenyl]ethyl] 4-[[[1-(2-fluorophenyl)-2-oxo-2-[(3R)-quinuclidin-3-yl]oxy-ethyl]amino]methyl]benzoate single diastereoisomer | $^1$H NMR (400 MHz, DMSO): δ 8.56 (s, 2 H), 7.94 (d, J = 8.1 Hz, 2 H), 7.55 (t, J = 7.5 Hz, 1 H), 7.46 (d, J = 8.0 Hz, 2 H), 7.41-7.34 (m, 1 H), 7.26-7.17 (m, 4 H), 7.10-7.06 (m, 1 H), 7.02 (t, J = 74.6 Hz, 1 H), 6.20 (dd, J = 9.2, 4.7 Hz, 1 H), 4.72-4.59 (m, 3 H), 3.78 (d, J = 6.1 Hz, 2 H), 3.61 (dd, J = 14.1, 9.1 Hz, 1 H), 3.36 (dd, J = 14.6, 5.2 Hz, 1 H), 3.12-2.85 (m, 2 H), 2.69-2.25 (m, 3 H), 2.17-2.10 (m, 1 H), 1.87-1.81 (m, 1 H), 1.59-1.37 (m, 3 H), 1.29 (d, J = 6.0 Hz, 3 H), 1.28-1.16 (m, 1 H), 1.23 (d, J = 6.0 Hz, 3 H). LCMS (Method 2): [MH+] = 802 at 3.68 min. |

| Ref. | Compound | Analytical Data |
|---|---|---|
| Ex. 84 (Single Diastereo-isomer 1) | [(3R)-quinuclidin-3-yl] 2-[[4-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-phenyl-acetate trifluoroacetate salt single diastereoisomer | $^1$H NMR (400 MHz, CD$_3$CN): δ 10.99 (br s, 1 H), 8.08 (s, 2 H), 7.79-7.72 (m, 2 H), 7.63-7.55 (m, 3 H), 7.34 (d, J = 7.8 Hz, 2 H), 7.24 (d, J = 8.2 Hz, 1 H), 7.20-7.16 (m, 1 H), 7.15-7.06 (m, 3 H), 6.82 (t, J = 75.4 Hz, 1 H), 6.12 (dd, J = 11.6, 4.2 Hz, 1 H), 5.26-5.17 (m, 2 H), 4.18 (d, J = 12.6 Hz, 1 H), 3.99 (d, J = 7.0 Hz, 2 H), 3.89 (d, J = 12.5 Hz, 1 H), 3.60-3.43 (m, 4 H), 3.31-3.09 (m, 6 H), 3.00-1.67 (m, 6 H), 1.36-1.26 (m, 1 H), 0.70-0.62 (m, 2 H), 0.44-0.38 (m, 2H). LCMS (Method 1): [MH+] = 810 at 2.73 min. |
| Ex. 85 (Single Diastereo-isomer 2) | [(3R)-quinuclidin-3-yl] 2-[[4-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-phenyl-acetate single diastereoisomer | $^1$H NMR (400 MHz, CD$_3$CN): δ 8.10 (s, 2 H), 7.49-7.43 (m, 2 H), 7.42-7.31 (m, 3 H), 7.29-7.24 (m, 2 H), 7.17-7.12 (m, 3 H), 7.02-6.92 (m, 2 H), 6.78 (t, J = 75.5 Hz, 1 H), 6.01 (dd, J = 9.8, 4.7 Hz, 1 H), 4.79-4.73 (m, 1 H), 4.42 (s, 1 H), 3.90-3.82 (m, 2 H), 3.73 (s, 2 H), 3.60 (d, J = 4.0 Hz, 2 H), 3.46 (dd, J = 14.1, 9.8 Hz, 1 H), 3.21 (dd, J = 14.2, 4.8 Hz, 1 H), 3.12 (ddd, J = 14.1, 7.8, 1.9 Hz, 1 H), 2.77-2.47 (m, 5 H), 1.82-1.78 (m, 1 H), 1.65-1.39 (m, 3 H), 1.31-1.17 (m, 2 H), 0.66-0.60 (m, 2 H), 0.40-0.34 (m, 2 H). LCMS (Method 1): [MH+] = 810 at 2.67 min. |

Example 86

[(1S)-1-[3-(cyclopropylmethoxy)-4-(difluoromethoxy)phenyl]-2-(3,5-dichloro-1-oxido-pyridin-1-ium-4-yl)ethyl] 2-hydroxy-3-[[[2-oxo-1-phenyl-2-[(3R)-quinuclidin-3-yl]oxy-ethyl]amino]methyl] benzoate formate salt

Step 1: Preparation of methyl 2-(benzyloxy)-3-formylbenzoate

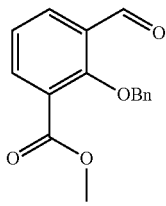 [SMILES: COC(=O)c1cccc(C=O)c1OCc1ccccc1]

A slurry of methyl 3-formyl-2-hydroxybenzoate (640 mg, 3.56 mmol), K$_2$CO$_3$ (982 mg, 7.12 mmol) and benzyl bromide (0.63 mL, 5.34 mmol) in DMF (3 mL) was stirred at room temperature for 16 hours and diluted with EtOAc (100 mL) and water (40 mL). The layers were separated and the organic phase dried over MgSO$_4$. After filtration and concentration in vacuo, the residue was purified via silica gel chromatography, eluting with 0-15% EtOAc in isohexane, to give the title compound as a white solid (598 mg, 62%).

$^1$H NMR (400 MHz, CDCl$_3$): δ 10.22 (s, 1H), 8.11 (dd, J=7.7, 1.9 Hz, 1H), 7.98 (dd, J=7.7, 1.9 Hz, 1H), 7.41-7.30 (m, 5H), 7.29-7.22 (m, 1H), 5.11 (s, 2H), 3.90 (s, 3H). LCMS (Method 1): [MH+]=271 at 4.19 min.

Step 2: Preparation of [(1S)-1-[3-(cyclopropylmethoxy)-4-(difluoromethoxy)phenyl]-2-(3,5-dichloro-1-oxido-pyridin-1-ium-4-yl)ethyl] 2-benzyloxy-3-formyl-benzoate

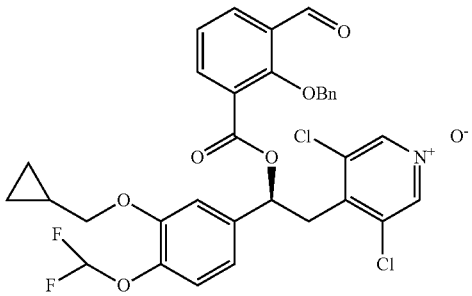

A solution of methyl 2-(benzyloxy)-3-formylbenzoate (598 mg, 2.21 mmol) in THF (4 mL) and MeOH (2 mL) and a solution of 4 N NaOH (1.10 mL, 4.43 mmol) was added at 0° C. and the reaction mixture stirred for 30 minutes. 2N HCl was then added at 0° C. to adjust the pH to ~2. After concentration in vacuo, the residue was azeotroped with toluene to dryness. The crude solid was dissolved in DMF (4.4 mL). To half of this solution (2.2 mL, 1.1 mmol) was added (S)-3,5-dichloro-4-(2-(3-(cyclopropylmethoxy)-4-(difluoromethoxy)phenyl)-2-hydroxyethyl)pyridine 1-oxide (553 mg, 1.32 mmol), 4-(dimethylamino)-pyridine (67 mg, 0.55 mmol) and N-(3-dimethylaminopropyl)-N'-ethylcarbodiimide hydrochloride (422 mg, 2.2 mmol and the resulting mixture was stirred at room temperature for 4 hours. The reaction mixture was diluted with DCM (100 mL), the organic phase washed with sat. NaHCO$_3$ (2×50 mL). The phases were separated over a hydrophobic frit and concentrated in vacuo. The residue was purified via silica gel chromatography, eluting with 0-100% EtOAc in isohexane to give the title compound as a white solid (784 mg, 54% over two steps).

$^1$H NMR (400 MHz, CDCl$_3$): δ 10.16 (s, 1H), 8.13 (s, 2H), 8.07 (dd, J=7.9, 1.6 Hz, 1H), 8.02-7.99 (m, 2H), 7.35-7.28 (m, 3H), 7.26-7.21 (m, 2H), 7.15 (d, J=8.4 Hz, 1H), 7.05-6.99 (m, 2H), 6.60 (t, J=75.3 Hz, 1H), 6.31 (dd, J=9.2, 5.0 Hz, 1H), 4.98-4.90 (m, 2H), 3.89-3.80 (m, 2H), 3.66 (dd, J=14.1, 9.2 Hz, 1H), 3.35 (dd, J=13.9, 5.1 Hz, 1H), 0.92-0.82 (m, 1H), 0.66-0.58 (m, 2H), 0.37-0.30 (m, 2H).

LCMS (Method 2): [MH+]=657 at 4.33 min.

Step 3: Preparation of [(1S)-1-[3-(cyclopropylmethoxy)-4-(difluoromethoxy)phenyl]-2-(3,5-dichloro-1-oxido-pyridin-1-ium-4-yl)ethyl] 3-formyl-2-hydroxy-benzoate

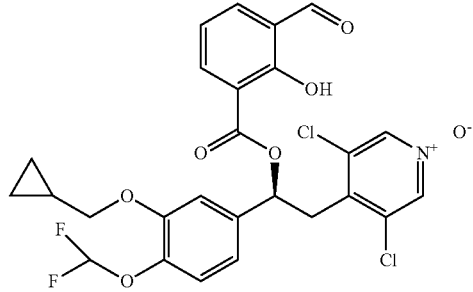

TFA (0.4 mL) was carefully added to a solution of [(1S)-1-[3-(cyclopropylmethoxy)-4-(difluoromethoxy)phenyl]-2-(3,5-dichloro-1-oxido-pyridin-1-ium-4-yl)ethyl] 2-benzyloxy-3-formyl-benzoate (116 mg, 0.18 mmol) in toluene (0.8 mL) at 0° C. The resulting mixture was stirred at 0° C. for 50 minutes. The solution was diluted with DCM (20 mL) and sat. NaHCO$_3$ (20 mL). The layers were separated over a hydrophobit fit and the organic phase concentrated in vacuo, the residue azeotroped with toluene to dryness. The yellow gum (120 mg) was used in the next step without further purification.

$^1$H NMR (400 MHz, CDCl$_3$): δ 11.20 (s, 1H), 10.38 (s, 1H), 8.15 (s, 2H), 8.00 (d, J=7.4 Hz, 1H), 7.29-7.22 (m, 2H), 7.24-6.98 (m, 3H), 6.60 (t, J=75.3 Hz, 1H), 6.30 (dd, J=9.8, 4.3 Hz, 1H), 3.90 (d, J=7.0 Hz, 2H), 3.72 (dd, J=14.2, 9.9 Hz, 1H), 3.35 (dd, J=14.2, 4.3 Hz, 1H), 1.35-1.23 (m, 1H), 0.69-0.62 (m, 2H), 0.40-0.34 (m, 2H). LCMS (Method 2): [MH+]=568 at 4.08 min.

167

Step 4: Preparation of [(1S)-1-[3-(cyclopropyl-methoxy)-4-(difluoromethoxy)phenyl]-2-(3,5-dichloro-1-oxido-pyridin-1-ium-4-yl)ethyl] 2-hydroxy-3-[[[2-oxo-1-phenyl-2-[(3R)-quinuclidin-3-yl]oxy-ethyl]amino]methyl]benzoate formate salt

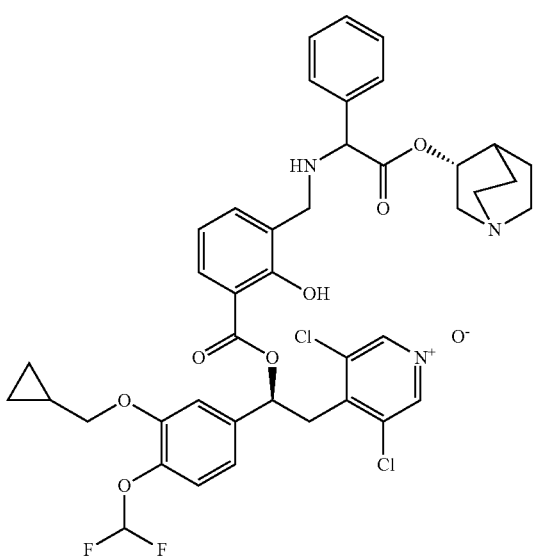

The title compound was synthesized from [(1S)-1-[3-(cyclopropylmethoxy)-4-(difluoromethoxy)phenyl]-2-(3,5-dichloro-1-oxido-pyridin-1-ium-4-yl)ethyl] 3-formyl-2-hydroxy-benzoate and Intermediate 8 via the same method described for Example 1.

¹H NMR (400 MHz, DMSO): δ 8.57 (s, 2H), 7.87 (d, J=8.0 Hz, 1H), 7.56 (d, J=7.4 Hz, 1H), 7.45-7.36 (m, 2H), 7.37-7.19 (m, 4H), 7.09 (dd, J=9.9, 0.4 Hz, 1H), 7.08 (t, J=75 Hz, 1H), 6.96 (t, J=7.7 Hz, 1H), 6.22 (dd, J=9.3, 4.5 Hz, 1H), 4.67-4.62 (m, 1H), 4.39 (d, J=7.1 Hz, 1H), 3.93 (d, J=6.9 Hz, 2H), 3.70-3.67 (m, 2H), 3.64 (dd, J=14.1, 9.5 Hz, 1H), 3.36 (dd, J=14.3, 5.0 Hz, 3H), 3.04 (dd, J=14.6, 8.2 Hz, 1H) †, 2.97 (dd, J=14.6, 8.2 Hz, 1H)*, 2.61-2.52 (m, 4H), 2.43 (d, J=15.7 Hz, 1H) †, 2.14 (d, J=14.7 Hz, 1H)*, 1.84-1.82 (m, 1H)*, 1.73-1.66 (m, 1H) †, 1.54-1.45 (m, 1H), 1.46-1.35 (m, 1H), 1.28-1.15 (m, 2H), 1.15-1.07 (m, 1H), 0.58-0.53 (m, 2H), 0.38-0.32 (m, 2H), † and * refer to different isomers.

LCMS (Method 1): [MH+]=812 at 2.72 min.

168

Example 87

[(1S)-2-(3,5-dichloro-1-oxido-pyridin-1-ium-4-yl)-1-(3,4-dimethoxyphenyl)ethyl]-4-[2-[[2-oxo-1-phenyl-2-[(3R)-quinuclidin-3-yl]oxy-ethyl]amino]ethyl]benzoate formate salt

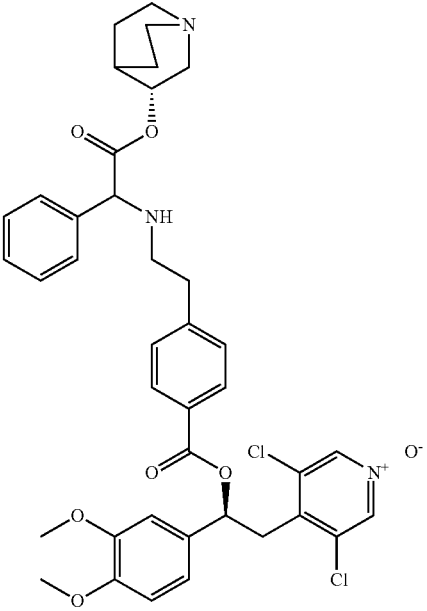

The title compound was obtained as a mixture of diastereoisomers following the procedure described in Example 32, starting from the appropriate amine. ¹H NMR (400 MHz, CDCl₃): δ 8.37 (s, 1H), 8.13 (s, 2H), 7.94 (dd, J=8.1, 2.1 Hz, 2H), 7.37-7.20 (m, 7H), 7.04-6.95 (m, 2H), 6.85 (d, J=8.2 Hz, 1H), 6.29 (dd, J=9.7, 4.6 Hz, 1H), 5.01-4.95 (m, 1H), 4.95-4.89 (m, 1H), 4.39 (s, 1H), 3.92-3.83 (m, 6H), 3.71 (dd, J=14.1, 9.7 Hz, 1H), 3.40-3.23 (m, 2H), 3.03-2.52 (m, 9H), 2.21 (s, 1H), 2.06 (s, 1H), 1.98-1.34 (m, 5H).

LCMS (Method 1): [MH+]=734 at 2.36 min.

Example 88

[(1S)-2-(3,5-dichloro-1-oxido-pyridin-1-ium-4-yl)-1-(3,4-dimethoxyphenyl)ethyl]-4-[2-[[1-(2-fluorophenyl)-2-oxo-2-[(3R)-quinuclidin-3-yl]oxy-ethyl]amino]ethyl]benzoate single diastereoisomer

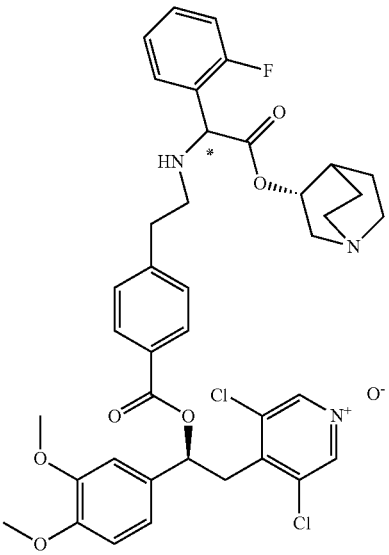

The title compound was obtained by chiral preparative SFC from the diastereoisomeric mixture (Example 32) ¹H NMR (400 MHz, CDCl₃): δ 8.12 (s, 2H), 7.94 (d, J=8.0 Hz, 2H), 7.32-7.21 (m, 4H), 7.13-6.95 (m, 4H), 6.85 (d, J=8.2 Hz, 1H), 6.29 (dd, J=9.7, 4.6 Hz, 1H), 4.85-4.79 (m, 1H), 4.73 (s, 1H), 3.90 (s, 3H), 3.87 (s, 3H), 3.74-3.63 (m, 1H), 3.34 (dd, J=14.0, 4.6 Hz, 1H), 3.18 (dd, J=14.7, 8.3 Hz, 1H), 3.00-2.63 (m, 9H), 2.03-1.09 (m, 6H).

LCMS (Method 1): [MH+]=752 at 2.45 min.

The following compounds can be prepared using the above procedures, or slightly modified procedures that the skilled person can easily apply.

| Ref | Compound | Analytical data |
| --- | --- | --- |
| Ex. 89 | 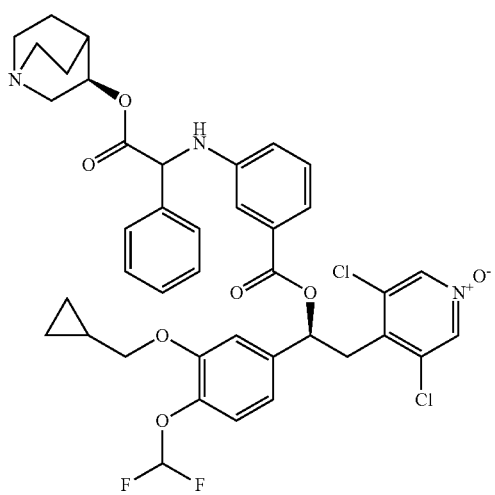 [(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]amino]benzoate trifluoroacetate salt | ¹H NMR (300 MHz, DMSO-d₆) δ ppm 9.36 and 0 9.50 (br. s., 1 H) 8.54 (s, 2 H) 7.49-7.68 (m, 3 H) 7.12-7.49 (m, 6 H) 6.90-7.12 (m, 3 H) 7.07 (t, 1 H) 6.75 (m, 1 H) 6.19 (dd, 1 H) 5.35 and 5.40 (d, 1 H) 4.95-5.13 (m, 1 H) 3.92 and 0 3.93 (d, 2 H) 3.48-3.77 (m, 2 H) 3.01-3.29 (m, 4 H) 2.67-2.80 (m, 1 H) 2.54-2.61 (m, 1 H) 1.94-2.08 and 2.20-2.26 (m, 1 H) 1.61-1.93 (m, 3 H) 1.36-1.57 (m, 1H) 1.08-1.36 (m, 1 H) 0.45-0.70 (m, 2 H) 0.25-0.45 (m, 2 H) LCMS: [MH+] = 782 |
| Ex. 90 | 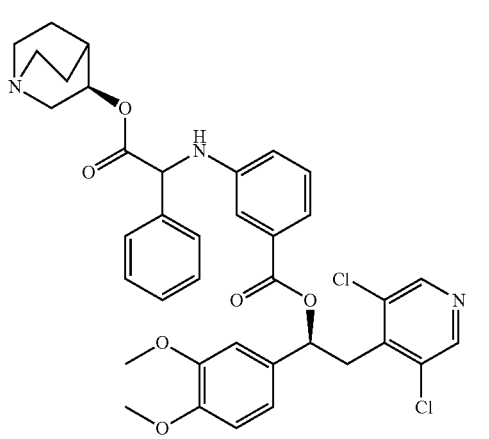 [SMILES: COc1ccc([C@H](Cc2c(Cl)cncc2Cl)OC(=O)c2cccc(NC(C(=O)O[C@H]3CN4CCC3CC4)c3ccccc3)c2)cc1OC] [(1S)-2-(3,5-dichloro-4-pyridyl)-1-(3,4-dimethoxyphenyl)ethyl] 3-[[2-oxo-1-phenyl-2-[(3R)-quinuclidin-3-yl]oxy-ethyl]amino]benzoate trifluoroacetate salt | ¹H NMR (300 MHz, DMSO-d₆) δ ppm 9.41 and 9.50 (br. s., 1 H), 8.57 and 8.58 (s, 2 H), 7.47-7.63 (m,2 H), 7.10-7.47 (m, 6 H), 6.88-7.08 (m, 4 H), 6.77 (d, 1 H), 6.26 (dd, 1 H), 5.30-5.42 (m, 1 H), 4.93-5.18 (m, 1 H), 3.76 (s, 3 H), 3.78 (s, 3 H), 3.54-3.74 (m, 3 H), 3.37-3.52 (m, 2 H), 2.99-3.24 (m, 3 H), 1.90-2.05 and 2.20-2.25 (m, 1 H), 1.63-1.90 (m, 2 H), 1.27-1.59 (m, 2 H) LCMS: [MH+] = 690 |

| Ref | Compound | Analytical data |
|---|---|---|
| Ex. 91 | 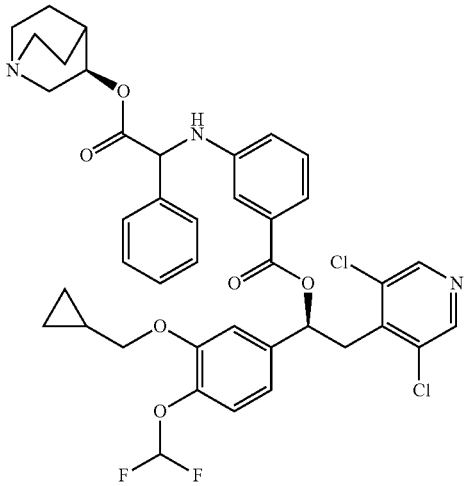 [SMILES: O=C(O[C@@H](Cc1c(Cl)cncc1Cl)c1ccc(OC(F)F)c(OCC2CC2)c1)c1cccc(NC(C(=O)O[C@H]2CN3CCC2CC3)c2ccccc2)c1]<br>[(1S)-1-[3-(cyclopropylmethoxy)-4-(difluoromethoxy)phenyl]-2-(3,5-dichloro-4-pyridyl)ethyl] 3-[[2-oxo-1-phenyl-2-[(3R)-quinuclidin-3-yl]oxy-ethyl]amino]benzoate trifluoroacetate salt | $^1$H NMR (300 MHz, DMSO-$d_6$) δ ppm 9.38 and 9.52 (br. s., 1 H), 8.58 and 8.59 (s, 2 H), 7.47-7.65 (m, 2 H), 7.11-7.47 (m, 8 H), 6.90-7.11 (m, 2 H), 7.07 (t, 1 H), 6.67 (br. s., 1 H), 6.25 (dd, 1 H), 5.32-5.41 (m, 1 H), 5.02-5.09 (m, 1 H), 3.81-4.04 (m, 2 H), 3.63-3.80 (m, 2 H), 3.34-3.47 (m, 1 H), 3.00-3.33 (m, 4 H), 2.65-2.79 (m, 1 H), 2.01 and 2.23 (br. s., 1 H), 0.96-1.93 (m, 5 H), 0.41-0.69 (m, 2 H), 0.15-0.41 (m, 2 H)<br>LCMS: [MH+] = 766 |
| Ex. 92 | 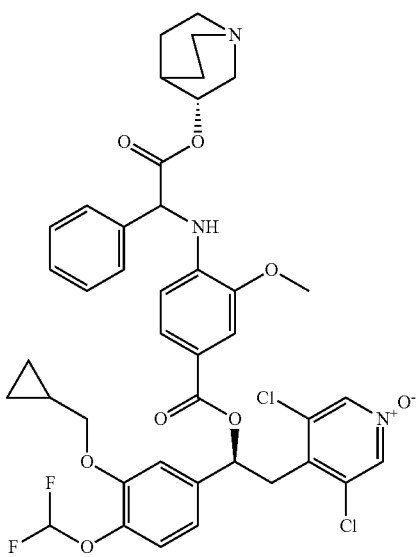<br>[(1S)-1-[3-(cyclopropylmethoxy)-4-(difluoromethoxy)phenyl]-2-(3,5-dichloro-1-oxido-pyridin-1-ium-4-yl)ethyl] 3-methoxy-4-[[2-oxo-1-phenyl-2-[(3R)-quinuclidin-3-yl]oxy-ethyl]amino]benzoate trifluoroacetate salt | $^1$H NMR (300 MHz, DMSO-$d_6$) δ ppm 9.37 (br. s., 1 H), 8.55 (s, 2 H), 7.47-7.59 (m, 2 H), 7.32-7.47 (m, 5 H), 7.18 (d, 1 H), 7.17 (d, 1 H), 7.03 (dd, 1 H), 7.04 (t, 1 H), 6.48 (d, 1 H), 6.13 (dd, 1 H), 6.07 (d, 1 H), 5.55 (d, 1 H), 5.00-5.16 (m, 1 H), 3.92 (s, 3 H), 3.91 (d, 2 H), 3.61-3.74 (m, 2 H), 3.04-3.36 (m, 5 H), 2.58-2.83 (m, 1 H), 2.20-2.43 (m, 1 H), 1.56-2.00 (m, 4 H), 0.97-1.32 (m, 1 H), 0.48-0.65 (m, 2 H), 0.23-0.41 (m, 2 H)<br>LCMS: [MH+] = 812 |

| Ref | Compound | Analytical data |
|---|---|---|
| Ex. 93 | 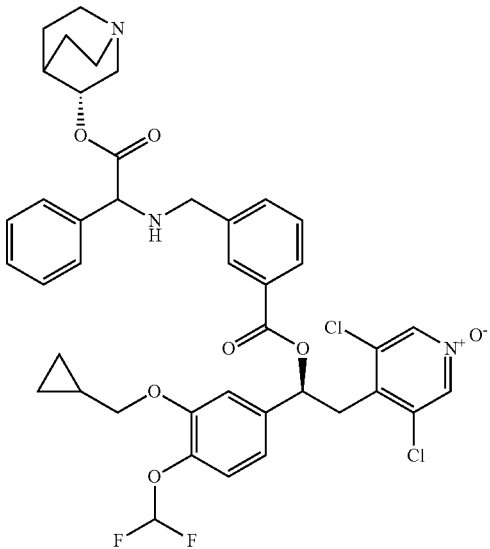<br>[(1S)-1-[3-(cyclopropylmethoxy)-4-(difluoromethoxy)phenyl]-2-(3,5-dichloro-1-oxido-pyridin-1-ium-4-yl)ethyl] 3-[[[2-oxo-1-phenyl-2-[(3R)-quinuclidin-3-yl]oxy-ethyl]amino]methyl]benzoate hydrobromide salt | $^1$H NMR (300 MHz, DMSO-d$_6$) δ ppm 9.44 and 9.55 (br. s., 1 H), 8.54 (s, 2 H), 7.89-8.11 (m, 2 H), 7.37-7.73 (m, 8 H), 7.19-7.27 (m, 2 H), 7.10 (dd, 1 H), 7.07 (t, 1 H), 6.16-6.31 (m, 1 H), 4.98-5.19 (m, 1 H), 4.03 (br. s., 2 H), 3.93 (d, 2 H), 3.57-3.77 (m, 1 H), 3.63 (dd, 1 H), 2.78-3.30 (m, 6 H), 2.00-2.14 and 2.32-2.45 (m, 1 H), 1.42-1.95 (m, 4 H), 1.06-1.28 (m, 1 H), 0.48-0.64 (m, 2 H), 0.23-0.45 (m, 2 H)<br>LCMS: [MH+] = 796 |
| Ex. 94 | 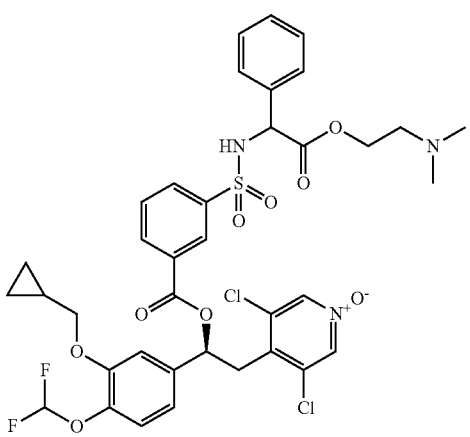<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-(2-dimethylaminoethyloxy)-2-oxo-1-phenyl-ethyl]sulfamoyl]benzoate trifluoroacetate salt | $^1$H NMR (300 MHz, DMSO-d$_6$) δ ppm 9.43 (br. s., 1 H), 9.10 (d, 1 H), 8.55 and 8.57 (s, 2 H), 8.16 and 8.17 (t, 1 H), 8.03-8.12 (m, 1 H), 7.86-7.97 (m, 1 H), 7.57 and 7.61 (t, 1 H), 6.78-7.38 (m, 9 H), 6.15-6.28 (m, 1 H), 5.18 and 5.20 (d, 1 H), 4.24-4.50 (m, 1 H), 4.07-4.24 (m, 1 H), 3.95 (d, 2 H), 3.64 (dd, 1 H), 3.37 (dd, 1 H), 3.29 (br. s., 2 H), 2.70 (br. s., 6 H), 1.10-1.33 (m, 1 H), 0.47-0.66 (m, 2 H), 0.18-0.47 (m, 2 H)<br>LCMS: [MH+] = 808 |

| Ref | Compound | Analytical data |
|---|---|---|
| Ex. 95 | 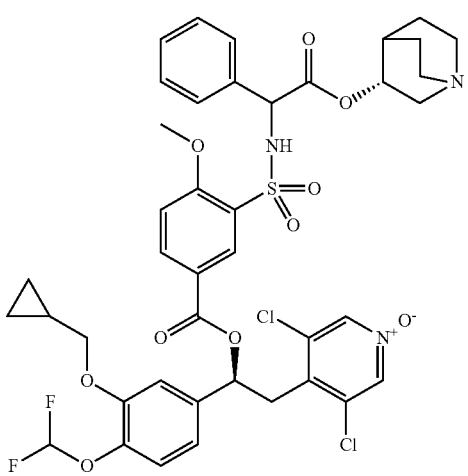<br>[(1S)-1-[3-(cyclopropylmethoxy)-4-(difluoromethoxy)phenyl]-2-(3,5-dichloro-1-oxido-pyridin-1-ium-4-yl)ethyl] 4-methoxy-3-[[2-oxo-1-phenyl-2-[(3R)-quinuclidin-3-yl]oxy-ethyl]sulfamoyl]benzoate trifluoroacetate salt | $^1$H NMR (300 MHz, DMSO-d$_6$) δ ppm 9.42 and 9.52 (br. s., 1 H), 8.81 (d, 1 H), 8.55 and 8.56 (s, 2 H), 8.30 and 8.32 (d, 1 H), 8.07 and 8.12 (dd, 1 H), 6.78-7.41 (m, 9 H), 7.08 (t, 1 H), 6.04-6.37 (m, 1 H), 5.21 and 5.23 (d, 1 H), 4.92-5.00 and 5.00-5.10 (m, 1 H), 3.95 (d, 2 H), 3.80 and 3.86 (s, 3 H), 3.58-3.71 (m, 2 H), 3.30-3.35 (m, 1 H), 2.75-3.29 (m, 5 H), 1.94-2.04 and 2.04-2.15 (m, 1 H), 1.03-1.90 (m, 5 H), 0.45-0.64 (m, 2 H), 0.28-0.44 (m, 2 H)<br>LCMS: [MH+] = 876 |
| Ex. 96 | 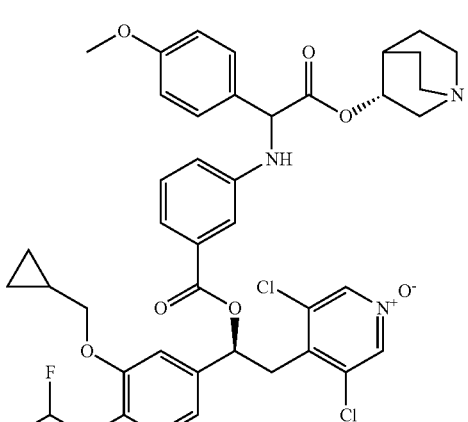<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-methoxyphenyl)-2-oxo-2-[(3R)-quinuclidin-3-yl]oxy-ethyl]amino]benzoate trifluoroacetate salt | $^1$H NMR (300 MHz, DMSO-d$_6$) δ ppm 932 and 9.46 (br. s., 1 H), 8.55 (s, 2 H), 1.40-7.56 (m, 2 H), 6.79-7.35 (m, 10 H), 6.62-6.77 (m, 1 H), 5.99-628 (m, 1 H), 5.13-5.41 (m, 1 H), 4.90-5.13 (m, 1 H), 3.92 and 3.93 (d, 2 H), 3.74 and 3.75 (s, 3 H), 3.48-3.69 (m, 4 H), 2.96-3.32 (m, 4 H), 2.13-2.25 and 1.99-2.08 (m, 1H), 1.39-1.96 (m, 4 H), 1.01-1.32 (m, 1 H), 0.44-0.63 (m, 2 H), 0.19-0.44 (m, 2 H)<br>LCMS: [MH+] = 812 |

-continued

| Ref | Compound | Analytical data |
|---|---|---|
| Ex. 97 | 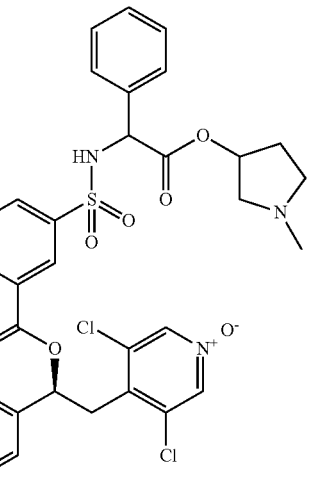<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-(1-methylpyrrolidin-3-yl)oxy-2-oxo-1-phenyl-ethyl]sulfamoyl]benzoate trifluoroacetate salt | $^1$H NMR (300 MHz, DMSO-$d_6$) δ ppm 9.96 (br. s., 1 H), 8.92-9.22 (m, 1 H), 8.55 and 8.57 (s, 2 H), 8.05-8.27 (m, 2 H), 7.81-8.05 (m, 1 H), 7.56-7.72 (m, 1 H), 7.01-7.30 (m, 8 H), 7.08 (t, 1 H), 6.05-6.31 (m, 1 H), 5.11-5.31 (m, 1 H), 4.84-5.11 (m, 1 H), 3.95 (d, 2 H), 3.64 (dd, 1 H), 3.46-3.59 (m, 1 H), 3.37 (dd, 1 H), 2.96-3.32 (m, 3 H), 2.81 (s, 3 H), 1.45-2.23 (m, 2 H), 1.08-1.33 (m, 1 H), 0.49-0.77 (m, 2 H), 0.21-0.49 (m, 2 H)<br>LCMS: [MH+] = 820 |
| Ex. 98 | 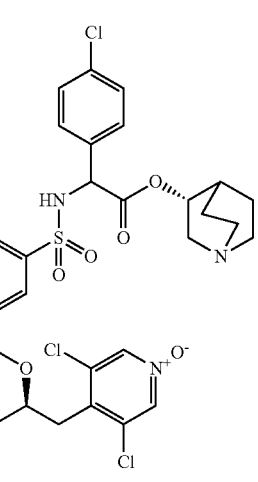<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-chlorophenyl)-2-oxo-2-[(3R)-quinuclidin-3-yl]oxy-ethyl]sulfamoyl]benzoate trifluoroacetate salt | $^1$H NMR (300 MHz, DMSO-$d_6$) δ ppm 9.51 and 9.59 (br. s., 1 H), 9.17 (d, 1 H), 8.55 and 8.56 (s, 2 H), 8.06-8.25 (m, 2 H), 7.86-8.05 (m, 1 H), 7.61 and 7.67 (t, 1 H), 6.77-7.46 (m, 8 H), 6.21 (dd, 1 H), 5.23 and 5.26 (d,1 H), 4.76-5.01 (m, 1 H), 3.95 (d, 2 H), 3.01-3.75 (m, 6 H), 2.68-2.99 (m, 2 H), 1.87-2.01 and 2.00-2.13 (m, 1 H), 1.40-1.87 (m, 4 H), 1.09-1.37 (m, 1 H), 0.46-0.69 (m, 2 H), 0.19-0.47 (m, 2 H)<br>LCMS: [MH+] = 880 |

| Ref | Compound | Analytical data |
|---|---|---|
| Ex. 99 | 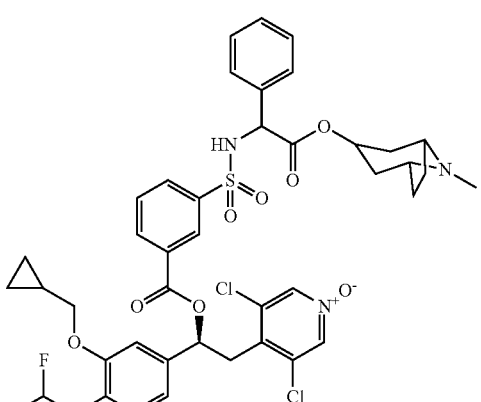<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-[(8-methyl-8-azabicyclo[3.2.1]octan-3-yl)oxy]-2-oxo-1-phenyl-ethyl]sulfamoyl]benzoate trifluoroacetate salt | $^1$H NMR (300 MHz, DMSO-$d_6$) δ ppm 9.24 (br. S., 1 H), 9.10 (d, 1 H), 8.55 and 8.56 (s, 2 H), 8.15-8.26 (m, 1 H), 8.03-8.15 (m, 1 H), 7.86-8.03 (m, 1 H), 7.58 and 7.61 (t, 1 H), 6.75-7.40 (m, 9 H), 6.12-6.29 (m, 1 H), 5.16 (d, 1 H), 4.66-4.92 (m, 1 H), 3.95 (d, 2 H), 3.56-3.82 (m, 3 H), 3.16-3.41 (m, 1 H), 2.57 and 2.59 (s, 3 H), 1.71-2.25 (m, 7 H), 1.46-1.66 (m, 1 H), 1.11-1.36 (m, 1 H), 0.45-0.69 (m, 2 H), 0.22-0.45 (m, 2 H)<br>LCMS: [MH+] = 860 |
| Ex. 100 | 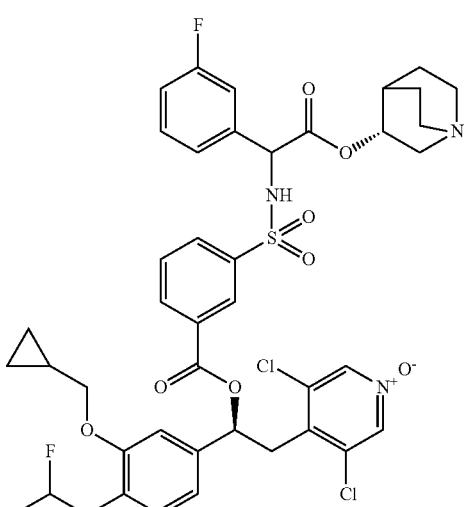<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-fluorophenyl)-2-oxo-2-[(3R)-quinuclidin-3-yl]oxy-ethyl]sulfamoyl]benzoate trifluoroacetate salt | $^1$H NMR (300 MHz, METHANOL-$d_4$) δ ppm 8.45 and 8.48 (s, 2 H), 8.24 and 8.33 (t, 1 H), 8.12 and 8.19 (dt, 1 H), 7.97 and 8.04 (ddd, 1 H), 7.56 and 7.62 (t, 1 H), 7.05-7.31 (m, 4 H), 6.80-7.02 (m, 3 H), 6.77 and 6.78 (t, 1 H), 6.31 and 6.35 (dd, 1 H), 5.19 and 5.24 (s, 1 H), 4.96-5.14 (m, 1 H), 3.87-4.06 (m, 2 H), 3.81 (dd, 1 H), 3.56-3.74 (m, 1 H), 3.44-3.56 (m, 2 H), 2.91-3.28 (m, 4 H), 2.09-2.19 and 2.24-2.32 (m, 1 H), 1.71-2.09 (m, 3 H), 1.56-1.71 (m, 1 H), 1.11-1.36 (m, 1 H), 0.51-0.74 (m, 2 H), 0.22-0.49 (m, 2 H)<br>LCMS: [MH+] = 864 |

| Ref | Compound | Analytical data |
|---|---|---|
| Ex. 101 (Single Diastereo-isomer 1) | [(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]sulfamoyl]benzoate trifluoroacetate salt single diasteroisomer | $^1$H NMR (300 MHz, DMSO-d$_6$) δ ppm 9.43 (br. s., 1 H), 9.14 (d, 1 H), 8.55 (s, 2 H), 8.23 (t, 1 H), 8.14 (dt, 1 H), 8.01 (dt, 1 H), 7.66 (t, 1 H), 7.15-7.31 (m, 7 H), 7.10 (dd, 1 H), 7.08 (t, 1 H), 6.21 (dd, 1 H), 5.16 (d, 1 H), 4.76-4.95 (m, 1 H), 3.95 (d, 2 H), 3.65 (dd, 1 H), 3.55-3.62 (m, 1 H), 3.37 (dd, 1 H), 3.02-3.28 (m, 3 H), 2.83-2.98 (m, 1 H), 2.75-2.83 (m, 1 H), 1.97-2.14 (m, 1 H), 1.48-1.87 (m, 4 H), 1.14-1.32 (m, 1 H), 0.47-0.68 (m, 2 H), 0.28-0.47 (m, 2 H) LCMS: [MH+] = 846 |
| Ex. 102 Single Diastero-isomer 2) | [(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]sulfamoyl]benzoate trifluoroacetate salt single diasteroisomer | $^1$H NMR (300 MHz, DMSO-d$_6$) δ ppm 9.52 (br. s., 1 H), 9.13 (d, 1 H), 8.57 (s, 2 H), 8.21 (t, 1 H), 8.07 (dt, 1 H), 7.93 (ddd, 1 H), 7.58 (t, 1 H), 7.16-7.27 (m, 5 H), 7.09-7.16 (m, 3 H), 7.08 (t, 1 H), 6.20 (dd, 1 H), 5.19 (d, 1 H), 4.84-5.02 (m, 1 H), 3.97 (dd, 1 H), 3.93 (dd, 1 H), 3.54-3.66 (m, 2 H), 3.37 (dd, 1 H), 2.93-3.26 (m, 5 H), 1.88-1.99 (m, 1 H), 1.62-1.87 (m, 2 H), 1.38-1.58 (m, 2 H), 1.15-1.24 (m, 1 H), 0.49-0.64 (m, 2 H), 0.25-0.43 (m, 2 H) LCMS: [MH+] = 846 |

| Ref | Compound | Analytical data |
|---|---|---|
| Ex. 103 | 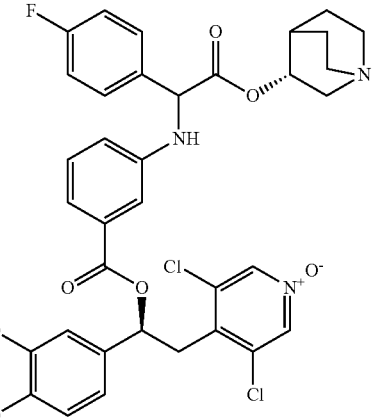<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-fluorophenyl)-2-oxo-2-[(3R)-quinuclidin-3-yl]oxy-ethyl]amino]benzoate trifluoroacetate salt | $^1$H NMR (300 MHz, DMSO-d$_6$) δ ppm 9.34 and 9.48 (br. s., 1 H), 8.55 (s, 2 H), 7.51-7.69 (m, 2 H), 7.12-7.31 (m, 8 H), 6.94-7_09 (m, 3 H), 7.07 (t, 1 H), 6.66-6.80 (m, 1 H), 6.19 (dd, 1 H), 5.31-5.51 (m, 1 H), 4.95-5.14 (m, 1 H), 3.92 and 3.93 (d, 2 H), 3.61-3.75 (m, 1 H), 2.95-3.43 (m, 5 H), 1.97-2.06 and 2.20-2.26 (m, 1 H), 1.36-1.96 (m, 4 H), 0.98-1.33 (m, 1 H), 0.49-0.69 (m, 2 H), 0.25-0.45 (m, 2 H)<br>LCMS: [MH+] = 800 |
| Ex. 104 | 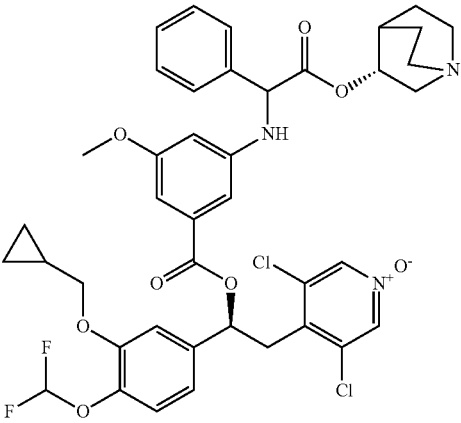<br>[(1S)-1-[3-(cyclopropylmethoxy)-4-(difluoromethoxy)phenyl]-2-(3,5-dichloro-1-oxido-pyridin-1-ium-4-yl)ethyl] 3-methoxy-5-[[2-oxo-1-phenyl-2-[(3R)-quinuclidin-3-yl]oxy-ethyl]amino]benzoate trifluoroacetate salt | $^1$H NMR (300 MHz, DMSO-d$_6$) δ ppm 9.55 and 9.67 (br. s., 1 H), 8.56 (s, 2 H), 7.49-7.61 (m, 2 H), 7.33-7.49 (m, 3 H), 7.13-7.26 (m, 2 H), 6.90-7.05 (m, 2 H), 7.07 (t, 1 H), 6.72-6.81 (m, 2 H), 6.51-6.61 (m, 1 H), 6.16 (dd, 1 H), 5.35 and 5.40 (d, 1 H), 4.95-5.12 (m, 1 H), 3.92 (d, 2 H), 3.71 and 3.72 (s, 3 H), 3.47-3.67 (m, 2 H), 3.01-3.26 (m, 5 H), 2.66-2.78 (m, 1 H), 1.97-2.08 and 2.19-2.26 (m, 1 H), 1.41-1.94 (m, 4 H), 1.07-1.32 (m, 1 H), 0.46-0.68 (m, 2 H), 0.22-0.46 (m, 2 H)<br>LCMS: [MH+] = 812 |

| Ref | Compound | Analytical data |
|---|---|---|
| Ex. 105 | 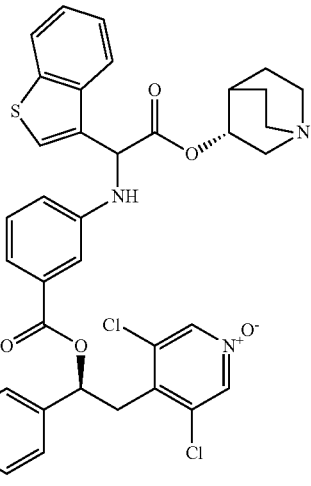<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(benzothiophen-3-yl)-2-oxo-2-[(3R)-quinuclidin-3-yl]oxy-ethyl]amino]benzoate trifluoroacetate salt | $^1$H NMR (300 MHz, DMSO-$d_6$) δ ppm 9.46 (br. s., 1 H), 8.53 (s, 2 H), 8.08-8.19 (m, 1 H), 8.00-8.06 (m, 1 H), 7.87 (s, 1 H), 6.99-7.05 (m, 1 H), 6.87 (d, 1 H), 6.75-7.58 (m, 9 H), 6.18 (dd, 1 H), 5.82 (d, 1 H), 4.98-5.17 (m, 1 H), 3.92 (d, 2 H), 3.59-3.76 (m, 1 H), 3.43-3.59 (m, 1 H), 2.81-3.28 (m, 6 H), 1.93-2.05 (m, 1 H), 0.82-1.88 (m, 5 H), 0.42-0.61 (m, 2 H), 0.18-0.40 (m, 2 H)<br>LCMS: [MH+] = 838 |
| Ex. 106 | 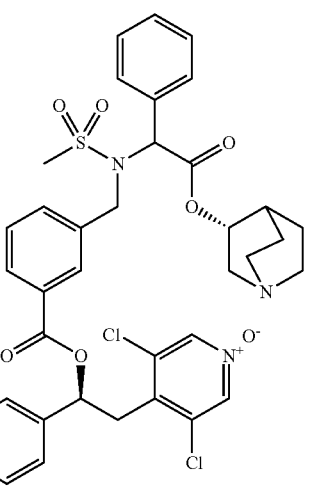<br>[(1S)-1-[3-(cyclopropylmethoxy)-4-(difluoromethoxy)phenyl]-2-(3,5-dichloro-1-oxido-pyridin-1-ium-4-yl)ethyl] 3-[[methylsulfonyl-[2-oxo-1-phenyl-2-[(3R)-quinuclidin-3-yl]oxy-ethyl]amino]methyl]benzoate trifluoroacetate salt | $^1$H NMR (300 MHz, DMSO-$d_6$) δ ppm 9.58 (br. s., 1 H), 8.55 (s, 2 H), 7.68-7.81 (m, 1 H), 7.62 (m, 1 H), 7.02-7.37 (m, 10 H), 7.07 (t, 1 H), 6.20 (dd, 1 H), 5.81 (s, 1 H), 5.01-5.31 (m, 1 H), 4.67 (dd, 1 H), 4.40 (d, 1 H), 3.94 (d, 2 H), 3.64-3.79 (m, 2 H), 3.34 (dd, 1 H), 3.12-3.29 (m, 4 H), 3.00-3.11 (m, 1 H), 3.07 (s, 3 H), 2.17-2.32 (m, 1 H), 1.86 (d, 3 H), 1.55-1.78 (m, 1 H), 1.13-1.30 (m, 1 H), 0.51-0.65 (m, 2 H), 0.36 (q, 2 H) LCMS: [MH+] = 874 |

| Ref | Compound | Analytical data |
|---|---|---|
| Ex. 107 | 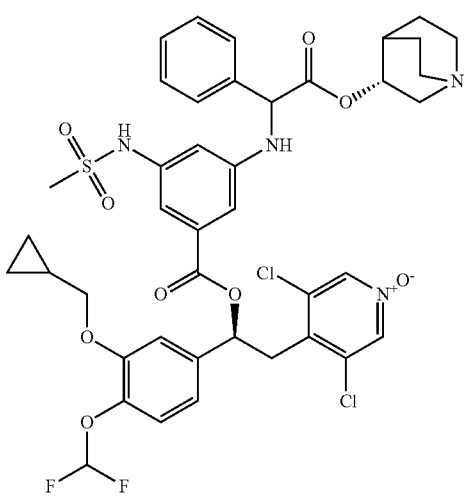<br>[(1S)-1-[3-(cyclopropylmethoxy)-4-(difluoromethoxy)phenyl]-2-(3,5-dichloro-1-oxido-pyridin-1-ium-4-yl)ethyl] 3-(methanesulfonamido)-5-[[2-oxo-1-phenyl-2-[(3R)-quinuclidin-3-yl]oxy-ethyl]amino]benzoate trifluoroacetate salt | $^1$H NMR (300 MHz, DMSO-d$_6$) δ ppm 9.78 (s, 1 H), 9.32-9.64 (m, 1 H), 8.54 (d, 2 H), 7.49-7.70 (m, 2 H), 7.28-7.49 (m, 3 H), 6.90-7.24 (m, 6 H), 6.82-6.89 (m, 1 H), 7.07 (t, 1 H), 6.15-6.22 (m, 1 H), 5.14-5.45 (m, 1 H), 4.75-5.14 (m, 1 H), 3.92 (dd, 2 H), 3.66 (br. s., 1 H), 3.26-3.44 (m, 2 H), 3.01-3.26 (m, 4 H), 2.96 (s, 3 H), 2.84-3.01 (m, 1 H), 1.95-2.11 (m, 1 H), 1.64-1.93 (m, 3 H), 1.33-1.64 (m, 1 H), 1.13-1.32 (m, 1 H), 0.46-0.69 (m, 2 H), 0.13-0.45 (m, 2 H)<br>LCMS: [MH+] = 875 |
| Ex. 108 | 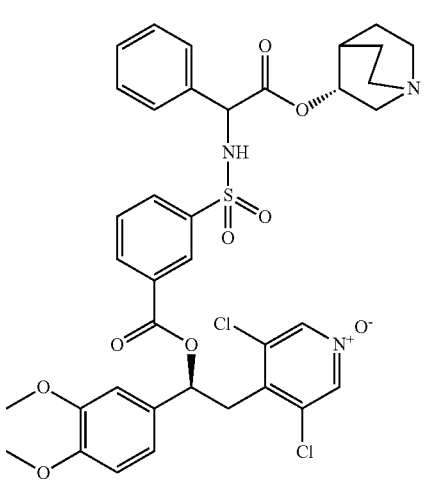<br>[(1S)-2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]sulfamoyl]benzoate trifluoroacetate salt | $^1$H NMR (300 MHz, DMSO-d$_6$) δ ppm 9.48 (br. s., 1 H), 9.13 and 9.14 (d, 1 H), 8.55 and 8.55 (s, 2 H), 8.20 and 8.24 (t, 1 H), 8.08 and 8.14 (dt, 1 H), 7.94 and 8.00 (dt, 1 H), 7.59 and 7.66 (t, 1 H), 6.89-7.38 (m, 8 H), 6.15-6.33 (m, 1 H), 5.15 and 5.18 (d, 1 H), 4.79-4.99 (m, 1 H), 3.80 (s, 3 H), 3.77 (s, 3 H), 3.61-3.72 (m, 1 H), 2.75-3.39 (m, 7 H), 1.87-1.98 and 2.07-2.17 (m, 1 H), 1.32-1.87 (m, 4 H)<br>LCMS: [MH+] = 770 |

| Ref | Compound | Analytical data |
|---|---|---|
| Ex. 109 | 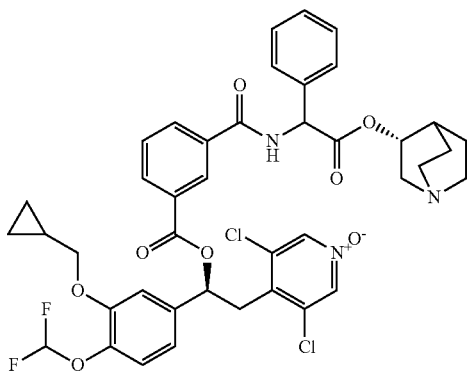<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]carbamoyl]benzoate trifluoroacetate salt | $^1$H NMR (300 MHz, DMSO-d$_6$) δ ppm 9.31-9.67 (m, 2 H), 8.52 (s, 2 H), 8.46 (d, 1 H), 8.19 (td, 2 H), 7.66 (t, 1 H), 7.48-7.60 (m, 2 H), 7.34-7.48 (m, 3 H), 7.16-7.34 (m, 2 H), 6.99-7.16 (m, 1 H), 6.85 (t, 1 H), 6.08-6.34 (m, 1 H), 5.70 (d, 1 H), 5.08 (dd, 1 H), 3.94 (d, 2 H), 3.65 (dd, 1 H), 3.55-3.71 (m, 1 H), 3.37 (dd, 1 H), 3.04-3.31 (m, 4 H), 2.76-3.04 (m, 1 H), 2.02-2.20 (m, 1 H), 1.66-2.01 (m, 3 H), 1.43-1.66 (m, 1 H), 1.00-1.32 (m, 1 H), 0.44-0.71 (m, 2 H), 0.22-0.43 (m, 2 H)<br>LCMS: [MH+] = 810 |
| Ex. 110 | 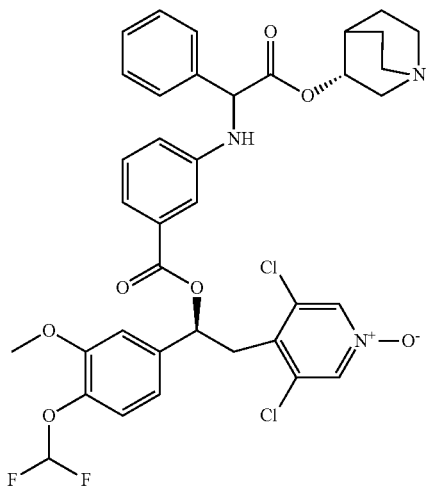 [SMILES: COc1cc([C@H](Cc2c(Cl)c[n+]([O-])cc2Cl)OC(=O)c2cccc(NC(C(=O)O[C@H]3CN4CCC3CC4)c3ccccc3)c2)ccc1OC(F)F]<br>[(1S)-2-(3,5-dichloro-1-oxido-pyridin-1-ium-4-yl)-1-[4-(difluoromethoxy)-3-methoxy-phenyl]ethyl] 3-[[2-oxo-1-phenyl-2-[(3R)-quinuclidin-3-yl]oxy-ethyl]amino]benzoate trifluoroacetate salt | $^1$H NMR (300 MHz, DMSO-d$_6$) δ ppm 9.48 and 9.61 (br s, 1 H), 8.54 and 8.55 (s, 2 H), 7.55 (d, 2 H), 7.18-7.50 (m, 8 H), 6.93-7.14 (m, 2 H), 7.06 (t, 1 H), 6.66-6.87 (m, 1 H), 6.22 (dd, 1 H), 5.38 (d, 1 H), 4.84-5.20 (m, 1 H), 3.85 and 3.86 (s, 3 H), 3.46-3.68 (m, 2 H), 3.35 (d, 1 H), 3.01-3.28 (m, 4 H), 2.67-2.83 (m, 1 H), 1.95-2.08 and 2.18-2.25 (m, 1 H), 1.72-1.95 (m, 3 H), 1.41-1.62 (m, 1 H)<br>LCMS: [MH+] = 742 |

| Ref | Compound | Analytical data |
|---|---|---|
| Ex. 111 | 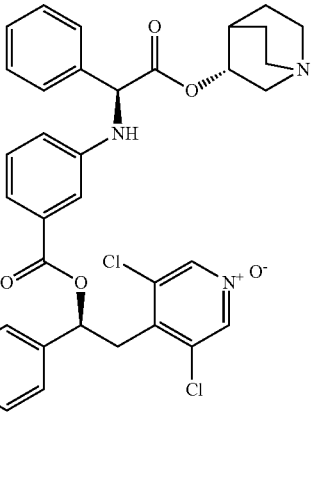<br>[(1S)-1-[3-(cyclopropylmethoxy)-4-(difluoromethoxy)phenyl]-2-(3,5-dichloro-1-oxido-pyridin-1-ium-4-yl)ethyl] 3-[[(1S)-2-oxo-1-phenyl-2-[(3R)-quinuclidin-3-yl]oxy-ethyl]amino]benzoate single stereoisomer | $^1$H NMR (300 MHz, DMSO-d$_6$) δ ppm 8.42 (s, 2 H), 7.52-7.64 (m, 2 H), 7.34-7.47 (m, 3 H), 7.27-7.34 (m, 2 H), 7.15-7.25 (m, 3 H), 7.10 (dd, 1 H), 6.98 (ddd, 1 H), 6.78 (t, 1 H), 6.34 (dd, 1 H), 5.22 (s, 1 H), 4.84-4.92 (m, 1 H), 3.96 (d, 2 H), 3.71 (dd, 1 H), 3.45 (dd, 1 H), 3.19 (dd, 1 H), 2.55-2.91 (m, 5 H), 1.74-1.88 (m, 1 H), 1.44-1.74 (m, 2 H), 1.04-1.37 (m, 3 H), 0.52-0.72 (m, 2 H), 0.26-0.51 (m, 2 H)<br>LCMS: [MH+] = 782 |
| Ex. 112 | 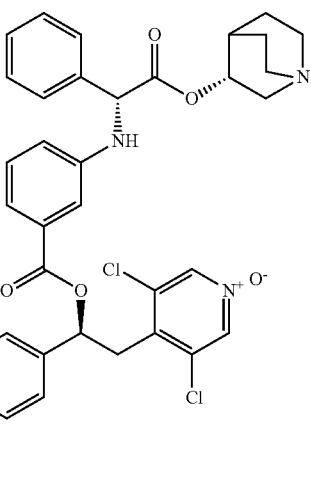<br>[(1S)-1-[3-(cyclopropylmethoxy)-4-(difluoromethoxy)phenyl]-2-(3,5-dichloro-1-oxido-pyridin-1-ium-4-yl)ethyl] 3-[[(1R)-2-oxo-1-phenyl-2-[(3R)-quinuclidin-3-yl]oxy-ethyl]amino]benzoate single stereoisomer | $^1$H NMR (300 MHz, METHANOL-d$_4$) δ ppm 8.43 (s, 2 H), 7.52-7.63 (m, 2 H), 7.27-7.49 (m, 6 H), 7.22 (t, 1 H), 7.17 (d, 1 H), 7.14 (d, 1 H), 7.04 (dd, 1 H), 6.99 (dd, 1 H), 6.77 (t, 2 H), 6.31 (dd, 1 H), 5.25 (s, 1 H), 4.83-5.01 (m, 2 H), 3.86-4.01 (m, 2 H), 3.74 (dd, 1 H), 3.47 (dd, 1 H), 3.10 (ddd, 1 H), 2.56-2.85 (m, 2 H), 2.30-2.47 (m, 1 H), 2.25 (ddd, 1 H), 1.97-2.09 (m, 1 H), 1.66-1.89 (m, 1 H), 1.49-1.67 (m, 1 H), 1.34-1.50 (m, 1 H), 1.13-1.33 (m, 1 H), 0.53-0.75 (m, 2 H), 0.15-0.50 (m, 2 H)<br>LCMS: [MH+] = 782 |

-continued

| Ref | Compound | Analytical data |
|---|---|---|
| Ex. 113 | 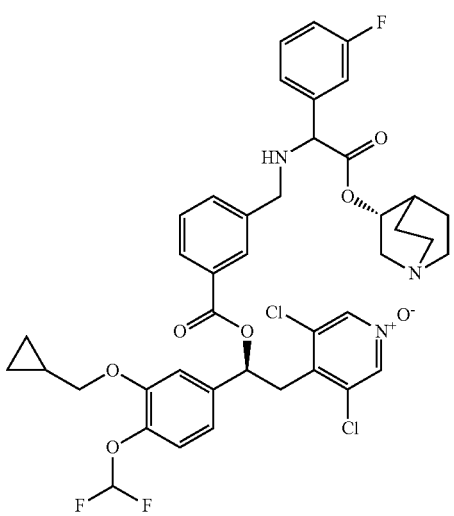<br>[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(3-fluorophenyl)-2-oxo-2-[(3R)-quinuclidin-3-yl]oxy-ethyl]amino]methyl]benzoate trifluoroacetate salt | $^1$H NMR (300 MHz, DMSO-d$_6$) δ ppm 9.67 (br. s., 1 H), 9.54 (br. S., 1 H), 8.54 (s, 2 H), 7.91-8.09 (m, 2 H), 7.63-7.72 (m, 1 H), 7.45-7.62 (m, 2 H), 7.25-7.45 (m, 3 H), 7.18-7.25 (m, 2 H), 7.10 (dd, 1 H), 7.07 (t, 1 H), 6.12-6.35 (m, 1 H), 4.96-5.24 (m, 2 H), 3.96-4.10 (m, 2 H), 3.94 (d, 2 H), 3.60-3.75 (m, 1 H), 3.62 (dd, 1 H), 3.36 (dd, 1 H), 2.84-3.30 (m, 5 H), 2.01-2.17 and 2.20-2.29 (m, 1 H), 1.32-1.97 (m, 4 H), 1.04-1.29 (m, 1 H), 0.48-0.65 (m, 2 H), 0.25-0.42 (m, 2 H)<br>LCMS: [MH+] = 814 |
| Ex. 114 | 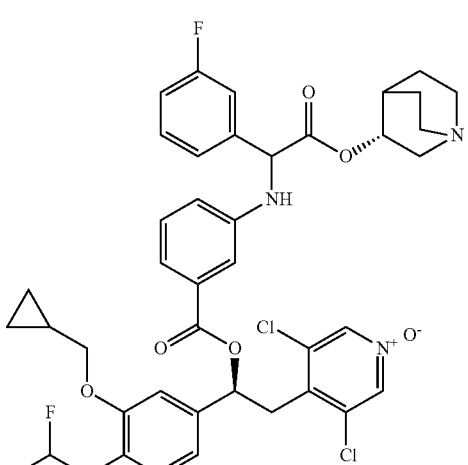<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-fluorophenyl)-2-oxo-2-[(3R)-quinuclidin-3-yl]oxy-ethyl]amino]benzoate trifluoroacetate salt | $^1$H NMR (300 MHz, DMSO-d$_6$) δ ppm 9.37 and 9.51 (br. s., 1 H), 8.54 (s, 2 H), 7.35-7.58 (m, 3 H), 7.12-7.35 (m, 4 H), 6.92-7.12 (m, 4 H), 7.06 (t, 1 H), 6.71-6.89 (m, 1 H), 6.09-6.28 (m, 1 H), 5.32-5.65 (m, 1 H), 4.95-5.17 (m, 1 H), 3.92 and 3.93 (d, 2 H), 3.45-3.73 (m, 3 H), 3.00-3.41 (m, 3 H), 2.57-2.86 (m, 2 H), 1.98-2.12 and 2.20-2.30 (m, 1 H), 1.41-1.95 (m, 3 H), 0.92-1.38 (m, 2 H), 0.47-0.69 (m, 2 H), 0.28-0.42 (m, 2 H)<br>LCMS: [MH+] = 800 |

| Ref | Compound | Analytical data |
|---|---|---|
| Ex. 115 | 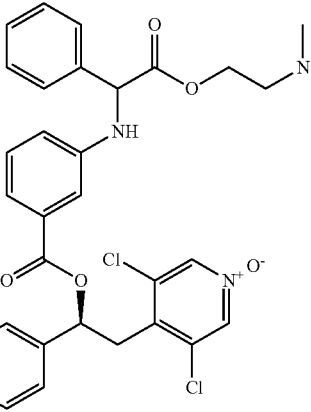<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-(2-dimethylaminoethyloxy)-2-oxo-1-phenyl-ethyl]amino]benzoate trifluoroacetate salt | $^1$H NMR (300 MHz, DMSO-d$_6$) δ ppm 9.53 (br. s., 1 H), 8.54 and 8.55 (s, 2 H), 7.48-7.61 (m, 2 H), 6.68-7.47 (m, 12 H), 6.65-6.81 (m, 1 H), 6.03-6.30 (m, 1 H), 5.17-5.47 (m, 0 H), 4.38-4.59 (m, 1 H), 4.20-4.38 (m, 1 H), 3.87-3.99 (m, 2 H), 3.47-3.62 (m, 2 H), 3.18-3.44 (m, 2 H), 2.72 (br. s., 6 H), 1.08-1.35 (m, 1 H), 0.46-0.65 (m, 2 H), 0.25-0.44 (m, 2 H)<br>LCMS: [MH+] = 744 |
| Ex. 116 | 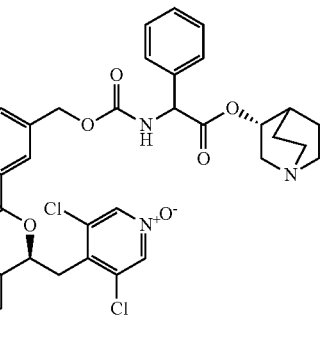<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]carbamoyloxy methyl]benzoate | $^1$H NMR (300 MHz, DMSO-d$_6$) δ ppm 8.53 (d, 2 H), 8.31 (dd, 1 H), 7.85-8.09 (m, 2 H), 7,66 (d, 1 H), 7.54 (d, 1 H), 7.41-7.48 (m, 2 H), 7.32-7.41 (m, 3 H), 7.20 (d, 2 H), 7.10 (dt, 1 H), 7.06 (t, 1 H), 6.22 (dd, 1 H), 5.28 (d, 1 H), 4.98-5.23 (m, 2 H), 4.68 (br. s., 1 H), 3.93 (d, 2 H), 3.62 (dd, 1 H), 3.36 (dd, 1 H), 2.88-3.13 (m, 1 H), 2.55-2.62 (m, 3 H), 2.30-2.42 (m, 1 H), 2.19 (d, 1 H), 1.69 (d, 1 H), 1.49-1.64 (m, 1 H), 1.32-1.49 (m, 1 H), 1.12-1.32 (m, 2 H), 0.95-1.10 (m, 1 H), 0.44-0.65 (m, 2 H), 0.17-0.43 (m, 2 H)<br>LCMS: [MH+] = 840 |
| Ex. 117 | 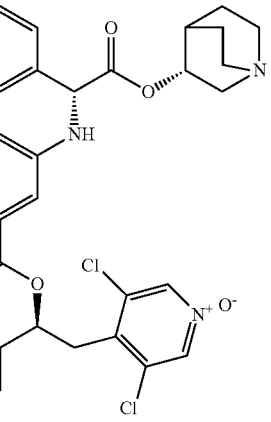<br>[(1S)-2-(3,5-dichloro-1-oxido-pyridin-1-ium-4-yl)-1-(3,4-dimethoxyphenyl)ethyl] 3-[[(1R)-2-oxo-1-phenyl-2-[(3R)-quinuclidin-3-yl]oxy-ethyl]amino]benzoate trifluoroacetae salt single stereoisomer | $^1$H NMR (300 MHz, DMSO-d$_6$) δ ppm 8.52 (s, 2 H), 7.54 (d, 2 H), 7.29-7.47 (m, 4 H), 7.11-7.29 (m, 2 H), 6.88-7.11 (m, 4 H), 6.68 (d, 1 H), 6.18 (dd, 1 H), 5.31 (d, 1 H), 4.69 (d, 1 H), 3.76 (s, 3 H), 3.77 (s, 3 H), 3.58 (dd, 1 H), 3.35-3.48 (m, 1 H), 2.95 (dd, 1 H), 2.54-2.64 (m, 2 H), 2.15-2.25 (m, 1 H), 2.04 (d, 1 H), 1.87 (br. s., 1 H), 1.48-1.71 (m, 2 H), 1.44 (br. s., 1 H), 1.23-1.31 (m, 1 H), 1.10-1.23 (m, 1 H)<br>LCMS: [MH+] = 706 |

-continued

| Ref | Compound | Analytical data |
|---|---|---|
| Ex. 118 | 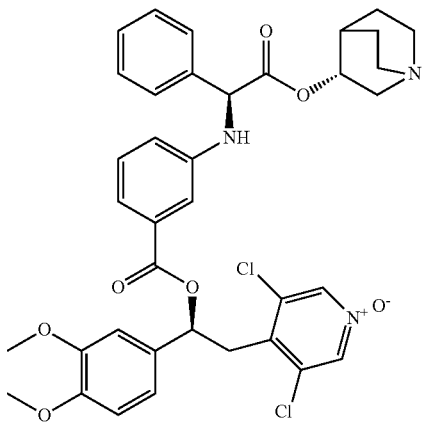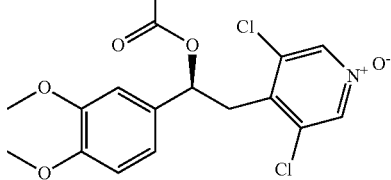<br>[(1S)-2-(3,5-dichloro-1-oxido-pyridin-1-ium-4-yl)-1-(3,4-dimethoxyphenyl)ethyl] 3-[[(1S)-2-oxo-1-phenyl-2-[(3R)-quinuclidin-3-yl]oxy-ethyl]amino]benzoate trifluoroacetate salt single stereoisomer | $^1$H NMR (300 MHz, DMSO-d$_6$) δ ppm 8.52 (s, 2 H), 7.45-7.64 (m, 2 H), 7.27-7.45 (m, 4 H), 7.13-7.27 (m, 2 H), 6.93-7.12 (m, 4 H), 6.69 (d, 1 H), 6.19 (dd, 1 H), 5.27 (d, 1 H), 4.52-4.86 (m, 1 H), 3.76 (s, 3 H), 3.79 (s, 3 H), 3.58 (dd, 1 H), 3.43 (s, 1 H), 3.06 (dd, 1 H), 2.54-2.66 (m, 5 H), 1.61-1.75 (m, 1 H), 1.36-1.58 (m, 2 H), 1.17 (br. s., 1 H), 0.96-1.11 (m, 1 H)<br>LCMS: [MH+] = 706 |
| Ex. 119 | 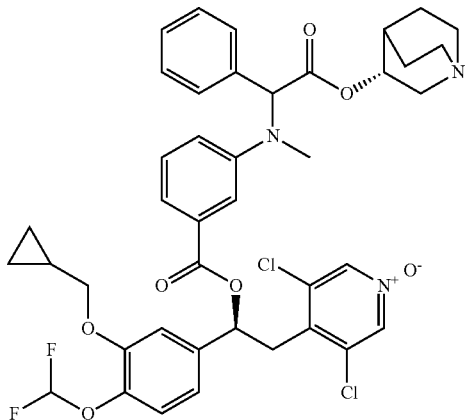<br>[(1S)-1-[3-(cyclopropylmethoxy)-4-(difluoromethoxy)phenyl]-2-(3,5-dichloro-1-oxido-pyridin-1-ium-4-yl)ethyl] 3-[methyl-[2-oxo-1-phenyl-2-[(3R)-quinuclidin-3-yl]oxy-ethyl]amino]benzoate | $^1$H NMR (300 MHz, DMSO-d$_6$) δ ppm 8.54 (d, 2 H), 7.33-7.50 (m, 8 H), 7.15-7.28 (m, 3 H), 7.06 (m, 1 H), 7.06 (t, 1 H), 6.20 (dd, 1 H), 5.91 (s, 1 H), 4.83 (t, 1 H), 3.92 (d, 2 H), 3.46-3.74 (m, 1 H), 3.36 (d, 1 H), 2.97-3.21 (m, 1 H), 2.78 (s, 3 H), 2.55-2.68 (m, 3 H), 2.33 (d, 1 H), 1.82 (dd, 1 H), 1.36-1.69 (m, 3 H), 1.02-1.36 (m, 3 H), 0.44-0.74 (m, 2 H), 0.15-0.44 (m, 2 H)<br>LCMS: [MH+] = 796 |

| Ref | Compound | Analytical data |
|---|---|---|
| Ex. 120 | [(1S)-1-[3-(cyclopropylmethoxy)-4-(difluoromethoxy)phenyl]-2-(3,5-dichloro-1-oxido-pyridin-1-ium-4-yl)ethyl] 3-carbamoyl-5-[[2-oxo-1-phenyl-2-[(3R)-quinuclidin-3-yl]oxy-ethyl]amino]benzoate trifluoroacetate salt | $^1$H NMR (300 MHz, DMSO-$d_6$) δ ppm 9.42 and 9.53 (br. s., 1 H), 8.53 and 8.54 (s, 2 H), 7.96 (br. s., 1 H), 7.73 (t, 1 H), 7.53-7.62 (m, 2 H), 7.49-7.54 (m, 1 H), 6.77-7.49 (m, 10 H), 6.21 (dd, 1 H), 5.43 and 5.47 (d, 1 H), 4.97-5.17 (m, 1 H), 3.88-3.98 (m, 2 H), 3.52-3.69 (m, 2 H), 3.30-3.40 (m, 1 H), 3.01-3.26 (m, 4 H), 2.74-2.84 (m, 1 H), 2.00-2.13 and 2.20-2.29 (m, 1 H), 1.72-1.94 (m, 2 H), 1.62-1.75 (m, 1 H), 1.41-1.62 (m, 1 H), 1.07-1.34 (m, 1 H), 0.45-0.67 (m, 2 H), 0.19-0.41 (m, 2 H)<br>LCMS: [MH+] = 825 |
| Ex. 121 | [(1S)-1-[3-(cyclopropylmethoxy)-4-(difluoromethoxy)phenyl]-2-(3,5-dichloro-1-oxido-pyridin-1-ium-4-yl)ethyl] 3-(dimethylcarbamoyl)-5-[[2-oxo-1-phenyl-2-[(3R)-quinuclidin-3-yl]oxy-ethyl]amino]benzoate trifluoroacetate salt | $^1$H NMR (300 MHz, DMSO-$d_6$) δ ppm 9.45 and 9.57 (br. s., 1 H), 8.54 (s, 2 H), 7.50-7.62 (m, 2 H), 7.35-7.48 (m, 2 H), 6.71-7.35 (m, 9 H), 6.19 (dd, 1 H), 5.43 and 5.47 (d, 1 H), 4.86-5.15 (m, 1 H), 3.86-4.08 (m, 2 H), 3.49-3.77 (m, 2 H), 3.28-3.42 (m, 1 H), 3.05-3.26 (m, 4 H), 2.97 (br. s., 3 H), 2.78-2.93 (m, 1 H), 2.82 (br. s., 3 H), 1.97-2.11 and 2.18-2.26 (m, 1 H), 1.36-1.95 (m, 4 H), 1.10-1.36 (m, 1 H), 0.45-0.72 (m, 2 H), 0.23-0.45 (m, 2 H)<br>LCMS: [MH+] = 853 |

| Ref | Compound | Analytical data |
|---|---|---|
| Ex. 122 | 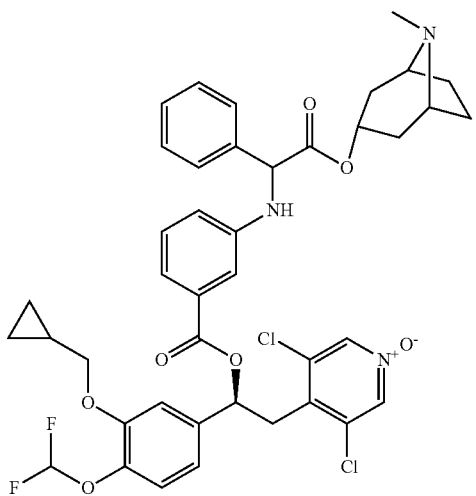<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-[(8-methyl-8-azabicyclo[3.2.1]octan-3-yl)oxy]-2-oxo-1-phenyl-ethyl]amino]benzoate trifluoroacetate salt | $^1$H NMR (300 MHz, DMSO-$d_6$) δ ppm 9.34 (br. s., 1 H), 8.54 (s, 2 H), 7.48-7.61 (m, 2 H), 7.03-7.11 (m, 1 H), 6.96-7.03 (m, 1 H), 6.80-7.47 (m, 9 H), 6.61-6.80 (m, 1 H), 6.07-6.28 (m, 1 H), 5.26-5.45 (m, 1 H), 4.76-5.05 (m, 1 H), 3.92 (d, 2 H), 3.50-3.85 (m, 3 H), 3.25-3.40 (m, 1 H), 2.60 (s, 3 H), 2.16-2.41 (m, 1 H), 1.65-2.33 (m, 5 H), 1.47-1.66 (m, 1 H), 1.04-1.41 (m, 2 H), 0.44-0.70 (m, 2 H), 0.24-0.43 (m, 2 H)<br>LCMS: [MH+] = 796 |
| Ex. 123 | 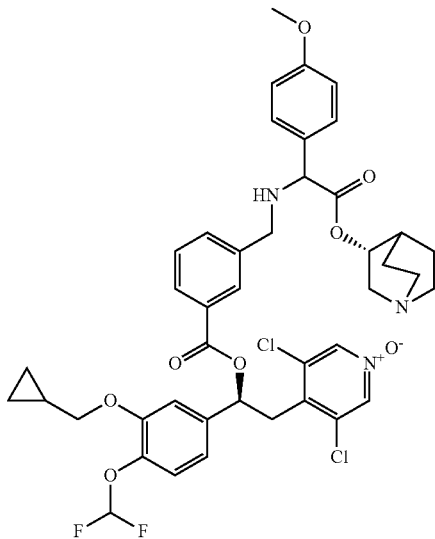<br>[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(4-methoxyphenyl)-2-oxo-2-[(3R)-quinuclidin-3-yl]oxy-ethyl]amino]methyl]benzoate trifluoroacetate salt | $^1$H NMR (300 MHz, DMSO-$d_6$) δ ppm 9.72 and 9.83 (br. s., 1 H), 8.54 (s, 2 H), 7.98-8.12 (m, 2 H), 7.66-7.78 (m, 1 H), 7.60 (t, 1 H), 7.41-7.53 (m, 2 H), 7.18-7.27 (m, 2 H), 6.99-7.16 (m, 3 H), 7.07 (t, 1 H), 6.14-6.34 (m, 1 H), 5.25 (br. s., 1 H), 5.12 (br. s., 1 H), 3.98-4.27 (m, 2 H), 3.93 (d, 2 H), 3.79 (s, 3 H), 3.67-3.76 (m, 1 H), 3.63 (dd, 1 H), 3.37 (dd, 1 H), 2.82-3.30 (m, 5 H), 2.02-2.13 and 2.20-2.35 (m, 1 H), 1.31-1.97 (m, 4 H), 1.08-1.30 (m, 1 H), 0.44-0.68 (m, 2 H), 0.22-0.44 (m, 2 H)<br>LCMS: [MH+] = 826 |

| Ref | Compound | Analytical data |
|---|---|---|
| Ex. 124 | 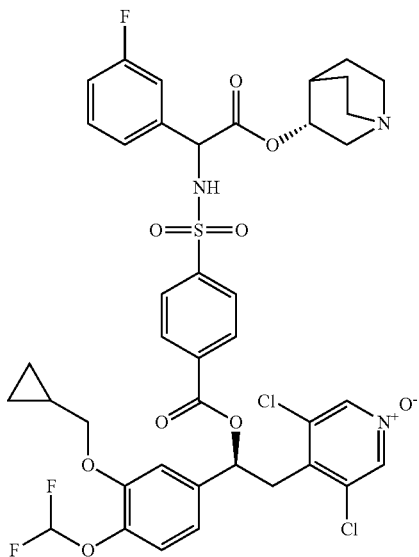<br>[(1S)-1-[3-(cyclopropylmethoxy)-4-(difluoromethoxy)phenyl]-2-(3,5-dichloro-1-oxido-pyridin-1-ium-4-yl)ethyl] 4-[[1-(3-fluorophenyl)-2-oxo-2-[(3R)-quinuclidin-3-yl]oxy-ethyl]sulfamoyl]benzoate | $^1$H NMR (300 MHz, DMSO-d$_6$) δ ppm 9.20 (br. s., 1 H), 8.55 (s, 2 H), 7.98-8.16 (m, 2 H), 7.72-7.92 (m, 2 H), 6.70-7.46 (m, 8 H), 6.01-6.44 (m, 1 H), 5.21 (s, 1 H), 4.38-4.67 (m, 1 H), 3.94 (d, 2 H), 3.63 (dd, 1 H), 3.36 (dd, 1 H), 2.82-3.06 (m, 1 H), 2.54-2.69 (m, 3 H), 1.99-2.44 (m, 2 H), 1.52-1.64 and 1.65-1.74 (m, 1 H), 1.10-1.52 (m, 5 H), 0.47-0.73 (m, 2 H), 0.14-0.42 (m, 2 H)<br>LCMS: [MH+] = 864 |
| Ex. 125 | 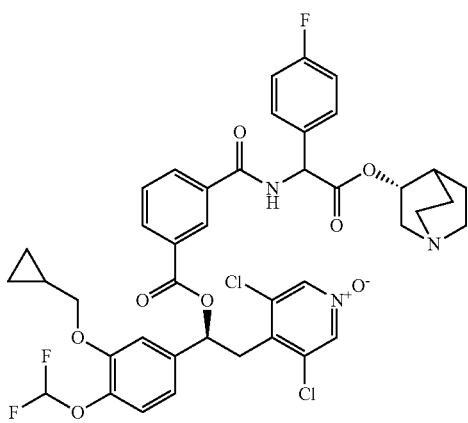<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-fluorophenyl)-2-oxo-2-[(3R)-quinuclidin-3-yl]oxy-ethyl]carbamoyl]benzoate<br>trifluoroacetate salt | $^1$H NMR (300 MHz, DMSO-d$_6$) δ ppm 9.54 and 9.62 (br. s., 1 H), 9.47 and 9.49 (d, 1 H), 8.53 and 8.54 (s, 2 H), 8.39-8.48 (m, 1 H), 8.02-8.28 (m, 2 H), 7.67 (t, 1 H), 7.51-7.63 (m, 2 H), 7.17-7.35 (m, 4 H), 7.10 (dd, 1 H), 7.07 (t, 1 H), 6.05-6.34 (m, 1 H), 5.70 and 5.75 (d, 1 H), 4.97-5.19 (m, 1 H), 3.93 and 3.94 (d, 2 H), 3.67-3.75 (m, 1 H), 3.65 (dd, 1 H), 3.37 (dd, 1 H), 2.81-3.31 (m, 5 H), 2.09-2.20 and 2.25-2.35 (m, 1 H), 1.49-1.98 (m, 4 H), 1.05-1.30 (m, 1 H), 0.44-0.65 (m, 2 H), 0.17-0.44 (m, 2 H)<br>LCMS: [MH+] = 828 |

| Ref | Compound | Analytical data |
|---|---|---|
| Ex. 126 | 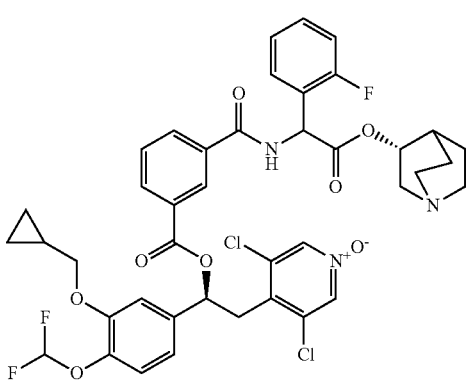<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-fluorophenyl)-2-oxo-2-[(3R)-quinuclidin-3-yl]oxy-ethyl]carbamoyl]benzoate trifluoroacetate salt | $^1$H NMR (300 MHz, DMSO-d$_6$) δ ppm 9.56 (d, 1 H), 9.52 (br. s., 1 H), 8.52 and 8.53 (s, 2 H), 8.42-8.49 (m, 1 H), 8.07-8.24 (m, 2 H), 7.67 (t, 1 H), 7.39-7.61 (m, 2 H), 7.18-7.34 (m, 4 H), 7.08-7.14 (m, 1 H), 7.06 (t, 1 H), 6.14-6.34 (m, 1 H), 5.97 and 6.03 (d, 1 H), 5.04-5.20 (m, 1 H), 3.93 and 3.94 (d, 2 H), 3.67-3.81 (m, 1 H), 3.65 (dd, 1 H), 3.37 (dd, 1 H), 2.82-3.31 (m, 5 H), 2.10-2.21 and 2.25-2.35 (m, 1 H), 1.48-1.98 (m, 4 H), 1.06-1.32 (m, 1 H), 0.47-0.76 (m, 2 H), 0.20-0.44 (m, 2 H)<br>LCMS: [MH+] = 828 |
| Ex. 127 | 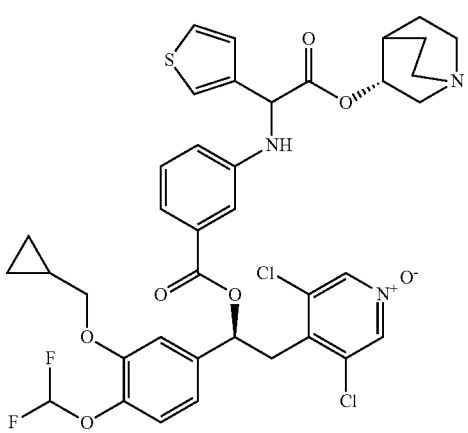<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-2-[(3R)-quinuclidin-3-yl]oxy-1-(3-thienyl)ethyl]amino]benzoate trifluoroacetate salt | $^1$H NMR (300 MHz, DMSO-d$_6$) δ ppm 9.39 and 9.49 (br. s., 1 H), 8.55 (s, 2 H), 7.62-7.68 (m, 1 H), 7.52-7.62 (m, 1 H), 7.24-7.38 (m, 3 H), 7.21 (d, 1 H), 7.19 (d, 1 H), 6.94-7.09 (m, 3 H), 7.07 (t, 1 H), 6.71 (d, 1 H), 6.11-6.32 (m, 1 H), 5.48 and 5.51 (d, 1 H), 4.91-5.18 (m, 1 H), 3.93 (d, 2 H), 3.54-3.71 (m, 2 H), 2.93-3.37 (m, 5 H), 2.70-2.90 (m, 1 H), 1.96-2.13 and 2.18-2.26 (m, 1 H), 1.40-2.00 (m, 4 H), 1.10-1.30 (m, 1 H), 0.47-0.71 (m, 2 H), 0.13-0.42 (m, 2 H)<br>LCMS: [MH+] = 788 |

| Ref | Compound | Analytical data |
|---|---|---|
| Ex. 128 | 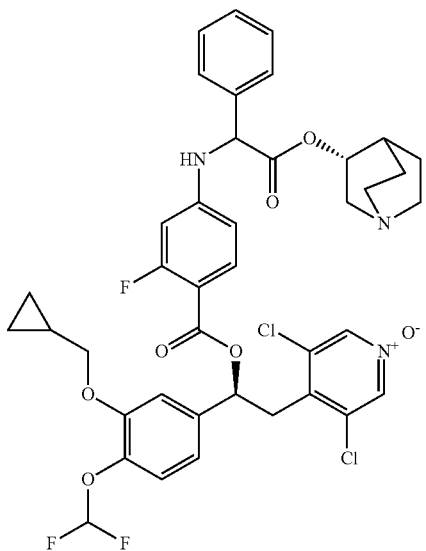<br>[(1S)-1-[3-(cyclopropylmethoxy)-4-(difluoromethoxy)phenyl]-2-(3,5-dichloro-1-oxido-pyridin-1-ium-4-yl)ethyl] 2-fluoro-4-[[2-oxo-1-phenyl-2-[(3R)-quinuclidin-3-yl]oxy-ethyl]amino]benzoate trifluoroacetate salt | $^1$H NMR (300 MHz, DMSO-$d_6$) δ ppm 9.43 and 9.55 (br. s., 1 H), 8.53 (s, 2 H), 7.67 and 7.68 (t, 1 H), 7.49-7.62 (m, 3 H), 7.33-7.49 (m, 3 H), 7.19 (d, 1 H), 7.15 (d, 1 H), 7.02 (dd, 1 H), 7.05 (t, 1 H), 6.59-6.70 (m, 1 H), 6.46-6.59 (m, 1 H), 6.10-6.24 (m, 1 H), 5.49 (d, 1 H), 5.00-5.20 (m, 1 H), 3.90 (d, 2 H), 3.57-3.76 (m, 1 H), 3.51 (dd, 1 H), 3.29 (dd, 1 H), 2.99-3.25 (m, 4 H), 2.70-2.85 (m, 1 H), 1.99-2.12 and 2.20-2.31 (m, 1 H), 1.34-1.98 (m, 4 H), 1.09-1.32 (m, 1 H), 0.47-0.66 (m, 2 H), 0.29-0.43 (m, 2 H)<br>LCMS: [MH+] = 800 |
| Ex. 129 | 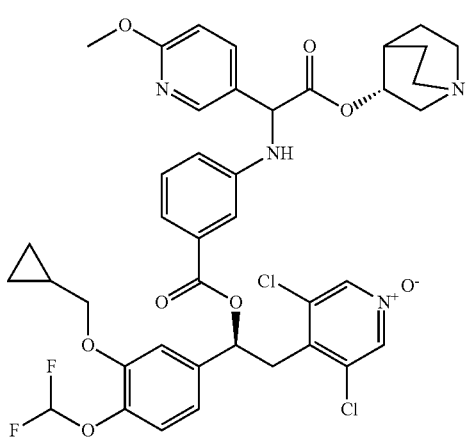<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(6-methoxy-3-pyridyl)-2-oxo-2-[(3R)-quinuclidin-3-yl]oxy-ethyl]amino]benzoate trifluoroacetate salt | $^1$H NMR (300 MHz, DMSO-$d_6$) δ ppm 9.32 and 9.51 (br. s., 1 H), 8.55 (s, 2 H), 8.34 (d, 1 H), 7.78-7.93 (m, 1 H), 7.14-7.36 (m, 4 H), 6.86 and 6.88 (d, 1 H), 6.81-7.27 (m, 4 H), 6.69-6.80 (m, 1 H), 6.20 (dd, 1 H), 5.39 and 5.43 (d, 1 H), 4.96-5.15 (m, 1 H), 3.92 and 3.94 (d, 2 H), 3.84 and 3.86 (s, 3 H), 3.50-3.70 (m, 2 H), 3.28-3.39 (m, 1 H), 3.01-3.28 (m, 4 H), 2.76-2.91 (m, 1 H), 2.05 (d, 1 H), 1.46-1.96 and 2.19-2.27 (m, 4 H), 1.12-1.31 (m, 1 H), 0.47-0.68 (m, 2 H), 0.23-0.44 (m, 2 H)<br>LCMS: [MH+] = 813 |

-continued

| Ref | Compound | Analytical data |
|---|---|---|
| Ex. 130 | 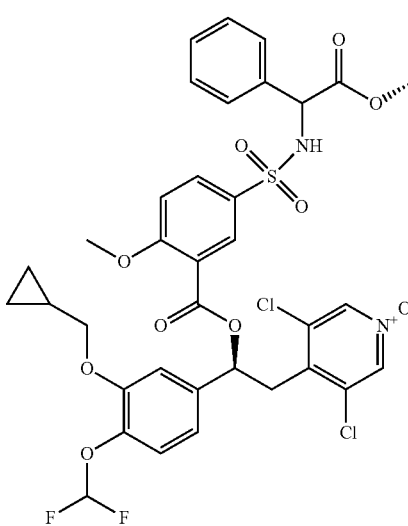<br>[(1S)-1-[3-(cyclopropylmethoxy)-4-(difluoromethoxy)phenyl]-2-(3,5-dichloro-1-oxido-pyridin-1-ium-4-yl)ethyl] 2-methoxy-5-[[2-oxo-1-phenyl-2-[(3R)-quinuclidin-3-yl]oxy-ethyl]sulfamoyl]benzoate | $^1$H NMR (300 MHz, DMSO-$d_6$) δ ppm 8.89 (br. s., 1 H), 8.55 and 8.56 (s, 2 H), 7.97 (d, 1 H), 7.79-7.93 (m, 1 H), 7.15-7.32 (m, 9 H), 7.05 (d, 1 H), 7.08 and 7.09 (t, 1 H), 6.17 (dd, 1 H), 5.01 (br. s., 1 H), 4.35-4.56 (m, 1 H), 3.87-3.99 (m, 2 H), 3.84 and 3.85 (s, 3 H), 3.52 (dd, 1 H), 3.33 (dd, 1 H), 2.77-2.99 (m, 1 H), 2.00-2.46 (m, 5 H), 1.52-1.60 and 1.60-1.70 (m, 1 H), 0.94-1.52 (m, 4 H), 0.48-0.67 (m, 2 H), 0.27-0.44 (m, 2 H)<br>LCMS: [MH+] = 876 |
| Ex. 131 | 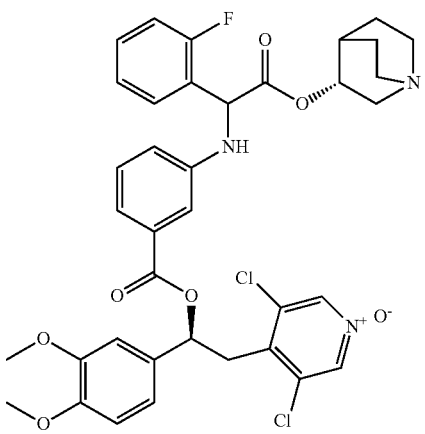<br>[(1S)-2-(3,5-dichloro-1-oxido-pyridin-1-ium-4-yl)-1-(3,4-dimethoxyphenyl)ethyl] 3-[[1-(2-fluorophenyl)-2-oxo-2-[(3R)-quinuclidin-3-yl]oxy-ethyl]amino]benzoate<br>trifluoroacetate salt | $^1$H NMR (300 MHz, DMSO-$d_6$) δ ppm 9.49 and 9.62 (br. s., 1 H), 8.51 and 8.53 (s, 2 H), 7.15-7.64 (m, 7 H), 6.92-7.10 (m, 4 H), 6.82 (br. s., 1 H), 6.07-6.28 (m, 1 H), 5.61 (br. s., 1 H), 5.00-5.20 (m, 1 H), 3.77 and 3.79 (s, 3 H), 3.76 (s, 3 H), 3.48-3.71 (m, 2 H), 2.97-3.42 (m, 5 H), 2.77-2.89 (m, 1 H), 1.96-2.06 and 2.20-2.30 (m, 1 H), 1.40-1.96 (m, 4 H)<br>LCMS: [MH+] = 724 |

| Ref | Compound | Analytical data |
|---|---|---|
| Ex. 132 | 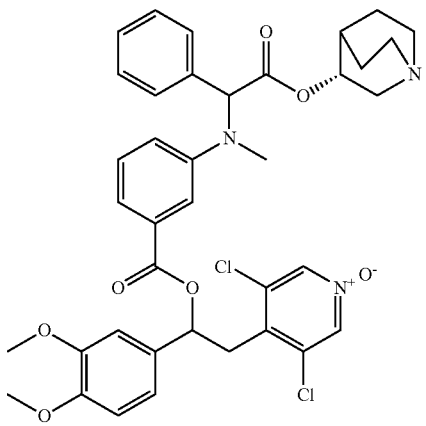<br>[2-(3,5-dichloro-1-oxido-pyridin-1-ium-4-yl)-1-(3,4-dimethoxyphenyl)ethyl] 3-[methyl-[2-oxo-1-phenyl-2-[(3R)-quinuclidin-3-yl]oxy-ethyl]amino]benzoate trifluoroacetate salt | $^1$H NMR (300 MHz, DMSO-$d_6$) δ ppm 9.45 (br. s., 1 H), 8.56 (s, 2 H), 7.13-7.62 (m, 9 H), 6.83-7.09 (m, 3 H), 6.09-6.30 (m, 1 H), 5.93-6.05 (m, 1 H), 4.98-5.29 (m, 1 H), 3.78 (s, 3 H), 3.76 (s, 3 H), 3.58-3.72 (m, 2 H), 3.33 (dd, 1 H), 2.85-3.26 (m, 5 H), 2.81 (s, 3 H), 1.97-2.19 (m, 1 H), 1.29-1.96 (m, 4 H)<br>LCMS: [MH+] = 720 |
| Ex. 133 | 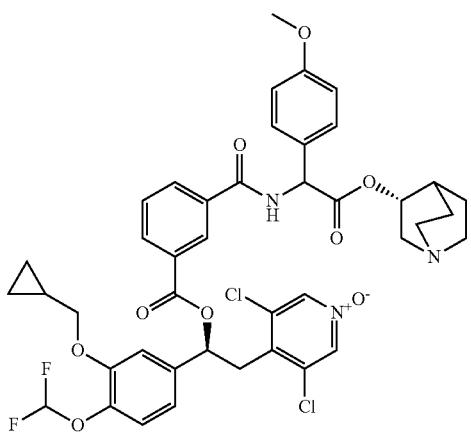<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-methoxyphenyl)-2-oxo-2-[(3R)-quinuclidin-3-yl]oxy-ethyl]carbamoyl]benzoate trifluoroacetate salt | $^1$H NMR (300 MHz, DMSO-$d_6$) δ ppm 9.37-9.48 (m, 1 H), 9.38 (d, 1 H), 8.52 and 8.54 (s, 2 H), 8.39-8.48 (m, 1 H), 8.07-8.26 (m, 2 H), 7.65 (t, 1 H), 7.38-7.53 (m, 2 H), 6.77-7.36 (m, 6 H), 6.17-6.35 (m, 1 H), 5.57 and 5.62 (d, 1 H), 5.06 (br. s., 1 H), 3.93 (d, 2 H), 3.77 (s, 3 H), 3.68-3.74 (m, 1 H), 3.64 (dd, 1 H), 3.37 (dd, 1 H), 3.04-3.30 (m, 4 H), 2.84-3.03 (m, 1 H), 2.05-2.18 and 2.29-2.38 (m, 1 H), 1.47-2.02 (m, 4 H), 1.10-1.34 (m, 1 H), 0.48-0.67 (m, 2 H), 0.22-0.42 (m, 2 H)<br>LCMS: [MH+] = 840 |

-continued

| Ref | Compound | Analytical data |
|---|---|---|
| Ex. 134 | [(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-methoxyphenyl)-2-oxo-2-[(3R)-quinuclidin-3-yl]oxy-ethyl]carbamoyl]benzoate trifluoroacetate salt | $^1$H NMR (300 MHz, DMSO-d$_6$) δ ppm 9.48 (br. s., 1 H), 9.43 and 9.44 (d, 1 H), 8.52 and 8.53 (s, 2 H), 8.38-8.48 (m, 1 H), 8.10-8.27 (m, 2 H), 7.66 (t, 1 H), 6.90-7.03 (m, 1 H), 6.75-7.47 (m, 7 H), 6.13-6.31 (m, 1 H), 5.64 and 5.70 (d, 1 H), 4.95-5.23 (m, 1 H), 3.93 and 3.94 (d, 2 H), 3.77 and 3.78 (s, 3 H), 3.66-3.74 (m, 1 H), 3.57-3.70 (m, 1 H), 3.38-3.52 (m, 1 H), 3.09-3.30 (m, 4 H), 2.84-3.05 (m, 1 H), 2.05-2.20 and 2.30-2.40 (m, 1 H), 1.50-1.99 (m, 4 H), 1.12-1.24 (m, 1 H), 0.48-0.69 (m, 2 H), 0.23-0.43 (m, 2 H)<br>LCMS: [MH+] = 840 |
| Ex. 135 | [(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-methoxyphenyl)-2-oxo-2-[(3R)-quinuclidin-3-yl]oxy-ethyl]carbamoyl]benzoate trifluoroacetate salt | $^1$H NMR (300 MHz, DMSO-d$_6$) δ ppm 9.41 (br. s., 1 H), 9.24 and 9.25 (d, 1 H), 8.51 and 8.53 (s, 2 H), 8.44 (t, 1 H), 8.07-8.25 (m, 2 H), 7.65 (t, 1 H), 7.18-7.27 (m, 2 H), 7.08-7.15 (m, 2 H), 6.94-7.04 (m, 1 H), 6.79-7.46 (m, 3 H), 6.16-6.31 (m, 1 H), 5.96 and 6.00 (d, 1 H), 5.08 (br. s., 1 H), 3.93 and 3.94 (d, 2 H), 3.84 (s, 3 H), 3.55-3.76 (m, 2 H), 3.34-3.46 (m, 1 H), 3.08-3.26 (m, 5 H), 2.07-2.40 (m, 1 H), 1.41-1.98 (m, 4 H), 1.11-1.22 (m, 1 H), 0.48-0.67 (m, 2 H), 0.21-0.44 (m, 2 H)<br>LCMS: [MH+] = 840 |
| Ex. 136 | [(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-fluorophenyl)-2-oxo-2-quinuclidin-3-yloxy-ethyl]carbamoyl]benzoate trifluoroacetate salt | $^1$H NMR (300 MHz, DMSO-d$_6$) δ ppm 9.57 (br. s., 1 H), 9.50 and 9.53 (d, 1 H), 8.52 and 8.53 (s, 2 H), 8.41-8.49 (m, 1 H), 8.14-8.28 (m, 2 H), 7.67 and 7.68 (t, 1 H), 7.34-7.55 (m, 3 H), 7.17-7.29 (m, 3 H), 7.08-7.16 (m, 1 H), 7.07 (t, 1 H), 6.24 (dd, 1 H), 5.75 and 5.81 (d, 1 H), 4.97-5.23 (m, 1 H), 3.93 and 3.94 (d, 2 H), 3.68-3.75 (m, 1 H), 3.65 (dd, 1 H), 3.37 (dd, 1 H), 2.85-3.29 (m, 5 H), 2.05-2.21 and 2.26-2.37 (m, 1 H), 1.47-2.00 (m, 4 H), 1.08-1.29 (m, 1 H), 0.45-0.65 (m, 2 H), 0.27-0.42 (m, 2 H)<br>LCMS: [MH+] = 828 |

| Ref | Compound | Analytical data |
|---|---|---|
| Ex. 137 | 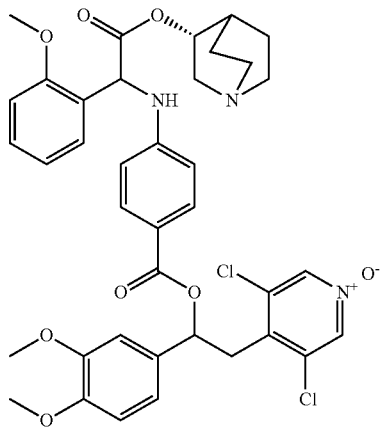<br>[2-(3,5-dichloro-1-oxido-pyridin-1-ium-4-yl)-1-(3,4-dimethoxyphenyl)ethyl] 4-[[1-(2-methoxyphenyl)-2-oxo-2-[(3R)-quinuclidin-3-yl]oxy-ethyl]amino]benzoate trifluoroacetate salt | $^1$H NMR (300 MHz, DMSO-$d_6$) δ ppm 9.42 and 9.49 (br. s., 1 H), 8.53 (s, 2 H), 7.66-7.75 (m, 2 H), 7.24-7.55 (m, 2 H), 6.87-7.16 (m, 6 H), 6.59-6.86 (m, 2 H), 6.11-6.24 (m, 1 H), 5.58 and 5.60 (br. s., 1 H), 4.89-5.18 (m, 1 H), 3.86 (s, 3 H), 3.77 (s, 3 H), 3.75 (s, 3 H), 3.51-3.72 (m, 2 H), 2.76-3.39 (m, 6 H), 1.98-2.15\f2 and 2.18 2.26 (m, 1 H), 1.40-1.96 (m, 4 H)<br>LCMS: [MH+] = 736 |
| Ex. 138 | 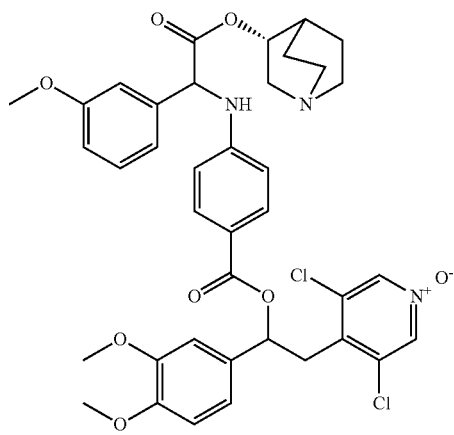<br>[2-(3,5-dichloro-1-oxido-pyridin-1-ium-4-yl)-1-(3,4-dimethoxyphenyl)ethyl] 4-[[1-(3-methoxyphenyl)-2-oxo-2-[(3R)-quinuclidin-3-yl]oxy-ethyl]amino]benzoate trifluoroacetate salt | $^1$H NMR (300 MHz, DMSO-$d_6$) δ ppm 9.45 and 9.58 (br. s., 1 H), 8.52 and 8.53 (s, 2 H), 7.60-7.88 (m, 2 H), 7.16-7.42 (m, 2 H), 7.04-7.15 (m, 2 H), 6.83-7.05 (m, 4 H), 6.64-6.83 (m, 2 H), 5.95-6.27 (m, 1 H), 5.23-5.55 (m, 1 H), 4.91-5.19 (m, 1 H), 3.77 (s, 3 H), 3.76 (s, 3 H), 3.74 (s, 3 H), 3.47-3.71 (m, 2 H), 2.99-3.39 (m, 5 H), 2.73 (dt, 1 H), 1.98-2.11 and 2.22-2.33 (m, 1 H), 1.64-1.98 (m, 3 H), 1.41-1.65 (m, 1 H)<br>LCMS: [MH+] = 736 |

| Ref | Compound | Analytical data |
|---|---|---|
| Ex. 139 | 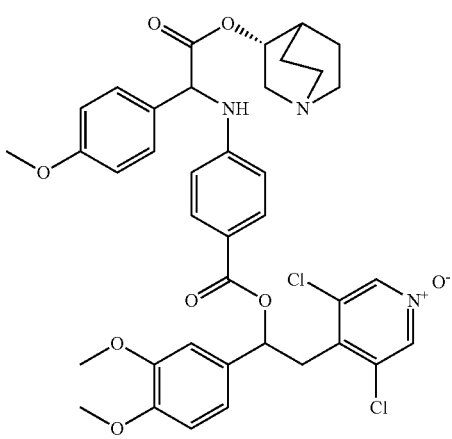<br>[2-(3,5-dichloro-1-oxido-pyridin-1-ium-4-yl)-1-(3,4-dimethoxyphenyl)ethyl] 4-[[1-(4-methoxyphenyl)-2-oxo-2-[(3R)-quinuclidin-3-yl]oxy-ethyl]amino]benzoate trifluoroacetate salt | $^1$H NMR (300 MHz, DMSO-d$_6$) δ ppm 9.41 and 9.54 (br. s., 1 H), 8.53 (s, 2 H), 7.64-7.84 (m, 2 H), 7.34-7.53 (m, 2 H), 7.11-7.25 (m, 1 H), 6.87-7.06 (m, 5 H), 6.57-6.79 (m, 2 H), 6.06-6.24 (m, 1 H), 5.39 (d, 1 H), 4.95-5.16 (m, 1 H), 3.77 (s, 3 H), 3.76 (s, 3 H), 3.75 (s, 3 H), 3.52-3.67 (m, 2 H), 3.28 (dd, 1 H), 3.00-3.24 (m, 4 H), 2.73-2.83 (m, 1 H), 1.98-2.12 and 2.16-2.34 (m, 1 H), 1.61-1.96 (m, 3 H), 1.45-1.63 (m, 1 H) LCMS: [MH+] = 736 |
| Ex. 140 | 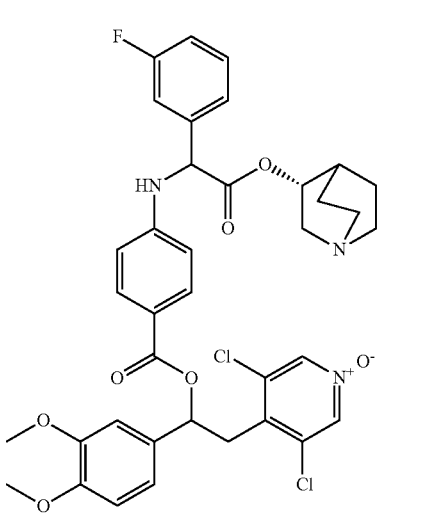<br>[2-(3,5-dichloro-1-oxido-pyridin-1-ium-4-yl)-1-(3,4-dimethoxyphenyl)ethyl] 4-[[1-(3-fluorophenyl)-2-oxo-2-[(3R)-quinuclidin-3-yl]oxy-ethyl]amino]benzoate trifluoroacetate salt | $^1$H NMR (300 MHz, DMSO-d$_6$) δ ppm 9.43 and 9.58 (br. s., 1 H), 8.52 (s, 2 H), 7.61-7.86 (m, 2 H), 7.35-7.57 (m, 3 H), 7.11-7.35 (m, 2 H), 6.88-7.08 (m, 3 H), 6.66-6.87 (m, 2 H), 6.03-6.25 (m, 1 H), 5.44-5.64 (m, 1 H), 4.95-5.22 (m, 1 H), 3.76 and 3.77 (s, 3 H), 3.74 (s, 3 H), 3.62-3.73 (m, 1 H), 3.57 (dd, 1 H), 3.04-3.36 (m, 5 H), 2.76-2.90 (m, 1 H), 2.01-2.11 and 2.23-2.32 (m, 1 H), 1.45-1.97 (m, 4 H) LCMS: [MH+] = 724 |

| Ref | Compound | Analytical data |
|---|---|---|
| Ex. 141 | 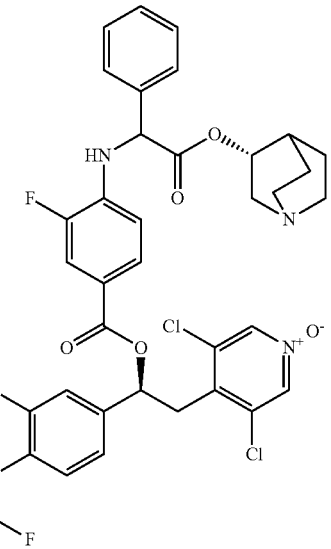<br>[(1S)-1-[3-(cyclopropylmethoxy)-4-(difluoromethoxy)phenyl]-2-(3,5-dichloro-1-oxido-pyridin-1-ium-4-yl)ethyl] 3-fluoro-4-[[2-oxo-1-phenyl-2-[(3R)-quinuclidin-3-yl]oxy-ethyl]amino]benzoate | $^1$H NMR (300 MHz, DMSO-$d_6$) δ ppm 9.49 and 9.61 (br. s., 1 H), 8.53 (s, 2 H), 7.50-7.76 (m, 5 H), 7.31-7.50 (m, 3 H), 7.14-7.25 (m, 1 H), 6.76-7.32 (m, 2 H), 6.56-6.78 (m, 2 H), 6.14 (dd, 1 H), 5.56 and 5.61 (d, 1 H), 4.99-5.20 (m, 1 H), 3.91 (d, 2 H), 3.42-3.73 (m, 2 H), 2.99-3.37 (m, 5 H), 2.76-2.95 (m, 1 H), 2.00-2.13 and 2.21-2.34 (m, 1 H), 1.37-1.98 (m, 4 H), 1.05-1.32 (m, 1 H), 0.44-0.74 (m, 2 H), 0.14-0.44 (m, 2 H)<br>LCMS: [MH+] = 800 |
| Ex. 142 | 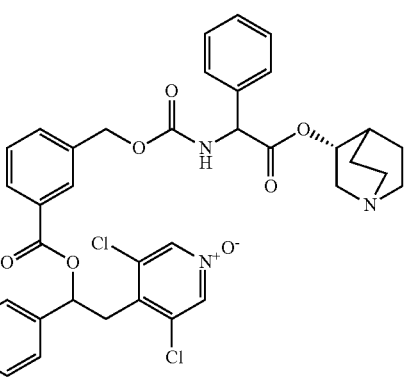<br>[2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]carbamoyloxymethyl]benzoate trifluoroacetate salt | $^1$H NMR (300 MHz, DMSO-$d_6$) δ ppm 9.42 and 9.51 (br. s., 1 H), 8.53 and 8.54 (s, 2 H), 8.41 (d, 1 H), 7.85-8.06 (m, 2 H), 7.23-7.76 (m, 6 H), 6.87-7.15 (m, 3 H), 6.23 (dd, 1 H), 5.34 and 5.37 (d, 1 H), 5.15 (s, 2 H), 5.01 (br. s., 1 H), 3.78 (s, 3 H), 3.76 (s, 3 H), 3.53-3.72 (m, 2 H), 3.35 (dd, 2 H), 2.97-3.27 (m, 4 H), 2.78-2.96 (m, 1 H), 1.95-2.07 and 2.20-2.27 (m, 1 H), 1.40-1.94 (m, 4 H)<br>LCMS: [MH+] = 764 |

| Ref | Compound | Analytical data |
|---|---|---|
| Ex. 143 | 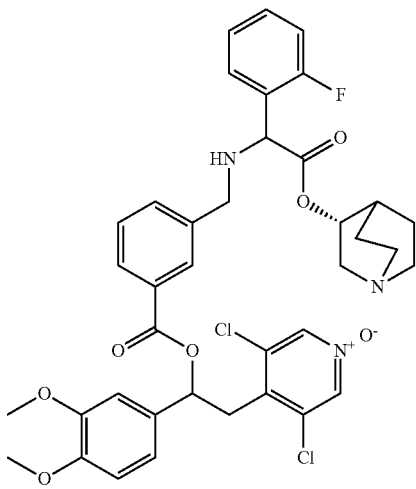<br>[2-(3,5-dichloro-1-oxido-pyridin-1-ium-4-yl)-1-(3,4-dimethoxyphenyl)ethyl] 3-[[[1-(2-fluorophenyl)-2-oxo-2-[(3R)-quinuclidin-3-yl]oxy-ethyl]amino]methyl]benzoate | $^1$H NMR (300 MHz, DMSO-d$_6$) δ ppm 8.51 (s, 2 H), 7.95 (s, 1 H), 7.78-7.90 (m, 1 H), 7.51-7.68 (m, 2 H), 7.46 (t, 1 H), 7.28-7.40 (m, 1 H), 7.12-7.28 (m, 2 H), 6.83-7.12 (m, 3 H), 6.01-6.38 (m, 1 H), 4.47-4.85 (m, 2 H), 3.77 (br. s., 3 H), 3.76 (s, 3 H), 3.77 (br. s., 2 H), 3.62 (dd, 1 H), 3.32-3.40 (m, 1 H), 2.90-3.12 (m, 1 H), 2.08-2.67 (m, 5 H), 1.68-1.94 (m, 1 H), 1.02-1.57 (m, 4 H)<br>LCMS: [MH+] = 738 |
| Ex. 144 | 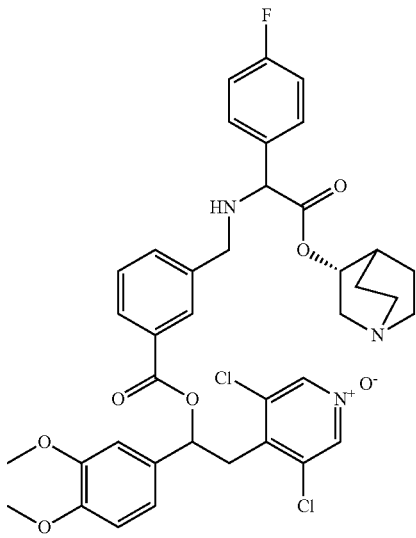<br>[2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate trifluoroacetate salt | $^1$H NMR (300 MHz, DMSO-d$_6$) δ ppm 9.62 and 9.75 (br. s., 1 H), 8.53 (s, 2 H), 7.91-8.22 (m, 2 H), 7.64-7.77 (m, 1 H), 7.47-7.64 (m, 3 H), 7.32 (m, 2 H), 6.86-7.17 (m, 3 H), 6.25 (dd, 1 H), 4.98-5.37 (m, 2 H), 3.78 (s, 3 H), 3.76 (s, 3 H), 3.71-4.24 (m, 3 H), 3.64 (dd, 1 H), 3.36 (dd, 1 H), 2.81-3.30 (m, 5 H), 2.00-2.16 and 2.22-2.31 (m, 1 H), 1.23-1.99 (m, 4 H) LCMS: [MH+] = 738 |

| Ref | Compound | Analytical data |
|---|---|---|
| Ex. 145 | 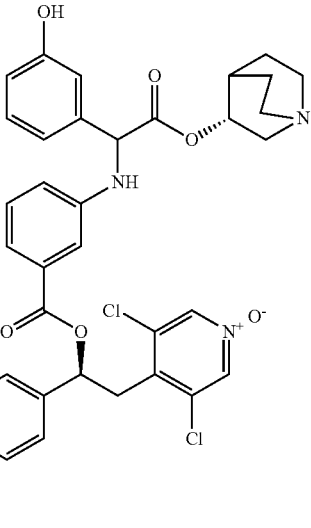<br>[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-hydroxyphenyl)-2-oxo-2-[(3R)-quinuclidin-3-yl]oxy-ethyl]amino]benzoate trifluoroacetate salt | $^1$H NMR (300 MHz, DMSO-$d_6$) δ ppm 9.35-9.65 (m, 2 H), 8.54 and 8.55 (s, 2 H), 7.12-7.38 (m, 6 H), 6.79-7.18 (m, 5 H), 6.60-6.79 (m, 2 H), 6.11-6.25 (m, 1 H), 5.22 and 5.28 (d, 1 H), 4.89-5.13 (m, 1 H), 3.92 and 3.93 (d, 2 H), 3.48-3.75 (m, 2 H), 2.97-3.34 (m, 5 H), 2.66-2.80 (m, 1 H), 1.97-2.14 and 2.20-2.30 (m, 1 H), 1.37-1.98 (m, 4 H), 1.09-1.30 (m, 1 H), 0.43-0.70 (m, 2 H), 0.15-0.46 (m, 2 H)<br>LCMS: [MH+] = 798 |
| Ex. 146 | 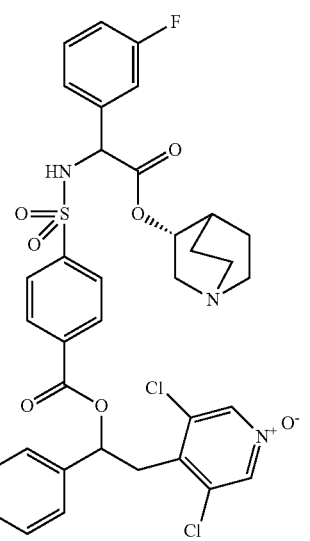<br>[2-(3,5-dichloro-1-oxido-pyridin-1-ium-4-yl)-1-(3,4-dimethoxyphenyl)ethyl] 4-[[1-(3-fluorophenyl)-2-oxo-2-[(3R)-quinuclidin-3-yl]oxy-ethyl]sulfamoyl]benzoate trifluoroacetate salt | $^1$H NMR (300 MHz, DMSO-$d_6$) δ ppm 9.69 (br. s., 1 H), 9.07-9.32 (m, 1 H), 8.48-8.72 (m, 2 H), 7.73-8.19 (m, 3 H), 7.23-7.45 (m, 1 H), 6.87-7.23 (m, 6 H), 6.23 (dd, 1 H), 5.18-5.52 (m, 1 H), 4.93 (d, 1 H), 4.33-4.55 (m, 1 H), 3.71-3.86 (m, 6 H), 3.45-3.71 (m, 2 H), 3.36 (dd, 1 H), 2.76-3.28 (m, 5 H), 1.88-2.14 (m, 1 H), 1.35-1.87 (m, 4 H)<br>LCMS: [MH+] = 788 |

| Ref | Compound | Analytical data |
|---|---|---|
| Ex. 147 | 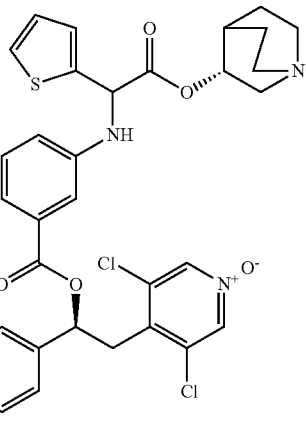<br>[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-2-[(3R)-quinuclidin-3-yl]oxy-1-(2-thienyl)ethyl]amino]benzoate trifluoroacetate salt | $^1$H NMR (300 MHz, DMSO-$d_6$) δ ppm 9.43 and 9.53 (br. s., 1 H), 8.54 and 8.55 (s, 2 H), 7.52 and 7.54 (dd, 1 H), 7.32-7.39 (m, 1 H), 6.70-7.33 (m, 10 H), 6.20 (dd, 1 H), 5.68 and 5.70 (d, 1 H), 5.10 (br. s., 1 H), 3.86-3.98 (m, 2 H), 3.58-3.76 (m, 2 H), 3.01-3.42 (m, 5 H), 2.77-2.91 (m, 1 H), 2.05-2.15 and 2.21-2.32 (m, 1 H), 1.49-1.99 (m, 4 H), 1.10-1.33 (m, 1 H), 0.45-0.68 (m, 2 H), 0.23-0.44 (m, 2 H)<br>LCMS: [MH+] = 788 |
| Ex. 148 | 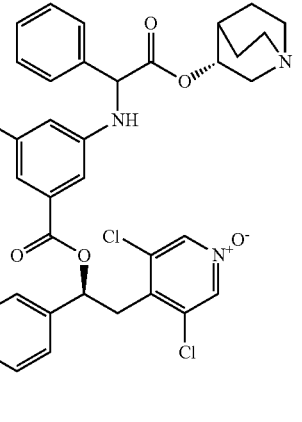<br>[(1S)-1-[3-(cyclopropylmethoxy)-4-(difluoromethoxy)phenyl]-2-(3,5-dichloro-1-oxido-pyridin-1-ium-4-yl)ethyl] 3-(methanesulfonamidomethyl)-5-[[2-oxo-1-phenyl-2-[(3R)-quinuclidin-3-yl]oxy-ethyl]amino]benzoate trifluoroacetate salt | $^1$H NMR (300 MHz, DMSO-$d_6$) δ ppm 9.44 and 9.58 (br. s., 1 H), 8.53 (s, 2 H), 7.15-7.67 (m, 10 H), 6.97-7.05 (m, 2 H), 6.83-6.92 (m, 1 H), 7.07 (t, 1 H), 6.19 (dd, 1 H), 5.33 and 5.38 (d, 1 H), 4.92-5.14 (m, 1 H), 4.08 (d, 2 H), 3.92 and 3.94 (d, 2 H), 3.46-3.76 (m, 2 H), 3.26-3.39 (m, 1 H), 3.02-3.26 (m, 4 H), 2.83 and 2.85 (s, 3 H), 2.69-2.80 (m, 1 H), 1.96-2.06 and 2.20-2.30 (m, 1 H), 1.59-1.95 (m, 3 H), 1.32-1.59 (m, 1 H), 1.06-1.30 (m, 1 H), 0.49-0.70 (m, 2 H), 0.26-0.44 (m, 2 H)<br>LCMS: [MH+] = 889 |

| Ref | Compound | Analytical data |
|---|---|---|
| Ex. 149 | [(3R)-quinuclidin-3-yl] 2-[3-[2-[2-(3,5-dichloro-1-oxido-pyridin-1-ium-4-yl)-1-(3,4-dimethoxyphenyl)ethoxy]-2-oxo-ethyl]anilino]-2-phenyl-acetate | $^1$H NMR (300 MHz, DMSO-d$_6$) δ ppm 9.48 and 9.51 (br. s., 1 H), 8.49 (s, 2 H), 7.48-7.63 (m, 2 H), 7.25-7.48 (m, 3 H), 6.88-7.07 (m, 2 H), 6.78-6.88 (m, 2 H), 6.20-6.70 (m, 4 H), 5.79-6.07 (m, 1 H), 5.16-5.39 (m, 1 H), 4.90-5.09 (m, 1 H), 3.74 (s, 6 H), 3.68 (s, 2 H), 3.29-3.64 (m, 2 H), 2.95-3.28 (m, 5 H), 2.60-2.85 (m, 1 H), 1.94-2.08 and 2.18-2.30 (m, 1 H), 1.29-1.94 (m, 4 H)<br>LCMS: [MH+] = 720 |

The following compounds were also prepared using procedures similar as those above described, applying the appropriate modifications, easily identifiable by the skilled person.

| Ref. | Compound | Analytical data |
|---|---|---|
| Ex. 150 | [2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[2-oxo-1-phenyl-2-[(3R)-quinuclidin-3-yl]oxy-ethyl]amino]benzoate | $^1$H NMR (300 MHz, DMSO-d$_6$) δ ppm 8.51 (s, 2 H), 7.47-7.65 (m, 2 H), 7.27-7.45 (m, 4 H), 7.14-7.27 (m, 3 H), 6.88-7.09 (m, 3 H), 7.07 (t, 1 H), 6.74 (d, 1 H), 6.04 (dd, 1 H), 5.32 (dd, 1 H), 4.91 (d, 1 H), 4.83 (d, 1 H), 4.62-4.76 (m, 1 H), 3.89 (dd, 2 H), 3.45 (dd, 1 H), 3.25 (dd, 1 H), 2.95 and 3.06 (dd, 1 H), 2.05-2.66 (m, 5 H), 1.67-1.78 and 1.84-1.92 (m, 1 H), 1.30-1.71 (m, 3 H), 1.22-1.30 (m, 2 H), 0.47-0.66 (m, 2 H), 0.22-0.42 (m, 2 H)<br>LCMS: [MH+] = 840 |

-continued

| Ref. | Compound | Analytical data |
|---|---|---|
| Ex. 151 | 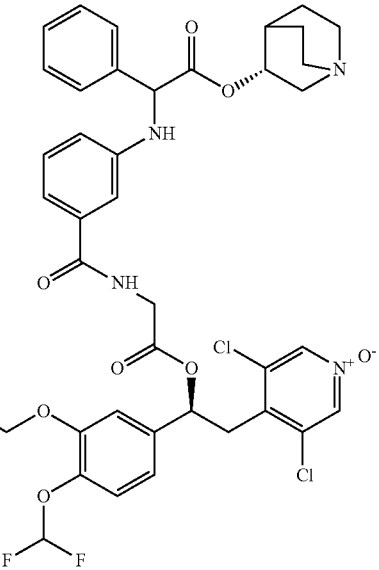<br>[(3R)-quinuclidin-3-yl] 2-[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]carbamoyl]anilino]-2-phenyl-acetate trifluoroacetate salt | $^1$H NMR (300 MHz, DMSO-d$_6$) δ ppm 9.42 (br. s., 1 H), 8.67 (t, 1 H), 8.51 (s, 2 H), 7.50-7.66 (m, 2 H), 7.33-7.48 (m, 3 H), 7.14-7.23 (m, 3 H), 7.04-7.13 (m, 2 H), 6.97 (dd, 1 H), 6.92 (dd, 1 H), 7.07 (t, 1 H), 6.62 (br. s., 1 H), 6.00 (dd, 1 H), 5.41 (br. s., 1 H), 4.86-5.11 (m, 1 H), 3.97 (t, 2 H), 3.90 (d, 2 H), 3.56-3.68 (m, 2 H), 3.24 (dd, 1 H), 3.03-3.18 (m, 3 H), 2.62-2.82 (m, 2 H), 2.18-2.26 (m, 1 H), 1.43-2.14 (m, 4 H), 1.07-1.34 (m, 1 H), 0.47-0.68 (m, 2 H), 0.21-0.44 (m, 2 H)<br>LCMS: [MH+] = 839 |
| Ex. 152 | 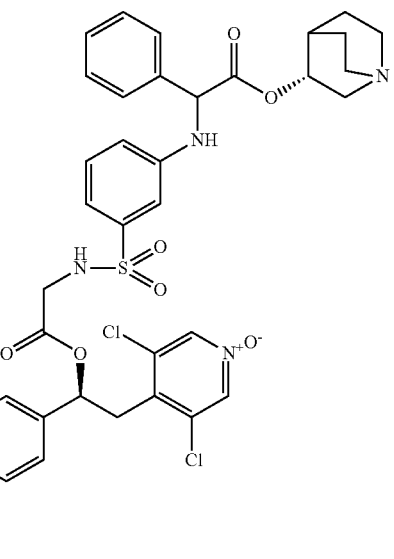<br>[(3R)-quinuclidin-3-yl] 2-[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl)sulfamoyl]anilino]-2-phenyl-acetate trifluoroacetate salt | $^1$H NMR (300 MHz, DMSO-d$_6$) δ ppm 9.43 and 9.55 (br. s., 1 H), 8.51 and 8.52 (s, 2 H), 8.00 and 8.01 (t, 1 H), 7.49-7.62 (m, 2 H), 7.33-7.47 (m, 3 H), 7.26 (dd, 1 H), 7.06-7.19 (m, 3 H), 6.87-7.02 (m, 4 H), 7.06 (t, 1 H), 5.83-6.05 (m, 1 H), 5.36 and 5.40 (d, 1 H), 4.88-5.14 (m, 1 H). 3.90 (d, 2 H), 3.52-3.77 (m, 6 H), 3.38 (dd, 1 H), 2.67-3.29 (m, 3 H), 1.98-2.13 and 2.22-2.32 (m, 1 H), 1.39-1.94 (m, 4 H), 1.10-1.30 (m, 1 H), 0.47-0.68 (m, 2 H), 0.15-0.45 (m, 2 H)<br>LCMS: [MH+] = 875 |

| Ref. | Compound | Analytical data |
|---|---|---|
| Ex. 153 | 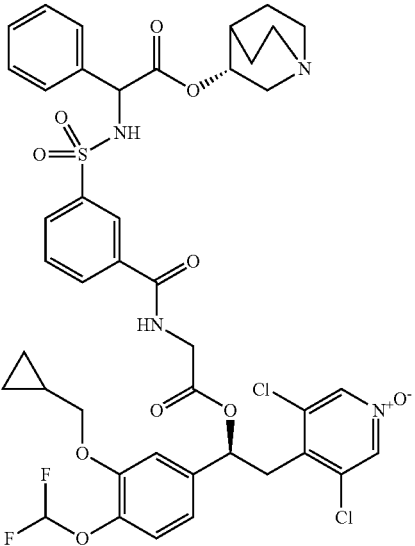<br>[(3R)-quinuclidin-3-yl] 2-[[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]carbamoyl]phenyl]sulfonylamino]-2-phenyl-acetate trifluoroacetate salt | $^1$H NMR (300 MHz, DMSO-$d_6$) δ ppm 9.46 and 9.51 (br. s., 1 H), 9.06-9.17 (m, 1 H), 9.06 and 9.08 (d, 1 H), 8.51 and 8.52 (s, 2 H), 8.23 and 8.25 (t, 1 H), 8.00 and 8.02 (dt, 1 H), 7.89 and 7.92 (dt, 1 H), 7.60 and 7.64 (t, 1 H), 7.23-7.37 (m, 5 H), 7.19 (d, 1 H), 7.12 (d, 1 H), 6.99 (dd, 1 H), 7.07 (t, 1 H), 6.02 (dd, 1 H), 5.14 and 5.20 (d, 1 H), 4.70-5.00 (m, 1 H), 3.99-4.14 (m, 2 H), 3.92 (d, 2 H), 3.54-3.66 (m, 1 H), 3.45 (dd, 1 H), 3.26 (dd, 1 H), 2.89-3.20 (m, 4 H), 2.81 (d, 1 H), 1.91-2.00 and 2.03-2.12 (m, 1 H), 1.57-1.89 (m, 3 H), 1.39-1.57 (m, 1 H), 1.10-1.31 (m, 1 H), 0.49-0.67 (m, 2 H), 0.26-0.41 (m, 2 H)<br>LCMS: [MH+] = 903 |
| Ex. 154 | 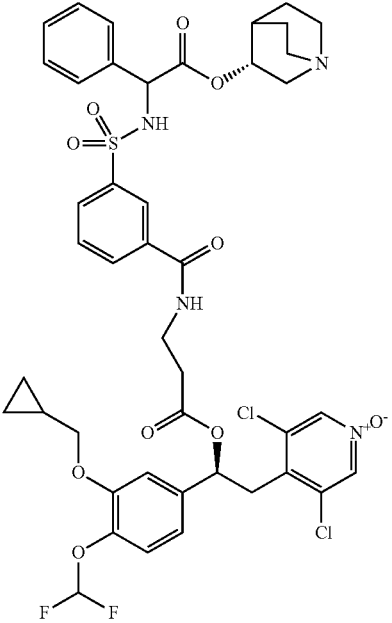<br>[(1S)-1-[3-(cyclopropylmethoxy)-4-(difluoromethoxy)phenyl]-2-(3,5-dichloro-1-oxido-pyridin-1-ium-4-yl)ethyl] 3-[[3-[[2-oxo-1-phenyl-2-[(3R)-quinuclidin-3-yl]oxy-ethyl]sulfamoyl]benzoyl]amino]propanoate trifluoroacetate salt | $^1$H NMR (300 MHz, DMSO-$d_6$) δ ppm 9.54 (br. s., 1 H), 9.04 and 9.06 (d, 1 H), 8.73 (t, 1 H), 8.51 (s, 2 H), 8.18 and 8.21 (t, 1 H), 7.91-8.00 (m, 1 H), 7.80-7.91 (m, 1 H), 7.56 and 7.60 (t, 1 H), 7.19-7.40 (m, 5 H), 7.14 (d, 1 H), 7.09 (d, 1 H), 6.96 (dd, 1 H), 7.04 (t, 1 H), 5.98 (dd, 1 H), 5.14 and 5.18 (d, 1 H), 4.65-4.96 (m, 1 H), 3.90 (d, 2 H), 3.33-3.70 (m, 3 H), 2.75-3.29 (m, 7 H), 2.64 (t, 2 H), 1.90-2.03 and 2.03-2.16 (m, 1 H), 1.56-1.90 (m, 3 H), 1.42-1.57 (m, 1 H), 1.14-1.33 (m, 1 H), 0.44-0.68 (m, 2 H), 0.22-0.40 (m, 2 H)<br>LCMS: [MH+] = 917 |

| Ref. | Compound | Analytical data |
|---|---|---|
| Ex. 155 | 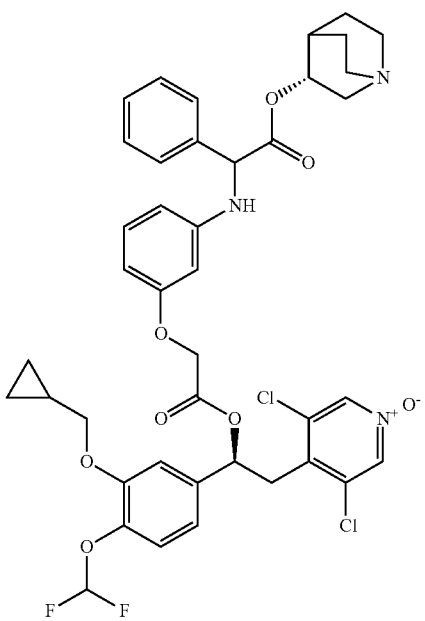<br>[(3R)-quinuclidin-3-yl] 2-[3-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethoxy]amino]-2-phenyl-acetate trifluoroacetate salt | $^1$H NMR (300 MHz, DMSO-$d_6$) δ ppm 9.49 and 9.60 (br. s., 1 H), 8.52 and 8.53 (s, 2 H), 7.49-7.57 (m, 2 H), 7.32-7.48 (m, 2 H), 7.17 (d, 1 H), 7.08 (d, 1 H), 6.85-7.01 (m, 2 H), 7.06 (t, 1 H), 6.42 (br. s., 1 H), 6.35 (d, 1 H), 6.20-6.30 (m, 1 H), 5.87-6.11 (m, 2 H), 5.16-5.39 (m, 1 H), 4.97-5.15 (m, 1 H), 4.70 and 4.71 (d, 1 H), 4.59 and 4.60 (d, 1 H), 3.89 (d, 2 H), 3.54-3.74 (m, 1 H), 3.46 (dd, 1 H), 2.94-3.30 (m, 5 H), 2.60-2.74 (m, 1 H), 1.96-2.07 and 2.20-2.30 (m, 1 H), 1.40-1.95 (m, 4 H), 1.14-1.27 (m, 2 H), 0.45-0.69 (m, 2 H), 0.17-0.42 (m, 2 H)<br>LCMS: [MH+] = 812 |
| Ex. 156 | 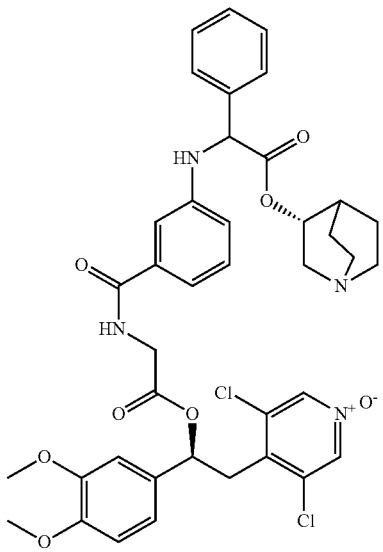<br>[(3R)-quinuclidin-3-yl] 2-[3-[[2-[(1S)-2-(3,5-dichloro-1-oxido-pyridin-1-ium-4-yl)-1-(3,4-dimethoxyphenyl)ethoxy]-2-oxo-ethyl]carbamoyl]amino]-2-phenyl-acetate trifluoroacetate salt | $^1$H NMR (300 MHz, DMSO-$d_6$) δ ppm 9.61 and 9.70 (br. s., 1 H), 8.66 (t, 1 H), 8.51 (s, 2 H), 7.49-7.70 (m, 2 H), 7.26-7.49 (m, 3 H), 7.12-7.26 (m, 2 H), 7.03-7.13 (m, 1 H), 6.82-7.01 (m, 4 H), 6.62 (br. s., 1 H), 6.01 (dd, 1 H), 5.38 and 5.41 (s, 1 H), 4.90-5.18 (m, 1 H), 3.85-4.13 (m, 2 H), 3.76 (s, 3 H), 3.75 (s, 3 H), 3.54-3.71 (m, 1 H), 3.36-3.54 (m, 1 H), 2.97-3.32 (m, 5 H), 2.65-2.88 (m, 1 H), 1.96-2.13 and 2.19-2.29 (m, 1 H), 1.45-1.95 (m, 4 H)<br>LCMS: [MH+] = 763 |

| Ref. | Compound | Analytical data |
|---|---|---|
| Ex. 157 | 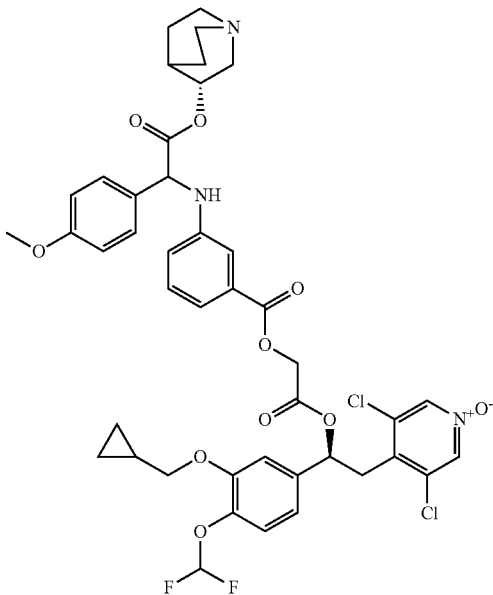<br>[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(4-methoxyphenyl)-2-oxo-2-[(3R)-quinuclidin-3-yl]oxy-ethyl]amino]benzoate trifluoroacetate salt | $^1$H NMR (300 MHz, DMSO-d$_6$) δ ppm 9.45 and 9.56 (br. s., 1 H), 8.52 (s, 2 H), 7.39-7.56 (m, 2 H), 7.29-7.38 (m, 1 H), 7.14-7.29 (m, 3 H), 7.06-7.12 (m, 1 H), 6.80-7.13 (m, 5 H), 6.72 (br. s., 1 H), 5.94-6.16 (m, 1 H), 5.30 and 5.33 (br. s., 1 H), 4.99-5.16 (m, 1 H), 4.91 (d, 1 H), 4.83 (d, 1 H), 3.88 and 3.90 (d, 2 H), 3.74 and 3.76 (s, 3 H), 3.55-3.72 (m, 1 H), 3.46 (dd, 1 H), 3.26 (dd, 1 H), 3.01-3.21 (m, 4 H), 2.71-2.89 (m, 1 H), 1.99-2.07 and 2.20-2.26 (m, 1 H), 1.61-1.98 (m, 3 H), 1.56 (d, 1 H), 1.08-1.29 (m, 1 H), 0.47-0.66 (m, 2 H), 0.27-0.43 (m, 2 H)<br>LCMS: [MH+] = 870 |
| Ex. 158 | 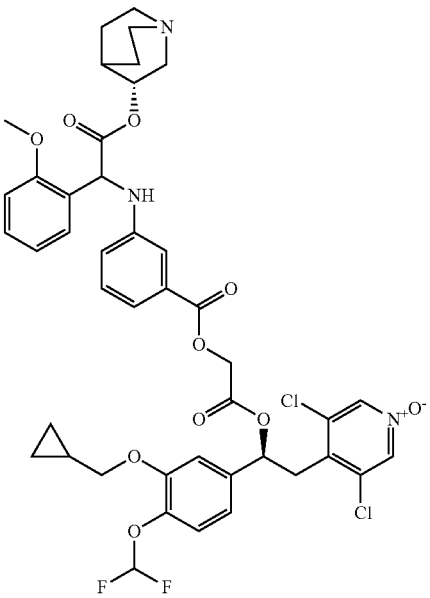<br>[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(2-methoxyphenyl)-2-oxo-2-[(3R)-quinuclidin-3-yl]oxy-ethyl]amino]benzoate trifluoroacetate salt | $^1$H NMR (300 MHz, DMSO-d$_6$) δ ppm 9.52 and 9.59 (br. s., 1 H), 8.51 (s, 2 H), 7.36-7.53 (m, 1 H), 7.13-7.36 (m, 5 H), 6.78 - 7.13 (m, 6 H), 6.63 (br. s., 1 H), 6.05 (dd, 1 H), 5.56 and 5.59 (s, 1 H), 4.99-5.14 (m, 1 H), 4.92 (d, 1 H), 4.84 (d, 1 H), 3.88 and 3.90 (d, 2 H), 3.85 (s, 3 H), 3.55-3.75 (m, 1 H), 3.45 (dd, 1 H), 3.26 (dd, 1 H), 2.97-3.21 (m, 4 H), 2.58-2.90 (m, 1 H), 1.96-2.11 and 2.18-2.27 (m, 1 H), 1.42-1.96 (m, 4 H), 0.97-1.36 (m, 1 H), 0.46-0.73 (m, 2 H), 0.08-0.46 (m, 2 H)<br>LCMS: [MH+] = 870 |

| Ref. | Compound | Analytical data |
|---|---|---|
| Ex. 159 | 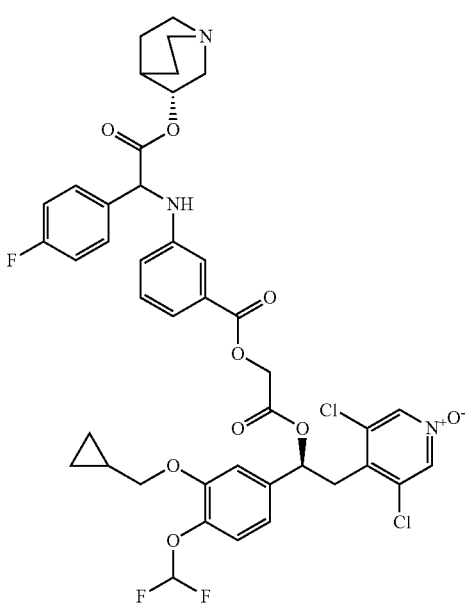<br>[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(4-fluorophenyl)-2-oxo-2-[(3R)-quinuclidin-3-yl]oxy-ethyl]amino]benzoate trifluoroacetate salt | $^1$H NMR (300 MHz, DMSO-d$_6$) δ ppm 9.63 and 9.75 (br. s., 1 H), 8.51 (s, 2 H), 7.49-7.76 (m, 2 H), 6.73-7.43 (m, 11 H), 5.83-6.21 (m, 1 H), 5.30-5.60 (m, 1 H), 4.99-5.12 (m, 1 H), 4.91 (d, 1 H), 4.84 (d, 1 H), 3.88 and 3.90 (d, 2 H), 3.55-3.76 (m, 1 H), 3.46 (dd, 1 H), 3.26 (dd, 1 H), 2.94-3.22 (m, 4 H), 2.71-2.90 (m, 1 H), 1.96-2.12 and 2.16-2.27 (m, 1 H), 1.42-1.97 (m, 4 H), 1.13-1.34 (m, 1 H), 0.48-0.67 (m, 2 H), 0.23-0.43 (m, 2 H)<br>LCMS: [MH+] = 858 |
| Ex. 160 | 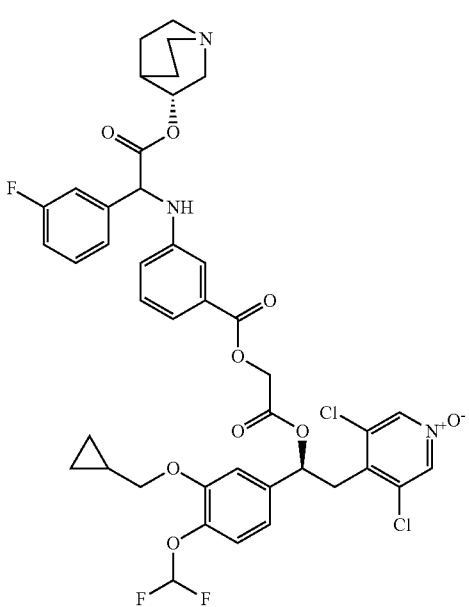<br>[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(3-fluorophenyl)-2-oxo-2-[(3R)-quinuclidin-3-yl]oxy-ethyl]amino]benzoate trifluoroacetate salt | $^1$H NMR (300 MHz, DMSO-d$_6$) δ ppm 9.40 and 9.50 (br. s., 1 H), 8.51 (s, 2 H), 7.36-7.51 (m, 2 H), 7.30-7.36 (m, 1 H), 7.19 (d, 1 H), 7.08 (d, 1 H), 6.99-7.06 (m, 1 H), 6.97 (dd, 1 H), 6.83-6.91 (m, 1 H), 6.75-7.30 (m, 5 H), 5.92-6.12 (m, 1 H), 5.49 and 5.52 (d, 1 H), 5.01-5.13 (m, 1 H), 4.91 (m, 1 H), 4.83 (d, 1 H), 3.88 and 3.90 (d, 2 H), 3.55-3.71 (m, 1 H), 3.39-3.51 (m, 1 H), 3.25 (dd, 1 H), 3.01-3.20 (m, 4 H), 2.76-2.91 (m, 1 H), 2.00-2.12 and 2.19-2.27 (m, 1 H), 1.46-1.98 (m, 4 H), 1.07-1.33 (m, 1 H), 0.45-0.69 (m, 2 H), 0.06-0.44 (m, 2 H)<br>LCMS: [MH+] = 858 |

| Ref. | Compound | Analytical data |
|---|---|---|
| Ex. 161 | 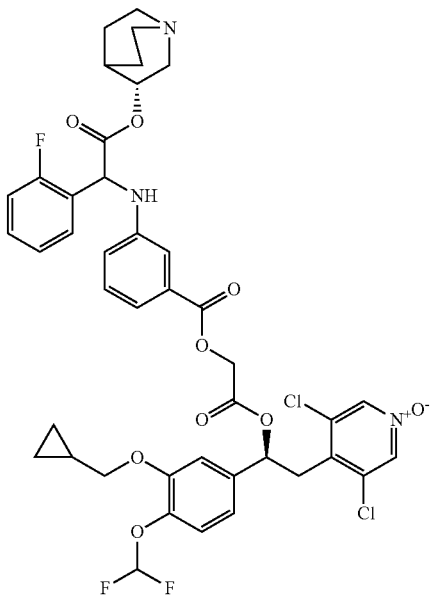<br>[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(2-fluorophenyl)-2-oxo-2-((3R)-quinuclidin-3-yl]oxy-ethyl]amino]benzoate trifluoroacetate salt | $^1$H NMR (300 MHz. DMSO-d$_6$) δ ppm 9.42 and 9.53 (br. s., 1 H), 8.50 and 8.51 (s, 2 H), 7.49-7.64 (m, 1 H), 7.37-7.48 (m, 1 H), 7.18 (d, 1 H), 6.96 (d, 1 H), 6.77-6.89 (m, 1 H), 6.74-7.38 (m, 8 H), 5.92-6.15 (m, 1 H), 5.61 and 5.64 (s, 1 H), 5.03-5.15 (m, 1 H), 4.92 (d, 1 H), 4.84 and 4.85 (d, 1 H), 3.88 and 3.90 (d, 2 H), 3.59-3.74 (m, 1 H), 3.38-3.50 (m, 1 H), 3.26 (dd, 1 H), 3.00-3.21 (m, 4 H), 2.76-2.93 (m, 1 H), 2.01-2.12 and 2.20-2.30 (m, 1 H), 1.44-1.95 (m, 4 H), 1.08-1.32 (m, 1 H), 0.48-0.67 (m, 2 H), 0.26-0.41 (m, 2 H)<br>LCMS: [MH+] = 858 |
| Ex. 162 | 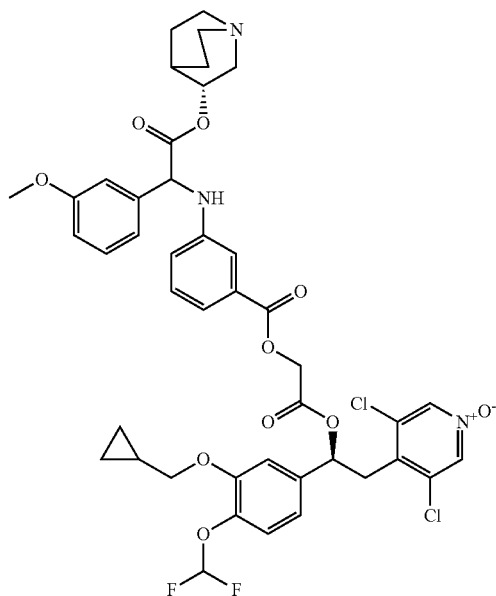<br>[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(3-methoxyphenyl)-2-oxo-2-[(3R)-quinuclidin-3-yl]oxy-ethyl]amino]benzoate trifluoroacetate salt | $^1$H NMR (300 MHz, DMSO-d$_6$) δ ppm 9.46 and 9.56 (br. s., 1 H), 8.51 (s, 2 H), 6.80-7.47 (m, 12 H), 6.78 (br.s., 1 H), 5.90-6.18 (m, 1 H), 5.31-5.46 (m, 1 H), 5.00-5.13 (m, 1 H), 4.92 (d, 1 H), 4.83 (d, 1 H), 3.88 and 3.89 (d, 2 H), 3.75 and 3.79 (s, 3 H), 3.56-3.72 (m, 1 H), 3.46 (dd, 1 H), 3.26 (dd, 1 H), 3.02-3.20 (m, 4 H), 2.68-2.87 (m, 1 H), 1.98-2.14 and 2.20-2.28 (m, 1 H), 1.45-1.99 (m, 4 H), 1.07-1.31 (m, 1 H), 0.49-0.65 (m, 2 H), 0.17-0.46 (m, 2 H)<br>LCMS: [MH+] = 870 |

| Ref. | Compound | Analytical data |
|---|---|---|
| Ex. 163 | 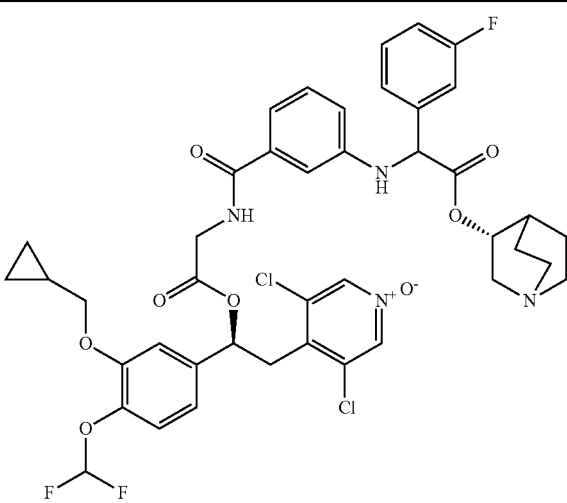<br>quinuclidin-3-yl 2-[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]carbamoyl]amino]-2-(3-fluorophenyl)acetate trifluoroacetate salt | $^1$H NMR (300 MHz, DMSO-$d_6$) δ ppm 9.33 and 9.46 (br. s., 1 H), 8.67 (t, 1 H), 8.51 (s, 2 H), 7.36-7.52 (m, 3 H), 6.94-7.00 (m, 1 H), 6.87-6.94 (m, 1 H), 6.78-7.34 (m, 7 H), 6.67 (d, 1 H), 5.90-6.11 (m, 1 H), 5.46 and 5.49 (d, 1 H), 4.90-5.15 (m, 1 H), 3.93-4.03 (m, 2 H), 3.85-3.94 (m, 2 H), 3.54-3.76 (m, 1 H), 2.99-3.30 (m, 6 H), 2.76-2.96 (m, 1 H), 2.02-2.12 and 2.20-2.30 (m, 1 H), 1.43-1.97 (m, 4 H), 1.06-1.26 (m, 1 H), 0.46-0.69 (m, 2 H), 0.27-0.46 (m, 2 H)<br>LCMS: [MH+] = 857 |
| Ex. 164 | 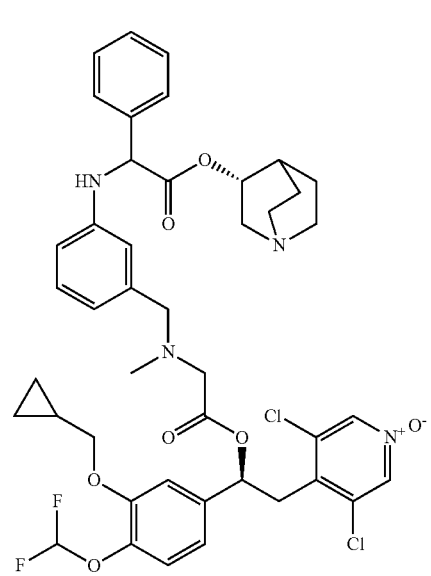<br>[(3R)-quinuclidin-3-yl] 2-[3-[[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]-methyl-amino]methyl]amino]-2-phenyl-acetate trifluoroacetate salt | $^1$H NMR (300 MHz, DMSO-$d_6$) δ ppm 9.69 and 9.80 (br. s., 1 H), 8.54 and 8.55 (s, 2 H), 7.49-7.58 (m, 2 H), 7.33-7.46 (m, 3 H), 7.20 (d, 1 H), 7.09-7.16 (m, 2 H), 6.99 (dd, 1 H), 7.07 (t, 1 H), 6.71-6.82 (m, 3 H), 6.48-6.66 (m, 1 H), 6.03 (dd, 1 H), 5.32 and 5.35 (s, 1 H), 4.97-5.12 (m, 1 H), 3.95-4.32 (m, 4H), 3.91 (d, 2H), 3.55-3.70 (m, 1 H), 3.41-3.54 (m, 1 H), 3.02-3.36 (m, 5 H), 2.55-2.80 (m, 4 H), 1.97-2.05 and 2.20-2.30 (m, 1 H), 1.32-1.95 (m, 4 H), 1.07-1.30 (m, 1 H), 0.48-0.68 (m, 2 H), 0.24-0.42 (m, 2 H)<br>LCMS: [MH+] = 839 |

| Ref. | Compound | Analytical data |
|---|---|---|
| Ex. 165 | 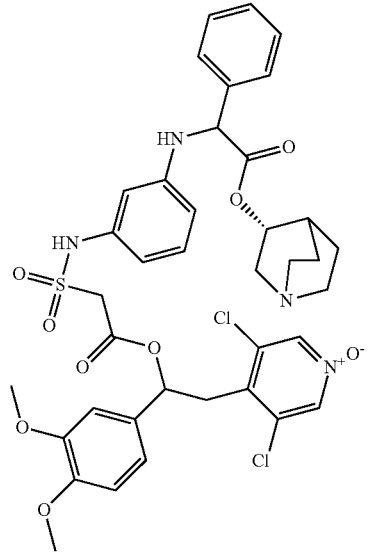<br>[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]sulfonylamino]amino]-2-phenyl-acetate trifluoroacetate salt | $^1$H NMR (300 MHz, DMSO-d$_6$) δ ppm 9.92 (s, 1 H), 9.42 and 9.55 (br. s., 1 H), 8.50 (s, 2 H), 7.28-7.61 (m, 5 H), 7.03 (t, 1 H), 6.94 (d, 1 H), 6.91 (d, 1 H), 6.81-6.87 (m, 1 H), 6.57-6.68 (m, 1 H), 6.53-6.58 (m, 1 H), 6.47-6.53 (m, 1 H), 6.43 (d, 1 H), 5.95 (dd, 1 H), 5.15-5.36 (m, 1 H), 4.92-5.15 (m, 1 H), 3.97-4.30 (m, 2 H), 3.75 (s, 3 H), 3.74 (s, 3 H), 3.55-3.71 (m, 1 H), 3.43 (dd, 1 H), 3.25 (dd, 1 H), 2.99-3.19 (m, 4 H), 2.60-2.84 (m, 1 H), 1.97-2.05 and 2.20-2.30 (m, 1 H), 1.39-1.96 (m, 4 H)<br>LCMS: [MH+] = 799 |
| Ex. 166 | 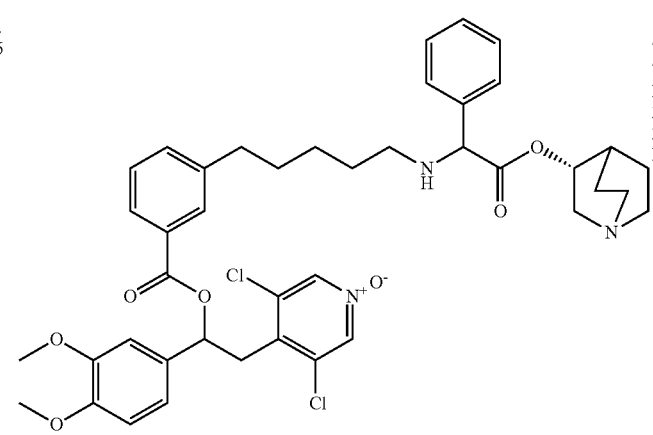<br>[2-(3,5-dichloro-1-oxido-pyridin-1-ium-4-yl)-1-(3,4-dimethoxyphenyl)ethyl] 3-[3-[[2-oxo-1-phenyl-2-[(3R)-quinuclidin-3-yl]oxy-ethyl]amino]propyl]benzoate | $^1$H NMR (300 MHz, DMSO-d$_6$) δ ppm 8.54 (s, 2 H), 7.72-7.84 (m, 2 H), 7.37-7.54 (m, 4 H), 7.21-7.37 (m, 3 H), 7.01-7.08 (m, 2 H), 6.98 (t, 1 H), 6.21 (dd, 1 H), 4.59-4.81 (m, 1 H), 4.38 (s, 1 H), 3.78 (s, 3 H), 3.75 (s, 3 H), 3.63 (dd, 1 H), 3.34 (dd, 1 H), 2.95-3.17 (m, 1 H), 2.55-2.82 (m, 7 H), 2.12-2.46 (m, 2 H), 1.66-1.89 (m, 3 H), 1.07-1.64 (m, 4 H)<br>LCMS: [MH+] = 748 |

| Ref. | Compound | Analytical data |
|---|---|---|
| Ex. 167 | 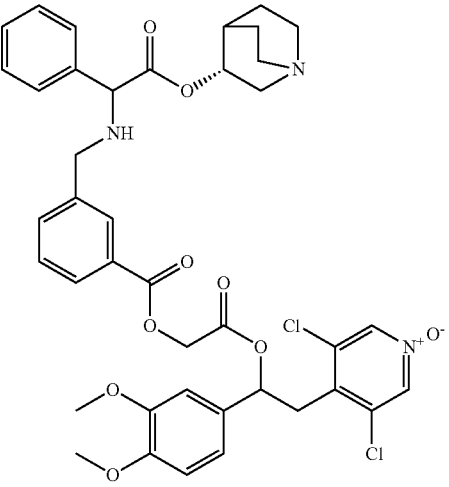<br>[2-[2-(3,5-dichloro-1-oxido-pyridin-1-ium-4-yl)-1-(3,4-dimethoxyphenyl)ethoxy]-2-oxo-ethyl] 3-[[[2-oxo-1-phenyl-2-[(3R)-quinuclidin-3-yl]oxy-ethyl]amino]methyl]benzoate trifluoroacetate salt | $^1$H NMR (300 MHz, DMSO-$d_6$) δ ppm 9.77 (br. s., 1 H), 8.50 (s, 2 H), 8.06 (s, 1 H), 7.99 (d, 1 H), 7.67-7.76 (m, 1 H), 7.59-7.66 (m, 1 H), 7.41-7.59 (m, 5 H), 6.85-7.05 (m, 3 H), 6.06 (dd, 1 H), 5.05-5.41 (m, 2 H), 4.97 (d, 1 H), 4.90 (d, 1 H), 4.02-4.31 (m, 2 H), 3.76 (s, 3 H), 3.76 (s, 3 H), 3.56-3.72 (m, 1 H), 3.50 (dd, 1 H), 3.26 (dd, 1 H), 2.77-3.22 (m, 5 H), 1.98-2.34 (m, 1 H), 1.21-2.00 (m, 4 H)<br>LCMS: [MH+] = 778 |
| Ex. 168 | 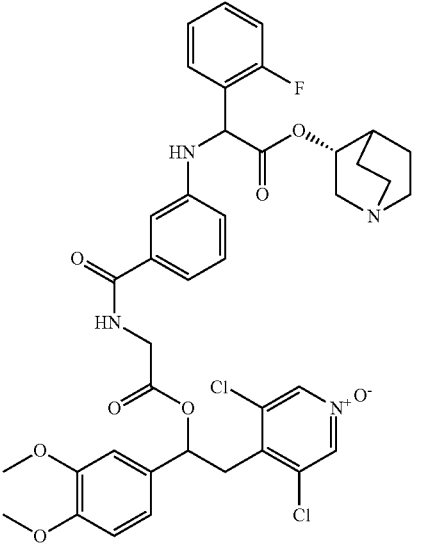<br>[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]carbamoyl]amino]-2-(2-fluorophenyl)acetate | $^1$H NMR (300 MHz, DMSO-$d_6$) δ ppm 9.54 and 9.63 (br. s., 1 H), 8.67 and 8.70 (d, 1 H), 8.51 (s, 2 H), 7.50-7.68 (m, 1 H), 7.34-7.48 (m, 1 H), 7.14-7.34 (m, 4 H), 7.05-7.14 (m, 1 H), 6.79-7.01 (m, 4 H), 6.65 (br. s., 1 H), 6.01 (dd, 1 H), 5.61 (s, 1 H), 4.96-5.17 (m, 1 H), 3.86-4.09 (m, 2 H), 3.72-3.79 (m, 6 H), 3.58-3.72 (m, 1 H), 3.46 (dd, 1 H), 3.00-3.28 (m, 5 H), 2.73-3.00 (m, 1 H), 2.00-2.15 and 2.19-2.30 (m, 1 H), 1.39-1.98 (m, 4 H)<br>LCMS: [MH+] = 781 |

| Ref. | Compound | Analytical data |
|---|---|---|
| Ex. 169 | 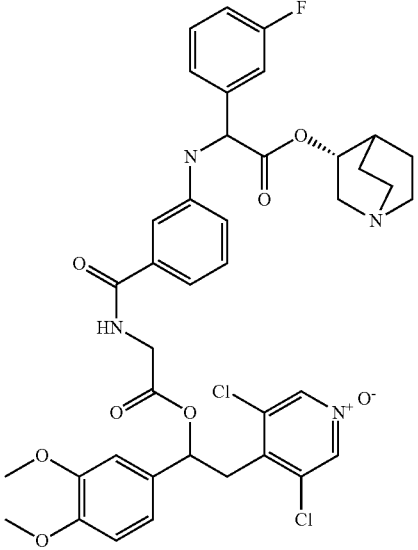<br>[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]carbamoyl]amino]-2-(3-fluorophenyl)acetate | $^1$H NMR (300 MHz, DMSO-d$_6$) δ ppm 9.48 and 9.58 (br. s., 1 H), 8.67 (br. s., 1 H), 8.51 (s, 2 H), 7.32-7.57 (m, 3 H), 7.14-7.33 (m, 3 H), 7.03-7.14 (m, 1 H), 6.83-6.98 (m, 4 H), 6.69 (br. s., 1 H), 6.01 (dd, 1 H), 5.39-5.54 (m, 1 H), 4.99-5.11 (m, 1 H), 3.86-4.05 (m, 2 H), 3.76 (s, 3 H), 3.75 (s, 3 H), 3.55-3.75 (m, 1 H), 3.46 (dd, 1 H), 2.99-3.34 (m, 5 H), 2.76-2.90 (m, 1 H), 2.02-2.13 and 2.21-2.28 (m, 1 H), 1.49-1.96 (m, 4 H)<br>LCMS: [MH+] = 781 |
| Ex. 170 | 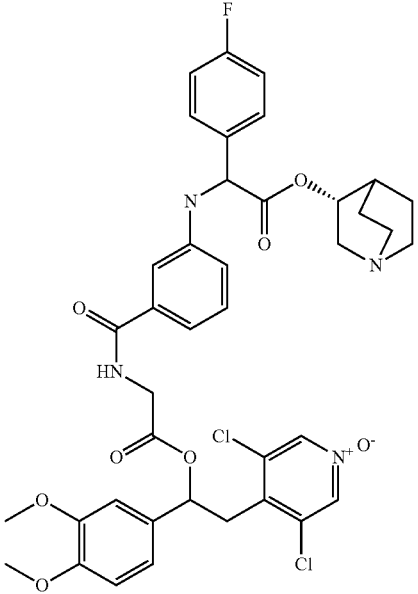<br>[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]carbamoyl]amino]-2-(4-fluorophenyl)acetate | $^1$H NMR (300 MHz, DMSO-d$_6$) δ ppm 9.47 and 9.58 (br. s., 1 H), 8.59-8.73 (m, 1 H), 8.51 (s, 2 H), 7.54-7.69 (m, 2 H), 7.13-7.33 (m, 4 H), 7.02-7.12 (m, 1 H), 6.84-6.99 (m, 4 H), 6.64 (d, 1 H), 6.01 (dd, 1 H), 5.30-5.56 (m, 1 H), 4.90-5.18 (m, 1 H), 3.87-4.08 (m, 2 H), 3.76 (s, 3 H), 3.75 (s, 3 H), 3.55-3.72 (m, 1 H), 3.46 (dd, 1 H), 3.06-3.31 (m, 5 H), 2.75-2.87 (m, 1 H), 1.98-2.13 and 2.19-2.25 (m, 1 H), 1.37-1.97 (m, 4 H)<br>LCMS: [MH+] = 781 |

| Ref. | Compound | Analytical data |
|---|---|---|
| Ex. 171 | 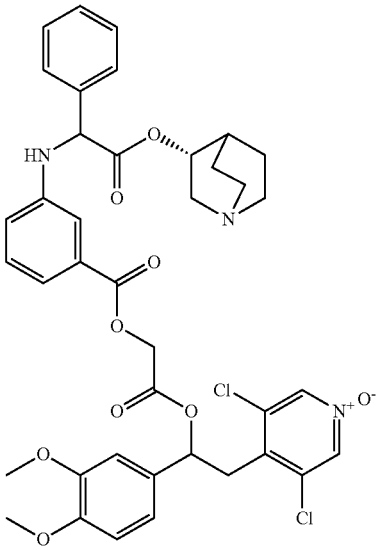<br><br>[2-[2-(3,5-dichloro-1-oxido-pyridin-1-ium-4-yl)-1-(3,4-dimethoxyphenyl)ethoxy]-2-oxo-ethyl] 3-[[2-oxo-1-phenyl-2-[(3R)-quinuclidin-3-yl]oxy-ethyl]amino]benzoate trifluoroacetate salt | $^1$H NMR (300 MHz, DMSO-$d_6$) δ ppm 9.44 and 9.55 (br. s., 1 H), 8.51 (s, 2 H), 7.50-7.63 (m, 2 H), 7.13-7.50 (m, 6 H), 7.02 (m, 1 H), 6.69-6.97 (m, 4 H), 5.87-6.15 (m, 1 H), 5.36-5.50 (m, 1 H), 4.99-5.13 (m, 1 H), 4.66-4.99 (m, 2 H), 3.76 (s, 3 H), 3.73 (s, 3 H), 3.55-3.71 (m, 1 H), 3.48 (dd, 1 H), 3.25 (dd, 1 H), 3.00-3.22 (m, 4 H), 2.70-2.82 (m, 1 H), 1.98-2.08 and 2.18-2.21 (m, 1 H), 1.40-1.95 (m, 4 H)<br>LCMS: [MH+] = 764 |

Pharmacological Activity of the Compounds of the Invention:
In Vitro Determination of PDE4 Inhibitory Activity:

In vitro determination of PDE4 inhibitory activity for compounds of the invention may be determined according to one of the protocols herebelow reported.

PDE4B2 HTRF Assay:

PDE4B2 activity is detected using the LANCE Ultra cAMP homogeneous time resolved fluorescence resonance energy transfer (TR-FRET) assay from Perkin Elmer. The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 μl Human recombinant PDE4B2 (80 μM) is incubated for 2 hours with 3 nM cAMP in buffer containing 1×HBSS, 5 mM HEPES, 3 mM $MgCl_2$, 0.1% BSA, pH 7.4 with or without test compounds. The enzymatic reactions are efficiently stopped by the addition of 500 μM IBMX present in the combined Stop/Detection buffer containing europium (Eu) chelate-labeled cAMP tracer and cAMP-specific monoclonal antibodies (mAb) labelled with the ULight™ dye. Samples are then further incubated for 1 h before plates are read at ex 340 nm and em at 665 nm and 615 nm on an EnVision reader. $IC_{50}$ values are determined from competition curves using a non-linear curve fitting program.

PDE4 Cell Free Assay Protocol:

PDE4 activity is determined in U937 human monocytic supernatants cells lysate. Cells are cultured, harvested and supernatant fraction prepared essentially as described in Torphy T J et al., J. Pharmacol. Exp. Ther. 1992; 263:1195-1205, which is incorporated herein by reference in its entirety. U937 cells are grown at 37° C., 5% $CO_2$ in RPMI 1640 with GlutaMAX™-I medium supplemented with 10% fetal bovine serum and 100 μg/mL Pen-strep (Gibco). Cells are harvested and washed twice by centrifugation (150×g, 8 min) in cold PBS. Washed cells are re-suspended in cold Krebs-Ringer-Henseleit buffer at a final concentration 20×10$^6$ cells/mL and sonicated. After centrifugation at 15000×g for 20 minutes, the supernatants are pooled, divided in aliquots and stored at −80° C.

PDE4 activity is determined in cells supernatants by assaying cAMP disappearance from the incubation mixtures.

The concentration of the test compounds ranges between 10$^{-12}$ M and 10$^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance ($IC_{50}$).

Percentage of inhibition of PDE4 activity is calculated, assuming cAMP disappearance in the absence of inhibitors as 100% and cAMP disappearance in heat inactivated samples as 0%.

Representative compounds of the invention, when tested in one of the above reported protocols, displayed an $IC_{50}$ lower than 100 nM.

In Vitro Determination of M3 Antagonism:

In vitro determination of M3 antagonism for compounds of the invention may be determined according to one of the protocols herebelow reported.

M3 Receptor Radioligand Binding Assay:

Human $M_3$ receptor membranes (15 μg/well) from Perkin Elmer are incubated with 0.52 nM Scopolamine Methyl Chloride, [N-methyl-3H] with or without test compounds, or a saturating concentration of Atropine (5 μM) for the determination of non-specific binding. The assay is carried out in 96-well polypropylene plates in a volume of 250 μl. The assay buffer used is 50 mM Tris-HCl, 154 mM NaCl (pH 7.4). The final assay concentration of DMSO is 0.5% (v/v). The plates are sealed and incubated for 2 hours at room temperature on an orbital shaker (slow speed). Membranes are harvested onto 96-well unifilter GF/C filter plates pre-treated with 0.5% polyethyleneimine (v/v), using a filter manifold, washed four times with 200 μl of assay buffer. The plates are dried before addition of 50 μl of microscint-0, sealed then read in a Trilux Microbeta scintillation counter. $IC_{50}$ values are determined from competition curves using a non-linear curve fitting program. $K_i$ values are calculated from $IC_{50}$ values by the Cheng and Prusoff equation.

M3 Binding Assay:

CHO-K1 clone cells expressing the human M3-receptor (Swissprot P20309) were harvested in $Ca^{++}/Mg^{++}$ free phosphate-buffered saline and collected by centrifugation at 1500 rpm for 3 minutes. The pellets were resuspended in ice cold buffer A (15 mM Tris-HCl pH 7.4, 2 mM $MgCl_2$, 0.3 mM EDTA, 1 mM EGTA) and homogenized by a PBI politron (setting 5 for 15 s). The crude membrane fraction was collected by two consecutive centrifugation steps at 40000 g for 20 min at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non selective muscarinic radioligand [$^3$H]-N-methyl scopolamine (see Mol. Pharmacol. 45:899-907, which is incorporated herein by reference in its entirety) was used to label the M3 binding sites. Binding experiments were performed in duplicate (ten point concentrations curves) in 96 well plates at radioligand concentration of 0.1-0.3 nM. The non specific binding was determined in the presence of cold N-methyl scopolamine 10 μM. Samples (final volume 0.75 mL) were incubated at room temperature for 90 minutes. The reaction was terminated by rapid filtration through GF/B Unifilter plates and two washes (0.75 mL) with cold buffer C using a Packard Filtermate Harvester. Radioactivity on the filters was measured by a microplate scintillation counter TriCarb 2500 (PerkinElmer).

Representative compounds of the invention, when tested in one of the above reported protocols, displayed an $IC_{50}$ lower than 100 nM.

Representative compounds of the invention displayed an $IC_{50}$ lower than 100 nM in both PDE4 cell free and M3 binding assays Where a numerical limit or range is stated herein, the endpoints are included.

Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound represented by formula (I):

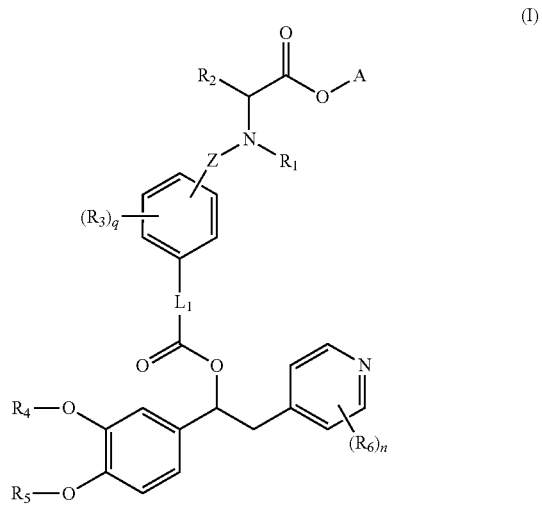

wherein
$R_1$ is hydrogen, $(C_1-C_4)$ alkyl, or $-SO_2(C_1-C_4)$alkyl;
$R_2$ is aryl or a 5 to 11 membered heteroaryl, wherein said aryl or heteroaryl is optionally substituted by 1 to 3 groups at each occurrence independently selected from the group consisting of halogen, $(C_1-C_4)$haloalkyl, hydroxy, $-SO_2NR_8R_9$, $-CN$, $-NR_{10}SO_2R_{11}$, $(C_1-C_4)$ alkyl, and $(C_1-C_4)$ alkoxy, wherein said $(C_1-C_4)$ alkyl or $(C_1-C_4)$ alkoxy are optionally substituted by one $(C_3-C_7)$ cycloalkyl group, and wherein
$R_8$ is hydrogen or $(C_1-C_6)$ alkyl;
$R_9$ is hydrogen or $(C_1-C_6)$ alkyl;
$R_{10}$ is hydrogen or $(C_1-C_6)$ alkyl;
$R_{11}$ is hydrogen or $(C_1-C_6)$ alkyl;
Z is a bond or a divalent radical selected from the group consisting of $-(CH2)_m-$, $-S-$, $-S(O)-$, $-S(O_2)-$, a group $-C(O)-$, and a group [1]-$(CH2)_m$, $-OC(O)$-[2] wherein [1] and [2] represent, respectively the point of attachment of group Z to phenyl ring and to the nitrogen atom, and m is an integer ranging from 1 to 4;
$L_1$ is:
a bond,
$-(CH2)_p-$,
[3]-$(CH_2)_p$—O-[4]
[3]-$(CH_2)_p$—$NR_{10}$—$(CH_2)_t$-[4]
[3]-$(CH_2)_p$—OC(O)-[4]
[3]-$(CH_2)_p$—$NR_{10}$C(O)-[4]
[3]-$(CH_2)_p$—$NR_{10}$S($O_2$)—[4] or
[3]-$(CH_2)_p$—S($O_2$)—N($R_{10}$)—[4]
wherein [3] and [4] represent, respectively the point of attachment of group $L_1$ to the carbonyl group and to the phenyl ring, and wherein
$R_{10}$ is as described above,
p is an integer ranging from 1 to 4 and
t is an integer ranging from 1 to 4 each $R_3$ is independently hydrogen, halogen, $(C_1-C_4)$ haloalkyl, hydroxy, aminocarbonyl, di-$(C_1-C_4)$ alkylaminocarbonyl, —$SO_2NR_{12}R_{13}$, —CN, —$NR_{14}SO_2R_{15}$, —$(CH2)_m$—$NR_{14}SO_2R_{15}$—, $(C_1-C_4)$ alkyl, or $(C_1-C_4)$ alkoxy, wherein said $(C_1-C_4)$ alkyl or $(C_1-C_4)$ alkoxy are optionally substituted by one $(C_3-C_7)$ cycloalkyl group, m is as described above and $R_{12}$ is hydrogen or $(C_1-C_6)$ alkyl;

$R_{13}$ is hydrogen or $(C_1-C_6)$ alkyl;

$R_{14}$ is hydrogen or $(C_1-C_6)$ alkyl;

$R_{15}$ is hydrogen or $(C_1-C_6)$ alkyl;

q is an integer ranging from 1 to 3;

$R_4$ and $R_5$ are the same of different and are independently:

H;

$(C_3-C_7)$ cycloalkylcarbonyl;

$(C_1-C_6)$ alkyl, optionally substituted by one or more substituents selected from $(C_3-C_7)$ cycloalkyl and $(C_5-C_7)$ cycloalkenyl;

$(C_1-C_6)$ haloalkyl;

$(C_3-C_7)$ cycloalkyl;

$(C_5-C_7)$ cycloalkenyl;

$(C_2-C_6)$ alkenyl; or $(C_2-C_6)$ alkynyl;

or $R_4$ and $R_5$, together with the interconnecting atoms, form a 2,2-difluoro-1,3-dioxolane ring of formula (r) fused to the phenyl moiety which bears groups —$OR_4$ and —$OR_5$, wherein asterisks indicate carbon atoms shared with said phenyl ring:

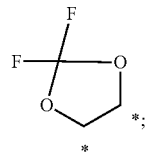
(r)

each $R_6$ is independently CN, $NO_2$, $CF_3$, or a halogen atom;

n is 0 or an integer ranging from 1 to 3;

A is a nitrogen containing group which is:

a group (a) which is —$(CH_2)_s$—$NR_{16}R_{17}$ wherein s is an integer ranging from 1 to 4 and $R_{16}$ and $R_{17}$ are independently hydrogen or $(C_1-C_4)$ alkyl; or a group (b) which is a saturated monocyclic, bicyclic or tricyclic heterocyclic ring system optionally substituted by one or two groups $R_{18}$ which are at each occurrence independently selected from $(C_1-C_4)$ alkyl and benzyl, or an N-oxide on the pyridine ring, a deuterated derivative, or a pharmaceutically acceptable salt thereof.

2. A compound, N-oxide, deuterated derivative, or pharmaceutically acceptable salt according to claim 1, which is represented by formula (IB):

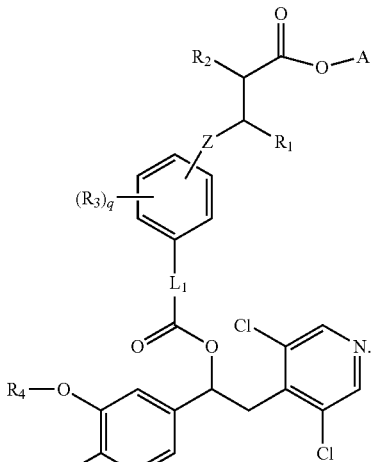
(IB)

3. A compound, N-oxide, deuterated derivative, or pharmaceutically acceptable salt according to claim 1, which is represented by formula (IA):

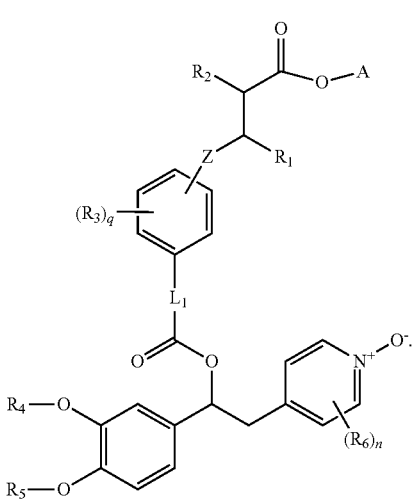
(IA)

4. A compound, N-oxide, deuterated derivative, or pharmaceutically acceptable salt according to claim 1, wherein $R_5$ is $(C_1-C_6)$ haloalkyl or $(C_1-C_6)$ alkyl, and $R_4$ is $(C_3-C_7)$ cycloalkyl or $(C_1-C_6)$ alkyl which is optionally substituted by $(C_3-C_7)$ cycloalkyl.

5. A compound, N-oxide, deuterated derivative, or pharmaceutically acceptable salt according to claim 1, which is represented by formula (ID):

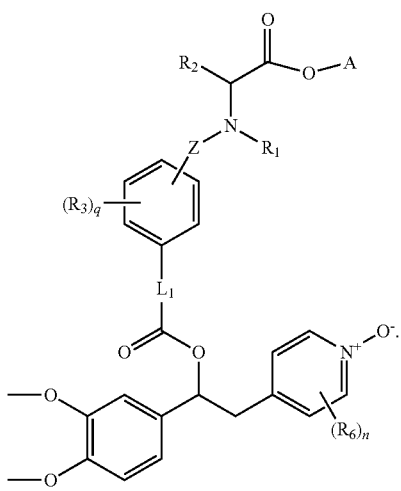

6. A compound, N-oxide, deuterated derivative, or pharmaceutically acceptable salt according to claim 1, which has the absolute configuration of carbon (1) shown in formula (I)':

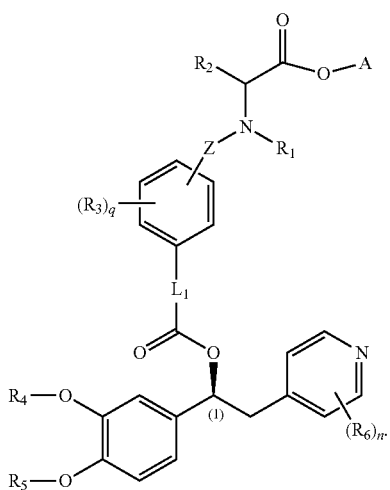

7. A compound, N-oxide, deuterated derivative, or pharmaceutically acceptable salt according to claim 1, which is a compound selected from the group consisting of:

[(1S)-2-(3,5-dichloro-1-oxido-pyridin-1-ium-4-yl)-1-(3,4-dimethoxyphenyl)ethyl] 3-[[[2-oxo-1-phenyl-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 3-fluoro-4-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 4-[[1-(3-fluorophenyl)-2-oxo-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 4-[[1-(2-fluorophenyl)-2-oxo-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 4-[[1-(3-fluorophenyl)-2-oxo-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 4-[[2-oxo-1-phenyl-2-[(3R)-quinuclidin-3-yl]oxy-ethyl]amino]benzoate single diastereoisomer;

[(1S)-2-(3,5-dichloro-1-oxido-pyridin-1-ium-4-yl)-1-(3,4-dimethoxyphenyl)ethyl] 4-[[2-oxo-1-phenyl-2-[(3R)-quinuclidin-3-yl]oxy-ethyl]amino]benzoate; single diastereoisomer

[(1S)-2-(3,5-dichloro-1-oxido-pyridin-1-ium-4-yl)-1-(3,4-dimethoxyphenyl)ethyl] 4-[[1-(2-fluorophenyl)-2-oxo-2-[(3R)-quinuclidin-3-yl]oxy-ethyl]amino]benzoate single diastereoisomer;

[(1S)-2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]amino]benzoate single diastereoisomer;

[(1S)-2-(3,5-dichloro-1-oxido-pyridin-1-ium-4-yl)-1-(3,4-dimethoxyphenyl)ethyl] 2-fluoro-4-[[2-oxo-1-phenyl-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]sulfamoyl]benzoate single diastereoisomer;

[(1S)-2-(3,5-dichloro-1-oxido-pyridin-1-ium-4-yl)-1-(3,4-dimethoxyphenyl)ethyl] 3-[[[1-(2-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 4-[[[2-oxo-1-phenyl-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 4-[[[1-(2-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 3-[[[2-oxo-1-phenyl-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[2-oxo-1-phenyl-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 4-[[[2-oxo-1-phenyl-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 4-[[[1-(4-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 4-[[[1-(4-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 4-[2-[[1-(2-fluorophenyl)-2-oxo-2-[(3R)-quinuclidin-3-yl]oxy-ethyl]amino]ethyl]benzoate;

[(1S)-2-(3,5-dichloro-1-oxido-pyridin-1-ium-4-yl)-1-[4-(difluoromethoxy)-3-methoxy-phenyl]ethyl] 3-[[[1-(2-fluorophenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(4-fluorophenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yD-ethyl] 3-[[[1-(3-methoxyphenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yD-ethyl] 3-[[[1-(2-methoxyphenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[[1-(2-fluorophenyl)-2-oxo-2-[(3R)-quinuclidin-3-yl]oxy-ethyl]amino]methyl]benzoate;

[2-(3,5-dichloro-1-oxido-pyridin-1-ium-4-yl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 4-[[[2-oxo-1-(3-pyridyl)-2-[(3R)-quinuclidin-3-yl]oxy-ethyl]amino]methyl]benzoate;

[(3R)-quinuclidin-3-yl] 2-[[4-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-(2-fluorophenyl)acetate;

[(3R)-quinuclidin-3-yl] 2-[[3-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-(2-fluorophenyl)acetate;

[(3R)-quinuclidin-3-yl] 2-[[3-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-phenyl-acetate;

[(3R)-quinuclidin-3-yl] 2-[[3-[2-[(1S)-2-(3,5-dichloro-1-oxido-pyridin-1-ium-4-yl)-1-(3,4-dimethoxyphenyl)ethoxy]-2-oxo-ethyl]phenyl]methylamino]-2-(2-fluorophenyl)acetate;

[(1S)-2-(3,5-dichloro-1-oxido-pyridin-1-ium-4-yl)-1-[4-(difluoromethoxy)-3-isopropoxy-phenyl]ethyl] 3-[[[1-(2-fluorophenyl)-2-oxo-2-[(3R)-quinuclidin-3-yl]oxy-ethyl]amino]methyl]benzoate;

[(1S)-2-(3,5-dichloro-1-oxido-pyridin-1-ium-4-yl)-1-[4-(difluoromethoxy)-3-isopropoxy-phenyl]ethyl] 4-[[[1-(2-fluorophenyl)-2-oxo-2-[(3R)-quinuclidin-3-yl]oxy-ethyl]amino]methyl]benzoate;

[(1R)-2-(3,5-dichloro-4-pyridyl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate;

[(1S)-2-(3,5-dichloro-4-pyridyl)-1-(3,4-dimethoxyphenyl)ethyl] 3-[[[1-(3-fluorophenyl)-2-oxo-2-[(3R)-quinuclidin-3-yl]oxy-ethyl]amino]methyl]benzoate;

[(1R)-2-(3,5-dichloro-4-pyridyl)-1-(3,4-dimethoxyphenyl)ethyl] 4-[[[1-(2-methoxyphenyl)-2-oxo-2-[(3R)-quinuclidin-3-yl]oxy-ethyl]amino]methyl]benzoate;

[(1S)-2-(3,5-dichloro-4-pyridyl)-1-(3,4-dimethoxyphenyl)ethyl] 4-[[[1-(2-methoxyphenyl)-2-oxo-2-[(3R)-quinuclidin-3-yl]oxy-ethyl]amino]methyl]benzoate;

[(1R)-2-(3,5-dichloro-4-pyridyl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate;

[(1S)-2-(3,5-dichloro-4-pyridyl)-1-(3,4-dimethoxyphenyl)ethyl] 3-[[[1-(2-methoxyphenyl)-2-oxo-2-[(3R)-quinuclidin-3-yl]oxy-ethyl]amino]methyl]benzoate;

[(1S)-2-(3,5-dichloro-4-pyridyl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate;

[(1R)-2-(3,5-dichloro-4-pyridyl)-1-(3,4-dimethoxyphenyl)ethyl] 4-[[[1-(3-fluorophenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 4-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)

ethyl] 4-[[1-(4-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 4-[[1-(2-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 4-[[1-(3-methoxyphenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 4-[[1-(4-methoxyphenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 4-[[1-(2-methoxyphenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(benzofuran-5-yl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-furyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 4-[[1-(2-fluorophenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 4-[[1-(4-fluorophenyl)-2-oxo-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 3-[[1-(3-fluorophenyl)-2-oxo-2-[(3R)-quinuclidin-3-yl]oxy-ethyl]amino]benzoate;

[(1S)-2-(3,5-dichloro-1-oxido-pyridin-1-ium-4-yl)-1-(3,4-dimethoxyphenyl)ethyl] 4-[[2-oxo-1-phenyl-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 3-[[1-(4-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-(p-tolyl)-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-fluorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-methoxyphenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-methoxyphenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-methoxyphenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3,4-difluorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 4-[[2-oxo-1-phenyl-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3,5)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-1-phenyl-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-fluorophenyl)-2-oxo-2-[(3R)-quinuclidin-3-yl]oxy-ethyl]sulfamoyl]benzoate;

[(1S)-2-(3,5-dichloro-1-oxido-pyridin-1-ium-4-yl)-1-[4-(difluoromethoxy)-3-methoxy-phenyl]ethyl] 3-[[[1-(2-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-[4-(difluoromethoxy)-3-methoxy-phenyl]ethyl] 3-[[[1-(2-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-(3,4-dimethoxyphenyl)ethyl] 4-[[[2-oxo-1-(3-pyridyl)-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-[4-(difluoromethoxy)-3-isopropoxy-phenyl]ethyl] 3-[[[1-(2-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-[4-(difluoromethoxy)-3-isopropoxy-phenyl]ethyl] 4-[[[1-(2-fluorophenyl)-2-oxo-2-[(3R)-quinuclidin-3-yl]oxy-ethyl]amino]methyl]benzoate single diastereoisomer;

[(1S)-2-(3,5-dichloro-1-oxido-pyridin-1-ium-4-yl)-1-[4-(difluoromethoxy)-3-isopropoxy-phenyl]ethyl] 4-[[[1-(2-fluorophenyl)-2-oxo-2-[(3R)-quinuclidin-3-yl]oxy-ethyl]amino]methyl]benzoate single diastereoisomer;

[(3R)-quinuclidin-3-yl] 2-[[4-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-phenyl-acetate single diastereoisomer;

[(3R)-quinuclidin-3-yl] 2-[[4-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]phenyl]methylamino]-2-phenyl-acetate single diastereoisomer;

[(1S)-1-[3-(cyclopropylmethoxy)-4-(difluoromethoxy)phenyl]-2-(3,5-dichloro-1-oxido-pyridin-1-ium-4-yl)ethyl] 2-hydroxy-3-[[[2-oxo-1-phenyl-2-[(3R)-quinuclidin-3-yl]oxy-ethyl]amino]methyl]benzoate;

[(1S)-2-(3,5-dichloro-1-oxido-pyridin-1-ium-4-yl)-1-(3,4-dimethoxyphenyl)ethyl] 4-[2-[[2-oxo-1-phenyl-2-[(3R)-quinuclidin-3-yl]oxy-ethyl]amino]ethyl]benzoate;

[(1S)-2-(3,5-dichloro-1-oxido-pyridin-1-ium-4-yl)-1-(3,4-dimethoxyphenyl)ethyl] 4-[2-[[1-(2-fluorophenyl)-2-oxo-2-[(3R)-quinuclidin-3-yl]oxy-ethyl]amino]ethyl]benzoate single diastereoisomer;

[(1S)-2-(3,5-dichloro-4-pyridyl)-1-(3,4-dimethoxyphenyl)ethyl] 3-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-4-pyridyl)ethyl] 3-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-methoxy-4-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[[2-oxo-1-phenyl-2-[(3R)-quinuclidin-3-yl] oxy-ethyl]amino]methyl]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[2-(2-dimethylaminoethyloxy)-2-oxo-1-phenyl-ethyl]sulfamoyl]benzoate;

[(1S)-1-[3-(cyclopropylmethoxy)-4-(difluoromethoxy) phenyl]-2-(3,5-dichloro-1-oxido-pyridin-1-ium-4-yl) ethyl]4-methoxy-3-[[2-oxo-1-phenyl-2-[(3R)-quinuclidin-3-yl]oxy-ethyl]sulfamoyl]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[1-(4-methoxyphenyl)-2-oxo-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yD-ethyl] 3-[[2-(1-methylpyrrolidin-3-yl)oxy-2-oxo-1-phenyl-ethyl]sulfamoyl]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[1-(4-chlorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[2-[(8-methyl-8-azabicyclo[3 0.2.1]octan-3-yl)oxy]-2-oxo-1-phenyl-ethyl]sulfamoyl]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[1-(3-fluorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[2-oxo-1-phenyl-2-[(3R)-quinuclidin-3-yl] oxy-ethyl]sulfamoyl]benzoate single diastereoisomer;

[(1S)-1-[3-(cyclopropylmethoxy)-4-(difluoromethoxy) phenyl]-2-(3,5-dichloro-1-oxido-pyridin-1-ium-4-yl) ethyl] 3-[[2-oxo-1-phenyl-2-[(3R)-quinuclidin-3-yl] oxy-ethyl]sulfamoyl]benzoate single diastereoisomer;

[(1S)-1-[3-(cyclopropylmethoxy)-4-(difluoromethoxy) phenyl]-2-(3,5-dichloro-1-oxido-pyridin-1-ium-4-yl) ethyl] 3-[[1-(4-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-methoxy-5-[ [2-oxo-1-phenyl-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[ 1-(benzothiophen-3-yl)-2-oxo-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[methylsulfonyl-[2-oxo-1-phenyl-2-[(3R)-quinuclidin-3-yl]oxy-ethyl]amino]methyl]benzoate;

[(1S)-1-[3-(cyclopropylmethoxy)-4-(difluoromethoxy) phenyl]-2-(3,5-dichloro-1-oxido-pyridin-1-ium-4-yD-ethyl] 3-(methanesulfonamido)-5-[[2-oxo-1-phenyl-2-[(3R)-quinuclidin-3-yl]oxy-ethyl]amino]benzoate;

[(1S)-2-(3,5-dichloro-1-oxido-pyridin-1-ium-4-yl)-1-(3, 4-dimethoxyphenyl)ethyl] 3-[[2-oxo-1-phenyl-2-[(3R)-quinuclidin-3-yl]oxy-ethyl]sulfamoyl]benzoate;

[(1S)-1-[3-(cyclopropylmethoxy)-4-(difluoromethoxy) phenyl]-2-(3,5-dichloro-1-oxido-pyridin-1-ium-4-yp-ethyl] 3-[[2-oxo-1-phenyl-2-[(3R)-quinuclidin-3-yl] oxy-ethyl]carbamoyl]benzoate;

[(1S)-2-(3,5-dichloro-1-oxido-pyridin-1-ium-4-yl)-1-[4-(difluoromethoxy)-3-methoxy-phenyl]ethyl] 3-[[2-oxo-1-phenyl-2-[(3R)-quinuclidin-3-yl]oxy-ethyl] amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[(1S)-2-oxo-1-phenyl-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[(1R)-2-oxo-1-phenyl-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[[1-(3-fluorophenyl)-2-oxo-2-[(3R)-quinuclidin-3-yl]oxy-ethyl]amino]methyl]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[1-(3-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[2-(2-dimethylaminoethyloxy)-2-oxo-1-phenyl-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[2-oxo-1-phenyl-2-[(3R)-quinuclidin-3-yl] oxy-ethyl]carbamoyloxy methyl]benzoate;

[(1S)-2-(3,5-dichloro-1-oxido-pyridin-1-ium-4-yl)-1-(3, 4-dimethoxyphenyl)ethyl] 3-[[(1R)-2-oxo-1-phenyl-2-[(3R)-quinuclidin-3-yl]oxy-ethyl]amino]benzoate;

[(1S)-2-(3,5-dichloro-1-oxido-pyridin-1-ium-4-yl)-1-(3, 4-dimethoxyphenyl)ethyl] 3-[[(1S)-2-oxo-1-phenyl-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[methyl-[2-oxo-1-phenyl-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-carbamoyl-5-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-(dimethylcarbamoyl)-5-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[2-[(8-methyl-8-azabicyclo[3.2.1]octan-3-yl) oxy]-2-oxo-1-phenyl-ethyl]amino]benzoate;

[(1S)-1-[3-(cyclopropylmethoxy)-4-(difluoromethoxy) phenyl]-2-(3,5-dichloro-1-oxido-pyridin-1-ium-4-yl) ethyl] 3-[[[1-(4-methoxyphenyl)-2-oxo-2-[(3R)-quinuclidin-3-yl]oxy-ethyl]amino]methyl]benzoate;

[(1S)-1-[3-(cyclopropylmethoxy)-4-(difluoromethoxy) phenyl]-2-(3,5-dichloro-1-oxido-pyridin-1-ium-4-yl) ethyl] 4-[[1-(3-fluorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[ [1-(4-fluorophenyl)-2-oxo-2-[(3R)-quinuclidin-3-yl]oxy-ethyl]carbamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-fluorophenyl)-2-oxo-2-[(3R)-quinuclidin-3-yl]oxy-ethyl]carbamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-2-[(3R)-quinuclidin-3-yl]oxy-1-(3-thienyl)ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 2-fluoro-4-[[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(6-methoxy-3-pyridyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 2-methoxy-5-[[2-oxo-1-phenyl-2-[(3R)-quinuclidin-3-yl]oxy-ethyl]sulfamoyl]benzoate;

[(1S)-2-(3,5-dichloro-1-oxido-pyridin-1-ium-4-yl)-1-(3,4-dimethoxyphenyl)ethyl] 3-[[1-(2-fluorophenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 3-[methyl-[2-oxo-1-phenyl-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(4-methoxyphenyl)-2-oxo-2-[(3R)-quinuclidin-3-yl]oxy-ethyl]carbamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-methoxyphenyl)-2-oxo-2-[(3R)-quinuclidin-3-yl]oxy-ethyl]carbamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(2-methoxyphenyl)-2-oxo-2-[(3R)-quinuclidin-3-yl]oxy-ethyl]carbamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-fluorophenyl)-2-oxo-2-quinuclidin-3-yloxy-ethyl]carbamoyl]benzoate;

[2-(3,5-dichloro-1-oxido-pyridin-1-ium-4-yl)-1-(3,4-dimethoxyphenyl)ethyl] 4-[[1-(2-methoxyphenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 4-[[1-(3-methoxyphenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl]4-[[1-(4-methoxyphenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 4-[[1-(3-fluorophenyl)-2-oxo-2-[(3R)-quinuclidin-3-yl]oxy-ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-fluoro-4-[[2-oxo-1-phenyl-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 3-[[2-oxo-1-phenyl-2-[(3R)-quinuclidin-3-yl]oxy-ethyl]carbamoyloxymethyl]benzoate;

[2-(3,5-dichloro-1-oxido-pyridin-1-ium-4-yl)-1-(3,4-dimethoxyphenyl)ethyl] 3-[[[1-(2-fluorophenyl)-2-oxo-2-[(3R)-quinuclidin-3-yl]oxy-ethyl]amino]methyl]benzoate;

[2-(3,5-dichloro-1-oxido-pyridin-1-ium-4-yl)-1-(3,4-dimethoxyphenyl)ethyl] 3-[[[1-(4-fluorophenyl)-2-oxo-2-[(3R)-quinuclidin-3-yl]oxy-ethyl]amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[1-(3-hydroxyphenyl)-2-oxo-2-[(3R)-quinuclidin-3-yl]oxy-ethyl]amino]benzoate;

[2-(3,5-dichloro-1-oxido-pyridin-1-ium-4-yl)-1-(3,4-dimethoxyphenyl)ethyl] 4-[[1-(3-fluorophenyl)-2-oxo-2-[(3R)-quinuclidin-3-yl]oxy-ethyl]sulfamoyl]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-[[2-oxo-2-[(3R)-quinuclidin-3-yl]oxy-1-(2-thienyl)ethyl]amino]benzoate;

[(1S)-1-[3-(cyclopropylmethoxy)-4-(difluoromethoxy)phenyl]-2-(3,5-dichloro-1-oxido-pyridin-1-ium-4-yl)ethyl] 3-(methanesulfonamidomethyl)-5-[[2-oxo-1-phenyl-2-[(3R)-quinuclidin-3-yl]oxy-ethyl]amino]benzoate;

[(3R)-quinuclidin-3-yl] 2-[3-[2-[2-(3,5-dichloro-1-oxido-pyridin-1-ium-4-yl)-1-(3,4-dimethoxyphenyl)ethoxy]-2-oxo-ethyl]anilino]-2-phenyl-acetate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[2-oxo-1-phenyl-2-[(3R)-quinuclidin-3-yl]oxy-ethyl]amino]benzoate;

[(3R)-quinuclidin-3-yl] 2-[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]carbamoyl]anilino]-2-phenyl-acetate;

[(3R)-quinuclidin-3-yl] 2-[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]sulfamoyl]anilino]-2-phenyl-acetate;

[(3R)-quinuclidin-3-yl] 2-[[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]carbamoyl]phenyl]sulfonylamino]-2-phenyl-acetate;

[(1S)-1-[3-(cyclopropylmethoxy)-4-(difluoromethoxy)phenyl]-2-(3,5-dichloro-1-oxido-pyridin-1-ium-4-yl)ethyl] 3-[[3-[[2-oxo-1-phenyl-2-[(3R)-quinuclidin-3-yl]oxy-ethyl]sulfamoyl]benzoyl]amino]propanoate;

[(3R)-quinuclidin-3-yl] 2-[3-[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethoxy]anilino]-2-phenyl-acetate;

[(3R)-quinuclidin-3-yl] 2-[3-[[2-[(1S)-2-(3,5-dichloro-1-oxido-pyridin-1-ium-4-yl)-1-(3,4-dimethoxyphenyl)ethoxy]-2-oxo-ethyl]carbamoyl]anilino]-2-phenyl-acetate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(4-methoxyphenyl)-2-oxo-2-[(3R)-quinuclidin-3-yl]oxy-ethyl]amino]benzoate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(2-methoxyphenyl)-2-oxo-2-[(3R)-quinuclidin-3-yl]oxy-ethyl]amino]benzoate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(4-fluorophenyl)-2-oxo-2-[(3R)-quinuclidin-3-yl]oxy-ethyl]amino]benzoate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(3-fluorophenyl)-2-oxo-2-[(3R)-quinuclidin-3-yl]oxy-ethyl]amino]benzoate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(2-fluorophenyl)-2-oxo-2-[(3R)-quinuclidin-3-yl]oxy-ethyl]amino]benzoate;

[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl] 3-[[1-(3-methoxyphenyl)-2-oxo-2-[(3R)-quinuclidin-3-yl]oxy-ethyl]amino]benzoate;

[(3R)-quinuclidin-3-yl] 2-[3-[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]carbamoyl]anilino]-2-(3-fluorophenyl)acetate;

[(3R)-quinuclidin-3-yl] 2-[3-[[[2-[(1S)-1-[3-(cyclopropylmethoxy)-4-(difluoromethoxy)phenyl]-2-(3,5-dichloro-1-oxido-pyridin-1-ium-4-yl)ethoxy]-2-oxo-ethyl]-methyl-amino]methyl]anilino]-2-phenylacetate;

[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]sulfonylamino]anilino]-2-phenylacetate;

[2-(3,5-dichloro-1-oxido-pyridin-1-ium-4-yl)-1-(3,4-dimethoxyphenyl)ethyl] 3-[3-[[2-oxo-1-phenyl-2-[(3R)-quinuclidin-3-yl]oxy-ethyl]amino]propyl]benzoate;

[2-[2-(3,5-dichloro-1-oxido-pyridin-1-ium-4-yl)-1-(3,4-dimethoxyphenyl)ethoxy]-2-oxo-ethyl] 3-[[[2-oxo-1-phenyl-2-[(3R)-quinuclidin-3-yl]oxy-ethyl]amino]methyl]benzoate;

[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]carbamoyl]anilino]-2-(2-fluorophenyl)acetate;

[(3R)-quinuclidin-3-yl] 2-[3-[ [2-[2-(3,5-dichloro-1-oxido-pyridin-1-ium-4-yl)-1-(3,4-dimethoxyphenyl)ethoxy]-2-oxo-ethyl]carbamoyl]anilino]-2-(3-fluorophenyl)acetate;

[(3R)-quinuclidin-3-yl] 2-[3-[[2-[2-(3,5-dichloro-1-oxido-pyridin-1-ium-4-yl)-1-(3,4-dimethoxyphenyl)ethoxy]-2-oxo-ethyl]carbamoyl]anilino]-2-(4-fluorophenyl)acetate; and

[2-[2-(3,5-dichloro-1-oxido-pyridin-1-ium-4-yl)-1-(3,4-dimethoxyphenyl)ethoxy]-2-oxo-ethyl] 3-[[2-oxo-1-phenyl-2-[(3R)-quinuclidin-3-yl]oxy-ethyl]amino]benzoate;

or a pharmaceutically acceptable salt of said compound.

8. A pharmaceutical composition, comprising a compound, N-oxide, deuterated derivative, or pharmaceutically acceptable salt according to claim 1 and one or more pharmaceutically acceptable carriers.

9. A pharmaceutical composition according to claim 8, further comprising another active ingredient.

10. A method for the treatment of a disease selected from the group consisting of asthma and COPD, comprising administering an effective amount of a compound, N-oxide, deuterated derivative, or pharmaceutically acceptable salt according to claim 1 to a subject in need thereof.

11. A method according to claim 10, wherein said disease is COPD.

12. An inhalation device, comprising a pharmaceutical composition according to claim 8.

13. A kit, comprising a pharmaceutical composition according to claim 8 and a device which is a single- or multi-dose dry powder inhaler, a metered dose inhaler or a nebulizer.

14. A method according to claim 10, wherein said disease is asthma.

* * * * *